US010260074B2

(12) United States Patent
Gall et al.

(10) Patent No.: US 10,260,074 B2
(45) Date of Patent: *Apr. 16, 2019

(54) AFFENADENOVIRUS (GORILLA) OR ADENOVIRAL VECTORS AND METHODS OF USE

(71) Applicant: GenVec, Inc., Gaithersburg, MD (US)

(72) Inventors: Jason G. D. Gall, Germantown, MD (US); Duncan McVey, Derwood, MD (US); Douglas E. Brough, Gaithersburg, MD (US)

(73) Assignee: GenVec, Inc., Gaithersburg, MD (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/650,289

(22) Filed: Jul. 14, 2017

(65) Prior Publication Data

US 2018/0066281 A1 Mar. 8, 2018

Related U.S. Application Data

(60) Continuation of application No. 14/992,152, filed on Jan. 11, 2016, now Pat. No. 9,725,738, which is a division of application No. 14/349,421, filed as application No. PCT/US2012/058956 on Oct. 5, 2012, now Pat. No. 9,233,153.

(60) Provisional application No. 61/543,638, filed on Oct. 5, 2011.

(51) Int. Cl.

| | |
|---|---|
| ***C12N 7/00*** | (2006.01) |
| ***A61K 48/00*** | (2006.01) |
| ***C12N 15/86*** | (2006.01) |
| ***A61K 39/155*** | (2006.01) |
| ***C07K 14/005*** | (2006.01) |

(52) U.S. Cl.

CPC ............ *C12N 15/86* (2013.01); *A61K 39/155* (2013.01); *C07K 14/005* (2013.01); *C12N 7/00* (2013.01); *A61K 48/00* (2013.01); *C12N 2710/10043* (2013.01); *C12N 2710/10322* (2013.01); *C12N 2710/10333* (2013.01); *C12N 2710/10343* (2013.01)

(58) Field of Classification Search

CPC ...................... C12N 15/86; C12N 7/00; C12N 2710/10043; C12N 2710/10322; C12N 2710/10343; C12N 2710/10333; A61K 39/155; A61K 48/00; C07K 14/005

See application file for complete search history.

(56) References Cited

U.S. PATENT DOCUMENTS

| | | | |
|---|---|---|---|
| 5,837,511 | A | 11/1998 | Falck-Pedersen et al. |
| 5,851,806 | A | 12/1998 | Kovesdi et al. |
| 5,994,106 | A | 11/1999 | Kovesdi et al. |
| 5,994,128 | A | 11/1999 | Fallaux et al. |
| 5,998,205 | A | 12/1999 | Hallenbeck et al. |
| 6,033,908 | A | 3/2000 | Bout et al. |
| 6,127,175 | A | 10/2000 | Vigne et al. |
| 6,225,289 | B1 | 5/2001 | Kovesdi et al. |
| 6,482,616 | B1 | 11/2002 | Kovesdi et al. |
| 6,514,943 | B2 | 2/2003 | Kovesdi et al. |
| 6,551,586 | B1 | 4/2003 | Davidson et al. |
| 6,677,156 | B2 | 1/2004 | Brough et al. |
| 6,682,929 | B2 | 1/2004 | Brough et al. |
| 7,195,896 | B2 | 3/2007 | Kovesdi et al. |
| 8,940,290 | B2 | 1/2015 | Roy et al. |
| 2003/0165820 | A1 | 9/2003 | Day et al. |
| 2004/0136963 | A1 | 7/2004 | Wilson et al. |
| 2008/0233650 | A1 | 9/2008 | Gall et al. |
| 2011/0123564 | A1 | 5/2011 | Mayall et al. |
| 2011/0223135 | A1 | 9/2011 | Roy et al. |
| 2014/0248307 | A1 | 9/2014 | Gall et al. |
| 2014/0248308 | A1 | 9/2014 | McVey et al. |
| 2014/0271711 | A1 | 9/2014 | Brough et al. |
| 2014/0314717 | A1 | 10/2014 | Brough et al. |
| 2015/0140025 | A1 | 5/2015 | Wei et al. |
| 2015/0152434 | A1 | 6/2015 | Roy et al. |
| 2015/0157700 | A1 | 6/2015 | Bruder et al. |
| 2017/0275339 | A1 | 9/2017 | Wei et al. |

FOREIGN PATENT DOCUMENTS

| | | | |
|---|---|---|---|
| WO | WO 1994/028152 | A1 | 12/1994 |
| WO | WO 1995/002697 | A2 | 1/1995 |
| WO | WO 1995/016772 | A1 | 6/1995 |
| WO | WO 1995/034671 | A1 | 12/1995 |
| WO | WO 1996/022378 | A1 | 7/1996 |
| WO | WO 1997/000326 | A1 | 1/1997 |
| WO | WO 1997/012986 | A2 | 4/1997 |
| WO | WO 1997/021826 | A2 | 6/1997 |
| WO | WO 2000/000628 | A1 | 1/2000 |
| WO | WO 2000/034444 | A2 | 6/2000 |
| WO | WO 01/58940 | A2 | 8/2001 |
| WO | WO 2003/020879 | A2 | 3/2003 |
| WO | WO 2003/022311 | A1 | 3/2003 |
| WO | WO 2005/075506 | A1 | 8/2005 |
| WO | WO 2006/065827 | A2 | 6/2006 |
| WO | WO 2007/027860 | A2 | 3/2007 |
| WO | WO 2008/011609 | A2 | 1/2008 |
| WO | WO 2010/051367 | A1 | 5/2010 |
| WO | WO 2010/086189 | A2 | 8/2010 |
| WO | WO 2011/057248 | A2 | 5/2011 |
| WO | WO 2012/021730 | A2 | 2/2012 |

OTHER PUBLICATIONS

Ahi et al., "Adenoviral Vector Immunity: Its Implications and Circumvention Strategies," *Curr. Gene Therapy*, 11(4): 307-320, Author Manuscript (Aug. 2011).

(Continued)

*Primary Examiner* — Rachel B Gill

(74) *Attorney, Agent, or Firm* — Leydig, Voit & Mayer, Ltd.

(57) ABSTRACT

The invention provides an adenovirus or adenoviral vector characterized by comprising one or more particular nucleic acid sequences or one or more particular amino acid sequences, or portions thereof, pertaining to, for example, an adenoviral pIX protein, DNA polymerase protein, penton protein, hexon protein, and/or fiber protein.

31 Claims, No Drawings

Specification includes a Sequence Listing.

(56) References Cited

OTHER PUBLICATIONS

Alonso-Padilla et al., "Development of Novel Adenoviral Vectors to Overcome Challenges Observed With HAdV-5-based Constructs," *Molecular Therapy*, 24(1): 6-16 (Nov. 2015).
McVey et al., "Adenoviruses isolated from wild gorillas are closely related to human species C viruses," *Virology*, 444: 119-123 (2013).
Seregin et al., "Overcoming pre-existing adenovirus immunity by genetic engineering of adenovirus-based vectors," *Expert Opinion on Biological Therapy*, 9(12): 1521-1531 (2009).
Fu et al., "A prime-boost vaccination strategy using attenuated *Salmonella typhimurium* and a replication-deficient recombinant adenovirus vector elicits protective immunity against human respiratory syncytial virus," *Biochem. and Biophys. Res. Comm.*, 395: 87-92 (2010).
Altschul et al., "Basic Local Alignment Search Tool," *J. Molecular Biol.*, 215(3): 403-410 (1990).
Altschul et al., "Gapped BLAST and PSI-BLAST: a new generation of protein database search programs," *Nucleic Acids Res.*, 25(17): 3389-3402 (1997).
Aubert et al., "Accumulation of Herpes Simplex Virus Type 1 Early and Leaky-Late Proteins Correlates with Apoptosis Prevention in infected Human Hep-2 Cells," *J. Virol.*, 75(2): 1013-1030 (2001).
Bai et al., "Mutations that alter an Arg-Gly-Asp (RGD) sequence in the adenovirus type 2 penton base protein abolish its cell-rounding activity and delay virus reproduction in flat cells," *J. Virol.*, 67(9): 5198-5205 (1993).
Biegert et al., "Sequence context-specific profiles for homology searching," *Proc. Natl. Acad. Sci. USA*, 106(10): 3770-3775 (2009).
Boulanger et al., "Characterization of adenovirus protein IX," *J. Gen. Virol.*, 44(3): 783-800 (1979).
Brough et al., "Activation of transgene expression by early region 4 is responsible for a high level of persistent transgene expression from adenovirus vectors in vivo," *J. Virol.*, 71(12): 9206-9213 (1997).
Cartier et al., "Hematopoietic stem cell gene therapy with a lentiviral vector in X-linked adrenoleukodystrophy," *Science*, 326(5954): 818-823 (2009).
Cavazzana-Calvo et al., "Gene therapy of human severe combined immunodeficiency (SCID)-X1 disease," *Science*, 288(5466): 669-672 (2000).
Chen et al., "Persistence in muscle of an adenoviral vector that lacks all viral genes," *Proc. Natl. Acad. Sci. USA*, 94(5): 1645-1650 (1997).
Chroboczek et al., "The sequence of the genome of adenovirus type 5 and its comparison with the genome of adenovirus type 2," *Virology*, 186(1): 280-285 (1992).
Crawford-Miksza et al., "Analysis of 15 adenovirus hexon proteins reveals the location and structure of seven hypervariable regions containing serotype-specific residues," *J. Virol.*, 70(3): 1836-1844 (1996).
Curiel et al., "High-efficiency gene transfer mediated by adenovirus coupled to DNA-polylysine complexes," *Hum. Gene Ther.*, 3(2): 147-154 (1992).
Devaux et al., "Structure of adenovirus fibre. I. Analysis of crystals of fibre from adenovirus serotypes 2 and 5 by electron microscopy and X-ray crystallography," *J. Molec. Biol.*, 215(4): 567-588 (1990).
Dey et al., "Molecular epidemiology of adenovirus infection among infants and children with acute gastroenteritis in Dhaka City, Bangladesh," *Infect. Genet. Evol.*, 9(4) 518-522 (2009).
Dolan et al., "The genome sequence of herpes simplex virus type 2," *J. Virol.*72(3): 2010-2021 (1998).
European Patent Office, International Search Report in International Patent Application No. PCT/US/2013/041358 (dated Dec. 11, 2014).
Field et al., "Properties of the adenovirus DNA polymerase," *J. Biol. Chem.*, 259(15): 9487-9495 (1984).
Gall et al., "Construction and characterization of hexon-chimeric adenoviruses: specification of adenovirus serotype," *J. Virol.*, 72(12): 10260-10264 (1998).
Genbank Accession No. ABU95388.1, "hexon, partial [Human adenovirus 9]," (Jun. 2009).
Genbank Accession No. ABX79578, "UL47 [Human herpesvirus 2]" (Apr. 14, 2009).
Genbank Accession No. CAB06743.1, "major capsid protein [Human herpesvirus 2]" (Nov. 14, 2006).
Genbank Accession No. EDA88859.1, "hypothetical protein GOS_1918841, partial [marine metagenome]," (Apr. 2007).
Genbank Accession No. EDL20708.1, "mCG1048340," (Jun. 2007).
Genbank Accession No. FJ025900, "Simian adenovirus 43, complete genome," (Jul. 2009).
Genbank Accession No. FJ025900.1, "Simian adenovirus 43, complete genome," (Mar. 2012).
Genbank Accession No. FJ025901, "Simian adenovirus 45, complete genome," (Jul. 2009).
Genbank Accession No. FJ025901.1, "Simian adenovirus 45, complete genome," (Mar. 2012).
Genbank Accession No. JN163990.1, "Gorilla gorilla beringei adenovirus 6 hexon gene, partial cds," (Dec. 2011).
Genbank Accession No. KC702813.1,"Gorilla beringei beringei adenovirus 7 isolate GC44 hexon gene, complete cds" (Sep. 2013).
Genbank Accession No. KC702815.1, "Gorilla beringei graueri adenovirus 9 isolate GC46 hexon gene, complete cds," (Sep. 2013).
Genbank Accession No. KC702816, "Gorilla beringei beringei adenovirus 7 isolate GC44 DNA polymerase gene, complete cds," (Sep. 2013).
Genbank Accession No. P89442.1, "Major capsid protein" (Nov. 2005).
Genbank Accession No. P89467, "Tegument protien and transactivator of immediate early genes," (Oct. 2006).
Ghosh-Choudhury et al., "Protein IX, a minor component of the human adenovirus capsid, is essential for the packaging of full length genomes," *EMBO J.*, 6(6): 1733-1739 (1987).
Ginsberg et al., "A proposed terminology for the adenovirus antigens and virion morphological subunits," *Virology*, 28(4): 782-783 (1966).
Goins et al., "Herpes simplex virus vector-mediated gene delivery for the treatment of lower urinary tract pain," *Gene Ther.*, 16(4): 558-569 (2009).
Graham et al., "Characteristics of a human cell line transformed by DNA from human adenovirus type 5," *J. Gen. Virol.*, 36(1): 59-72 (1977).
Green et al., "Evidence for a repeating cross-beta sheet structure in the adenovirus fibre," *EMBO J.*, 2(8): 1357-1365 (1983).
Hacein-Bey-Abina et al., "A serious adverse event after successful gene therapy for X-linked severe combined immunodeficiency," *N. Engl. J. Med.*, 348(3): 255-256 (2003).
Henry et al., "Characterization of the knob domain of the adenovirus type 5 fiber protein expressed in *Escherichia coli," J. Virol.*, 68(8): 5239-5246 (1994).
Horvath et al., "Nonpermissivity of human peripheral blood lymphocytes to adenovirus type 2 infection," *J. Virology*, 62(1): 341-345 (1988).
Jornvall et al., "The adenovirus hexon protein. The primary structure of the polypeptide and its correlation with the hexon gene," *J. Biol. Chem.*, 256(12): 6181-6186 (1981).
Kannan et al., "Structural and functional diversity of the microbial kinome," *PLoS Biol.*, 5(3) E17 (2007).
Kay et al., "Viral vectors for gene therapy: the art of turning infectious agents into vehicles of therapeutics," *Nature Medicine*, 7(1): 33-40 (2001).
Kochanek et al., "High-capacity adenoviral vectors for gene transfer and somatic gene therapy," *Hum. Gene Ther.*, 10(15): 2451-2459 (1999).
Koelle et al., "CD4 T-cell responses to herpes simplex virus type 2 major capsid protein VP5: Comparison with responses to tegument and envelope glycoproteins", *J. Virol.*, 74(23):11422-11425 (2000).
Kohlmann et al., "Protective efficacy and immunogenictiy of an adenoviral vector vaccine encoding the codon-optimized F protein of respiratory syncytial virus," *J Virol.* 83(23): 12601-12610 (2009).
Lasaro et al., "New insights on adenovirus as vaccine vectors," *Molecular Therapy*, 17(8): 1333-1339 (2009).

(56) References Cited

OTHER PUBLICATIONS

Lutz et al., "The product of the adenovirus intermediate gene IX is a transcriptional activator," *J. Virol.*, 71(7): 5102-5109 (1997).
Mayrhofer et al., "Nonreplicating vaccinia virus vectors expressing the H5 influenza virus hemagglutinin produced in modified Vero cells induce robust protection," *J. Virol.*, 83(10): 5192-5203 (2009).
Mease et al., "Safety, tolerability, and clinical outcomes after intraarticular injection of a recombinant adeno-associated vector containing a tumor necrosis factor antagonist gene: results of a phase 1/2 Study," *Journal of Rheumatology*, 37(4): 692-703 (2010).
Morsy et al., An adenoviral vector deleted for all viral coding sequences results in enhanced safety and extended expression of a leptin transgene, *Proc. Natl. Acad. Sci. USA*, 95: 7866-7871 (1998).
Muller et al., "Herpes simplex virus type 2 tegument proteins contain subdominant T-cell epitopes detectable in BALB/c mice after DNA immunization and infection", *J. Virol.*, 90 (5): 1153-1163 (2009).
Narum et al., "Codon Optimization of Gene Fragments Encoding Plasmodium falciparum Merzoite Proteins Enhances DNA Vaccine Protein Expression and Immunogenicity in Mice," *Infect Immun*, 69(12): 7250-7253 (2001).
NCBI reference sequence AP_000218, "E3 12.5K [Human adenovirus 5]," (Dec. 2008).
NCBI reference sequence AP_000224.1, "*Homo sapiens* genomic DNA, chromosome 21q21.2, LL56-APP region, clone:B2017A3, complete sequence," (Nov. 1991).
Neumann et al., "Determination of the nucleotide sequence for the penton-base gene of human adenovirus type 5," *Gene*, 69(1) 153-157 (1988).
Novelli et al., "Deletion analysis of functional domains in baculovirus-expressed adenovirus type 2 fiber," *Virology*, 185(1): 365-376 (1991).
Roberts et al., "Three-dimensional structure of the adenovirus major coat protein hexon," *Science*, 232(4754): 1148-1151 (1986).
Roy et al., "Generation of an adenoviral vaccine vector based on simian adenovirus 21," *Journal of General Virology* 87: 2477-2485 (2006).
Roy et al., "Isolation and Characterization of Adenoviruses Persistently Shed from the Gastrointestinal Tract of Non-Human Primates," *PLOS Pathogens*, 5(7): E1000503, 1-9, (2009).
Rusch et al., "The Sorcerer II Global Ocean Sampling expedition: northwest Atlantic through eastern tropical Pacific," *PLoS Biol.*, 5(3) E77 (2007).
Rux et al., "Structural and phylogenetic analysis of adenovirus hexons by use of high-resolution x-ray crystallographic, molecular modeling, and sequence-based methods," *J. Virol.*, 77(17): 9553-9566 (2003).
Signas et al., Adenovirus 3 Fiber Polypeptide Gene: Implications for the Structure of the Fiber Protein, *J. Virol.*, 53(2): 672-678 (1985).
Silver et al., "Interaction of human adenovirus serotype 2 with human lymphoid cells," *Virology*, 165(2): 377-387 (1968).
Soding, "Protein homology detection by HMM-HMM comparison," *Bioinformatics*, 21(7): 951-960 (2005).
Stewart et al., "Difference imaging of adenovirus: bridging the resolution gap between X-ray crystallography and electron microscopy," *EMBO J.*, 12(7): 2589-99 (1993).
Stewart et al., "Image reconstruction reveals the complex molecular organization of adenovirus," *Cell*, 67(1): 145-154 (1991).
Subak-Sharpe et al., "HSV Molecular Biology: General Aspects of Herpes Simplex Virus Molecular Biology", *Virus Genes*, 16(3): 239-251 (1998).
Thomas et al., "Progress and problems with the use of viral vectors for gene therapy," *Nature Review Genetics*, 4(5): 346-358 (2003).
Van Oostrum et al, "Molecular composition of the adenovirus type 2 virion," *J. Virol.*, 56(2): 439-448 (1985).
Wevers et al., "A novel adenovirus of Western lowland gorillas (*Gorilla gorilla gorilla*)," *J. Virology*, 7(1): 1-8 (2010).
Wevers et al., "Novel Adenoviruses in Wild Primates: a High Level of Genetic Diversity and Evidence of Zoonotic Transmissions," *J. Virology*, 85(20): 10774-10784, (2011).
Yeh et al., "Human adenovirus type 41 contains two fibers," *Virus Res.*, 33(2): 179-198 (1994).
Yooseph et al., "The Sorcerer II Global Ocean Sampling expedition: expanding the universe of protein families," *PLoS Biol.*, 5(3) E16, (2007).

AFFENADENOVIRUS (GORILLA) OR ADENOVIRAL VECTORS AND METHODS OF USE

CROSS-REFERENCE TO RELATED APPLICATIONS

This patent application is a continuation of U.S. patent application Ser. No. 14/992,152, filed Jan. 11, 2016, now U.S. Pat. No. 9,725,738, which is a divisional of U.S. patent application Ser. No. 14/349,421, filed Apr. 3, 2014, now U.S. Pat. No. 9,233,153, which is a U.S. National Phase of International Patent Application No. PCT/US2012/058956, filed Oct. 5, 2012, which claims the benefit of U.S. Provisional Patent Application No. 61/543,638, filed Oct. 5, 2011, all of which are incorporated by reference.

INCORPORATION-BY-REFERENCE OF MATERIAL SUBMITTED ELECTRONICALLY

Incorporated by reference in its entirety herein is a computer-readable nucleotide/amino acid sequence listing submitted concurrently herewith and identified as follows: One 285,400 Byte ASCII (Text) file named "730337_ST25.txt," created Jul. 14, 2017.

BACKGROUND OF THE INVENTION

In vivo delivery of proteins in biologically relevant forms and amounts has been an obstacle to drug and vaccine development for decades. One solution that has proven to be a successful alternative to traditional protein delivery approaches is the delivery of exogenous nucleic acid sequences for production of proteins in vivo. Gene transfer vectors ideally enter a wide variety of cell types, have the capacity to accept large nucleic acid sequences, are safe, and can be produced in quantities required for treating patients. Viral vectors are gene transfer vectors with these advantageous properties (see, e.g., Thomas et al., *Nature Review Genetics,* 4: 346-358 (2003)). Furthermore, while many viral vectors are engineered to infect a broad range of cell types, viral vectors also can be modified to target specific cell types, which can enhance the therapeutic efficacy of the vector (see, e.g., Kay et al., *Nature Medicine,* 7(1): 33-40 (2001).

Viral vectors that have been used with some success to deliver exogenous proteins to mammalian cells for therapeutic purposes include, for example, Retrovirus (see, e.g., Cavazzana-Calvo et al., *Science,* 288 (5466): 669-672 (2000)), Lentivirus (see, e.g., Cartier et al., *Science,* 326: 818-823 (2009)), Adeno-associated virus (AAV) (see, e.g., Mease et al., *Journal of Rheumatology,* 27(4): 692-703 (2010)), Herpes Simplex Virus (HSV) (see, e.g., Goins et al., *Gene Ther.,* 16(4): 558-569 (2009)), Vaccinia Virus (see, e.g., Mayrhofer et al., *J. Virol.,* 83(10): 5192-5203 (2009)), and Adenovirus (see, e.g., Lasaro and Ertl, *Molecular Therapy,* 17(8): 1333-1339 (2009)).

Despite their advantageous properties, widespread use of viral gene transfer vectors is hindered by several factors. In this respect, certain cells are not readily amenable to gene delivery by currently available viral vectors. For example, lymphocytes are impaired in the uptake of adenoviruses (Silver et al., *Virology,* 165: 377-387 (1988), and Horvath et al., *J. Virology,* 62(1): 341-345 (1988)). In addition, viral vectors that integrate into the host cell's genome (e.g., retroviral vectors) have the potential to cause insertion mutations in oncogenes (see, e.g., Cavazzana-Calvo et al., supra, and Hacein-Bey-Abina et al., *N. Engl. J. Med.,* 348: 255-256 (2003)).

The use of viral vectors for gene transfer also is impeded by the immunogenicity of viral vectors. A majority of the U.S. population has been exposed to wild-type forms of many of the viruses currently under development as gene transfer vectors (e.g., adenovirus). As a result, much of the U.S. population has developed pre-existing immunity to certain virus-based gene transfer vectors. Such vectors are quickly cleared from the bloodstream, thereby reducing the effectiveness of the vector in delivering biologically relevant amounts of a gene product. Moreover, the immunogenicity of certain viral vectors prevents efficient repeat dosing, which can be advantageous for "boosting" the immune system against pathogens when viral vectors are used in vaccine applications, thereby resulting in only a small fraction of a dose of the viral vector delivering its payload to host cells.

Thus, there remains a need for improved viral vectors that can be used to efficiently deliver genes to mammalian cells in vivo. The invention provides such viral vectors.

BRIEF SUMMARY OF THE INVENTION

The invention provides an adenovirus or adenoviral vector. The adenovirus or adenoviral vector comprises one or more of the nucleic acid sequences selected from the group consisting of (a) the nucleic acid sequence of SEQ ID NO: 1, (b) a nucleic acid sequence that is at least 98.5% identical to SEQ ID NO: 2, (c) a nucleic acid sequence that is at least 90% identical to SEQ ID NO: 3, (d) a nucleic acid sequence that is at least 80% identical to SEQ ID NO: 4, and (e) a nucleic acid sequence that is at least 89% identical to SEQ ID NO: 5.

The invention provides an adenovirus or adenoviral vector comprising one or more of the nucleic acid sequences selected from the group consisting of (a) a nucleic acid sequence that is at least 98.6% identical to SEQ ID NO: 6, (b) a nucleic acid sequence that is at least 99.06% identical to SEQ ID NO: 7, (c) a nucleic acid sequence that is at least 97.13% identical to SEQ ID NO: 8, (d) a nucleic acid sequence that is at least 90.7% identical to SEQ ID NO: 9, and (e) a nucleic acid sequence that is at least 96.6% identical to SEQ ID NO: 10.

The invention provides an adenovirus or adenoviral vector comprising one or more of the nucleic acid sequences selected from the group consisting of (a) a nucleic acid sequence comprising at least 121 contiguous nucleotides of SEQ ID NO: 6, (b) a nucleic acid sequence comprising at least 462 contiguous nucleotides of SEQ ID NO: 7, (c) a nucleic acid sequence comprising at least 234 contiguous nucleotides of SEQ ID NO: 8, (d) a nucleic acid sequence comprising at least 606 contiguous nucleotides of SEQ ID NO: 9, and (e) a nucleic acid sequence comprising at least 188 contiguous nucleotides of SEQ ID NO: 10.

The invention provides an adenovirus or adenoviral vector comprising one or more of the amino acid sequences selected from the group consisting of (a) the amino acid sequence of SEQ ID NO: 11, (b) an amino acid sequence that is at least 82% identical to SEQ ID NO: 13, (c) an amino acid sequence that is at least 80% identical to SEQ ID NO: 14, and (d) an amino acid sequence that is at least 83% identical to SEQ ID NO: 15.

The invention provides an adenovirus or adenoviral vector comprising one or more of the nucleic acid sequences selected from the group consisting of (a) a nucleic acid sequence encoding the amino acid sequence of SEQ ID NO: 11, (b) a nucleic acid sequence encoding an amino acid sequence that is at least 99% identical to SEQ ID NO: 12, (c) a nucleic acid sequence encoding an amino acid sequence that is at least 82% identical to SEQ ID NO: 13, (d) a nucleic acid sequence encoding an amino acid sequence that is at least 80% identical to SEQ ID NO: 14, and (e) a nucleic acid sequence encoding an amino acid sequence that is at least 83% identical to SEQ ID NO: 15.

The invention provides an adenovirus or adenoviral vector comprising one or more of the amino acid sequences selected from the group consisting of (a) the amino acid sequence of SEQ ID NO: 16, (b) an amino acid sequence that is at least 97.8% identical to SEQ ID NO: 18, (c) an amino acid that is at least 93.4% identical to SEQ ID NO: 19, and (d) an amino acid sequence that is at least 98.2% identical to SEQ ID NO: 20.

The invention provides an adenovirus or adenoviral vector comprising one or more of the nucleic acid sequences selected from the group consisting of (a) a nucleic acid sequence encoding the amino acid sequence of SEQ ID NO: 16, (b) a nucleic acid sequence encoding an amino acid sequence that is at least 99.78% identical to SEQ ID NO: 17, (c) a nucleic acid sequence encoding an amino acid sequence that is at least 97.8% identical to SEQ ID NO: 18, (d) a nucleic acid sequence encoding an amino acid that is at least 93.4% identical to SEQ ID NO: 19, and (e) a nucleic acid sequence encoding an amino acid sequence that is at least 98.2% identical to SEQ ID NO: 20.

The invention provides an adenovirus or adenoviral vector comprising one or more of the amino acid sequences selected from the group consisting of (a) an amino acid sequence comprising at least 89 contiguous amino acid residues of SEQ ID NO: 16, (b) an amino acid sequence comprising at least 247 contiguous amino acid residues of SEQ ID NO: 18, (c) an amino acid sequence comprising at least 370 contiguous amino acid residues of SEQ ID NO: 19, and (d) an amino acid sequence comprising at least 192 contiguous amino acid residues of SEQ ID NO: 20.

The invention provides an adenovirus or adenoviral vector comprising one or more of the nucleic acid sequences selected from the group consisting of (a) a nucleic acid sequence encoding an amino acid sequence comprising at least 89 contiguous amino acid residues of SEQ ID NO: 16, (b) a nucleic acid sequence encoding an amino acid sequence comprising at least 428 contiguous amino acid residues of SEQ ID NO: 17, (c) a nucleic acid sequence encoding an amino acid sequence comprising at least 247 contiguous amino acid residues of SEQ ID NO: 18, (d) a nucleic acid sequence encoding an amino acid sequence comprising at least 370 contiguous amino acid residues of SEQ ID NO: 19, and (e) a nucleic acid sequence encoding an amino acid sequence comprising at least 192 contiguous amino acid residues of SEQ ID NO: 20.

DETAILED DESCRIPTION OF THE INVENTION

Adenoviruses are generally associated with benign pathologies in humans, and the genomes of adenoviruses isolated from a variety of species, including humans, have been extensively studied. Adenovirus is a medium-sized (90-100 nm), nonenveloped icosohedral virus containing approximately 36 kb of double-stranded DNA. The adenovirus capsid mediates the key interactions of the early stages of the infection of a cell by the virus, and is required for packaging adenovirus genomes at the end of the adenovirus life cycle. The capsid comprises 252 capsomeres, which includes 240 hexons, 12 penton base proteins, and 12 fibers (Ginsberg et al., *Virology,* 28: 782-83 (1966)). The hexon comprises three identical proteins, namely polypeptide II (Roberts et al., *Science,* 232: 1148-51 (1986)). The penton base comprises five identical proteins and the fiber comprises three identical proteins. Proteins IIIa, VI, and IX are present in the adenoviral coat and are believed to stabilize the viral capsid (Stewart et al., *Cell,* 67: 145-54 (1991), and Stewart et al., *EMBO J.,* 12(7): 2589-99 (1993)). The expression of the capsid proteins, with the exception of pIX, is dependent on the adenovirus polymerase protein. Therefore, major components of an adenovirus particle are expressed from the genome only when the polymerase protein gene is present and expressed.

Several features of adenoviruses make them ideal vehicles for transferring genetic material to cells for therapeutic applications (i.e. "gene therapy"), or for use as antigen delivery systems for vaccine applications. For example, adenoviruses can be produced in high titers (e.g., about $10^{13}$ particle units (pu)), and can transfer genetic material to nonreplicating and replicating cells. The adenoviral genome can be manipulated to carry a large amount of exogenous DNA (up to about 8 kb), and the adenoviral capsid can potentiate the transfer of even longer sequences (Curiel et al., *Hum. Gene Ther.,* 3: 147-154 (1992)). Additionally, adenoviruses generally do not integrate into the host cell chromosome, but rather are maintained as a linear episome, thereby minimizing the likelihood that a recombinant adenovirus will interfere with normal cell function.

The invention is predicated, at least in part, on the discovery and isolation of an adenovirus that has not previously been identified or isolated. The adenovirus described herein was isolated from a *gorilla*. There are four widely recognized *gorilla* subspecies within the two species of Eastern *Gorilla* (*Gorilla beringei*) and Western *Gorilla* (*Gorilla gorilla*). The Western *Gorilla* species includes the subspecies Western Lowland *Gorilla* (*Gorilla gorilla gorilla*) and Cross River *Gorilla* (*Gorilla gorilla diehli*). The Eastern *Gorilla* species includes the subspecies Mountain *Gorilla* (*Gorilla beringei beringei*) and Eastern Lowland *Gorilla* (*Gorilla beringei graueri*) (see, e.g., Wilson and Reeder, eds., *Mammalian Species of the World,* 3rd ed., Johns Hopkins University Press, Baltimore, Md. (2005)). The adenovirus of the invention was isolated from Mountain *Gorilla* (*Gorilla beringei beringei*).

The genomes of several such adenoviruses have been analyzed, and it has been determined that the adenovirus can have the nucleic acid sequence of, for example, SEQ ID NO: 21, SEQ ID NO: 22, SEQ ID NO: 23, SEQ ID NO: 24, or SEQ ID NO: 25, each of which includes a number of sub-sequences that serve to uniquely define the adenovirus, namely the nucleic acid sequences SEQ ID NOs: 1-10, and amino acid sequences SEQ ID NOs: 11-20. SEQ ID NOs: 6-10 encode the amino acid sequences of SEQ ID NOs: 16-20, respectively. SEQ ID NOs: 1-5 are a subset of the nucleic acid sequences of SEQ ID NOs: 6-10, respectively. SEQ ID NOs: 11-15 are a subset of the amino acid sequences of SEQ ID NOs: 16-20, respectively.

The adenovirus can be modified in the same manner as previously known adenoviruses to be used as an adenoviral vector, e.g., a gene delivery vehicle.

The term "adenovirus," as used herein, refers to an adenovirus that retains the ability to participate in the adenovirus life cycle and has not been physically inactivated by, for example, disruption (e.g., sonication), denaturing (e.g., using heat or solvents), or cross-linkage (e.g., via formalin cross-linking). The "adenovirus life cycle" includes (1) virus binding and entry into cells, (2) transcription of the adenoviral genome and translation of adenovirus proteins, (3) replication of the adenoviral genome, and (4) viral particle assembly (see, e.g., Fields Virology, $5^{th}$ ed., Knipe et al. (eds.), Lippincott Williams & Wilkins, Philadelphia, Pa. (2006)).

The term "adenoviral vector," as used herein, refers to an adenovirus in which the adenoviral genome has been manipulated to accommodate a nucleic acid sequence that is non-native with respect to the adenoviral genome. Typically, an adenoviral vector is generated by introducing one or more mutations (e.g., a deletion, insertion, or substitution) into the adenoviral genome of the adenovirus so as to accommodate the insertion of a non-native nucleic acid sequence, for example, for gene transfer, into the adenovirus.

The adenovirus and adenoviral vector can be replication-competent, conditionally replication-competent, or replication-deficient.

A replication-competent adenovirus or adenoviral vector can replicate in typical host cells, i.e., cells typically capable of being infected by an adenovirus. A replication-competent adenovirus or adenoviral vector can have one or more mutations as compared to the wild-type adenovirus (e.g., one or more deletions, insertions, and/or substitutions) in the adenoviral genome that do not inhibit viral replication in host cells. For example, the adenovirus or adenoviral vector can have a partial or entire deletion of the adenoviral early region known as the E3 region, which is not essential for propagation of the adenovirus or adenoviral genome.

A conditionally-replicating adenovirus or adenoviral vector is an adenovirus or adenoviral vector that has been engineered to replicate under pre-determined conditions. For example, replication-essential gene functions, e.g., gene functions encoded by the adenoviral early regions, can be operably linked to an inducible, repressible, or tissue-specific transcription control sequence, e.g., promoter. In such an embodiment, replication requires the presence or absence of specific factors that interact with the transcription control sequence. Conditionally-replicating adenoviral vectors are further described in U.S. Pat. No. 5,998,205.

A replication-deficient adenovirus or adenoviral vector is an adenovirus or adenoviral vector that requires complementation of one or more gene functions or regions of the adenoviral genome that are required for replication, as a result of, for example, a deficiency in one or more replication-essential gene function or regions, such that the adenovirus or adenoviral vector does not replicate in typical host cells, especially those in a human to be infected by the adenovirus or adenoviral vector.

A deficiency in a gene function or genomic region, as used herein, is defined as a disruption (e.g., deletion) of sufficient genetic material of the adenoviral genome to obliterate or impair the function of the gene (e.g., such that the function of the gene product is reduced by at least about 2-fold, 5-fold, 10-fold, 20-fold, 30-fold, or 50-fold) whose nucleic acid sequence was disrupted (e.g., deleted) in whole or in part. Deletion of an entire gene region often is not required for disruption of a replication-essential gene function. However, for the purpose of providing sufficient space in the adenoviral genome for one or more transgenes, removal of a majority of one or more gene regions may be desirable. While deletion of genetic material is preferred, mutation of genetic material by addition or substitution also is appropriate for disrupting gene function. Replication-essential gene functions are those gene functions that are required for adenovirus replication (e.g., propagation) and are encoded by, for example, the adenoviral early regions (e.g., the E1, E2, and E4 regions), late regions (e.g., the L1, L2, L3, L4, and L5 regions), genes involved in viral packaging (e.g., the IVa2 gene), and virus-associated RNAs (e.g., VA-RNA-1 and/or VA-RNA-2).

Whether the adenovirus or adenoviral vector is replication-competent or replication-deficient, the adenovirus or adenoviral vector retains at least a portion of the adenoviral genome. The adenovirus or adenoviral vector can comprise any portion of the adenoviral genome, including protein coding and non-protein coding regions. Desirably, the adenovirus or adenoviral vector comprises at least one nucleic acid sequence that encodes an adenovirus protein. The adenovirus or adenoviral vector can comprise a nucleic acid sequence that encodes any suitable adenovirus protein, such as, for example, a protein encoded by any one of the early region genes (i.e., E1A, E1B, E2A, E2B, E3, and/or E4 regions), or a protein encoded by any one of the late region genes, which encode the virus structural proteins (i.e., L1, L2, L3, L4, and L5 regions).

The adenovirus or adenoviral vector desirably comprises one or more nucleic acid sequences that encode the pIX protein, the DNA polymerase protein, the penton protein, the hexon protein, and/or the fiber protein. The adenovirus or adenoviral vector can comprise a full-length nucleic acid sequence that encodes a full-length amino acid sequence of an adenovirus protein. Alternatively, the adenovirus or adenoviral vector can comprise a portion of a full-length nucleic acid sequence that encodes a portion of a full-length amino acid sequence of an adenovirus protein.

A "portion" of a nucleic acid sequence comprises at least ten nucleotides (e.g., about 10 to about 5000 nucleotides). Preferably, a "portion" of a nucleic acid sequence comprises 10 or more (e.g., 15 or more, 20 or more, 25 or more, 30 or more, 35 or more, 40 or more, 45 or more, 50 or more, or 100 or more) nucleotides, but less than 5,000 (e.g., 4900 or less, 4000 or less, 3000 or less, 2000 or less, 1000 or less, 800 or less, 500 or less, 300 or less, or 100 or less) nucleotides. Preferably, a portion of a nucleic acid sequence is about 10 to about 3500 nucleotides (e.g., about 10, 20, 30, 50, 100, 300, 500, 700, 1000, 1500, 2000, 2500, or 3000 nucleotides), about 10 to about 1000 nucleotides (e.g., about 25, 55, 125, 325, 525, 725, or 925 nucleotides), or about 10 to about 500 nucleotides (e.g., about 15, 30, 40, 50, 60, 70, 80, 90, 150, 175, 250, 275, 350, 375, 450, 475, 480, 490, 495, or 499 nucleotides), or a range defined by any two of the foregoing values. More preferably, a "portion" of a nucleic acid sequence comprises no more than about 3200 nucleotides (e.g., about 10 to about 3200 nucleotides, about 10 to about 3000 nucleotides, or about 30 to about 500 nucleotides, or a range defined by any two of the foregoing values).

A "portion" of an amino acid sequence comprises at least three amino acids (e.g., about 3 to about 1,200 amino acids). Preferably, a "portion" of an amino acid sequence comprises 3 or more (e.g., 5 or more, 10 or more, 15 or more, 20 or more, 25 or more, 30 or more, 40 or more, or 50 or more) amino acids, but less than 1,200 (e.g., 1,000 or less, 800 or less, 700 or less, 600 or less, 500 or less, 400 or less, 300 or less, 200 or less, or 100 or less) amino acids. Preferably, a portion of an amino acid sequence is about 3 to about 500 amino acids (e.g., about 10, 100, 200, 300, 400, or 500 amino acids), about 3 to about 300 amino acids (e.g., about 20, 50, 75, 95, 150, 175, or 200 amino acids), or about 3 to about 100 amino acids (e.g., about 15, 25, 35, 40, 45, 60, 65, 70, 80, 85, 90, 95, or 99 amino acids), or a range defined by any two of the foregoing values. More preferably, a "portion" of an amino acid sequence comprises no more than about 500 amino acids (e.g., about 3 to about 400 amino acids, about 10 to about 250 amino acids, or about 50 to about 100 amino acids, or a range defined by any two of the foregoing values).

The adenovirus pIX protein is present in the adenovirus capsid, has been shown to strengthen hexon nonamer interactions, and is essential for the packaging of full-length genomes (see, e.g., Boulanger et al., *J. Gen. Virol.,* 44: 783-800 (1979); Horwitz M. S., "Adenoviridae and their replication" in *Virology,* $2^{nd}$ ed., B. N. Fields et al. (eds.), Raven Press, Ltd., New York, pp. 1679-1721 (1990), Ghosh-Choudhury et al., *EMBO J.,* 6: 1733-1739 (1987), and van Oostrum et al, *J. Virol.,* 56: 439-448 (1985)). In addition to its contribution to adenovirus structure, pIX also has been shown to exhibit transcriptional properties, such as stimulation of adenovirus major late promoter (MLP) activity (see, e.g., Lutz et al., *J. Virol.,* 71(7): 5102-5109 (1997)). Nucleic acid sequences that encode all or a portion of an adenovirus pIX protein include, for example, SEQ ID NO: 6 and SEQ ID NO: 1. Amino acid sequences that comprise a full-length pIX protein, or a portion thereof, include, for example, SEQ ID NO: 16 and SEQ ID NO: 11.

The adenovirus DNA polymerase protein is essential for viral DNA replication both in vitro and in vivo. The polymerase co-purifies in a complex with the precursor (pTP) of the terminal protein (TP), which is covalently attached to the 5' ends of adenovirus DNA (Field et al., *J. Biol. Chem.,* 259: 9487-9495 (1984)). Both the adenovirus DNA polymerase and pTP are encoded by the E2 region. The polymerase protein is required for the expression of all the structural proteins except for pIX. Without the gene sequence for polymerase protein, polymerase protein is not produced. As a result, the viral genome is not replicated, the Major Late Promoter is not activated, and the capsid proteins are not expressed. Nucleic acid sequences that encode all or a portion of an adenovirus DNA polymerase protein include, for example, SEQ ID NO: 7 and SEQ ID NO: 2. Amino acid sequences that comprise a full-length adenovirus DNA polymerase, or a portion thereof, include, for example, SEQ ID NO: 17 and SEQ ID NO: 12.

The adenovirus hexon protein is the largest and most abundant protein in the adenovirus capsid. The hexon protein is essential for virus capsid assembly, determination of the icosahedral symmetry of the capsid (which in turn defines the limits on capsid volume and DNA packaging size), and integrity of the capsid. In addition, hexon is a primary target for modification in order to reduce neutralization of adenoviral vectors (see, e.g., Gall et al., *J. Virol.,* 72: 10260-264 (1998), and Rux et al., *J. Virol.,* 77(17): 9553-9566 (2003)). The major structural features of the hexon protein are shared by adenoviruses across serotypes, but the hexon protein differs in size and immunological properties between serotypes (Jornvall et al., *J. Biol. Chem.,* 256(12): 6181-6186 (1981)). A comparison of 15 adenovirus hexon proteins revealed that the predominant antigenic and serotype-specific regions of the hexon appear to be in loops 1 and 2 (i.e., LI or 11, and LII or 12, respectively), within which are seven discrete hypervariable regions (HVR1 to HVR7) varying in length and sequence between adenoviral serotypes (Crawford-Miksza et al., *J. Virol.,* 70(3): 1836-1844 (1996)). Nucleic acid sequences that encode all or a portion of an adenovirus hexon protein include, for example, SEQ ID NO: 9 and SEQ ID NO: 4. Amino acid sequences that comprise a full-length adenovirus hexon protein, or a portion thereof, include, for example, SEQ ID NO: 19 and SEQ ID NO: 14.

The adenovirus fiber protein is a homotrimer of the adenoviral polypeptide IV that has three domains: the tail, shaft, and knob. (Devaux et al., *J. Molec. Biol.,* 215: 567-88 (1990), Yeh et al., *Virus Res.,* 33: 179-98 (1991)). The fiber protein mediates primary viral binding to receptors on the cell surface via the knob and the shaft domains (Henry et al., *J. Virol.,* 68(8): 5239-46 (1994)). The amino acid sequences for trimerization are located in the knob, which appears necessary for the amino terminus of the fiber (the tail) to properly associate with the penton base (Novelli et al., *Virology,* 185: 365-76 (1991)). In addition to recognizing cell receptors and binding the penton base, the fiber contributes to serotype identity. Fiber proteins from different adenoviral serotypes differ considerably (see, e.g., Green et al., *EMBO J.,* 2: 1357-65 (1983), Chroboczek et al., *Virology,* 186: 280-85 (1992), and Signas et al., *J. Virol.,* 53: 672-78 (1985)). Thus, the fiber protein has multiple functions key to the life cycle of adenovirus. Nucleic acid sequences that encode all or a portion of an adenovirus fiber protein include, for example, SEQ ID NO: 10 and SEQ ID NO: 5. Amino acid sequences that comprise a full-length adenovirus fiber protein, or a portion thereof, include, for example, SEQ ID NO: 20 and SEQ ID NO: 15.

The adenovirus penton base protein is located at the vertices of the icosahedral capsid and comprises five identical monomers. The penton base protein provides a structure for bridging the hexon proteins on multiple facets of the icosahedral capsid, and provides the essential interface for the fiber protein to be incorporated in the capsid. Each monomer of the penton base contains an RGD tripeptide motif (Neumann et al., *Gene,* 69: 153-157 (1988)). The RGD tripeptide mediates binding to av integrins and adenoviruses that have point mutations in the RGD sequence of the penton base are restricted in their ability to infect cells (Bai et al., *J. Virol.,* 67: 5198-5205 (1993)). Thus, the penton base protein is essential for the architecture of the capsid and for maximum efficiency of virus-cell interaction. Nucleic acid sequences that encode all or a portion of an adenovirus penton base protein include, for example, SEQ ID NO: 8 and SEQ ID NO: 3. Amino acid sequences that comprise a full-length adenovirus penton base protein, or a portion thereof, include, for example, SEQ ID NO: 18 and SEQ ID NO: 13.

Nucleic acid or amino acid sequence "identity," as described herein, can be determined by comparing a nucleic acid or amino acid sequence of interest to a reference nucleic acid or amino acid sequence. The number of nucleotides or amino acid residues that have been changed and/or modified (such as, e.g., by point mutations, insertions, or deletions) in the reference sequence so as to result in the sequence of interest are counted. The total number of such changes is subtracted from the total length of the sequence of interest, and the difference is divided by the length of the sequence of interest and expressed as a percentage. A number of mathematical algorithms for obtaining the optimal alignment and calculating identity between two or more sequences are known and incorporated into a number of available software programs. Examples of such programs include CLUSTAL-W, T-Coffee, and ALIGN (for alignment of nucleic acid and amino acid sequences), BLAST programs (e.g., BLAST 2.1, BL2SEQ, and later versions thereof) and FASTA programs (e.g., FASTA3×, FASTM, and SSEARCH) (for sequence alignment and sequence similarity searches). Sequence alignment algorithms also are disclosed in, for example, Altschul et al., *J. Molecular Biol.,* 215(3): 403-410 (1990), Beigert et al., *Proc. Natl. Acad. Sci. USA,* 106(10): 3770-3775 (2009), Durbin et al., eds., *Bio-*

*logical Sequence Analysis: Probalistic Models of Proteins and Nucleic Acids*, Cambridge University Press, Cambridge, UK (2009), Soding, *Bioinformatics,* 21(7): 951-960 (2005), Altschul et al., *Nucleic Acids Res.,* 25(17): 3389-3402 (1997), and Gusfield, *Algorithms on Strings, Trees and Sequences*, Cambridge University Press, Cambridge UK (1997)).

In one embodiment, the adenovirus or adenoviral vector comprises one or more of the following nucleic acid sequences: (a) the nucleic acid sequence of SEQ ID NO: 1, (b) a nucleic acid sequence that is at least 98.5% identical (e.g., at least 98.73%, at least 98.96%, at least 99.18%, at least 99.41%, at least 99.64%, at least 99.87%, or 100% identical) to SEQ ID NO: 2, (c) a nucleic acid sequence that is at least 90% identical (e.g., at least 92.94%, at least 95.88%, 98.82%, or 100% identical) to SEQ ID NO: 3, (d) a nucleic acid sequence that is at least 80% identical (e.g., at least 80.83%, at least 83.06%, at least 85.28%, at least 87.50%, at least 89.72%, at least 91.94%, at least 94.17%, at least 96.39%, at least 98.61%, or 100% identical) to SEQ ID NO: 4, and (e) a nucleic acid sequence that is at least 89% identical (e.g., at least 92.33%, at least 95.67%, at least 99%, or 100% identical) to SEQ ID NO: 5.

The adenovirus or adenoviral vector can comprise one, two, three, four, or all five of the aforementioned sequences alone or in any combination. In this respect, the adenovirus or adenoviral vector can comprise any combination of any two of the aforementioned sequences, any combination of any three of the aforementioned sequences, any combination of any four of the aforementioned sequences, or all five of the aforementioned sequences. For example, the adenovirus or adenoviral vector can comprise the nucleic acid sequence of SEQ ID NO: 1. The adenovirus or adenoviral vector can comprise a nucleic acid sequence that is at least 98.5% identical to SEQ ID NO: 2 and a nucleic acid sequence that is at least 90% identical to SEQ ID NO: 3. The adenovirus or adenoviral vector can comprise the nucleic acid sequence of SEQ ID NO: 1, a nucleic acid sequence that is at least 90% identical to SEQ ID NO: 3, and a nucleic acid sequence that is at least 89% identical to SEQ ID NO: 5. The adenovirus or adenoviral vector can comprise (a) the nucleic acid sequence of SEQ ID NO: 1, (b) the nucleic acid sequence SEQ ID NO: 2, (c) the nucleic acid sequence of SEQ ID NO: 3, (d) the nucleic acid sequence of SEQ ID NO: 4, or (e) the nucleic acid sequence of SEQ ID NO: 5. The adenovirus or adenoviral vector can comprise (a) the nucleic acid sequence of SEQ ID NO: 1, (b) a nucleic acid sequence that is at least 98.5% identical to SEQ ID NO: 2, (c) a nucleic acid sequence that is at least 90% identical to SEQ ID NO: 3, (d) a nucleic acid sequence that is at least 80% identical to SEQ ID NO: 4, and (e) a nucleic acid sequence that is at least 89% identical to SEQ ID NO: 5. The adenovirus or adenoviral vector can comprise (a) the nucleic acid sequence of SEQ ID NO: 1, (b) the nucleic acid sequence SEQ ID NO: 2, (c) the nucleic acid sequence of SEQ ID NO: 3, (d) the nucleic acid sequence of SEQ ID NO: 4, and (e) the nucleic acid sequence of SEQ ID NO: 5.

In another embodiment, the adenovirus or adenoviral vector comprises one or more of the following nucleic acid sequences: (a) a nucleic acid sequence that is at least 98.6% identical (e.g., at least 98.85%, at least 99.10%, at least 99.35%, at least 99.60%, or 100% identical) to SEQ ID NO: 6, (b) a nucleic acid sequence that is at least 99.06% identical (e.g., at least 99.09%, at least 99.12%, at least 99.15%, at least 99.19%, at least 99.22%, at least 99.25%, at least 99.28%, at least 99.31%, at least 99.34%, at least 99.38%, at least 99.41%, at least 99.44%, at least 99.47%, at least 99.50%, at least 99.53%, at least 99.57%, at least 99.60%, at least 99.63%, at least 99.66%, at least 99.69%, at least 99.72%, at least 99.75%, at least 99.79%, at least 99.82%, at least 99.85%, at least 99.88%, at least 99.91%, at least 99.94%, at least 99.98%, or 100% identical) to SEQ ID NO: 7, (c) a nucleic acid sequence that is at least 97.13% identical (e.g., at least 97.18%, at least 97.23%, at least 97.28%, at least 97.33%, at least 97.38%, at least 97.43%, at least 97.48%, at least 97.5% at least 97.54%, at least 97.59%, at least 97.6%, at least 97.64%, at least 97.69%, at least 97.7%, at least 97.74%, at least 97.79%, at least 97.8%, at least 97.84%, at least 97.89%, at least 97.9%, at least 97.94%, at least 97.99%, at least 98%, at least 98.04%, at least 98.09%, at least 98.1%, at least 98.14%, at least 98.19%, at least 98.2%, at least 98.24%, at least 98.30%, at least 98.35%, at least 98.40%, at least 98.45%, at least 98.50%, at least 98.55%, at least 98.60%, at least 98.70%, at least 98.75%, at least 98.80%, at least 98.85%, at least 98.90%, at least 98.95%, at least 99.00%, at least 99.06%, at least 99.11%, at least 99.16%, at least 99.2%, at least 99.21%, at least 99.26%, at least 99.3%, at least 99.31%, at least 99.36%, at least 99.4%, at least 99.41%, at least 99.46%, at least 99.5%, at least 99.51%, at least 99.56%, at least 99.6%, at least 99.61%, at least 99.66%, at least 99.7%, at least 99.71%, at least 99.76%, at least 99.8%, at least 99.81%, at least 99.87%, at least 99.9%, at least 99.92%, at least 99.95%, at least 99.97%, or 100% identical) to SEQ ID NO: 8, (d) a nucleic acid sequence that is at least 90.7% identical (e.g., at least 90.73%, at least 90.77%, at least 90.80%, at least 90.84%, at least 90.87%, at least 90.91%, at least 90.94%, at least 90.98%, at least 91.01%, at least 91.05%, at least 91.08%, at least 91.12%, at least 91.15%, at least 91.19%, at least 91.22%, at least 91.26%, at least 91.29%, at least 91.33%, at least 91.36%, at least 91.40%, at least 91.43%, at least 91.46%, at least 91.50%, at least 91.53%, at least 91.57%, at least 91.60%, at least 91.64%, at least 91.67%, at least 91.71%, at least 91.74%, at least 91.78%, at least 91.81%, at least 91.85%, at least 91.88%, at least 91.92%, at least 91.95%, at least 91.99%, at least 92.02%, at least 92.06%, at least 92.09%, at least 92.13%, at least 92.16%, at least 92.19%, at least 92.23%, at least 92.26%, at least 92.30%, at least 92.33%, at least 92.37%, at least 92.40%, at least 92.44%, at least 92.47%, at least 92.51%, at least 92.54%, at least 92.58%, at least 92.61%, at least 92.65%, at least 92.68%, at least 92.72%, at least 92.75%, at least 92.79%, at least 92.82%, at least 92.86%, at least 92.89%, at least 92.92%, at least 92.96%, at least 92.99%, at least 93.03%, at least 93.06%, at least 93.10%, at least 93.13%, at least 93.17%, at least 93.20%, at least 93.24%, at least 93.27%, at least 93.31%, at least 93.34%, at least 93.38%, at least 93.41%, at least 93.45%, at least 93.48%, at least 93.52%, at least 93.55%, at least 93.58%, at least 93.62%, at least 93.65%, at least 93.69%, at least 93.72%, at least 93.76%, at least 93.79%, at least 93.83%, at least 93.86%, at least 93.90%, at least 93.93%, at least 93.97%, at least 94.00%, at least 94.04%, at least 94.07%, at least 94.11%, at least 94.14%, at least 94.18%, at least 94.21%, at least 94.25%, at least 94.28%, at least 94.31%, at least 94.35%, at least 94.38%, at least 94.42%, at least 94.45%, at least 94.49%, at least 94.52%, at least 94.56%, at least 94.59%, at least 94.63%, at least 94.66%, at least 94.70%, at least 94.73%, at least 94.77%, at least 94.80%, at least 94.84%, at least 94.87%, at least 94.91%, at least 94.94%, at least 94.98%, at least 95.01%, at least 95.04%, at least 95.08%, at least 95.11%, at least 95.15%, at least 95.18%, at least 95.22%, at least 95.25%, at least 95.29%, at least 95.32%, at least 95.36%, at least 95.39%, at least 95.43%, at least 95.46%, at least 95.50%, at least 95.53%, at least 95.57%, at least 95.60%, at least 95.64%, at least 95.67%, at least 95.71%, at least 95.74%, at least 95.77%, at least 95.81%, at least 95.84%, at least 95.88%, at least 95.91%, at least 95.95%, at least 95.98%, at least 96.02%, at least 96.05%, at least 96.09%, at least 96.12%, at least 96.16%, at least 96.19%, at least 96.23%, at least 96.26%, at least 96.30%, at least 96.33%, at least 96.37%, at least 96.40%, at least 96.44%, at least 96.47%, at least 96.50%, at least 96.54%, at least 96.57%, at least 96.61%, at least 96.64%, at least 96.68%, at least 96.71%, at least 96.75%, at least 96.78%, at least 96.82%, at least 96.85%, at least 96.89%, at least 96.92%, at least 96.96%, at least 96.99%, at least 97.03%, at least 97.06%, at least 97.10%, at least 97.13%, at least 97.17%, at least 97.20%, at least 97.23%, at least 97.27%, at least 97.30%, at least 97.34%, at least 97.37%, at least 97.41%, at least 97.44%, at least 97.48%, at least 97.51%, at least 97.55%, at least 97.58%, at least 97.62%, at least 97.65%, at least 97.69%, at least 97.72%, at least 97.76%, at least 97.79%, at least 97.83%, at least 97.86%, at least 97.89%, at least 97.93%, at least 97.96%, at least 98.00%, at least 98.03%, at least 98.07%, at least 98.10%, at least 98.14%, at least 98.17%, at least 98.21%, at least 98.24%, at least 98.28%, at least 98.31%, at least 98.35%, at least 98.38%, at least 98.42%, at least 98.45%, at least 98.49%, at least 98.52%, at least 98.56%, at least 98.59%, at least 98.62%, at least 98.66%, at least 98.69%, at least 98.73%, at least 98.76%, at least 98.80%, at least 98.83%, at least 98.87%, at least 98.90%, at least 98.94%, at least 98.97%, at least 99.01%, at least 99.04%, at least 99.08%, at least 99.11%, at least 99.15%, at least 99.18%, at least 99.22%, at least 99.25%, at least 99.29%, at least 99.32%, at least 99.35%, at least 99.39%, at least 99.42%, at least 99.46%, at least 99.49%, at least 99.53%, at least 99.56%, at least 99.60%, at least 99.63%, at least 99.67%, at least 99.70%, at least 99.74%, at least 99.77%, at least 99.81%, at least 99.84%, at least 99.88%, at least 99.91%, at least 99.95%, at least 99.98%, or 100% identical) to SEQ ID NO: 9, and (e) a nucleic acid sequence that is at least 96.6% identical (e.g., at least 96.66%, at least 96.71%, at least 96.77%, at least 96.83%, at least 96.89%, at least 96.94%, at least 97.00%, at least 97.06%, at least 97.11%, at least 97.17%, at least 97.23%, at least 97.29%, at least 97.34%, at least 97.40%, at least 97.46%, at least 97.51%, at least 97.57%, at least 97.63%, at least 97.69%, at least 97.74%, at least 97.80%, at least 97.86%, at least 97.92%, at least 97.97%, at least 98.03%, at least 98.09%, at least 98.14%, at least 98.20%, at least 98.26%, at least 98.32%, at least 98.37%, at least 98.43%, at least 98.49%, at least 98.54%, at least 98.60%, at least 98.66%, at least 98.72%, at least 98.77%, at least 98.83%, at least 98.89%, at least 98.94%, at least 99.00%, at least 99.06%, at least 99.12%, at least 99.17%, at least 99.23%, at least 99.29%, at least 99.34%, at least 99.40%, at least 99.46%, at least 99.52%, at least 99.57%, at least 99.63%, at least 99.69%, at least 99.74%, at least at least 99.80%, at least 99.86%, at least 99.92%, at least 99.97%, or 100% identical) to SEQ ID NO: 10.

The adenovirus or adenoviral vector can comprise one, two, three, four, or all five of the aforementioned sequences alone or in any combination. In this respect, the adenovirus or adenoviral vector can comprise any combination of any two of the aforementioned sequences, any combination of any three of the aforementioned sequences, any combination of any four of the aforementioned sequences, or all five of the aforementioned sequences. For example, the adenovirus or adenoviral vector can comprise a nucleic acid sequence that is at least 98.6% identical to SEQ ID NO: 6. The adenovirus or adenoviral vector can comprise a nucleic acid sequence that is at least 99.06% identical to SEQ ID NO: 7 and a nucleic acid sequence that is at least 97.13% identical to SEQ ID NO: 8. The adenovirus or adenoviral vector can comprise a nucleic acid sequence that is at least 97.13% identical to SEQ ID NO: 8, a nucleic acid sequence that is at least 90.7% identical to SEQ ID NO: 9, and a nucleic acid sequence that is at least 96.6% identical to SEQ ID NO: 10. The adenovirus or adenoviral vector can comprise (a) the nucleic acid sequence of SEQ ID NO: 6, (b) the nucleic acid sequence SEQ ID NO: 7, (c) the nucleic acid sequence of SEQ ID NO: 8, (d) the nucleic acid sequence of SEQ ID NO: 9, or (e) the nucleic acid sequence of SEQ ID NO: 10. The adenovirus or adenoviral vector can comprise (a) a nucleic acid sequence that is at least 98.6% identical to SEQ ID NO: 6, (b) a nucleic acid sequence that is at least 99.06% identical to SEQ ID NO: 7, (c) a nucleic acid sequence that is at least 97.13% identical to SEQ ID NO: 8, (d) a nucleic acid sequence that is at least 90.7% identical to SEQ ID NO: 9, and (e) a nucleic acid sequence that is at least 96.6% identical to SEQ ID NO: 10. The adenovirus or adenoviral vector can comprise (a) the nucleic acid sequence of SEQ ID NO: 6, (b) the nucleic acid sequence SEQ ID NO: 7, (c) the nucleic acid sequence of SEQ ID NO: 8, (d) the nucleic acid sequence of SEQ ID NO: 9, and (e) the nucleic acid sequence of SEQ ID NO: 10.

In another embodiment, the adenovirus or adenoviral vector comprises one or more of the following nucleic acid sequences: (a) a nucleic acid sequence comprising at least 121 contiguous nucleotides of SEQ ID NO: 6, (b) a nucleic acid sequence comprising at least 462 contiguous nucleotides of SEQ ID NO: 7, (c) a nucleic acid sequence comprising at least 234 contiguous nucleotides of SEQ ID NO: 8, (d) a nucleic acid sequence comprising at least 606 contiguous nucleotides of SEQ ID NO: 9, or (e) a nucleic acid sequence comprising at least 188 contiguous nucleotides of SEQ ID NO: 10.

The adenovirus or adenoviral vector can comprise a nucleic acid sequence comprising at least 121 (e.g., 125 or more, 130 or more, 150 or more, 200 or more, 250 or more, or 300 or more) contiguous nucleotides of SEQ ID NO: 6, but no more than 399 (e.g., 398 or less, 350 or less, or 275 or less) contiguous nucleotides of SEQ ID NO: 6. Preferably, the adenovirus or adenoviral vector comprises a nucleic acid sequence comprising 121 to 300 contiguous nucleotides (e.g., 125, 150, 175, 200, 250, or 275 contiguous nucleotides), 121 to 200 contiguous nucleotides (e.g., 130, 140, 145, 160, 165, 170, 180, 185, 190, 195, or 199 contiguous nucleotides), or 121 to 150 contiguous nucleotides (e.g., 122, 123, 124, 125, 126, 127, 128, 129, 130, 131, 132, 133, 134, 135, 136, 137, 138, 139, 140, 141, 142, 143, 144, 145, 146, 147, 148, or 149 contiguous nucleotides) of SEQ ID NO: 6, or a range defined by any two of the foregoing values.

The adenovirus or adenoviral vector can comprise a nucleic acid sequence comprising at least 462 (e.g., 470 or more, 500 or more, 600 or more, 700 or more, 800 or more, 900 or more, or 1,000 or more) contiguous nucleotides of SEQ ID NO: 7, but no more than 3168 (e.g., 3,100 or less, 3,000 or less, 2,500 or less, 2,000 or less, or 1,500 or less) contiguous nucleotides of SEQ ID NO: 7. Preferably, the adenovirus or adenoviral vector comprises a nucleic acid sequence comprising 462 to 2,000 contiguous nucleotides (e.g., 475, 500, 700, 1,000, 1,200, 1,500, or 1,700 contiguous nucleotides), 462 to 1,000 contiguous nucleotides (e.g., 490, 525, 575, 600, 650, 675, 725, 750, 800, 850, 900, or 950 contiguous nucleotides), or 462 to 800 contiguous nucleotides (e.g., 480, 485, 490, 495, 499, 510, 515, 530, 540, 550, 560, 565, 570, 580, 585, 590, 595, 615, 625, 630, 640, 660, 665, 670, 680, 685, 690, 695, 705, 715, 730, 740, 755, 760, 765, 770, 775, 780, 785, 790, 795, or 799 contiguous nucleotides) of SEQ ID NO: 7, or a range defined by any two of the foregoing values.

The adenovirus or adenoviral vector can comprise a nucleic acid sequence comprising at least 234 (e.g., 235 or more, 250 or more, 300 or more, 350 or more, 400 or more, 450 or more, or 500 or more) contiguous nucleotides of SEQ ID NO: 8, but no more than 1,974 (e.g., 1,900 or less, 1,800 or less, 1,500 or less, 1,200 or less, 1,000 or less, 850 or less, 800 or less, 750 or less, or 700 or less) contiguous nucleotides of SEQ ID NO: 8. Preferably, the adenovirus or adenoviral vector comprises a nucleic acid sequence comprising 234 to 1,500 contiguous nucleotides (e.g., 290, 300, 400, 500, 600, 700, 800, 900, 1,000, or 1,200 contiguous nucleotides), 234 to 1,000 contiguous nucleotides (e.g., 295, 350, 450, 550, 650, 750, 850, or 950 contiguous nucleotides), or 234 to 500 contiguous nucleotides (e.g., 290, 305, 310, 315, 325, 340, 345, 360, 365, 370, 375, 380, 385, 390, 395, 405, 425, 430, 440, 455, 460, 465, 470, 475, 480, 485, 490, 495, or 499 contiguous nucleotides) of SEQ ID NO: 8, or a range defined by any two of the foregoing values.

The adenovirus or adenoviral vector can comprise a nucleic acid sequence comprising at least 606 (e.g., 610 or more, 650 or more, 700 or more, 800 or more, or 1,000 or more) contiguous nucleotides of SEQ ID NO: 9, but no more than 2877 (2,800 or less, 2,500 or less, 2,000 or less, 1,800 or less, or 1,500 or less) contiguous nucleotides of SEQ ID NO: 9. Preferably, the adenovirus or adenoviral vector comprises a nucleic acid sequence comprising 606 to 2,000 contiguous nucleotides (e.g., 615, 650, 700, 800, 900, 1,000, 1,200, 1,500, 1,700, or 1,900 contiguous nucleotides), 606 to 1,000 contiguous nucleotides (e.g., 630, 645, 665, 675, 725, 750, 775, 825, 850, 875, 925, 950, or 975 contiguous nucleotides), or 606 to 800 contiguous nucleotides (e.g., 620, 635, 640, 655, 660, 670, 680, 685, 690, 695, 699, 705, 715, 730, 735, 740, 745, 755, 760, 765, 770, 785, 790, 795, or 799 contiguous nucleotides) of SEQ ID NO: 9, or a range defined by any two of the foregoing values.

The adenovirus or adenoviral vector can comprise a nucleic acid sequence comprising at least 188 (e.g., 189 or more, 200 or more, 300 or more, 500 or more, 700 or more, or 900 or more) contiguous nucleotides of SEQ ID NO: 10, but no more than 1,749 (1,700 or less, 1,500 or less, 1,200 or less, or 1,000 or less) contiguous nucleotides of SEQ ID NO: 10. Preferably, the adenovirus or adenoviral vector comprises a nucleic acid sequence comprising 188 to 1,500 contiguous nucleotides (e.g., 200, 400, 600, 800, 1,000, 1,200, or 1,400 contiguous nucleotides), 188 to 1,000 contiguous nucleotides (e.g., 195, 250, 350, 450, 550, 650, 750, 850, or 950 contiguous nucleotides), or 188 to 500 contiguous nucleotides (e.g., 190, 225, 230, 240, 255, 260, 265, 270, 275, 315, 325, 330, 340, 355, 360, 365, 370, 375, 380, 385, 390, 395, 415, 425, 430, 440, 455, 460, 465, 470, 475, 480, 485, 490, 495, or 499 contiguous nucleotides) of SEQ ID NO: 10, or a range defined by any two of the foregoing values.

The adenovirus or adenoviral vector can comprise one, two, three, four, or all five of the aforementioned sequences alone, or in any combination. In this respect, the adenovirus or adenoviral vector can comprise any combination of any two of the aforementioned sequences, any combination of any three of the aforementioned sequences, any combination of any four of the aforementioned sequences, or all five of the aforementioned sequences. For example, the adenovirus or adenoviral vector can comprise a nucleic acid sequence comprising at least 121 contiguous nucleotides of SEQ ID NO: 6. The adenovirus or adenoviral vector can comprise a nucleic acid sequence comprising at least 234 contiguous nucleotides of SEQ ID NO: 8, and a nucleic acid sequence comprising at least 188 contiguous nucleotides of SEQ ID NO: 10. The adenovirus or adenoviral vector can comprise a nucleic acid sequence comprising at least 462 contiguous nucleotides of SEQ ID NO: 7, a nucleic acid sequence comprising at least 606 contiguous nucleotides of SEQ ID NO: 9, and a nucleic acid sequence comprising at least 188 contiguous nucleotides of SEQ ID NO: 10. The adenovirus or adenoviral vector can comprise a nucleic acid sequence comprising at least 121 contiguous nucleotides of SEQ ID NO: 6, a nucleic acid sequence comprising at least 462 contiguous nucleotides of SEQ ID NO: 7, a nucleic acid sequence comprising at least 234 contiguous nucleotides of SEQ ID NO: 8, and a nucleic acid sequence comprising at least 606 contiguous nucleotides of SEQ ID NO: 9. The adenovirus or adenoviral vector can comprise (a) a nucleic acid sequence comprising at least 121 contiguous nucleotides of SEQ ID NO: 6, (b) a nucleic acid sequence comprising at least 462 contiguous nucleotides of SEQ ID NO: 7, (c) a nucleic acid sequence comprising at least 234 contiguous nucleotides of SEQ ID NO: 8, (d) a nucleic acid sequence comprising at least 606 contiguous nucleotides of SEQ ID NO: 9, and (e) a nucleic acid sequence comprising at least 188 contiguous nucleotides of SEQ ID NO: 10.

In another embodiment, the adenovirus or adenoviral vector comprises one or more of the following amino acid sequences: (a) the amino acid sequence of SEQ ID NO: 11, (b) an amino acid sequence that is at least 82% identical (e.g., at least 88.67%, at least 95.33%, or 100% identical) to SEQ ID NO: 13, (c) an amino acid sequence that is at least 80% identical (e.g., at least 81%, at least 82%, at least 83%, at least 83.06%, at least 84%, at least 85%, at least 85.28%, at least 86%, at least 87%, at least 87.5%, at least 88%, at least 88.67%, at least 89%, at least 89.72% at least 90%, at least 91%, at least 91.94%, at least 92%, at least 92.33%, at least 93%, at least 94%, at least 94.17%, at least 95%, at least 95.33%, at least 95.67%, at least 96%, at least 96.39%, at least 97%, at least 98%, at least 98.61%, at least 99%, at least 99.5%, or 100% identical) to SEQ ID NO: 14, and (d) an amino acid sequence that is at least 83% identical (e.g., at least 89.67%, at least 96.33%, or 100% identical) to SEQ ID NO: 15.

The adenovirus or adenoviral vector can comprise one, two, three, or all four of the aforementioned amino acid sequences alone or in any combination. In this respect, the adenovirus or adenoviral vector can comprise any combination of any two of the aforementioned sequences, any combination of any three of the aforementioned sequences, or all four of the aforementioned sequences. For example, the adenovirus or adenoviral vector can comprise the amino acid sequence of SEQ ID NO: 11. The adenovirus or adenoviral vector can comprise an amino acid sequence of SEQ ID NO: 11, and an amino acid sequence that is at least 82% identical to SEQ ID NO: 13. The adenovirus or adenoviral vector can comprise the amino acid sequence of SEQ ID NO: 11, an amino acid sequence that is at least 82% identical to SEQ ID NO: 13, and an amino acid sequence that is at least 83% identical to SEQ ID NO: 15. The adenovirus or adenoviral vector can comprise (a) the amino acid sequence of SEQ ID NO: 11, (b) the amino acid sequence of SEQ ID NO: 13, (c) the amino acid sequence of SEQ ID NO: 14, or (d) the amino acid sequence of SEQ ID NO: 15. The adenovirus or adenoviral vector can comprise (a) the amino acid sequence of SEQ ID NO: 11, (b) an amino acid sequence that is at least 82% identical to SEQ ID NO: 13, (c) an amino acid sequence that is at least 80% identical to SEQ ID NO: 14, and (d) an amino acid sequence that is at least 83% identical to SEQ ID NO: 15. The adenovirus or adenoviral vector can comprise (a) the amino acid sequence of SEQ ID NO: 11, (b) the amino acid sequence of SEQ ID NO: 13, (c) the amino acid sequence of SEQ ID NO: 14, and (d) the amino acid sequence of SEQ ID NO: 15.

In another embodiment, the adenovirus or adenoviral vector comprises one or more of the following amino acid sequences: (a) the amino acid sequence of SEQ ID NO: 16, (b) an amino acid sequence that is at least 97.8% identical (e.g., at least 97.95%, at least 98.10%, at least 98.26%, at least 98.41%, at least 98.56%, at least 98.71%, at least 98.86%, at least 99.02%, at least 99.17%, at least 99.32%, at least 99.47%, at least 99.62%, at least 99.78%, or 100% identical) to SEQ ID NO: 18, (c) an amino acid sequence that is at least 93.4% identical (e.g., at least 93.50%, at least 93.61%, at least 93.71%, at least 93.82%, at least 93.92%, at least 94.03%, at least 94.13%, at least 94.23%, at least 94.34%, at least 94.44%, at least 94.55%, at least 94.65%, at least 94.76%, at least 94.86%, at least 94.96%, at least 95.07%, at least 95.17%, at least 95.28%, at least 95.38%, at least 95.49%, at least 95.59%, at least 95.69%, at least 95.80%, at least 95.90%, at least 96.01%, at least 96.11%, at least 96.22%, at least 96.32%, at least 96.42%, at least 96.53%, at least 96.63%, at least 96.74%, at least 96.84%, at least 96.95%, at least 97.05%, at least 97.15%, at least 97.26%, at least 97.36%, at least 97.47%, at least 97.57%, at least 97.68%, at least 97.78%, at least 97.88%, at least 97.99%, at least 98.09%, at least 98.20%, at least 98.30%, at least 98.41%, at least 98.51%, at least 98.61%, at least 98.72%, at least 98.82%, at least 98.93%, at least 99.03%, at least 99.14%, at least 99.24%, at least 99.34%, at least 99.45%, at least 99.55%, at least 99.66%, at least 99.76%, at least 99.87%, at least 99.97%, or 100% identical) to SEQ ID NO: 19, and (d) an amino acid sequence that is at least 98.2% identical (e.g., at least 98.37%, at least 98.54%, at least 98.71%, at least 98.89%, at least 99.06%, at least 99.23%, at least 99.40%, at least 99.57%, at least 99.74%, at least 99.92%, or 100% identical) to SEQ ID NO: 20.

The adenovirus or adenoviral vector can comprise one, two, three, or all four of the aforementioned amino acid sequences alone or in any combination. In this respect, the adenovirus or adenoviral vector can comprise any combination of any two of the aforementioned sequences, any combination of any three of the aforementioned sequences, or all four of the aforementioned sequences. For example, the adenovirus or adenoviral vector can comprise the amino acid sequence of SEQ ID NO: 16. The adenovirus or adenoviral vector can comprise the amino acid sequence of SEQ ID NO: 16, and an amino acid sequence that is at least 93.4% identical to SEQ ID NO: 19. The adenovirus or adenoviral vector can comprise the amino acid sequence of SEQ ID NO: 16, an amino acid sequence that is at least 93.4% identical to SEQ ID NO: 19, and an amino acid sequence that is at least 98.2% identical to SEQ ID NO: 20. The adenovirus or adenoviral vector can comprise (a) the amino acid sequence of SEQ ID NO: 16, (b) the amino acid sequence of SEQ ID NO: 18, (c) the amino acid sequence of SEQ ID NO: 19, or (d) the amino acid sequence of SEQ ID NO: 20. The adenovirus or adenoviral vector can comprise (a) the amino acid sequence of SEQ ID NO: 16, (b) an amino acid sequence that is at least 97.8% identical to SEQ ID NO: 18, (c) an amino acid that is at least 93.4% identical to SEQ ID NO: 19, and (d) an amino acid sequence that is at least 98.2% identical to SEQ ID NO: 20. The adenovirus or adenoviral vector can comprise (a) the amino acid sequence of SEQ ID NO: 16, (b) the amino acid sequence of SEQ ID NO: 18, (c) the amino acid sequence of SEQ ID NO: 19, and (d) the amino acid sequence of SEQ ID NO: 20.

In another embodiment, the adenovirus or adenoviral vector comprises one or more of the following amino acid sequences: (a) an amino acid sequence comprising at least 89 contiguous amino acid residues of SEQ ID NO: 16, (b) an amino acid sequence comprising at least 247 contiguous amino acid residues of SEQ ID NO: 18, (c) an amino acid sequence comprising at least 370 contiguous amino acid residues of SEQ ID NO: 19, and (d) an amino acid sequence comprising at least 192 contiguous amino acid residues of SEQ ID NO: 20.

The adenovirus or adenoviral vector can comprise an amino acid sequence comprising at least 89 (e.g., 90 or more, 100 or more, or 110 or more) contiguous amino acid residues of SEQ ID NO: 16, but no more than 133 (e.g., 130 or less, 125 or less, 120 or less, or 115 or less) contiguous amino acid residues of SEQ ID NO: 16. Preferably, the adenovirus or adenoviral vector comprises an amino acid sequence comprising 89 to 130 contiguous amino acid residues (e.g., 90, 100, 110, 115, 120, or 125 contiguous amino acid residues) of SEQ ID NO: 16, 89 to 115 contiguous amino acid residues of SEQ ID NO: 16 (e.g., 95, 110, or 112 contiguous amino acid residues), or 89 to 100 contiguous amino acid residues (e.g., 89, 90, 91, 92, 93, 94, 95, 96, 97, 98, or 99 contiguous amino acid residues) of SEQ ID NO: 16, or a range defined by any two of the foregoing values.

The adenovirus or adenoviral vector can comprise an amino acid sequence comprising at least 247 (e.g., 250 or more, 275 or more, 300 or more, or 400 or more) contiguous amino acid residues of SEQ ID NO: 18, but no more than 658 (e.g., 650 or less, 550 or less, or 450 or less) contiguous amino acid residues of SEQ ID NO: 18. Preferably, the adenovirus or adenoviral vector comprises an acid sequence comprising 247 to 600 contiguous amino acid residues (e.g., 255, 275, 300, 400, or 500 contiguous amino acid residues) of SEQ ID NO: 18, 247 to 500 contiguous amino acid residues of SEQ ID NO: 18 (e.g., 325, 350, 375, 425, 450, or 475 contiguous amino acid residues), or 247 to 400 contiguous amino acid residues (e.g., 265, 280, 285, 290, 295, 360, 365, 380, 385, 390, 395, or 399 contiguous amino acid residues) of SEQ ID NO: 18, or a range defined by any two of the foregoing values.

The adenovirus or adenoviral vector can comprise an amino acid sequence comprising at least 370 (e.g., 380 or more, 400 or more, or 500 or more) contiguous amino acid residues of SEQ ID NO: 19, but no more than 959 (e.g., 950 or less, 900 or less, 800 or less, 700 or less, or 600 or less) contiguous amino acid residues of SEQ ID NO: 19. Preferably, the adenovirus or adenoviral vector comprises an acid sequence comprising 370 to 800 contiguous amino acid residues (e.g., 390, 400, 500, 600, or 700 contiguous amino acid residues) of SEQ ID NO: 19, 370 to 600 contiguous amino acid residues (e.g., 375, 385, 395, 425, 445, 450, 465, 475, 525, 545, 550, 565 or 575 contiguous amino acid residues) of SEQ ID NO: 19, or 370 to 500 contiguous amino acid residues (e.g., 385, 389, 395, 399, 415, 435, 440, 460, 470, 480, or 499 contiguous amino acid residues) of SEQ ID NO: 19, or a range defined by any two of the foregoing values.

The adenovirus or adenoviral vector can comprise an amino acid sequence comprising at least 192 (e.g., 193 or more, 200 or more, or 300 or more) contiguous amino acid residues of SEQ ID NO: 20, but no more than 583 (e.g., 580 or less, 550 or less, 500 or less, 450 or less, or 400 or less) contiguous amino acid residues of SEQ ID NO: 20. Preferably, the adenovirus or adenoviral vector comprises an acid sequence comprising 192 to 500 contiguous amino acid residues (e.g., 198, 200, 300, or 400 contiguous amino acid residues) of SEQ ID NO: 20, 192 to 300 contiguous amino acid residues (e.g., 194, 196, 200, 210, 220, 230, 240, 250, 260, 270, 280, or 290 contiguous amino acid residues) of SEQ ID NO: 20, or 192 to 250 contiguous amino acid residues (e.g., 195, 199, 215, 225, 235, or 245 contiguous amino acid residues) of SEQ ID NO: 20, or a range defined by any two of the foregoing values.

The adenovirus or adenoviral vector can comprise one, two, three, or all four of the aforementioned amino acid sequences alone or in any combination. In this respect, the adenovirus or adenoviral vector can comprise any combination of any two of the aforementioned sequences, any combination of any three of the aforementioned sequences, or all four of the aforementioned sequences. For example, the adenovirus or adenoviral vector can comprise an amino acid sequence comprising at least 89 contiguous amino acid residues of SEQ ID NO: 16. The adenovirus or adenoviral vector can comprise an amino acid sequence comprising at least 89 contiguous amino acid residues of SEQ ID NO: 16, and an amino acid sequence comprising at least 370 contiguous amino acid residues of SEQ ID NO: 19. The adenovirus or adenoviral vector can comprise an amino acid sequence comprising at least 89 contiguous amino acid residues of SEQ ID NO: 16, an amino acid sequence comprising at least 247 contiguous amino acid residues of SEQ ID NO: 18, and an amino acid sequence comprising at least 370 contiguous amino acid residues of SEQ ID NO: 19. The adenovirus or adenoviral vector can comprise an amino acid sequence comprising at least 89 contiguous amino acid residues of SEQ ID NO: 16, an amino acid sequence comprising at least 247 contiguous amino acid residues of SEQ ID NO: 18, and an amino acid sequence comprising at least 192 contiguous amino acid residues of SEQ ID NO: 20. The adenovirus or adenoviral vector can comprise (a) an amino acid sequence comprising at least 89 contiguous amino acid residues of SEQ ID NO: 16, (b) an amino acid sequence comprising at least 247 contiguous amino acid residues of SEQ ID NO: 18, (c) an amino acid sequence comprising at least 370 contiguous amino acid residues of SEQ ID NO: 19, and (d) an amino acid sequence comprising at least 192 contiguous amino acid residues of SEQ ID NO: 20.

In other embodiments, the adenovirus or adenoviral vector comprises one or more nucleic acid sequences that encode one or more of any of the aforementioned amino acid sequences, e.g., the amino acid sequences of any of SEQ ID NOs: 11-20 or any of the variants and/or portions thereof as described herein. For example, the adenovirus or adenoviral vector can comprise a nucleic acid sequence encoding an amino acid sequence that is at least 99.78% identical (e.g., at least 99.87%, at least 99.97%, or 100% identical) to SEQ ID NO: 17, or a nucleic acid sequence encoding an amino acid sequence that is at least 99% identical (e.g., at least 99.68% or 100% identical) to SEQ ID NO: 12.

The adenovirus or adenoviral vector can comprise the nucleic acid sequence of, for example, SEQ ID NO: 21, SEQ ID NO: 22, SEQ ID NO: 23, SEQ ID NO: 24, or SEQ ID NO: 25.

As discussed herein, the adenovirus or adenoviral vector can be replication-competent, conditionally-replicating, or replication-deficient. Preferably, the adenovirus or adenoviral vector is replication-deficient, such that the replication-deficient adenovirus or adenoviral vector requires complementation of at least one replication-essential gene function of one or more regions of the adenoviral genome for propagation (e.g., to form adenoviral vector particles).

The replication-deficient adenovirus or adenoviral vector can be modified in any suitable manner to cause the deficiencies in the one or more replication-essential gene functions in one or more regions of the adenoviral genome for propagation. The complementation of the deficiencies in the one or more replication-essential gene functions of one or more regions of the adenoviral genome refers to the use of exogenous means to provide the deficient replication-essential gene functions. Such complementation can be effected in any suitable manner, for example, by using complementing cells and/or exogenous DNA (e.g., helper adenovirus) encoding the disrupted replication-essential gene functions.

The adenovirus or adenoviral vector can be deficient in one or more replication-essential gene functions of only the early regions (i.e., E1-E4 regions) of the adenoviral genome, only the late regions (i.e., L1-L5 regions) of the adenoviral genome, both the early and late regions of the adenoviral genome, or all adenoviral genes (i.e., a high capacity adenovector (HC-Ad). See Morsy et al., *Proc. Natl. Acad. Sci. USA,* 95: 965-976 (1998); Chen et al., *Proc. Natl. Acad. Sci. USA,* 94: 1645-1650 (1997); and Kochanek et al., *Hum. Gene Ther.,* 10: 2451-2459 (1999). Examples of replication-deficient adenoviral vectors are disclosed in U.S. Pat. Nos. 5,837,511; 5,851,806; 5,994,106; 6,127,175; 6,482,616; and 7,195,896, and International Patent Application Publications WO 1994/028152, WO 1995/002697, WO 1995/016772, WO 1995/034671, WO 1996/022378, WO 1997/012986, WO 1997/021826, and WO 2003/022311.

The early regions of the adenoviral genome include the E1, E2, E3, and E4 regions. The E1 region comprises the E1A and E1B subregions, and one or more deficiencies in replication-essential gene functions in the E1 region can include one or more deficiencies in replication-essential gene functions in either or both of the E1A and E1B subregions, thereby requiring complementation of the E1A subregion and/or the E1B subregion of the adenoviral genome for the adenovirus or adenoviral vector to propagate (e.g., to form adenoviral vector particles). The E2 region comprises the E2A and E2B subregions, and one or more deficiencies in replication-essential gene functions in the E2 region can include one or more deficiencies in replication-essential gene functions in either or both of the E2A and E2B subregions, thereby requiring complementation of the E2A subregion and/or the E2B subregion of the adenoviral genome for the adenovirus or adenoviral vector to propagate (e.g., to form adenoviral vector particles).

The E3 region does not include any replication-essential gene functions, such that a deletion of the E3 region in part or in whole does not require complementation of any gene functions in the E3 region for the adenovirus or adenoviral vector to propagate (e.g., to form adenoviral vector particles). In the context of the invention, the E3 region is defined as the region that initiates with the open reading frame that encodes a protein with high homology to the 12.5K protein from the E3 region of human adenovirus 5 (NCBI reference sequence AP_000218) and ends with the open reading frame that encodes a protein with high homology to the 14.7K protein from the E3 region of human adenovirus 5 (NCBI reference sequence AP_000224.1). The E3 region may be deleted in whole or in part, or retained in whole or in part. The size of the deletion may be tailored so as to retain an adenovirus or adenoviral vector whose genome closely matches the optimum genome packaging size. A larger deletion will accommodate the insertion of larger heterologous nucleic acid sequences in the adenovirus or adenoviral genome. In one embodiment of the invention, the L4 polyadenylation signal sequences, which reside in the E3 region, are retained.

The E4 region comprises multiple open reading frames (ORFs). An adenovirus or adenoviral vector with a deletion of all of the open reading frames of the E4 region except ORF6, and in some cases ORF3, does not require complementation of any gene functions in the E4 region for the adenovirus or adenoviral vector to propagate (e.g., to form adenoviral vector particles). Conversely, an adenovirus or adenoviral vector with a disruption or deletion of ORF6, and in some cases ORF3, of the E4 region (e.g., with a deficiency in a replication-essential gene function based in ORF6 and/or ORF3 of the E4 region), with or without a disruption or deletion of any of the other open reading frames of the E4 region or the native E4 promoter, polyadenylation sequence, and/or the right-side inverted terminal repeat (ITR), requires complementation of the E4 region (specifically, of ORF6 and/or ORF3 of the E4 region) for the adenovirus or adenoviral vector to propagate (e.g., to form adenoviral vector particles). The late regions of the adenoviral genome include the L1, L2, L3, L4, and L5 regions. The adenovirus or adenoviral vector also can have a mutation in the major late promoter (MLP), as discussed in International Patent Application Publication WO 2000/000628, which can render the adenovirus or adenoviral vector replication-deficient if desired.

The one or more regions of the adenoviral genome that contain one or more deficiencies in replication-essential gene functions desirably are one or more early regions of the adenoviral genome, i.e., the E1, E2, and/or E4 regions, optionally with the deletion in part or in whole of the E3 region.

The replication-deficient adenovirus or adenoviral vector also can have one or more mutations as compared to the wild-type adenovirus (e.g., one or more deletions, insertions, and/or substitutions) in the adenoviral genome that do not inhibit viral replication in host cells. Thus, in addition to one or more deficiencies in replication-essential gene functions, the adenovirus or adenoviral vector can be deficient in other respects that are not replication-essential. For example, the adenovirus or adenoviral vector can have a partial or entire deletion of the adenoviral early region known as the E3 region, which is not essential for propagation of the adenovirus or adenoviral genome.

In one embodiment, the adenovirus or adenoviral vector is replication-deficient and requires, at most, complementation of the E1 region or the E4 region of the adenoviral genome, for propagation (e.g., to form adenoviral vector particles). Thus, the replication-deficient adenovirus or adenoviral vector requires complementation of at least one replication-essential gene function of the E1A subregion and/or the E1B region of the adenoviral genome (denoted an E1-deficient adenoviral vector) or the E4 region of the adenoviral genome (denoted an E4-deficient adenoviral vector) for propagation (e.g., to form adenoviral vector particles). The adenovirus or adenoviral vector can be deficient in at least one replication-essential gene function (desirably all replication-essential gene functions) of the E1 region of the adenoviral genome and at least one gene function of the nonessential E3 region of the adenoviral genome (denoted an E1/E3-deficient adenoviral vector). The adenovirus or adenoviral vector can be deficient in at least one replication-essential gene function (desirably all replication-essential gene functions) of the E4 region of the adenoviral genome and at least one gene function of the nonessential E3 region of the adenoviral genome (denoted an E3/E4-deficient adenoviral vector).

In one embodiment, the adenovirus or adenoviral vector is replication-deficient and requires, at most, complementation of the E2 region, preferably the E2A subregion, of the adenoviral genome, for propagation (e.g., to form adenoviral vector particles). Thus, the replication-deficient adenovirus or adenoviral vector requires complementation of at least one replication-essential gene function of the E2A subregion of the adenoviral genome (denoted an E2A-deficient adenoviral vector) for propagation (e.g., to form adenoviral vector particles). The adenovirus or adenoviral vector can be deficient in at least one replication-essential gene function (desirably all replication-essential gene functions) of the E2A region of the adenoviral genome and at least one gene function of the nonessential E3 region of the adenoviral genome (denoted an E2A/E3-deficient adenoviral vector).

In one embodiment, the adenovirus or adenoviral vector is replication-deficient and requires, at most, complementation of the E1 and E4 regions of the adenoviral genome for propagation (e.g., to form adenoviral vector particles). Thus, the replication-deficient adenovirus or adenoviral vector requires complementation of at least one replication-essential gene function of both the E1 and E4 regions of the adenoviral genome (denoted an E1/E4-deficient adenoviral vector) for propagation (e.g., to form adenoviral vector particles). The adenovirus or adenoviral vector can be deficient in at least one replication-essential gene function (desirably all replication-essential gene functions) of the E1 region of the adenoviral genome, at least one replication-essential gene function of the E4 region of the adenoviral genome, and at least one gene function of the nonessential E3 region of the adenoviral genome (denoted an E1/E3/E4-deficient adenoviral vector). The adenovirus or adenoviral vector preferably requires, at most, complementation of the E1 region of the adenoviral genome for propagation, and does not require complementation of any other deficiency of the adenoviral genome for propagation. More preferably, the adenovirus or adenoviral vector requires, at most, complementation of the E1 and E4 regions of the adenoviral genome for propagation, and does not require complementation of any other deficiency of the adenoviral genome for propagation.

The adenovirus or adenoviral vector, when deficient in multiple replication-essential gene functions of the adenoviral genome (e.g., an E1/E4-deficient adenoviral vector), can include a spacer sequence to provide viral growth in a complementing cell line similar to that achieved by adenoviruses or adenoviral vectors deficient in a single replication-essential gene function (e.g., an E1-deficient adenoviral vector). The spacer sequence can contain any nucleotide sequence or sequences which are of a desired length, such as sequences at least about 15 base pairs (e.g., between about 15 nucleotides and about 12,000 nucleotides), preferably about 100 nucleotides to about 10,000 nucleotides, more preferably about 500 nucleotides to about 8,000 nucleotides, even more preferably about 1,500 nucleotides to about 6,000 nucleotides, and most preferably about 2,000 to about 3,000 nucleotides in length, or a range defined by any two of the foregoing values. The spacer sequence can be coding or non-coding and native or non-native with respect to the adenoviral genome, but does not restore the replication-essential function to the deficient region. The spacer also can contain an expression cassette. More preferably, the spacer comprises a polyadenylation sequence and/or a gene that is non-native with respect to the adenovirus or adenoviral vector. The use of a spacer in an adenoviral vector is further described in, for example, U.S. Pat. No. 5,851,806 and International Patent Application Publication WO 1997/021826.

By removing all or part of the adenoviral genome, for example, the E1, E3, and E4 regions of the adenoviral genome, the resulting adenovirus or adenoviral vector is able to accept inserts of exogenous nucleic acid sequences while retaining the ability to be packaged into adenoviral capsids. An exogenous nucleic acid sequence can be inserted at any position in the adenoviral genome so long as insertion in the position allows for the formation of adenovirus or the adenoviral vector particle. The exogenous nucleic acid sequence preferably is positioned in the E1 region, the E3 region, or the E4 region of the adenoviral genome.

The replication-deficient adenovirus or adenoviral vector of the invention can be produced in complementing cell lines that provide gene functions not present in the replication-deficient adenovirus or adenoviral vector, but required for viral propagation, at appropriate levels in order to generate high titers of viral vector stock. Such complementing cell lines are known and include, but are not limited to, 293 cells (described in, e.g., Graham et al., *J. Gen. Virol.,* 36: 59-72 (1977)), PER.C6 cells (described in, e.g., International Patent Application Publication WO 1997/000326, and U.S. Pat. Nos. 5,994,128 and 6,033,908), and 293-ORF6 cells (described in, e.g., International Patent Application Publication WO 95/34671 and Brough et al., *J. Virol.,* 71: 9206-9213 (1997)). Other suitable complementing cell lines to produce the replication-deficient adenovirus or adenoviral vector of the invention include complementing cells that have been generated to propagate adenoviral vectors encoding transgenes whose expression inhibits viral growth in host cells (see, e.g., U.S. Patent Application Publication No. 2008/0233650). Additional suitable complementing cells are described in, for example, U.S. Pat. Nos. 6,677,156 and 6,682,929, and International Patent Application Publication WO 2003/020879. In some instances, the cellular genome need not comprise nucleic acid sequences, the gene products of which complement for all of the deficiencies of a replication-deficient adenoviral vector. One or more replication-essential gene functions lacking in a replication-deficient adenoviral vector can be supplied by a helper virus, e.g., an adenoviral vector that supplies in trans one or more essential gene functions required for replication of the replication-deficient adenovirus or adenoviral vector. Alternatively, the inventive adenovirus or adenoviral vector can comprise a non-native replication-essential gene that complements for the one or more replication-essential gene functions lacking in the inventive replication-deficient adenovirus or adenoviral vector. For example, an E1/E4-deficient adenoviral vector can be engineered to contain a nucleic acid sequence encoding E4 ORF 6 that is obtained or derived from a different adenovirus (e.g., an adenovirus of a different serotype than the inventive adenovirus or adenoviral vector, or an adenovirus of a different species than the inventive adenovirus or adenoviral vector).

The adenovirus or adenoviral vector can further comprise a transgene. The term "transgene" is defined herein as a non-native nucleic acid sequence that is operably linked to appropriate regulatory elements (e.g., a promoter), such that the non-native nucleic acid sequence can be expressed to produce a protein (e.g., peptide or polypeptide). The regulatory elements (e.g., promoter) can be native or non-native to the adenovirus or adenoviral vector.

A "non-native" nucleic acid sequence is any nucleic acid sequence (e.g., DNA, RNA, or cDNA sequence) that is not a naturally occurring nucleic acid sequence of an adenovirus in a naturally occurring position. Thus, the non-native nucleic acid sequence can be naturally found in an adenovirus, but located at a non-native position within the adenoviral genome and/or operably linked to a non-native promoter. The terms "non-native nucleic acid sequence," "heterologous nucleic acid sequence," and "exogenous nucleic acid sequence" are synonymous and can be used interchangeably in the context of the invention. The non-native nucleic acid sequence preferably is DNA and preferably encodes a protein (i.e., one or more nucleic acid sequences encoding one or more proteins).

The non-native nucleic acid sequence can encode a therapeutic protein that can be used to prophylactically or therapeutically treat a mammal for a disease. Examples of suitable therapeutic proteins include cytokines, toxins, tumor suppressor proteins, growth factors, hormones, receptors, mitogens, immunoglobulins, neuropeptides, neurotransmitters, and enzymes. Alternatively, the non-native nucleic acid sequence can encode an antigen of a pathogen (e.g., a bacterium or a virus), and the adenovirus or adenoviral vector can be used as a vaccine.

The invention provides a composition comprising the adenovirus or adenoviral vector described herein and a carrier therefor (e.g., a pharmaceutically acceptable carrier). The composition desirably is a physiologically acceptable (e.g., pharmaceutically acceptable) composition, which comprises a carrier, preferably a physiologically (e.g., pharmaceutically) acceptable carrier, and the adenovirus or adenoviral vector. Any suitable carrier can be used within the context of the invention, and such carriers are well known in the art. The choice of carrier will be determined, in part, by the particular use of the composition (e.g., administration to an animal) and the particular method used to administer the composition. Ideally, in the context of replication-deficient adenoviral vectors, the pharmaceutical composition preferably is free of replication-competent adenovirus. The pharmaceutical composition optionally can be sterile.

Suitable compositions include aqueous and non-aqueous isotonic sterile solutions, which can contain anti-oxidants, buffers, and bacteriostats, and aqueous and non-aqueous sterile suspensions that can include suspending agents, solubilizers, thickening agents, stabilizers, and preservatives. The composition can be presented in unit-dose or multi-dose sealed containers, such as ampules and vials, and can be stored in a freeze-dried (lyophilized) condition requiring only the addition of the sterile liquid carrier, for example, water, immediately prior to use. Extemporaneous solutions and suspensions can be prepared from sterile powders, granules, and tablets. Preferably, the carrier is a buffered saline solution. More preferably, the adenovirus or adenoviral vector is part of a composition formulated to protect the adenovirus or adenoviral vector from damage prior to administration. For example, the composition can be formulated to reduce loss of the adenovirus or adenoviral vector on devices used to prepare, store, or administer the adenovirus or adenoviral vector, such as glassware, syringes, or needles. The composition can be formulated to decrease the light sensitivity and/or temperature sensitivity of the adenovirus or adenoviral vector. To this end, the composition preferably comprises a pharmaceutically acceptable liquid carrier, such as, for example, those described above, and a stabilizing agent selected from the group consisting of polysorbate 80, L-arginine, polyvinylpyrrolidone, trehalose, and combinations thereof. Use of such a composition will extend the shelf life of the adenovirus or adenoviral vector, and facilitate its administration. Formulations for adenovirus or adenoviral vector-containing compositions are further described in, for example, U.S. Pat. No. 6,225,289, U.S. Pat. No. 6,514,943, and International Patent Application Publication WO 2000/034444.

The composition also can be formulated to enhance transduction efficiency. In addition, one of ordinary skill in the art will appreciate that the adenovirus or adenoviral vector can be present in a composition with other therapeutic or biologically-active agents. For example, factors that control inflammation, such as ibuprofen or steroids, can be part of the composition to reduce swelling and inflammation associated with in vivo administration of the adenovirus or adenoviral vector. If the adenovirus or adenoviral vector is used to deliver an antigen-encoding nucleic acid sequence to a host, immune system stimulators or adjuvants, e.g., interleukins, lipopolysaccharide, or double-stranded RNA, can be administered to enhance or modify any immune response to the antigen. Antibiotics, i.e., microbicides and fungicides, can be present to treat existing infection and/or reduce the risk of future infection, such as infection associated with gene transfer procedures.

The following examples further illustrate the present invention and, of course, should not be construed as in any way limiting its scope.

EXAMPLE 1

This example demonstrates the immunogenicity of an adenoviral vector encoding a Respiratory Syncytial Virus (RSV) F protein in cotton rats.

A *gorilla* adenovirus having the nucleic acid sequence of SEQ ID NO: 22 was modified by genetic engineering to (1) be rendered replication-deficient by deletion of the E1 region, and (2) express the human Respiratory Syncytial Virus (RSV) Fusion (F) glycoprotein. Because RSV replicates in the cytoplasm of cells, the gene encoding the F protein was modified for expression in a cell nucleus by removing RNA processing signals (e.g., RNA splicing sites), and was codon-optimized for expression in a mammalian cell. The expression of the F protein from the adenoviral vector was verified by infection of HEK-293 cells in vitro, and by a Western blot assay using protein extracts of the infected cells and a commercially available anti-RSV polyclonal antibody (Pab7133P, Maine Biotechnology, Portland, Me.).

Cotton rats (*Sigmodon hispidus*) were injected in the tibialis muscle with a single administration of $10^7$ particle units (pu) of the E1-deleted adenoviral vector expressing the RSV F glycoprotein. The animals were then challenged 28 days later with live human RSV ($10^6$ particle forming units (pfu) administered intranasally). At 5 days post-challenge, the viral load of RSV in the lungs of the animals was measured. The animals that were immunized with the adenoviral vector expressing the F protein did not have detectable RSV in the lungs (limit of detection 70 pfu/gram of lung tissue).

The results of this example demonstrate that the inventive adenoviral vector encoding an RSV F protein is immunogenic in vivo and can confer complete protection against RSV infection in cotton rats.

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

The invention claimed is:

1. An adenovirus or adenoviral vector comprising a non-native nucleic acid sequence encoding an immunogenic protein and one or more of the nucleic acid sequences selected from the group consisting of:

(a) the nucleic acid sequence of SEQ ID NO: 1, (b) a nucleic acid sequence that is at least 98.5% identical to SEQ ID NO: 2, (c) a nucleic acid sequence that is at least 90% identical to SEQ ID NO: 3, (d) a nucleic acid sequence that is at least 80/o identical to SEQ ID NO: 4, and (e) a nucleic acid sequence that is at least 89% identical to SEQ ID NO: 5.

2. The adenovirus or adenoviral vector of claim 1, which comprises the nucleic acid sequence of SEQ ID NO: 1.

3. The adenovirus or adenoviral vector of claim 1, which comprises a nucleic acid sequence that is at least 98.5% identical to SEQ ID NO: 2.

4. The adenovirus or adenoviral vector of claim 3, which comprises the nucleic acid sequence of SEQ ID NO: 2.

5. The adenovirus or adenoviral vector of claim 1, which comprises a nucleic acid sequence that is at least 90% identical to SEQ ID NO: 3.

6. The adenovirus or adenoviral vector of claim 5, which comprises the nucleic acid sequence of SEQ ID NO: 3.

7. The adenovirus or adenoviral vector of claim 1, which comprises a nucleic acid sequence that is at least 80% identical to SEQ ID NO: 4.

8. The adenovirus or adenoviral vector of claim 7, which comprises the nucleic acid sequence of SEQ ID NO: 4.

9. The adenovirus or adenoviral vector of claim 1, which comprises a nucleic acid sequence that is at least 89% identical to SEQ ID NO: 5.

10. The adenovirus or adenoviral vector of claim 9, which comprises the nucleic acid sequence of SEQ ID NO: 5.

11. An adenovirus or adenoviral vector comprising a non-native nucleic acid sequence encoding an immunogenic protein and one or more of the amino acid sequences selected from the group consisting of:

(a) the amino acid sequence of SEQ ID NO: 11, (b) an amino acid sequence that is at least 82% identical to SEQ ID NO: 13, (c) an amino acid sequence that is at least 80% identical to SEQ ID NO: 14, and (d) an amino acid sequence that is at least 83% identical to SEQ ID NO: 15.

12. The adenovirus or adenoviral vector of claim 11, which comprises the amino acid sequence of SEQ ID NO: 11.

13. The adenovirus or adenoviral vector of claim 11, which comprises an amino acid sequence that is at least 82% identical to SEQ ID NO: 13.

14. The adenovirus or adenoviral vector of claim 13, which comprises the amino acid sequence of SEQ ID NO: 13.

15. The adenovirus or adenoviral vector of claim 11, which comprises an amino acid sequence that is at least 80% identical to SEQ ID NO: 14.

16. The adenovirus or adenoviral vector of claim 15, which comprises the amino acid sequence of SEQ ID NO: 14.

17. The adenovirus or adenoviral vector of claim 11, which comprises an amino acid sequence that is at least 83% identical to SEQ ID NO: 15.

18. The adenovirus or adenoviral vector of claim 17, which comprises the amino acid sequence of SEQ ID NO: 15.

19. An adenovirus or adenoviral vector comprising a non-native nucleic acid sequence encoding an immunogenic protein and one or more of the nucleic acid sequences selected from the group consisting of:

(a) a nucleic acid sequence encoding the amino acid sequence of SEQ ID NO: 11, (b) a nucleic acid sequence encoding an amino acid sequence that is at least 99% identical to SEQ ID NO: 12, (c) a nucleic acid sequence encoding an amino acid sequence that is at least 82% identical to SEQ ID NO: 13, (d) a nucleic acid sequence encoding an amino acid sequence that is at least 80% identical to SEQ ID NO: 14, and (e) a nucleic acid sequence encoding an amino acid sequence that is at least 83% identical to SEQ ID NO: 15.

20. The adenovirus or adenoviral vector of claim 19, which comprises a nucleic acid sequence encoding the amino acid sequence of SEQ ID NO: 11.

21. The adenovirus or adenoviral vector of claim 19, which comprises a nucleic acid sequence encoding an amino acid sequence that is at least 99% identical to SEQ ID NO: 12.

22. The adenovirus or adenoviral vector of claim 21, which comprises a nucleic acid sequence encoding the amino acid sequence of SEQ ID NO: 12.

23. The adenovirus or adenoviral vector of claim 19, which comprises a nucleic acid sequence encoding an amino acid sequence that is at least 82% identical to SEQ ID NO: 13.

24. The adenovirus or adenoviral vector of claim 23, which comprises a nucleic acid sequence encoding the amino acid sequence of SEQ ID NO: 13.

25. The adenovirus or adenoviral vector of claim 19, which comprises a nucleic acid sequence encoding an amino acid sequence that is at least 80% identical to SEQ ID NO: 14.

26. The adenovirus or adenoviral vector of claim 25, which comprises a nucleic acid sequence encoding the amino acid sequence of SEQ ID NO: 14.

27. The adenovirus or adenoviral vector of claim 19, which comprises a nucleic acid sequence encoding an amino acid sequence that is at least 83% identical to SEQ ID NO: 15.

28. The adenovirus or adenoviral vector of claim 27, which comprises a nucleic acid sequence encoding the amino acid sequence of SEQ ID NO: 15.

29. A composition comprising the adenovirus or adenoviral vector of claim 1 and a pharmaceutically acceptable carrier.

30. A composition comprising the adenovirus or adenoviral vector of claim 11 and a pharmaceutically acceptable carrier.

31. A composition comprising the adenovirus or adenoviral vector of claim 19 and a pharmaceutically acceptable carrier.

* * * * *

SEQUENCE LISTING

```
<160> NUMBER OF SEQ ID NOS: 25

<210> SEQ ID NO 1
<211> LENGTH: 30
<212> TYPE: DNA
<213> ORGANISM: Gorilla beringei beringei

<400> SEQUENCE: 1

agctctttgg tggcgagcgg cgcggcctct                                    30
```

<210> SEQ ID NO 2
<211> LENGTH: 439
<212> TYPE: DNA
<213> ORGANISM: Gorilla beringei beringei

<400> SEQUENCE: 2
aacatcaata cctcaaagtc atggtcaggg acactttcgc cctcacccac acctccctcc 60
gcaaggcggc gcaggcctac gcgctgcccg tggagaaggg ctgttgcccc taccaggccg 120
tcaaccagtt ctacatgcta ggctcttacc gttcggacac ggacgggttt cccctccaag 180
agtactggaa agaccgcgaa gagttcgtcc tcaaccgcga gctgtggaaa aagaaggggg 240
aggataagta tgacatcatc cgcgagaccc tcgactactg cgcgctcgac gtccaggtca 300
ccgccgagct ggtgcacaag ctgcgcgagt cctacgcctc cttcgtcagg gactcggtgg 360
gcttgcaaga agcaagcttc aacgtcttcc agcggcccac catctcctcc aactcccatg 420
ccatcttcag gcagatcgc 439

<210> SEQ ID NO 3
<211> LENGTH: 34
<212> TYPE: DNA
<213> ORGANISM: Gorilla beringei beringei

<400> SEQUENCE: 3
actgaggctg cggctaaggc tgaggtcgaa gcca 34

<210> SEQ ID NO 4
<211> LENGTH: 45
<212> TYPE: DNA
<213> ORGANISM: Gorilla beringei beringei

<400> SEQUENCE: 4
ataggtgtgg atgccacaca ggcgggagat aaccctatat atgct 45

<210> SEQ ID NO 5
<211> LENGTH: 30
<212> TYPE: DNA
<213> ORGANISM: Gorilla beringei beringei

<400> SEQUENCE: 5
gtagcaggcc ccctagctgt ggccaatggc 30

<210> SEQ ID NO 6
<211> LENGTH: 399
<212> TYPE: DNA
<213> ORGANISM: Gorilla beringei beringei

<400> SEQUENCE: 6
atgagcgaca ccggcaacag ctttgatgga agcatcttta gcccctatct gacagtgcgc 60
atgcctcact gggctggagt gcgtcagaat gtgatgggtt ccaacgtgga tggacgcccc 120
gttctgcctt caaattcgtc tacaatggcc tacgcgaccg tgggaggaac tccgctggac 180
gccgcgacct ccgccgccgc ctccgccgcc gccgcgaccg cgcgcagcat ggctacggac 240
ctttacagct ctttggtggc gagcggcgcg gcctctcgcg cgtctgctcg ggatgagaaa 300
ctgaccgctc tgctgcttaa actggaagac ttgacccggg agctgggtca actgacccag 360
caggtctcca gcttgcgtga gagcagcctt gcctccccc 399

<210> SEQ ID NO 7
<211> LENGTH: 3168
<212> TYPE: DNA

-continued

<213> ORGANISM: Gorilla beringei beringei

<400> SEQUENCE: 7
atggacagct ccaatgtgcg cgatgtcgtc atcaaactcc gcccgccgag cgccgagatc 60
tggacctgcg gctctcgcgg cgtggtggtc tgctccacca tcgccctcca ggagacagat 120
gctggcggcc agacaaccaa agtagaagac caccagccac acgggacccc aggcggggga 180
cttagattcc cgctgcgctt cctcgtcaga ggtcgccagg ttcacctcgt gcaagatata 240
caacccgtgc agcgctgcca gtactgcggt cgcttttaca aaagccagca cgagtgctcg 300
gcccgcagac gggacttcta ctttcaccac atcaacagcc aatcctccaa ctggtggcgg 360
gagatccagt tcttcccgat cggctctcat cctcgcacgg agcgcctctt tgtcacctac 420
gatgtagaga cctacacttg gatgggagcc tttggcaagc agctcgtgcc cttcatgctg 480
gtcatgaaac tgggggggcga cgaggctctg gtcgccgccg cgcgcgacct cgcccgagag 540
ctcagatggg accccctgga gaaagacccc ctcaccttct actgcatcac ccccgaaaag 600
atggccgtgg ggcgacagtt cagaaccttc cgcgaccgcc tgcagaccct catggcccgc 660
gacctctggc gatccttcct ggcggccaac cctcacttgc aagactgggc cctggaggag 720
cacggcctgg aatcgcccga ggagctcacc tacgaggaac tcaaaaagct cccctccatc 780
aagggccagc cccgcttttt ggagctctac atcgtgggcc acaacataaa cggctttgac 840
gagatcgtcc tggccgccca ggtcatcaac aaccgctcct cggtcccagg gccctttcgc 900
atcaccagaa acttcatgcc tcgagcgggg aagatcctct tcaatgacct caccttctcc 960
ctgcccaacc cgcgctccaa aaagcgcacg gactacaccc tgtgggaaca gggcggctgc 1020
gatgacacag acttcaaaca tcaatacctc aaagtcatgg tcagggacac tttcgccctc 1080
acccacacct ccctccgcaa ggcggcgcag gcctacgcgc tgcccgtgga gaagggctgt 1140
tgcccctacc aggccgtcaa ccagttctac atgctaggct cttaccgttc ggacacggac 1200
gggtttcccc tccaagagta ctggaaagac cgcgaagagt tcgtcctcaa ccgcgagctg 1260
tggaaaaaga agggggagga taagtatgac atcatccgcg agaccctcga ctactgcgcg 1320
ctcgacgtcc aggtcaccgc cgagctggtg cacaagctgc gcgagtccta cgcctccttc 1380
gtcagggact cggtgggctt gcaagaagca agcttcaacg tcttccagcg gcccaccatc 1440
tcctccaact cccatgccat cttcaggcag atcgccttcc gcgccgagcg cccccagcgc 1500
accaacctcg ggcccaacat gctggccccc tcccacgagc tctatgacta cgtgcgcgcc 1560
agcatccgcg gggggcgctg ctaccccacc tacctcggca tcctcaggga acccctgtac 1620
gtgtatgaca tctgcggcat gtacgcctcc gcgctcaccc accccatgcc ctggggcccg 1680
cccctcaacc cctacgagcg cgcgctcgcc gcccgcgaat ggcagcgggc tctggacatg 1740
caagcttgca agatcgacta ctttgacccg cgcttgctcc ccggggtctt caccatcgac 1800
gcggaccccc caaacgagga ccagctggac cccctacccc ccttctgctc gcgcaagggc 1860
ggccgcctct gctggaccaa cgagcgcctg cgcggcgagg tcgccaccag cgtcgacatg 1920
gtcaccctgc acaaccgagg ctggagggtg cgcctaatcc cagacgagcg caccaccgtc 1980
ttccccgagt ggaagtgcgt ggcccgcgag tacgtgcaac tcaacatcgc ggccaaggag 2040
cgagccgacc gcgacaaaaa ccagaccctg cgctccatcg ccaagctgct ctccaacgcc 2100
ctctacgggt cgttcgccac caagcttgac aacaaaaaaa tagtgttttc tgaccagatg 2160
gacccaggta ccctcaaagg tatcacctcc ggacaggtga acatcaaatc ctcctcattt 2220
ttagaaactg acaacctgag cgctgaggtc atgcccgcct tcgagaggga atacttaccc 2280
cagcagctgg ccctcgcaga cagcgatgcg gaagagagtg aagatgaaag ggcgcccacc 2340 ccctttttata cccccccgtc gggaaccccc ggtcacgtgt cctacaccta caagccaatc 2400
acttttctgg acgcggagga gggggacatg tgcctgcaca ccctggagaa ggtggacccg 2460
ctagtggaca acgaccgcta cccctcccac gtggcctcct tcgtcctggc ctggacgcgg 2520
gccttcgtct cagagtggtc agagtttctc tacgaggagg acagaggcac tccgctggaa 2580
gacaggcccc tgaagtcggt ctacggggac acggacagcc tcttcgtcac cgagaaggga 2640
caccgcctca tggagagccg aggtaagaaa cgcatcaaaa agcatggggg caacctggtt 2700
tttgaccctg accgcccgga gctcacttgg ctggtggaat gcgagacggt ctgcgcttcc 2760
tgcggcgcgg acgcctactc cccagagtcc gtgtttctcg ctcccaagct ctacgccctg 2820
aagagcctgc agtgcccctc gtgcggcgcc acctccaagg gaaagctccg cgccaagggg 2880
cacgccgccg agggtctcga ctacgagacc atggtcaaat gctacctggc cgacgcgcag 2940
ggcgaagagc ggcagcgatt cagcaccagc agaaccagcc tcaagcgcac cctggccagc 3000
gcccaacccg gagcgcaccc cttcaccgtg acccagacca ccctgacgag gaccctgcgc 3060
ccatggaagg acatgactct ggccccgctg gacgcccatc ggctggtgcc ctacagcgaa 3120
agccgcccca acccgcgaaa cgaggagatc tgctggatcg agatgccg 3168

<210> SEQ ID NO 8
<211> LENGTH: 1974
<212> TYPE: DNA
<213> ORGANISM: Gorilla beringei beringei

<400> SEQUENCE: 8
atgcggcgcg cggcgatgtt cgaggagggg cctccccccct cttacgagag cgcgatgggg 60
atttctcctg cggcgcccct gcagcctccc tacgtgcctc ctcggtacct gcaacctaca 120
ggggggagaa atagcatctg ttactctgag ctgcagcccc tgtacgatac caccagactg 180
tacctggtgg acaacaagtc cgcggacgtg gcctccctga actaccagaa cgaccacagc 240
gattttttga ccacggtgat ccaaaacaac gacttcaccc caaccgaggc cagcacccag 300
accataaacc tggataacag gtcgaactgg ggcggcgacc tgaagaccat cttgcacacc 360
aacatgccca acgtgaacga gttcatgttc accaactctt ttaaggcgcg ggtgatggtg 420
gcgcgcgagc agggggaggc gaagtacgag tgggtggact tcacgctgcc cgagggcaac 480
tactcagaga ccatgactct cgacctgatg aacaatgcga tcgtggaaca ctatctgaaa 540
gtgggcaggc agaacggggt gaaggaaagc gatatcgggg tcaagtttga caccagaaac 600
ttccgtctgg gctgggaccc cgtgaccggg ctggtcatgc cgggggtcta caccaacgag 660
gcctttcatc ccgacatagt gcttctgccc ggctgtgggg tggacttcac ccagagccgg 720
ctgagcaacc tgctgggcat tcgcaagcgg cagcctttcc aggagggttt caagatcacc 780
tatgaggatc tgaagggggg caacattccc gcgctccttg atctggacgc ctacgaggag 840
agcttgaaac ccgaggagag cgctggcgac agcggcgaga gtggcgagga gcaagccggc 900
ggcggtggcg gcgcgtcggt agaaaacgaa agtacgcccg cagtggcggc ggacgctgcg 960
gaggtcgagc cggaggccat gcagcaggac gcagaggagg gcgcacagga gggcgcgcag 1020
aaggacatga acgatgggga gatcagggga gacacattcg ccacccgggg cgaagaaaaa 1080
gaggcagagg cggcggcggc ggcgacggcg gaggccgaaa ccgaggttga ggcagaggca 1140
gagcccgaga ccgaagttat ggaagacatg aatgatggag aacgtagggg cgacacgttc 1200

-continued

```
gccacccggg gcgaagagaa ggcggcggag gcagaagccg cggctgagga ggcggctgcg   1260

gctgcggcca agactgaggc tgcggctaag gctgaggtcg aagccaatgt tgcggttgag   1320

gctcaggctg aggaggaggc ggcggctgaa gcagttaagg aaaaggccca ggcagagcag   1380

gaagagaaaa aacctgtcat tcaacctcta aaagaagata gcaaaaagcg cagttacaac   1440

gtcatcgagg gcagcacctt tacccagtac cgcagctggt acctggcgta caactacggc   1500

gacccggtca agggggtgcg ctcgtggacc ctgctctgca cgccggacgt cacctgcggc   1560

tccgagcaga tgtactggtc gctgccgaac atgatgcaag acccggtgac cttccgctcc   1620

acgcggcagg ttagcaactt cccggtggtg ggcgccgaac tgctgcccgt gcactccaag   1680

agtttttaca acgagcaggc cgtctactcc cagctgatcc gccaggccac ctctctgacc   1740

cacgtgttca atcgctttcc cgagaaccag attttggcgc gcccgccggc ccccaccatc   1800

accaccgtga gtgaaaacgt tcctgccctc acagatcacg ggacgctacc gctgcgcaac   1860

agcatctcag gagtccagcg agtgaccatt actgacgcca gacgccggac ctgcccctac   1920

gtttacaagg ccttgggcat agtctcgccg cgcgtcctct ccagtcgcac tttt         1974
```

<210> SEQ ID NO 9
<211> LENGTH: 2877
<212> TYPE: DNA
<213> ORGANISM: Gorilla beringei beringei

<400> SEQUENCE: 9

```
atggcgaccc catcgatgat gcctcagtgg tcgtacatgc acatctcggg ccaggacgct     60

tcggagtacc tgagccccgg gctggtgcag ttcgcccgcg ccacagacac ctacttcaac    120

atgagtaaca agttcaggaa ccccactgtg gcgcccaccc acgatgtgac cacggaccgg    180

tcgcagcgcc tgacgctgcg gttcatcccc gtggatcggg aggacaccgc ctactcttac    240

aaggcgcggt tcacgctggc cgtgggcgac aaccgcgtgc tggacatggc ctccacttac    300

tttgacatca ggggggtgct ggacaggggc cccaccttca agccctactc gggtactgcc    360

tacaactccc tggcccccaa gggcgctccc aattcttgcg agtgggaaca agatgaacca    420

gctcaggcag caatagctga agatgaagaa gaacttgaag aagaacaagc tcaggacgaa    480

caggcgccca ctaagaaaac ccatgtatac gcccaggcac ctctttctgg tgaaaaaatt    540

actaaggatg gtttgcaaat aggtgtggat gccacacagg cgggagataa ccctatatat    600

gctgataaaa cattccaacc cgaacctcag ataggtgagt ctcagtggaa cgaggctgat    660

gccacagtag caggaggcag agtcttaaaa aagaccaccc ctatgagacc ttgctatgga    720

tcctatgcca aacctactaa tgccaatggc ggtcaaggga tcatggtggc caatgatcag    780

ggagcgcttg aatctaaagt tgagatgcaa tttttctcca ccacaacgtc tcttaatgta    840

agggaaggtg aaaacaatct tcagccaaaa gtagtgctat acagcgaaga tgttaacttg    900

gaatcccctg acactcattt gtcttacaaa cctaaaaagg atgacaccaa ctctaaaatc    960

atgttgggtc agcaagccat gcccaacaga cccaacctca ttgcttttag ggacaacttt   1020

attggactta tgtactacaa cagcacaggc aacatgggag tgctggcagg acaggcctcc   1080

cagctaaacg ctgtggtaga cttgcaagac agaaacacag agctgtcata ccaactgatg   1140

cttgattcca ttggagacag atcaagatac ttttccatgt ggaaccaggc agtggacagc   1200

tatgacccag atgtcagaat cattgaaaac catggggttg aagatgagct gcccaactat   1260

tgctttcccc tgggcggtat tggaattaca gacacatacc agtgcataaa accaaccgca   1320

gctgctaata acactacatg gtctaaggat gaagaattta gtgatcgcaa tgaaataggg   1380
```

gtgggaaaca acttcgccat ggagatcaac atccaggcca acctctggag gaacttcctc 1440
tatgcgaacg tggggctcta cctgccagac aagctcaagt acaaccccac caacgtggac 1500
atctctgaca accccaacac ctatgactac atgaacaagc gtgtggtggc tcccggcctg 1560
gtggactgct ttgtcaatgt gggagccagg tggtccctgg actacatgga caacgtcaac 1620
cccttcaacc accaccgcaa tgcgggtctg cgctaccgct ccatgatcct gggcaacggg 1680
cgctacgtgc ccttccacat tcaggtgccc cagaagttct ttgccatcaa gaacctcctc 1740
ctcctgccgg gctcctacac ttacgagtgg aacttcagga aggatgtcaa catggtcctg 1800
cagagctctc tgggcaatga ccttagggtg gacggggcca gcatcaagtt tgacagcgtc 1860
accctctatg ctaccttctt ccccatggct cacaacaccg cctccacgct cgaggccatg 1920
ctgaggaacg acaccaacga ccagtccttc aatgactacc tctctggggc caacatgctc 1980
taccccatcc ccgccaaggc caccaacgtg cccatctcca ttccctctcg caactgggcc 2040
gccttcagag gctgggcctt tacccgcctt aagaccaagg aaacccccctc cctgggctcg 2100 ggttttgacc cctactttgt ctactcggga tccatcccct acctggatgg caccttctac 2160
ctcaaccaca cttttaagaa gatatccatc atgtatgact cctccgtcag ctggccgggc 2220
aatgaccgcc tgctcacccc caatgagttc gaggtcaagc gcgccgtgga cggcgagggc 2280
tacaacgtgg cccagtgcaa catgaccaag gactggttcc tggtgcagat gctggccaac 2340
tacaacatag gctaccaggg cttctacatc ccagagagct acaaggacag gatgtactcc 2400
ttcttcagaa atttccaacc catgagcagg caggtggtgg acgagaccaa atacaaggac 2460
tatcaggcca ttggcatcac tcaccagcac aacaactcgg gattcgtggg ctacctggct 2520
cccaccatgc gcgaggggca ggcctacccc gccaacttcc cctacccgtt gataggcaaa 2580
accgcggtcg acagcgtcac ccagaaaaag ttcctctgcg accgcaccct ctggcgcatc 2640
cccttctcta gcaacttcat gtccatgggt gcgctcacgg acctgggcca gaacctgctc 2700
tatgccaact ccgcccatgc gctggacatg acttttgagg tggaccccat ggacgagccc 2760
acccttctct atattgtgtt tgaagtgttc gacgtggtca gagtgcacca gccgcaccgc 2820
ggtgtcatcg agaccgtgta cctgcgcacg cccttctcgg ccggcaacgc caccacc 2877

<210> SEQ ID NO 10
<211> LENGTH: 1749
<212> TYPE: DNA
<213> ORGANISM: Gorilla beringei beringei

<400> SEQUENCE: 10
atgaaacgcg cgagatcgtc tgacgagacc ttcaaccccg tgtaccccta cgataccgag 60
atcgctccga cttctgtccc tttccttacc cctccctttg tgtcatccgc aggaatgcaa 120
gaaaatccag ctggggtgct gtccctgcac ttgtcagagc cccttaccac ccacaatggg 180
gccctgactc taaaaatggg gggcggcctg accctggaca aggaagggaa tctcacttcc 240
caaaacatca ccagtgtcga tccccctctc aaaaaaagca agaacaacat cagccttcag 300
accgccgcac ccctcgccgt cagctccggg gccctaacac tttttgccac tcccccccta 360
gcggtcagtg gtgacaacct tactgtgcag tctcaggccc ctctcacttt ggaagactca 420
aaactaactc tggccaccaa aggaccccta actgtgtccg aaggcaaact tgtcctagaa 480
acagaggctc ccctgcatgc aagtgacagc agcagcctgg gccttagcgt tacggcccca 540
cttagcatta acaatgacag cctaggacta gatctgcagg cacccattgt ctctcaaaat 600

-continued

```
ggaaaactgg ctctaaatgt agcaggcccc ctagctgtgg ccaatggcat taatgctttg    660

acagtaggca caggcaaagg tattggtcta aatgaaacca gcactcactt gcaagcaaag    720

ttggtcgccc ccctaggctt tgataccaat ggcaacatta agctaagcgt tgcaggaggc    780

atgagactaa ataatgacac acttatacta gatgtaaact acccatttga agctcaaggc    840

caactaagtc taagagtggg ccagggtccg ctgtatgtag attctagcag ccataacctg    900

accattagat gccttagagg attatacata acatcgtcta ataaccaaac cggtctagag    960

gccaacataa aactaacaaa aggccttgtc tatgatggaa atgccatagc agtcaatgtt   1020

ggtcaaggat tgcaatacag cactactgcc acatcggaag gtgtgtatcc tatacagtct   1080

aagataggtt tgggaatgga atatgatacc aacggagcca tgatgacaaa actaggctct   1140

ggactaagct ttgacaattc aggagccatt gtagtgggaa acaaaaatga tgacaggctt   1200

actctgtgga ctacaccaga cccatctcct aactgtagaa tttattctga aaaagatact   1260

aaactaacct tggtgctgac taagtgtggc agccaaatcc taggcacagt atctgccctt   1320

gctgtcagag gcagccttgc gcccatcact aatgcatcca gcatagtcca aatatttcta   1380

agatttgatg aaaatggact attgatgagc aactcatcgc tagacggtga ttactggaat   1440

tacagaaatg ggactccac taatagcaca ccatatacaa atgcagtagg ctttatgcct   1500

aatctagcag cctatcctaa aggtcaggct acagctgcaa aaagcagtat tgtaagccag   1560

gtatacatgg atggtgacac tactaaacct ataacactaa aaataaactt caatggcatt   1620

gatgaaacaa cagaaaatac ccctgttagt aaatattcca tgacattctc atggagctgg   1680

cccaccgcaa gctacatagg ccacactttt gcaacaaact cttttacttt ctcctacatc   1740

gcccaagaa                                                           1749
```

```
<210> SEQ ID NO 11
<211> LENGTH: 10
<212> TYPE: PRT
<213> ORGANISM: Gorilla beringei beringei

<400> SEQUENCE: 11

Ser Ser Leu Val Ala Ser Gly Ala Ala Ser
1               5                   10


<210> SEQ ID NO 12
<211> LENGTH: 147
<212> TYPE: PRT
<213> ORGANISM: Gorilla beringei beringei

<400> SEQUENCE: 12

Lys His Gln Tyr Leu Lys Val Met Val Arg Asp Thr Phe Ala Leu Thr
1               5                   10                  15

His Thr Ser Leu Arg Lys Ala Ala Gln Ala Tyr Ala Leu Pro Val Glu
            20                  25                  30

Lys Gly Cys Cys Pro Tyr Gln Ala Val Asn Gln Phe Tyr Met Leu Gly
        35                  40                  45

Ser Tyr Arg Ser Asp Thr Asp Gly Phe Pro Leu Gln Glu Tyr Trp Lys
    50                  55                  60

Asp Arg Glu Glu Phe Val Leu Asn Arg Glu Leu Trp Lys Lys Lys Gly
65                  70                  75                  80

Glu Asp Lys Tyr Asp Ile Ile Arg Glu Thr Leu Asp Tyr Cys Ala Leu
                85                  90                  95

Asp Val Gln Val Thr Ala Glu Leu Val His Lys Leu Arg Glu Ser Tyr
            100                 105                 110
```

```
Ala Ser Phe Val Arg Asp Ser Val Gly Leu Gln Glu Ala Ser Phe Asn
        115                 120                 125

Val Phe Gln Arg Pro Thr Ile Ser Ser Asn Ser His Ala Ile Phe Arg
    130                 135                 140

Gln Ile Ala
145


<210> SEQ ID NO 13
<211> LENGTH: 15
<212> TYPE: PRT
<213> ORGANISM: Gorilla beringei beringei

<400> SEQUENCE: 13

Lys Thr Glu Ala Ala Ala Lys Ala Glu Val Glu Ala Asn Val Ala
1               5                   10                  15


<210> SEQ ID NO 14
<211> LENGTH: 15
<212> TYPE: PRT
<213> ORGANISM: Gorilla beringei beringei

<400> SEQUENCE: 14

Ile Gly Val Asp Ala Thr Gln Ala Gly Asp Asn Pro Ile Tyr Ala
1               5                   10                  15


<210> SEQ ID NO 15
<211> LENGTH: 15
<212> TYPE: PRT
<213> ORGANISM: Gorilla beringei beringei

<400> SEQUENCE: 15

Leu Asn Val Ala Gly Pro Leu Ala Val Ala Asn Gly Ile Asn Ala
1               5                   10                  15


<210> SEQ ID NO 16
<211> LENGTH: 133
<212> TYPE: PRT
<213> ORGANISM: Gorilla beringei beringei

<400> SEQUENCE: 16

Met Ser Asp Thr Gly Asn Ser Phe Asp Gly Ser Ile Phe Ser Pro Tyr
1               5                   10                  15

Leu Thr Val Arg Met Pro His Trp Ala Gly Val Arg Gln Asn Val Met
            20                  25                  30

Gly Ser Asn Val Asp Gly Arg Pro Val Leu Pro Ser Asn Ser Ser Thr
        35                  40                  45

Met Ala Tyr Ala Thr Val Gly Gly Thr Pro Leu Asp Ala Ala Thr Ser
    50                  55                  60

Ala Ala Ala Ser Ala Ala Ala Ala Thr Ala Arg Ser Met Ala Thr Asp
65                  70                  75                  80

Leu Tyr Ser Ser Leu Val Ala Ser Gly Ala Ala Ser Arg Ala Ser Ala
                85                  90                  95

Arg Asp Glu Lys Leu Thr Ala Leu Leu Leu Lys Leu Glu Asp Leu Thr
            100                 105                 110

Arg Glu Leu Gly Gln Leu Thr Gln Gln Val Ser Ser Leu Arg Glu Ser
        115                 120                 125

Ser Leu Ala Ser Pro
    130
```

-continued

<210> SEQ ID NO 17
<211> LENGTH: 1056
<212> TYPE: PRT
<213> ORGANISM: Gorilla beringei beringei

<400> SEQUENCE: 17

```
Met Asp Ser Ser Asn Val Arg Asp Val Val Ile Lys Leu Arg Pro Pro
1               5                   10                  15

Ser Ala Glu Ile Trp Thr Cys Gly Ser Arg Gly Val Val Val Cys Ser
            20                  25                  30

Thr Ile Ala Leu Gln Glu Thr Asp Ala Gly Gly Gln Thr Thr Lys Val
        35                  40                  45

Glu Asp His Gln Pro His Gly Thr Pro Gly Gly Gly Leu Arg Phe Pro
    50                  55                  60

Leu Arg Phe Leu Val Arg Gly Arg Gln Val His Leu Val Gln Asp Ile
65                  70                  75                  80

Gln Pro Val Gln Arg Cys Gln Tyr Cys Gly Arg Phe Tyr Lys Ser Gln
                85                  90                  95

His Glu Cys Ser Ala Arg Arg Arg Asp Phe Tyr Phe His His Ile Asn
            100                 105                 110

Ser Gln Ser Ser Asn Trp Trp Arg Glu Ile Gln Phe Phe Pro Ile Gly
        115                 120                 125

Ser His Pro Arg Thr Glu Arg Leu Phe Val Thr Tyr Asp Val Glu Thr
    130                 135                 140

Tyr Thr Trp Met Gly Ala Phe Gly Lys Gln Leu Val Pro Phe Met Leu
145                 150                 155                 160

Val Met Lys Leu Gly Gly Asp Glu Ala Leu Val Ala Ala Ala Arg Asp
                165                 170                 175

Leu Ala Arg Glu Leu Arg Trp Asp Pro Trp Glu Lys Asp Pro Leu Thr
            180                 185                 190

Phe Tyr Cys Ile Thr Pro Glu Lys Met Ala Val Gly Arg Gln Phe Arg
        195                 200                 205

Thr Phe Arg Asp Arg Leu Gln Thr Leu Met Ala Arg Asp Leu Trp Arg
    210                 215                 220

Ser Phe Leu Ala Ala Asn Pro His Leu Gln Asp Trp Ala Leu Glu Glu
225                 230                 235                 240

His Gly Leu Glu Ser Pro Glu Glu Leu Thr Tyr Glu Glu Leu Lys Lys
                245                 250                 255

Leu Pro Ser Ile Lys Gly Gln Pro Arg Phe Leu Glu Leu Tyr Ile Val
            260                 265                 270

Gly His Asn Ile Asn Gly Phe Asp Glu Ile Val Leu Ala Ala Gln Val
        275                 280                 285

Ile Asn Asn Arg Ser Ser Val Pro Gly Pro Phe Arg Ile Thr Arg Asn
    290                 295                 300

Phe Met Pro Arg Ala Gly Lys Ile Leu Phe Asn Asp Leu Thr Phe Ser
305                 310                 315                 320

Leu Pro Asn Pro Arg Ser Lys Lys Arg Thr Asp Tyr Thr Leu Trp Glu
                325                 330                 335

Gln Gly Gly Cys Asp Asp Thr Asp Phe Lys His Gln Tyr Leu Lys Val
            340                 345                 350

Met Val Arg Asp Thr Phe Ala Leu Thr His Thr Ser Leu Arg Lys Ala
        355                 360                 365

Ala Gln Ala Tyr Ala Leu Pro Val Glu Lys Gly Cys Cys Pro Tyr Gln
    370                 375                 380
```

-continued

```
Ala Val Asn Gln Phe Tyr Met Leu Gly Ser Tyr Arg Ser Asp Thr Asp
385                 390                 395                 400

Gly Phe Pro Leu Gln Glu Tyr Trp Lys Asp Arg Glu Glu Phe Val Leu
                405                 410                 415

Asn Arg Glu Leu Trp Lys Lys Lys Gly Glu Asp Lys Tyr Asp Ile Ile
            420                 425                 430

Arg Glu Thr Leu Asp Tyr Cys Ala Leu Asp Val Gln Val Thr Ala Glu
        435                 440                 445

Leu Val His Lys Leu Arg Glu Ser Tyr Ala Ser Phe Val Arg Asp Ser
    450                 455                 460

Val Gly Leu Gln Glu Ala Ser Phe Asn Val Phe Gln Arg Pro Thr Ile
465                 470                 475                 480

Ser Ser Asn Ser His Ala Ile Phe Arg Gln Ile Ala Phe Arg Ala Glu
                485                 490                 495

Arg Pro Gln Arg Thr Asn Leu Gly Pro Asn Met Leu Ala Pro Ser His
            500                 505                 510

Glu Leu Tyr Asp Tyr Val Arg Ala Ser Ile Arg Gly Gly Arg Cys Tyr
        515                 520                 525

Pro Thr Tyr Leu Gly Ile Leu Arg Glu Pro Leu Tyr Val Tyr Asp Ile
    530                 535                 540

Cys Gly Met Tyr Ala Ser Ala Leu Thr His Pro Met Pro Trp Gly Pro
545                 550                 555                 560

Pro Leu Asn Pro Tyr Glu Arg Ala Leu Ala Ala Arg Glu Trp Gln Arg
                565                 570                 575

Ala Leu Asp Met Gln Ala Cys Lys Ile Asp Tyr Phe Asp Pro Arg Leu
            580                 585                 590

Leu Pro Gly Val Phe Thr Ile Asp Ala Asp Pro Pro Asn Glu Asp Gln
        595                 600                 605

Leu Asp Pro Leu Pro Pro Phe Cys Ser Arg Lys Gly Gly Arg Leu Cys
    610                 615                 620

Trp Thr Asn Glu Arg Leu Arg Gly Glu Val Ala Thr Ser Val Asp Met
625                 630                 635                 640

Val Thr Leu His Asn Arg Gly Trp Arg Val Arg Leu Ile Pro Asp Glu
                645                 650                 655

Arg Thr Thr Val Phe Pro Glu Trp Lys Cys Val Ala Arg Glu Tyr Val
            660                 665                 670

Gln Leu Asn Ile Ala Ala Lys Glu Arg Ala Asp Arg Asp Lys Asn Gln
        675                 680                 685

Thr Leu Arg Ser Ile Ala Lys Leu Leu Ser Asn Ala Leu Tyr Gly Ser
    690                 695                 700

Phe Ala Thr Lys Leu Asp Asn Lys Lys Ile Val Phe Ser Asp Gln Met
705                 710                 715                 720

Asp Pro Gly Thr Leu Lys Gly Ile Thr Ser Gly Gln Val Asn Ile Lys
                725                 730                 735

Ser Ser Ser Phe Leu Glu Thr Asp Asn Leu Ser Ala Glu Val Met Pro
            740                 745                 750

Ala Phe Glu Arg Glu Tyr Leu Pro Gln Gln Leu Ala Leu Ala Asp Ser
        755                 760                 765

Asp Ala Glu Glu Ser Glu Asp Glu Arg Ala Pro Thr Pro Phe Tyr Thr
    770                 775                 780

Pro Pro Ser Gly Thr Pro Gly His Val Ser Tyr Thr Tyr Lys Pro Ile
785                 790                 795                 800

Thr Phe Leu Asp Ala Glu Glu Gly Asp Met Cys Leu His Thr Leu Glu
```

```
                805                 810                 815

Lys Val Asp Pro Leu Val Asp Asn Asp Arg Tyr Pro Ser His Val Ala
            820                 825                 830

Ser Phe Val Leu Ala Trp Thr Arg Ala Phe Val Ser Glu Trp Ser Glu
        835                 840                 845

Phe Leu Tyr Glu Glu Asp Arg Gly Thr Pro Leu Glu Asp Arg Pro Leu
    850                 855                 860

Lys Ser Val Tyr Gly Asp Thr Asp Ser Leu Phe Val Thr Glu Lys Gly
865                 870                 875                 880

His Arg Leu Met Glu Ser Arg Gly Lys Lys Arg Ile Lys Lys His Gly
                885                 890                 895

Gly Asn Leu Val Phe Asp Pro Asp Arg Pro Glu Leu Thr Trp Leu Val
            900                 905                 910

Glu Cys Glu Thr Val Cys Ala Ser Cys Gly Ala Asp Ala Tyr Ser Pro
        915                 920                 925

Glu Ser Val Phe Leu Ala Pro Lys Leu Tyr Ala Leu Lys Ser Leu Gln
    930                 935                 940

Cys Pro Ser Cys Gly Ala Thr Ser Lys Gly Lys Leu Arg Ala Lys Gly
945                 950                 955                 960

His Ala Ala Glu Gly Leu Asp Tyr Glu Thr Met Val Lys Cys Tyr Leu
                965                 970                 975

Ala Asp Ala Gln Gly Glu Glu Arg Gln Arg Phe Ser Thr Ser Arg Thr
            980                 985                 990

Ser Leu Lys Arg Thr Leu Ala Ser  Ala Gln Pro Gly Ala  His Pro Phe
        995                 1000                 1005

Thr Val  Thr Gln Thr Thr Leu  Thr Arg Thr Leu Arg  Pro Trp Lys
    1010                 1015                 1020

Asp Met  Thr Leu Ala Pro Leu  Asp Ala His Arg Leu  Val Pro Tyr
    1025                 1030                 1035

Ser Glu  Ser Arg Pro Asn Pro  Arg Asn Glu Glu Ile  Cys Trp Ile
    1040                 1045                 1050

Glu Met  Pro
    1055


<210> SEQ ID NO 18
<211> LENGTH: 658
<212> TYPE: PRT
<213> ORGANISM: Gorilla beringei beringei

<400> SEQUENCE: 18

Met Arg Arg Ala Ala Met Phe Glu Glu Gly Pro Pro Pro Ser Tyr Glu
1               5                   10                  15

Ser Ala Met Gly Ile Ser Pro Ala Ala Pro Leu Gln Pro Pro Tyr Val
            20                  25                  30

Pro Pro Arg Tyr Leu Gln Pro Thr Gly Gly Arg Asn Ser Ile Cys Tyr
        35                  40                  45

Ser Glu Leu Gln Pro Leu Tyr Asp Thr Thr Arg Leu Tyr Leu Val Asp
    50                  55                  60

Asn Lys Ser Ala Asp Val Ala Ser Leu Asn Tyr Gln Asn Asp His Ser
65                  70                  75                  80

Asp Phe Leu Thr Thr Val Ile Gln Asn Asn Asp Phe Thr Pro Thr Glu
                85                  90                  95

Ala Ser Thr Gln Thr Ile Asn Leu Asp Asn Arg Ser Asn Trp Gly Gly
            100                 105                 110
```

```
Asp Leu Lys Thr Ile Leu His Thr Asn Met Pro Asn Val Asn Glu Phe
        115                 120                 125

Met Phe Thr Asn Ser Phe Lys Ala Arg Val Met Val Ala Arg Glu Gln
    130                 135                 140

Gly Glu Ala Lys Tyr Glu Trp Val Asp Phe Thr Leu Pro Glu Gly Asn
145                 150                 155                 160

Tyr Ser Glu Thr Met Thr Leu Asp Leu Met Asn Asn Ala Ile Val Glu
                165                 170                 175

His Tyr Leu Lys Val Gly Arg Gln Asn Gly Val Lys Glu Ser Asp Ile
            180                 185                 190

Gly Val Lys Phe Asp Thr Arg Asn Phe Arg Leu Gly Trp Asp Pro Val
        195                 200                 205

Thr Gly Leu Val Met Pro Gly Val Tyr Thr Asn Glu Ala Phe His Pro
    210                 215                 220

Asp Ile Val Leu Leu Pro Gly Cys Gly Val Asp Phe Thr Gln Ser Arg
225                 230                 235                 240

Leu Ser Asn Leu Leu Gly Ile Arg Lys Arg Gln Pro Phe Gln Glu Gly
                245                 250                 255

Phe Lys Ile Thr Tyr Glu Asp Leu Lys Gly Gly Asn Ile Pro Ala Leu
            260                 265                 270

Leu Asp Leu Asp Ala Tyr Glu Glu Ser Leu Lys Pro Glu Glu Ser Ala
        275                 280                 285

Gly Asp Ser Gly Glu Ser Gly Glu Glu Gln Ala Gly Gly Gly Gly Gly
    290                 295                 300

Ala Ser Val Glu Asn Glu Ser Thr Pro Ala Val Ala Ala Asp Ala Ala
305                 310                 315                 320

Glu Val Glu Pro Glu Ala Met Gln Gln Asp Ala Glu Glu Gly Ala Gln
                325                 330                 335

Glu Gly Ala Gln Lys Asp Met Asn Asp Gly Glu Ile Arg Gly Asp Thr
            340                 345                 350

Phe Ala Thr Arg Gly Glu Glu Lys Glu Ala Glu Ala Ala Ala Ala Ala
        355                 360                 365

Thr Ala Glu Ala Glu Thr Glu Val Glu Ala Glu Ala Glu Pro Glu Thr
    370                 375                 380

Glu Val Met Glu Asp Met Asn Asp Gly Glu Arg Arg Gly Asp Thr Phe
385                 390                 395                 400

Ala Thr Arg Gly Glu Glu Lys Ala Ala Glu Ala Glu Ala Ala Ala Glu
                405                 410                 415

Glu Ala Ala Ala Ala Ala Ala Lys Thr Glu Ala Ala Ala Lys Ala Glu
            420                 425                 430

Val Glu Ala Asn Val Ala Val Glu Ala Gln Ala Glu Glu Glu Ala Ala
        435                 440                 445

Ala Glu Ala Val Lys Glu Lys Ala Gln Ala Glu Gln Glu Glu Lys Lys
    450                 455                 460

Pro Val Ile Gln Pro Leu Lys Glu Asp Ser Lys Lys Arg Ser Tyr Asn
465                 470                 475                 480

Val Ile Glu Gly Ser Thr Phe Thr Gln Tyr Arg Ser Trp Tyr Leu Ala
                485                 490                 495

Tyr Asn Tyr Gly Asp Pro Val Lys Gly Val Arg Ser Trp Thr Leu Leu
            500                 505                 510

Cys Thr Pro Asp Val Thr Cys Gly Ser Glu Gln Met Tyr Trp Ser Leu
        515                 520                 525

Pro Asn Met Met Gln Asp Pro Val Thr Phe Arg Ser Thr Arg Gln Val
```

```
    530                 535                 540

Ser Asn Phe Pro Val Val Gly Ala Glu Leu Leu Pro Val His Ser Lys
545                 550                 555                 560

Ser Phe Tyr Asn Glu Gln Ala Val Tyr Ser Gln Leu Ile Arg Gln Ala
                565                 570                 575

Thr Ser Leu Thr His Val Phe Asn Arg Phe Pro Glu Asn Gln Ile Leu
            580                 585                 590

Ala Arg Pro Pro Ala Pro Thr Ile Thr Thr Val Ser Glu Asn Val Pro
        595                 600                 605

Ala Leu Thr Asp His Gly Thr Leu Pro Leu Arg Asn Ser Ile Ser Gly
    610                 615                 620

Val Gln Arg Val Thr Ile Thr Asp Ala Arg Arg Arg Thr Cys Pro Tyr
625                 630                 635                 640

Val Tyr Lys Ala Leu Gly Ile Val Ser Pro Arg Val Leu Ser Ser Arg
                645                 650                 655

Thr Phe


<210> SEQ ID NO 19
<211> LENGTH: 959
<212> TYPE: PRT
<213> ORGANISM: Gorilla beringei beringei

<400> SEQUENCE: 19

Met Ala Thr Pro Ser Met Met Pro Gln Trp Ser Tyr Met His Ile Ser
1               5                   10                  15

Gly Gln Asp Ala Ser Glu Tyr Leu Ser Pro Gly Leu Val Gln Phe Ala
            20                  25                  30

Arg Ala Thr Asp Thr Tyr Phe Asn Met Ser Asn Lys Phe Arg Asn Pro
        35                  40                  45

Thr Val Ala Pro Thr His Asp Val Thr Thr Asp Arg Ser Gln Arg Leu
    50                  55                  60

Thr Leu Arg Phe Ile Pro Val Asp Arg Glu Asp Thr Ala Tyr Ser Tyr
65                  70                  75                  80

Lys Ala Arg Phe Thr Leu Ala Val Gly Asp Asn Arg Val Leu Asp Met
                85                  90                  95

Ala Ser Thr Tyr Phe Asp Ile Arg Gly Val Leu Asp Arg Gly Pro Thr
            100                 105                 110

Phe Lys Pro Tyr Ser Gly Thr Ala Tyr Asn Ser Leu Ala Pro Lys Gly
        115                 120                 125

Ala Pro Asn Ser Cys Glu Trp Glu Gln Asp Glu Pro Ala Gln Ala Ala
    130                 135                 140

Ile Ala Glu Asp Glu Glu Glu Leu Glu Glu Glu Gln Ala Gln Asp Glu
145                 150                 155                 160

Gln Ala Pro Thr Lys Lys Thr His Val Tyr Ala Gln Ala Pro Leu Ser
                165                 170                 175

Gly Glu Lys Ile Thr Lys Asp Gly Leu Gln Ile Gly Val Asp Ala Thr
            180                 185                 190

Gln Ala Gly Asp Asn Pro Ile Tyr Ala Asp Lys Thr Phe Gln Pro Glu
        195                 200                 205

Pro Gln Ile Gly Glu Ser Gln Trp Asn Glu Ala Asp Ala Thr Val Ala
    210                 215                 220

Gly Gly Arg Val Leu Lys Lys Thr Thr Pro Met Arg Pro Cys Tyr Gly
225                 230                 235                 240

Ser Tyr Ala Lys Pro Thr Asn Ala Asn Gly Gly Gln Gly Ile Met Val
```

-continued

```
                245                 250                 255

Ala Asn Asp Gln Gly Ala Leu Glu Ser Lys Val Glu Met Gln Phe Phe
            260                 265                 270

Ser Thr Thr Thr Ser Leu Asn Val Arg Glu Gly Glu Asn Asn Leu Gln
        275                 280                 285

Pro Lys Val Val Leu Tyr Ser Glu Asp Val Asn Leu Glu Ser Pro Asp
    290                 295                 300

Thr His Leu Ser Tyr Lys Pro Lys Lys Asp Asp Thr Asn Ser Lys Ile
305                 310                 315                 320

Met Leu Gly Gln Gln Ala Met Pro Asn Arg Pro Asn Leu Ile Ala Phe
                325                 330                 335

Arg Asp Asn Phe Ile Gly Leu Met Tyr Tyr Asn Ser Thr Gly Asn Met
            340                 345                 350

Gly Val Leu Ala Gly Gln Ala Ser Gln Leu Asn Ala Val Val Asp Leu
        355                 360                 365

Gln Asp Arg Asn Thr Glu Leu Ser Tyr Gln Leu Met Leu Asp Ser Ile
    370                 375                 380

Gly Asp Arg Ser Arg Tyr Phe Ser Met Trp Asn Gln Ala Val Asp Ser
385                 390                 395                 400

Tyr Asp Pro Asp Val Arg Ile Ile Glu Asn His Gly Val Glu Asp Glu
                405                 410                 415

Leu Pro Asn Tyr Cys Phe Pro Leu Gly Gly Ile Gly Ile Thr Asp Thr
            420                 425                 430

Tyr Gln Cys Ile Lys Pro Thr Ala Ala Ala Asn Asn Thr Thr Trp Ser
        435                 440                 445

Lys Asp Glu Glu Phe Ser Asp Arg Asn Glu Ile Gly Val Gly Asn Asn
    450                 455                 460

Phe Ala Met Glu Ile Asn Ile Gln Ala Asn Leu Trp Arg Asn Phe Leu
465                 470                 475                 480

Tyr Ala Asn Val Gly Leu Tyr Leu Pro Asp Lys Leu Lys Tyr Asn Pro
                485                 490                 495

Thr Asn Val Asp Ile Ser Asp Asn Pro Asn Thr Tyr Asp Tyr Met Asn
            500                 505                 510

Lys Arg Val Val Ala Pro Gly Leu Val Asp Cys Phe Val Asn Val Gly
        515                 520                 525

Ala Arg Trp Ser Leu Asp Tyr Met Asp Asn Val Asn Pro Phe Asn His
    530                 535                 540

His Arg Asn Ala Gly Leu Arg Tyr Arg Ser Met Ile Leu Gly Asn Gly
545                 550                 555                 560

Arg Tyr Val Pro Phe His Ile Gln Val Pro Gln Lys Phe Phe Ala Ile
                565                 570                 575

Lys Asn Leu Leu Leu Leu Pro Gly Ser Tyr Thr Tyr Glu Trp Asn Phe
            580                 585                 590

Arg Lys Asp Val Asn Met Val Leu Gln Ser Ser Leu Gly Asn Asp Leu
        595                 600                 605

Arg Val Asp Gly Ala Ser Ile Lys Phe Asp Ser Val Thr Leu Tyr Ala
    610                 615                 620

Thr Phe Phe Pro Met Ala His Asn Thr Ala Ser Thr Leu Glu Ala Met
625                 630                 635                 640

Leu Arg Asn Asp Thr Asn Asp Gln Ser Phe Asn Asp Tyr Leu Ser Gly
                645                 650                 655

Ala Asn Met Leu Tyr Pro Ile Pro Ala Lys Ala Thr Asn Val Pro Ile
            660                 665                 670
```

Ser Ile Pro Ser Arg Asn Trp Ala Ala Phe Arg Gly Trp Ala Phe Thr
675 680 685

Arg Leu Lys Thr Lys Glu Thr Pro Ser Leu Gly Ser Gly Phe Asp Pro
690 695 700

Tyr Phe Val Tyr Ser Gly Ser Ile Pro Tyr Leu Asp Gly Thr Phe Tyr
705 710 715 720

Leu Asn His Thr Phe Lys Lys Ile Ser Ile Met Tyr Asp Ser Ser Val
725 730 735

Ser Trp Pro Gly Asn Asp Arg Leu Leu Thr Pro Asn Glu Phe Glu Val
740 745 750

Lys Arg Ala Val Asp Gly Glu Gly Tyr Asn Val Ala Gln Cys Asn Met
755 760 765

Thr Lys Asp Trp Phe Leu Val Gln Met Leu Ala Asn Tyr Asn Ile Gly
770 775 780

Tyr Gln Gly Phe Tyr Ile Pro Glu Ser Tyr Lys Asp Arg Met Tyr Ser
785 790 795 800

Phe Phe Arg Asn Phe Gln Pro Met Ser Arg Gln Val Val Asp Glu Thr
805 810 815

Lys Tyr Lys Asp Tyr Gln Ala Ile Gly Ile Thr His Gln His Asn Asn
820 825 830

Ser Gly Phe Val Gly Tyr Leu Ala Pro Thr Met Arg Glu Gly Gln Ala
835 840 845

Tyr Pro Ala Asn Phe Pro Tyr Pro Leu Ile Gly Lys Thr Ala Val Asp
850 855 860

Ser Val Thr Gln Lys Lys Phe Leu Cys Asp Arg Thr Leu Trp Arg Ile
865 870 875 880

Pro Phe Ser Ser Asn Phe Met Ser Met Gly Ala Leu Thr Asp Leu Gly
885 890 895

Gln Asn Leu Leu Tyr Ala Asn Ser Ala His Ala Leu Asp Met Thr Phe
900 905 910

Glu Val Asp Pro Met Asp Glu Pro Thr Leu Leu Tyr Ile Val Phe Glu
915 920 925

Val Phe Asp Val Val Arg Val His Gln Pro His Arg Gly Val Ile Glu
930 935 940

Thr Val Tyr Leu Arg Thr Pro Phe Ser Ala Gly Asn Ala Thr Thr
945 950 955

<210> SEQ ID NO 20
<211> LENGTH: 583
<212> TYPE: PRT
<213> ORGANISM: Gorilla beringei beringei

<400> SEQUENCE: 20

Met Lys Arg Ala Arg Ser Ser Asp Glu Thr Phe Asn Pro Val Tyr Pro
1 5 10 15

Tyr Asp Thr Glu Ile Ala Pro Thr Ser Val Pro Phe Leu Thr Pro Pro
20 25 30

Phe Val Ser Ser Ala Gly Met Gln Glu Asn Pro Ala Gly Val Leu Ser
35 40 45

Leu His Leu Ser Glu Pro Leu Thr Thr His Asn Gly Ala Leu Thr Leu
50 55 60

Lys Met Gly Gly Gly Leu Thr Leu Asp Lys Glu Gly Asn Leu Thr Ser
65 70 75 80

Gln Asn Ile Thr Ser Val Asp Pro Pro Leu Lys Lys Ser Lys Asn Asn

-continued

```
                85                  90                  95

Ile Ser Leu Gln Thr Ala Ala Pro Leu Ala Val Ser Ser Gly Ala Leu
            100                 105                 110

Thr Leu Phe Ala Thr Pro Pro Leu Ala Val Ser Gly Asp Asn Leu Thr
        115                 120                 125

Val Gln Ser Gln Ala Pro Leu Thr Leu Glu Asp Ser Lys Leu Thr Leu
    130                 135                 140

Ala Thr Lys Gly Pro Leu Thr Val Ser Glu Gly Lys Leu Val Leu Glu
145                 150                 155                 160

Thr Glu Ala Pro Leu His Ala Ser Asp Ser Ser Ser Leu Gly Leu Ser
                165                 170                 175

Val Thr Ala Pro Leu Ser Ile Asn Asn Asp Ser Leu Gly Leu Asp Leu
            180                 185                 190

Gln Ala Pro Ile Val Ser Gln Asn Gly Lys Leu Ala Leu Asn Val Ala
        195                 200                 205

Gly Pro Leu Ala Val Ala Asn Gly Ile Asn Ala Leu Thr Val Gly Thr
    210                 215                 220

Gly Lys Gly Ile Gly Leu Asn Glu Thr Ser Thr His Leu Gln Ala Lys
225                 230                 235                 240

Leu Val Ala Pro Leu Gly Phe Asp Thr Asn Gly Asn Ile Lys Leu Ser
                245                 250                 255

Val Ala Gly Gly Met Arg Leu Asn Asn Asp Thr Leu Ile Leu Asp Val
            260                 265                 270

Asn Tyr Pro Phe Glu Ala Gln Gly Gln Leu Ser Leu Arg Val Gly Gln
        275                 280                 285

Gly Pro Leu Tyr Val Asp Ser Ser Ser His Asn Leu Thr Ile Arg Cys
    290                 295                 300

Leu Arg Gly Leu Tyr Ile Thr Ser Ser Asn Asn Gln Thr Gly Leu Glu
305                 310                 315                 320

Ala Asn Ile Lys Leu Thr Lys Gly Leu Val Tyr Asp Gly Asn Ala Ile
                325                 330                 335

Ala Val Asn Val Gly Gln Gly Leu Gln Tyr Ser Thr Thr Ala Thr Ser
            340                 345                 350

Glu Gly Val Tyr Pro Ile Gln Ser Lys Ile Gly Leu Gly Met Glu Tyr
        355                 360                 365

Asp Thr Asn Gly Ala Met Met Thr Lys Leu Gly Ser Gly Leu Ser Phe
    370                 375                 380

Asp Asn Ser Gly Ala Ile Val Val Gly Asn Lys Asn Asp Asp Arg Leu
385                 390                 395                 400

Thr Leu Trp Thr Thr Pro Asp Pro Ser Pro Asn Cys Arg Ile Tyr Ser
                405                 410                 415

Glu Lys Asp Thr Lys Leu Thr Leu Val Leu Thr Lys Cys Gly Ser Gln
            420                 425                 430

Ile Leu Gly Thr Val Ser Ala Leu Ala Val Arg Gly Ser Leu Ala Pro
        435                 440                 445

Ile Thr Asn Ala Ser Ser Ile Val Gln Ile Phe Leu Arg Phe Asp Glu
    450                 455                 460

Asn Gly Leu Leu Met Ser Asn Ser Ser Leu Asp Gly Asp Tyr Trp Asn
465                 470                 475                 480

Tyr Arg Asn Gly Asp Ser Thr Asn Ser Thr Pro Tyr Thr Asn Ala Val
                485                 490                 495

Gly Phe Met Pro Asn Leu Ala Ala Tyr Pro Lys Gly Gln Ala Thr Ala
            500                 505                 510
```

-continued

Ala Lys Ser Ser Ile Val Ser Gln Val Tyr Met Asp Gly Asp Thr Thr
515 520 525

Lys Pro Ile Thr Leu Lys Ile Asn Phe Asn Gly Ile Asp Glu Thr Thr
530 535 540

Glu Asn Thr Pro Val Ser Lys Tyr Ser Met Thr Phe Ser Trp Ser Trp
545 550 555 560

Pro Thr Ala Ser Tyr Ile Gly His Thr Phe Ala Thr Asn Ser Phe Thr
565 570 575

Phe Ser Tyr Ile Ala Gln Glu
580

<210> SEQ ID NO 21
<211> LENGTH: 37229
<212> TYPE: DNA
<213> ORGANISM: Gorilla beringei beringei

<400> SEQUENCE: 21
catcatcaat aatatacctt attttggatt gtggccaata tgataatgag gtgggcgggg 60
agaggcgggg cgggtgacgt aggacgcgcg agtagggttg ggaggtgtgg cggaagtgtg 120
gcatttgcaa gtgggaggag ctcacatgca agcttccgtc gcggaaaatg tgacgttttt 180
gatgagcgcc gcctacctcc ggaagtgcca attttcgcgc gcttttcacc ggatatcgta 240
gtaattttgg gcgggaccat gtaagatttg gccattttcg cgcgaaaagt gaaacgggga 300
agtgaaaact gaataatagg gcgttagtca tagcgcgtaa tatttaccga gggccgaggg 360
actttgaccg attacgtgga ggactcgccc aggtgttttt tacgtgaatt tccgcgttcc 420
gggtcaaagt ctccgttttt attgtcaccg tcatttgacg cggagggtat ttaaacccgc 480
tgcgctcctc aagaggccac tcttgagtgc cagcgagaag agttttctcc tctgctccgc 540
ttcggtgatc gaaaaatgag acacatagcc tgcactccgg gtcttttgtc cggtcgggcg 600
gcggccgagc ttttggacgc tttgatcaat gatgtcctaa gcgatgattt tccgtctact 660
acccacttta gcccacctac tcttcacgaa ctgtacgatc tggatgtact ggtggatgtg 720
aacgatccca acgaggaggc ggtttctgcg tttttcccg agtctgcgct gttggccgct 780
caggagggat ttgacctaca cactccgccg cctattttag agtctccgct gccggagccc 840
agtggtatac cttatatgcc tgaactgctt cccgaagtgg tagacctgac ctgccacgag 900
cctggctttc cgcccagcga cgatgagggt gagccttttg ttttagactt tgctgagata 960
cctgggcacg gttgcaggtc ttgtgcatat catcagaggg ttaccggaga ccccgaggtt 1020
aagtgttcgc tgtgctatat gaggatgacc tcttccttta tctacagtaa gtttttgtct 1080
aggtgggctt ttgggtaggt gggttttgtg tcagaacagg tgtaaacgtt gcttgtgttt 1140
tttgtacctg taggtccggt gtccgagcca gacccggagc ccgaccgcga tcccgagccg 1200
gatcccgagc ctcctcgcag gacaaggaaa ctaccttcca ttctgtgcaa gtctcagaca 1260
cctgtaagga ccagcgaggc agacagcacc gactctggca cttctacctc tccccctgaa 1320
attcacccag tggttcctct gggtatacat aaacctgttg ctgttaaagt ttgcgggcga 1380
cgccctgcag tacagtgcat tgaggacttg cttcacgatc ccgaggaacc tttggacttg 1440
agccttaaac gccctaggca ataaacccca cctaagtaat aaaccccacc taagtaataa 1500
accctgccgc ccttggttat tgagatgacg cccaatgttt gcttttgaat gacttcatgt 1560
gtgtaataaa agtgagtgtg atcataggtc tcttgtttgt ctgggcgggg cttaagggta 1620
tataagtctc ttggggctaa acttggttac acttgacccc aatggaggcg tgggggtgct 1680
tggaggagtt tgcggacgtg cgccgtttgc tggacgagag ctctagcaat acctatacta 1740
tttggaggta tctgtggggc tctactcagg ccaagttggt ttccagaatt aagcaggatt 1800
acaagtgcga ttttgaagag ctttttagtt cctgcggtga gcttttgcaa tccttgaatc 1860
tgggccatca ggctattttc caggaaaagg ttctctcgac tttggatttt tccactcccg 1920
ggcgcaccgc cgcttgtgtg gcttttgtgt cttttgtgca agataaatgg agcgaggaga 1980
cccacctgag tcacggctac gtactggatt tcatggcgat ggctctttgg agggctcaca 2040
acaaatggaa gattcagaag gaactgtacg gttccgccct acgtcgtcca cttctgtcgc 2100
gacaggggct gaggtttccc gaccatcggc agcatcagaa tctggaagac gagtcggagg 2160
agcgagcgga ggagaagatc agcttgagag ccggcctgga ccctcctcag gaggaatgaa 2220
tctcccgcag gtggttgacc tgtttccaga actgagacgg gtcctgacta tcagggagga 2280
tggtcagttt gtgaagaagt ttaagaggga tcggggtgag ggagatgatg aggcggctag 2340
caatttagct tttagtctga tgactcgcca ccgaccggaa tgtattacct atcagcagat 2400
taaggagagt tgtgccaacg agctggatct tttgggtcag aagtatagca tagaacagct 2460
taccacttac tggcttcagc ctggggatga ttgggaagag gcgatcaggg tgtatgcaaa 2520
ggtggccctg cggcccgatt gcaagtataa gattactaag ttggttaata ttagaaactg 2580
ctgctatatt tctgggaacg gggccgaagt ggagatagat actcaggaca gggtggcttt 2640
taggtgttgc atgataaaca tgtggcccgg gatactgggg atggatgggg tggtattcat 2700
gaatgtgagg tttacgggcc ccaactttaa tggcacggtg ttcatgggca acaccaactt 2760
gctcctgcat ggtgcgagtt tctatgggtt taataacacc tgtatagagg cctggaccga 2820
tgtaaaggtt cgaggttgtt ccttttatag ctgttggaag gcggtggtgt gtcgccctaa 2880
aagcaggggt tctgtgaaaa aatgcttgtt tgaaaggtgc accttaggca tcctctctga 2940
gggcaactcc agggtgcgcc ataatgtggc ttcgaactgc ggttgcttca tgcaagtgaa 3000
gggggtgagc gttatcaagc ataactcggt gtgtggaaac tgcgaggatc gcgcctccca 3060
gatgctgacc tgctttgatg gcaactgtca cctgttgaag accattcata taagcagcca 3120
ccccagaaag gcctggcccg tgtttgagca taacatcttg acccgctgct ccttgcatct 3180
gggggtcagg aggggtatgt tcctgcctta ccagtgtaac tttagccaca ctaaaatcct 3240
gctggaaccc gagtgcatga ccaaggtcag cctgaatggt gtgtttgatg tgactctgaa 3300
aatctggaag gtgctgaggt atgatgagac caggaccagg tgccgaccct gcgagtgcgg 3360
cggcaagcac atgagaaatc agcctgtgat gttggatgtg accgaggagc ttaggcctga 3420
ccatctggtg ctggcctgca ccagggccga gtttgggtct agcgatgagg ataccgattg 3480
aggtgggtaa ggtgggcgtg gctagaaggg tggggcgtgt ataaattggg ggtctaaggg 3540
tctctctgtt ttgtcttgca acagccgccg ccatgagcga caccggcaac agctttgatg 3600
gaagcatctt tagcccctat ctgacagtgc gcatgcctca ctgggctgga gtgcgtcaga 3660
atgtgatggg ttccaacgtg gatggacgcc ccgttctgcc ttcaaattcg tctacaatgg 3720
cctacgcgac cgtgggagga actccgctgg acgccgcgac ctccgccgcc gcctccgccg 3780
ccgccgcgac cgcgcgcagc atggctacgg acctttacag ctctttggtg gcgagcggcg 3840
cggcctctcg cgcgtctgct cgggatgaga aactgaccgc tctgctgctt aaactggaag 3900
acttgacccg ggagctgggt caactgaccc agcaggtctc cagcttgcgt gagagcagcc 3960
ttgcctcccc ctaatggccc ataatataaa taaaagccag tctgtttgga ttaagcaagt 4020

-continued

```
gtatgttctt tatttaactc tccgcgcgcg gtaagcccgg gaccagcggt ctcggtcgtt   4080
tagggtgcgg tggattcttt ccaacacgtg gtacaggtgg ctctggatgt ttagatacat   4140
gggcatgagt ccatccctgg ggtggaggta gcaccactgc agagcttcgt gctcgggggt   4200
ggtgttgtat atgatccagt cgtagcagga gcgctgggcg tggtgctgaa aaatgtcctt   4260
aagcaagagg cttatagcta gggggaggcc cttggtgtaa gtgtttacaa atctgctcag   4320
ttgggagggg tgcatccggg ggatataat gtgcatcttg gactggattt ttaggttggc   4380
tatgttccca cccagatccc ttctgggatt catgttgtgc aggaccacca gcacggtata   4440
tccagtgcac ttgggaaatt tatcgtggag cttagacggg aatgcatgga agaacttgga   4500
gacgcccttg tggcctccca gattttccat acattcgtcc atgatgatgg caatgggccc   4560
gtgggaagct gcctgagcaa aaatgtttct gggatcgctc acatcgtagt tatgttccag   4620
ggtgaggtca tcataggaca tctttacgaa tcgggggcgg agggtcccgg actgggggat   4680
gatggtaccc tcgggccccg gggcgtagtt cccctcacag atctgcatct cccaggcttt   4740
catttcagag ggagggatca tatccacctg cggagcgatg aaaaacacag tttctggcgc   4800
aggggagatt aactgggatg agagcaggtt tctgagcagc tgtgactttc cacagccggt   4860
gggcccatat atcacgccta tcaccggctg cagctggtag ttaagagagc tgcagctgcc   4920
gtcctcccgg agcagggggg ccacctcgtt cagcatatcc ctgacgtgga tgttctccct   4980
gaccaattcc gccagaaggc gctcgccgcc cagcgaaagc agctcttgca aggaagcaaa   5040
atttttcagc ggttttaggc cgtcggccgt gggcatgttt ttcagcgtct gggtcagcag   5100
ttccagcctg tcccacagct cggtgatgtg ctctacggca tctcgatcca gcagatctcc   5160
tcgtttcgcg ggttggggcg gctttcgctg tagggcacca gccgatgggc gtccagcggg   5220
gccagagtca tgtccttcca tgggcgcagg gtcctcgtca gggtggtctg ggtcacggtg   5280
aaggggtgcg ctccgggttg ggcgctggcc agggtgcgct tgaggctggt tctgctggtg   5340
ctgaatcgct gccgctcttc gccctgcgcg tcggccaggt agcatttgac catggtctcg   5400
tagtcgagac cctcggcggc gtgccccttg gcgcggagct ttcccttgga ggtggcgccg   5460
cacgaggggc actgcaggct cttcagggcg tagagcttgg gagcgagaaa cacggactct   5520
ggggagtagg cgtccgcgcc gcaggaagcg cagaccgtct cgcattccac cagccaagtg   5580
agctccgggc ggtcagggtc aaaaaccagg ttgcccccat gctttttgat gcgtttctta   5640
cctcggctct ccatgaggcg gtgtcccttc tcggtgacga agaggctgtc cgtgtccccg   5700
tagaccgact tcaggggcct gtcttccagc ggagtgcctc tgtcctcctc gtagagaaac   5760
tctgaccact ctgagacgaa ggcccgcgtc caggccagga cgaaggaggc cacgtgggag   5820
gggtagcggt cgttgtccac tagcgggtcc accttctcca gggtgtgcag gcacatgtcc   5880
ccctcctccg cgtccagaaa agtgattggc ttgtaggtgt aggacacgtg accgggggtt   5940
cccgacgggg gggtataaaa gggggtgggc gccctttcat cttcactctc ttccgcatcg   6000
ctgtctgcga gggccagctg ctggggtaag tattccctct cgaaggcggg catgacctca   6060
gcgctcaggt tgtcagtttc taaaaatgag gaggatttga tgttcacctg tccggaggtg   6120
ataccttttga gggtacctgg gtccatctgg tcagaaaaca ctatttttt gttgtcaagc   6180
ttggtggcga acgacccgta gagggcgttg gagagcagct tggcgatgga gcgcagggtc   6240
tggtttttgt cgcggtcggc tcgctccttg gccgcgatgt tgagttgcac gtactcgcgg   6300
gccacgcact tccactcggg gaagacggtg gtgcgctcgt ctgggattag gcgcaccctc   6360
cagcctcggt tgtgcagggt gaccatgtcg acgctggtgg cgacctcgcc gcgcaggcgc   6420
```

tcgttggtcc agcagaggcg gccgcccttg cgcgagcaga agggggggtag ggggtccagc 6480
tggtcctcgt ttggggggtc cgcgtcgatg gtgaagaccc cggggagcaa gcgcgggtca 6540
aagtagtcga tcttgcaagc ttgcatgtcc agagcccgct gccattcgcg ggcggcgagc 6600
gcgcgctcgt aggggttgag ggcgggcccc cagggcatgg ggtgggtgag cgcggaggcg 6660
tacatgccgc agatgtcata cacgtacagg ggttccctga ggatgccgag gtaggtgggg 6720
tagcagcgcc ccccgcggat gctggcgcgc acgtagtcat agagctcgtg ggagggggcc 6780
agcatgttgg gcccgaggtt ggtgcgctgg gggcgctcgg cgcggaaggc gatctgcctg 6840
aagatggcat gggagttgga ggagatggtg ggccgctgga agacgttgaa gcttgcttct 6900
tgcaagccca ccgagtccct gacgaaggag gcgtaggact cgcgcagctt gtgcaccagc 6960
tcggcggtga cctggacgtc gagcgcgcag tagtcgaggg tctcgcggat gatgtcatac 7020
ttatcctccc ccttcttttt ccacagctcg cggttgagga cgaactcttc gcggtctttc 7080
cagtactctt ggaggggaaa cccgtccgtg tccgaacggt aagagcctag catgtagaac 7140
tggttgacgg cctggtaggg gcaacagccc ttctccacgg gcagcgcgta ggcctgcgcc 7200
gccttgcgga gggaggtgtg ggtgagggcg aaagtgtccc tgaccatgac tttgaggtat 7260
tgatgtttga agtctgtgtc atcgcagccg ccctgttccc acagggtgta gtccgtgcgc 7320
tttttggagc gcgggttggg cagggagaag gtgaggtcat tgaagaggat cttccccgct 7380
cgaggcatga agtttctggt gatgcgaaag ggccctggga ccgaggagcg gttgttgatg 7440
acctgggcgg ccaggacgat ctcgtcaaag ccgtttatgt tgtggcccac gatgtagagc 7500
tccaaaaagc ggggctggcc cttgatggag gggagctttt tgagttcctc gtaggtgagc 7560
tcctcgggcg attccaggcc gtgctcctcc agggcccagt cttgcaagtg agggttggcc 7620
gccaggaagg atcgccagag gtcgcgggcc atgagggtct gcaggcggtc gcggaaggtt 7680
ctgaactgtc gccccacggc catcttttcg gggtgatgc agtagaaggt gagggggtct 7740
ttctcccagg ggtcccatct gagctctcgg gcgaggtcgc gcgcggcggc gaccagagcc 7800
tcgtcgcccc ccagtttcat gaccagcatg aagggcacga gctgcttgcc aaaggctccc 7860
atccaagtgt aggtctctac atcgtaggtg acaaagaggc gctccgtgcg aggatgagag 7920
ccgatcggga agaactggat ctcccgccac cagttggagg attggctgtt gatgtggtga 7980
aagtagaagt cccgtctgcg ggccgagcac tcgtgctggc ttttgtaaaa gcgaccgcag 8040
tactggcagc gctgcacggg ttgtatatct tgcacgaggt gaacctggcg acctctgacg 8100
aggaagcgca gcgggaatct aagtcccccg cctggggtcc cgtgtggctg gtggtcttct 8160
actttggttg tctggccgcc agcatctgtc tcctggaggg cgatggtgga gcagaccacc 8220
acgccgcgag agccgcaggt ccagatctcg gcgctcggcg ggcggagttt gatgacgaca 8280
tcgcgcacat tggagctgtc catggtctcc agctcccgcg gcggcaggtc agctgggagt 8340
tcctggaggt tcacctcgca gagacgggtc aaggcgcggg cagtgttgag atggtatctg 8400
atttcaaggg gcgtgttggc ggcggagtcg atggcttgca ggaggccgca gccccggggg 8460
gccacgatgg ttccccgcgg ggcgcgaggg gaggcggaag ctgggggtgt gttcagaagc 8520
ggtgacgcgg gcgggccccc ggaggtaggg ggggttccgg ccccacaggc atgggcggca 8580
ggggcacgtc ttcgccgcgc gcgggcaggg gctggtgctg gctccgaaga gcgcttgcgt 8640
gcgcgacgac gcgacggttg gtgtcctgta tctgacgcct ctgagtgaag accacgggtc 8700
ccgtgacctt gaacctgaaa gagagttcga cagaatcaat ctcggcatcg ttgacagcgg 8760

-continued

```
cctggcgcag gatctcctgc acgtcgcccg agttgtcctg gtaggcgatc tctgccatga   8820
actgctcgat ctcttcttcc tggagatctc ctcgtccggc gcgctccacg gtggccgcca   8880
ggtcgttgga gatgcgaccc atgagctgtg agaaggcgtt gagcccgccc tcgttccaga   8940
cccggctgta gaccacgccc ccctcggcgt cgcgagcgcg catgaccacc tgggccaggt   9000
tgagctccac gtgtcgcgtg aagacggcgt agttgcgcag gcgctggaaa aggtagttca   9060
gggtggtggc ggtgtgctcg gcgacgaaga agtacatgac ccagcgccgc aacgtggatt   9120
cattgatgtc ccccaaggcc tccaggcgct ccatggcctc gtagaagtcc acggcgaagt   9180
tgaaaaactg ggagttgcga gcggacacgg tcaactcctc ctccagaaga cggatgagct   9240
cggcgacagt gttgcgcacc tcgcgctcga aggccacggg gggcgcttct tcctcttcca   9300
cctcttcttc catgatcgct tcttcttctt cctcagccgg gacgggaggg ggcggcggcg   9360
gcgggggagg ggcgcggcgg cggcggcggc gcaccgggag gcggtcgatg aagcgctcga   9420
tcatctcccc ccgcatgcgg cgcatggtct cggtgacggc gcggccgttc tcccgggggc   9480
gcagctcgaa gacgccgcct ctcatctcgc cgcggggcga gcggccgtga ggtagcgaga   9540
cggcgctgac tatgcatctt aacaattgct gtgtaggtac accgccgagg gacctgattg   9600
agtccagatc caccggatcc gaaaaccttt ggaggaaagc gtctatccag tcgcagtcgc   9660
aaggtaggct gagcaccgtg gcgggcgggg gcgggtctgg agagttcctg gcggagatgc   9720
tgctgatgat gtaattaaag taggcggtct tgagaaggcg gatggtggac aggagcacca   9780
tgtctttggg tccggcctgt tggatgcgga ggcggtcggc catgccccag gcctcgttct   9840
gacaccggcg caggtctttg tagtagtctt gcatgagtct ttccaccggc acctcttctc   9900
cttcctcttc tccatctcgc cggtggtttc tcgcgccgcc catgcgcgtg accccaaagc   9960
ccctgagcgg ctgcagcagg gccaggtcgg cgaccacgcg ctcggccaag atggcctgct  10020
gcacctgagt gagggtcctc tcgaagtcat ccatgtccac gaagcggtgg taggcgcccg  10080
tgttgatggt gtaggtgcag ttggccatga cggaccagtt gacggtctgg tgtcccggct  10140
gcgagagctc cgtgtaccgc aggcgcgaga aggcgcggga atcgaacacg tagtcgttgc  10200
aagtccgcac cagatactgg tagcccacca ggaagtgcgg cggaggttgg cgatagaggg  10260
gccagcgctg ggtggcgggg gcgccgggcg ccaggtcttc cagcatgagg cggtggtatc  10320
cgtagatgta cctggacatc caggtgatgc cggcggcggt ggtggtggcg cgcgcgtagt  10380
cgcggacccg gttccagatg tttcgcaggg gcgagaagtg ttccatggtc ggcacgctct  10440
ggccggtgag gcgcgcgcag tcgttgacgc tctatacaca cacaaaaacg aaagcgttta  10500
cagggctttc gttctgtagc ctggaggaaa gtaaatgggt tgggttgcgg tgtgccccgg  10560
ttcgagacca agctgagctc ggccggctga agccgcagct aacgtggtat tggcagtccc  10620
gtctcgaccc aggccctgta tcctccagga tacggtcgag agcccttttg ctttcttggc  10680
caagcgcccg tggcgcgatc tgggatagat ggtcgcgatg agaggacaaa agcggctcgc  10740
ttccgtagtc tggagaaaca atcgccaggg ttgcgttgcg gcgtaccccg gttcgagccc  10800
ctatggcggc ttgaatcggc cggaaccgcg gctaacgagg gccgtggcag ccccgtcctc  10860
aggaccccgc cagccgactt ctccagttac gggagcgagc cccttttgtt ttttattttt  10920
tagatgcatc ccgtgctgcg gcagatgcgc ccctcgcccc ggcccgatca gcagcagcaa  10980
cagcaggcat gcagaccccc ctctcccctt tccgccccgg tcaccacggc cgcggcggcc  11040
gtgtcgggcg cggggggcgc gctggagtca gatgagccac cgcggcggcg acctaggcag  11100
tatctggact tggaagaggg cgagggactg gcgcggctgg gggcgaactc tccagagcgc  11160
```

cacccgcggg tgcagttgaa aagggacgcg cgcgaggcgt acctgccgcg gcagaacctg 11220
tttcgcgacc gcgggggcga ggagcccgag gagatgcgag actgcaggtt ccaagcgggg 11280
cgcgagctgc ggcgcgggct ggacagacag cgcctgctgc gcgaggagga ctttgagccc 11340
gacacgcaga cgggcatcag ccccgcgcgc gcgcacgtag ccgcggccga cctggtgacc 11400
gcctacgagc agacggtaaa ccaggagcgc aacttccaaa agagcttcaa caaccacgtg 11460
cgcacgctgg tggcgcgcga ggaggtgacc ctgggtctca tgcatctgtg ggacctggtg 11520
gaggcgatcg tgcagaaccc cagcagcaag cccctgaccg cgcagctgtt cctggtggtg 11580
cagcacagca gggacaacga ggccttcagg gaggcgctgc tgaacatcac cgagccggag 11640
gggcgctggc tcctggacct gataaacatc ctgcagagca tagtggtgca ggagcgcagc 11700
ctgagcctgg ccgagaaggt ggcggccatc aactactcta tgctgagcct gggcaagttc 11760
tacgcccgca agatctacaa gaccccctac gtgcccatag acaaggaggt gaagatagac 11820
agcttctaca tgcgcatggc gctgaaggtg ctgaccctga gcgacgacct gggagtgtac 11880
cgcaacgagc gcatccacaa ggccgtgagc gccagccggc ggcgcgagct gagcgaccgc 11940
gagctgatgc acagtctgca gcgcgcgctg accggcgcgg gcgagggcga cagggaggtc 12000
gagtcctact tcgacatggg ggccgacctg cactggcagc cgagccgccg cgccctggag 12060
gcggcggggg cgtacggcgg ccccctggcg gccgatgacc aggaagagga ggactatgag 12120
ctagaggagg gcgagtacct ggaggactga cctggctggt ggtgttttgg tatagatgca 12180
agatccgaac gtggcggacc cggcggtccg ggcggcgctg caaagccagc cgtccggcat 12240
taactcctct gacgactggg ccgcggccat gggtcgcatc atggccctga ccgcgcgcaa 12300
ccccgaggct ttcaggcagc agcctcaggc caaccggctg gcggccatct tggaagcggt 12360
agtgcccgcg cgctccaacc ccacccacga gaaggtgctg gccatagtca acgcgctggc 12420
ggagagcagg gccatccgcg cggacgaggc cggactggtg tacgatgcgc tgctgcagcg 12480
ggtggcgcgg tacaacagcg gcaacgtgca gaccaacctg gaccgcctgg tgacggacgt 12540
gcgcgaggcc gtggcgcagc gcgagcgctt gcatcaggac ggtaacctgg gctcgctggt 12600
ggcgctaaac gccttcctca gcacccagcc ggccaacgta ccgcgggggc aggaggacta 12660
caccaacttt ttgagcgcgc tgcggctgat ggtgaccgag gtccctcaga gcgaggtgta 12720
ccagtcgggg cccgactact tcttccagac cagcagacag ggcttgcaaa ccgtgaacct 12780
gagccaggct ttcaagaacc tgcgggggct gtggggagtg aaggcgccca ccggcgaccg 12840
ggctacggtg tccagcctgc taacccccaa ctcgcgcctg ctgctgctgc tgatcgcgcc 12900
cttcacggac agcgggagcg tctcgcggga gacctatctg ggccacctgc tgacgctgta 12960
ccgcgaggcc atcgggcagg cgcaggtgga cgagcacacc ttccaagaga tcaccagcgt 13020
gagccacgcg ctggggcagg aggacacggg cagcctgcag gcgaccctga actacctgct 13080
gaccaacagg cggcagaaga ttcccacgct gcacagcctg acccaggagg aggagcgcat 13140
cttgcgctac gtgcagcaga gcgtgagcct gaacctgatg cgcgacggcg tgacgcccag 13200
cgtggcgctg gacatgaccg cgcgcaacat ggaaccgggc atgtacgcct cccaccggcc 13260
gtttatcaac cgcctgatgg actacttgca tcgggcggcg gccgtgaacc ccgagtactt 13320
cactaatgcc attctgaatc cccactggat gccccctccg ggtttctaca acggggactt 13380
tgaggtgccc gaggtcaacg acgggttcct ctgggatgac atggatgaca gtgtgttctc 13440
acccaacccg ctgcgcgccg cgtctctgcg attgaaggag ggctctgaca gggaaggacc 13500

-continued

```
gaggagtctg gcctcctccc tggctctggg agcggtgggc gccacgggcg cggcggcgcg  13560
gggcagtagc cccttcccca gcctggcaga ctctctgaac agcgggcggg tgagcaggcc  13620
ccgcttgcta ggcgaggagg agtatctgaa caactccctg ctgcagcccg cgagggacaa  13680
gaacgctcag cggcagcagt ttcccaacaa tgggatagag agcctggtgg acaagatgtc  13740
cagatggaag acgtatgcgc aggagtacaa ggagtgggag gaccgccagc cgcggcccctt 13800
gccgcccccct aggcagcgct ggcagcggcg cgcgtccaac cgccgctgga ggcaggggcc 13860
cgaggacgat gatgactctg cagatgacag cagcgtgttg gacctgggcg ggagcgggaa  13920
cccctttcg cacctgcgcc cacgcctggg caagatgttt taaaagaaaa aaaaaataaa  13980
actcaccaag gccatggcga cgagcgttgg tttttgttc ccttccttag tatgcggcgc  14040
gcggcgatgt tcgaggaggg gcctcccccc tcttacgaga gcgcgatggg gatttctcct  14100
gcggcgcccc tgcagcctcc ctacgtgcct cctcggtacc tgcaacctac aggggggaga  14160
aatagcatct gttactctga gctgcagccc ctgtacgata ccaccagact gtacctggtg  14220
gacaacaagt ccgcggacgt ggcctccctg aactaccaga acgaccacag cgatttttttg 14280
accacggtga tccaaaacaa cgacttcacc ccaaccgagg ccagcaccca gaccataaac  14340
ctggataaca ggtcgaactg gggcggcgac ctgaagacca tcttgcacac caacatgccc  14400
aacgtgaacg agttcatgtt caccaactct tttaaggcgc gggtgatggt ggcgcgcgag  14460
caggggggagg cgaagtacga gtgggtggac ttcacgctgc ccgagggcaa ctactcagag 14520
accatgactc tcgacctgat gaacaatgcg atcgtggaac actatctgaa agtgggcagg  14580
cagaacgggg tgaaggaaag cgatatcggg gtcaagtttg acaccagaaa cttccgtctg  14640
ggctgggacc ccgtgaccgg gctggtcatg ccgggggtct acaccaacga ggcctttcat  14700
cccgacatag tgcttctgcc cggctgtggg gtggacttca cccagagccg gctgagcaac  14760
ctgctgggca ttcgcaagcg gcagcctttc caggagggtt tcaagatcac ctatgaggat  14820
ctgaaggggg gcaacattcc cgcgctcctt gatctggacg cctacgagga gagcttgaaa  14880
cccgaggaga gcgctggcga cagcggcgag agtggcgagg agcaagccgg cggcggtggc  14940
ggcgcgtcgg tagaaaacga aagtacgccc gcagtggcgg cggacgctgc ggaggtcgag  15000
ccggaggcca tgcagcagga cgcagaggag ggcgcacagg agggcgcgca gaaggacatg  15060
aacgatgggg agatcagggg agacacattc gccacccggg gcgaagaaaa agaggcagag  15120
gcggcggcgg cggcgacggc ggaggccgaa accgaggttg aggcagaggc agagcccgag  15180
accgaagtta tggaagacat gaatgatgga gaacgtaggg gcgacacgtt cgccacccgg  15240
ggcgaagaga aggcggcgga ggcagaagcc gcggctgagg aggcggctgc ggctgcggcc  15300
aagactgagg ctgcggctaa ggctgaggtc gaagccaatg ttgcggttga ggctcaggct  15360
gaggaggagg cggcggctga agcagttaag gaaaaggccc aggcagagca ggaagagaaa  15420
aaacctgtca ttcaacctct aaaagaagat agcaaaaagc gcagttacaa cgtcatcgag  15480
ggcagcacct ttacccagta ccgcagctgg tacctggcgt acaactacgg cgacccggtc  15540
aagggggtgc gctcgtggac cctgctctgc acgccggacg tcacctgcgg ctccgagcag  15600
atgtactggt cgctgccgaa catgatgcaa gacccggtga ccttccgctc cacgcggcag  15660
gttagcaact tcccggtggt gggcgccgaa ctgctgcccg tgcactccaa gagtttttac  15720
aacgagcagg ccgtctactc ccagctgatc cgccaggcca cctctctgac ccacgtgttc  15780
aatcgctttc ccgagaacca gattttggcg cgcccgccgg cccccaccat caccaccgtg  15840
agtgaaaacg ttcctgccct cacagatcac gggacgctac cgctgcgcaa cagcatctca  15900
```

-continued

```
ggagtccagc gagtgaccat tactgacgcc agacgccgga cctgccccta cgtttacaag  15960
gccttgggca tagtctcgcc gcgcgtcctc tccagtcgca ctttttaaaa cacatctacc  16020
cacacgttcc aaaatcatgt ccgtactcat ctcacccagc aacaacaccg gctgggggct  16080
gcgcgcgccc agcaagatgt ttggaggggc gaggaagcgc tccgaccagc accctgtgcg  16140
cgtgcgcggc cactaccgcg cgccctgggg agcgcacaag cgcgggcgca cagggcgcac  16200
cactgtggac gacgtcattg actccgtagt ggagcaagcg cgccactaca cacccggcgc  16260
gccgaccgcc cccgccgtgt ccaccgtgga ccaggcgatc gaaagcgtgg tacagggcgc  16320
gcggcactat gccaacctta aaagtcgccg ccgccgcgtg gcccgccgcc atcgccggag  16380
accccgggcc accgccgccg cgcgccttac taaggctctg ctcaggcgcg ccaggcgaac  16440
tggccaccgg gccgccatga gggccgcacg gcgggctgcc gctgccgcaa gcgtcgtggc  16500
cccgcgggca cgaaggcgcg cggccgctgc cgccgccgcc gccatttcca gcttggcctc  16560
gacgcggcgc ggtaacatat actgggtgcg cgactcggta accggcacgc gggtacccgt  16620
gcgctttcgc cccccgcgga attagcacaa gacaacatac acactgagtc tcctgctgtt  16680
gtgtatccca gcggcgaccg tcagcagcgg cgacatgtcc aagcgcaaaa ttaaagaaga  16740
gatgctccag gtcatcgcgc cggagatcta tgggcccccg aagaaggagg aggatgatta  16800
caagccccgc aagctaaagc gggtcaaaaa gaaaaagaaa gatgatgatg acgaggcggt  16860
ggagtttgtc cgccgcatgg cacccaggcg ccccgtgcag tggaagggcc ggcgcgtgca  16920
gcgcgttttg cgccccggca ccgcggtggt cttcacgccc ggcgagcgct ccacgcgcac  16980
tttcaagcgg gtgtacgatg aggtgtacgg cgacgaggac ctgttggagc aggccaacca  17040
gcgctttggg gagtttgcat atgggaaacg gccccgcgag agtctaaaag aggacctgct  17100
ggcgctaccg ctggacgagg gcaatcccac cccgagtctg aagccggtaa ccctgcaaca  17160
ggtgctgcct ttgagcgcgc ccagcgagca taagcgaggg ttgaagcgcg aaggcgggga  17220
cctggcgccc accgtgcagt tgatggtgcc caagcggcag aagctggagg acgtgctgga  17280
gaaaatgaaa gtagagcccg ggatccagcc cgagatcaag gtccgcccca tcaagcaggt  17340
ggcgcccggc gtgggagtcc agaccgtgga cgttaggatt cccacggagg agatggaaac  17400
ccaaaccgcc actccctctt cggcggccag cgccaccacc ggcaccgctt cggtagaggt  17460
gcagacggac ccctggctac ccgccaccgc tgttgccgcc gccgcccccc gttcgcgcgg  17520
gcgcaagaga aattatccag cggccagcgc gctcatgccc cagtacgcac tgcatccatc  17580
catcgtgccc acccccggct accgcgggta ctcgtaccgc ccgcgcagat cagccggcac  17640
tcgcggccgc cgccgccgtg cgaccacaac cagccgccgc cgtcgccgcc gccgccagcc  17700
agtgctgacc cccgtgtctg taaggaaggt ggctcgctcg gggagcacgc tggtggtgcc  17760
cagagcgcgc taccacccca gcatcgttta aagccggtct ctgtatggtt cttgcagata  17820
tggccctcac ttgtcgcctc cgcttcccgg tgccgggata ccgaggaaga actcaccgcc  17880
gcagaggcat ggcgggcagc ggtctccgcg gcggccgtcg ccatcgccgg cgcgcaaaaa  17940
gcaggcgcat gcgcggcggt gtgctgcctc tgctaatccc gctaatcgcc gcggcgatcg  18000
gtgccgtacc cgggatcgcc tccgtggccc tgcaggcgtc ccagaaacgt tgactcttgc  18060
aaccttgcaa gcttgcattt tttggaggaa aaataaaaaa aagtctagac tctcacgctc  18120
gcttggtcct gtgactattt tgtagaaaaa aagatggaag acatcaactt tgcgtcgctg  18180
gccccgcgtc acggctcgcg cccgttcatg ggagactgga cagatatcgg caccagcaat  18240
```

-continued

```
atgagcggtg gcgccttcag ctggggcagt ctgtggagcg gccttaaaaa ttttggttcc  18300
accattaaga actatggcaa caaagcgtgg aacagcagca cgggccagat gctgagagac  18360
aagttgaaag agcagaactt ccaggagaag gtggcgcagg gcctggcctc tggcatcagc  18420
ggggtggtgg acatagctaa ccaggccgtg cagaaaaaga taaacagtca tctggacccc  18480
cgtcctcagg tggaggaaat gcctccagcg atggagacgg tgtctcccga gggcaaaggc  18540
gaaaagcgcc cgcggcccga cagagaagag accctggtgt cacacaccga ggagccgccc  18600
tcttacgagg aggcagtcaa ggccggcctg cccaccactc gccccatagc ccccatggcc  18660
accggtgtgg tgggccacag gcaacacact cccgcaacac tagatctgcc cccgccgtcc  18720
gagccgccgc gccagccaaa ggcggcgacg gtgcccgctc cctccacttc cgccgccaac  18780
agagtgcccc tgcgccgcgc cgcgagcggc ccccgggcct cgcgagttag cggcaactgg  18840
cagagcacac tgaacagcat cgtgggcctg ggagtgagga gtgtgaagcg ccgccgttgc  18900
tactgaatga gcaagctagc taacgtgttg tatgtgtgta tgcgtcctat gtcgccgcca  18960
gaggagctgt tgagccgccg gcgccgtctg cactccagcg aatttcaaga tggcgacccc  19020
atcgatgatg cctcagtggt cgtacatgca catctcgggc caggacgctt cggagtacct  19080
gagccccggg ctggtgcagt tcgcccgcgc cacagacacc tacttcaaca tgagtaacaa  19140
gttcaggaac cccactgtgg cgcccaccca cgatgtgacc acggaccggt cgcagcgcct  19200
gacgctgcgg ttcatccccg tggatcggga ggacaccgcc tactcttaca aggcgcggtt  19260
cacgctggcc gtgggcgaca accgcgtgct ggacatggcc tccacttact ttgacatcag  19320
gggggtgctg gacaggggcc ccaccttcaa gccctactcg ggtactgcct acaactccct  19380
ggcccccaag ggcgctccca attcttgcga gtgggaacaa gatgaaccag ctcaggcagc  19440
aatagctgaa gatgaagaag aacttgaaga agaacaagct caggacgaac aggcgcccac  19500
taagaaaacc catgtatacg cccaggcacc tctttctggt gaaaaaatta ctaaggatgg  19560
tttgcaaata ggtgtggatg ccacacaggc gggagataac cctatatatg ctgataaaac  19620
attccaaccc gaacctcaga taggtgagtc tcagtggaac gaggctgatg ccacagtagc  19680
aggaggcaga gtcttaaaaa agaccacccc tatgagacct tgctatggat cctatgccaa  19740
acctactaat gccaatggcg gtcaagggat catggtggcc aatgatcagg gagcgcttga  19800
atctaaagtt gagatgcaat ttttctccac cacaacgtct cttaatgtaa gggaaggtga  19860
aaacaatctt cagccaaaag tagtgctata cagcgaagat gttaacttgg aatcccctga  19920
cactcatttg tcttacaaac ctaaaaagga tgacaccaac tctaaaatca tgttgggtca  19980
gcaagccatg cccaacagac ccaacctcat tgcttttagg gacaacttta ttggacttat  20040
gtactacaac agcacaggca acatgggagt gctggcagga caggcctccc agctaaacgc  20100
tgtggtagac ttgcaagaca gaaacacaga gctgtcatac caactgatgc ttgattccat  20160
tggagacaga tcaagatact tttccatgtg gaaccaggca gtggacagct atgacccaga  20220
tgtcagaatc attgaaaacc atggggttga agatgagctg cccaactatt gctttcccct  20280
gggcggtatt ggaattacag acacatacca gtgcataaaa ccaaccgcag ctgctaataa  20340
cactacatgg tctaaggatg aagaatttag tgatcgcaat gaaatagggg tgggaaacaa  20400
cttcgccatg gagatcaaca tccaggccaa cctctggagg aacttcctct atgcgaacgt  20460
ggggctctac ctgccagaca agctcaagta caaccccacc aacgtggaca tctctgacaa  20520
ccccaacacc tatgactaca tgaacaagcg tgtggtggct cccggcctgg tggactgctt  20580
tgtcaatgtg ggagccaggt ggtccctgga ctacatggac aacgtcaacc ccttcaacca  20640
```

-continued

```
ccaccgcaat gcgggtctgc gctaccgctc catgatcctg ggcaacgggc gctacgtgcc  20700
cttccacatt caggtgcccc agaagttctt tgccatcaag aacctcctcc tcctgccggg  20760
ctcctacact tacgagtgga acttcaggaa ggatgtcaac atggtcctgc agagctctct  20820
gggcaatgac cttagggtgg acggggccag catcaagttt gacagcgtca ccctctatgc  20880
taccttcttc cccatggctc acaacaccgc ctccacgctc gaggccatgc tgaggaacga  20940
caccaacgac cagtccttca atgactacct ctctggggcc aacatgctct accccatccc  21000
cgccaaggcc accaacgtgc ccatctccat tccctctcgc aactgggccg ccttcagagg  21060
ctgggccttt acccgcctta agaccaagga aacccccctcc ctgggctcgg gttttgaccc  21120
ctactttgtc tactcgggat ccatccccta cctggatggc accttctacc tcaaccacac  21180
ttttaagaag atatccatca tgtatgactc ctccgtcagc tggccgggca atgaccgcct  21240
gctcaccccc aatgagttcg aggtcaagcg cgccgtggac ggcgagggct acaacgtggc  21300
ccagtgcaac atgaccaagg actggttcct ggtgcagatg ctggccaact acaacatagg  21360
ctaccagggc ttctacatcc cagagagcta caaggacagg atgtactcct tcttcagaaa  21420
tttccaaccc atgagcaggc aggtggtgga cgagaccaaa tacaaggact atcaggccat  21480
tggcatcact caccagcaca acaactcggg attcgtgggc tacctggctc ccaccatgcg  21540
cgaggggcag gcctaccccg ccaacttccc ctacccgttg ataggcaaaa ccgcggtcga  21600
cagcgtcacc cagaaaaagt tcctctgcga ccgcaccctc tggcgcatcc ccttctctag  21660
caacttcatg tccatgggtg cgctcacgga cctgggccag aacctgctct atgccaactc  21720
cgcccatgcg ctggacatga cttttgaggt ggaccccatg gacgagccca cccttctcta  21780
tattgtgttt gaagtgttcg acgtggtcag agtgcaccag ccgcaccgcg gtgtcatcga  21840
gaccgtgtac ctgcgcacgc ccttctcggc cggcaacgcc accacctaag gagacagcgc  21900
cgccgcctgc atgacgggtt ccaccgagca agagctcagg gccatcgcca gagacctggg  21960
atgcggaccc tatttttgg gcacctatga caaacgcttc ccgggcttca tctcccgaga  22020
caagctcgcc tgcgccatcg tcaacacggc cgcgcgcgag accgggggcg tgcactggct  22080
ggcctttggc tgggacccgc gctccaaaac ctgctacctc ttcgacccct ttggcttctc  22140
cgatcagcgc ctcagacaga tctatgagtt tgagtacgag gggctgctgc gccgcagcgc  22200
gcttgcctcc tcgcccgacc gctgcatcac ccttgagaag tccaccgaga ccgtgcaggg  22260
gccccactcg gccgcctgcg gtctcttctg ctgcatgttt ttgcacgcct ttgtgcgctg  22320
gccccagagt cccatggatc gcaaccccac catgaacttg ctcaagggag tgcccaacgc  22380
catgctccag agcccccagg tccagcccac cctgcgccac aaccaggaac agctctaccg  22440
cttcctggag cgccactccc cctacttccg cagtcacagc gcgcacatcc ggggggccac  22500
ctctttctgc cacttgcaag aaaacatgca agacggaaaa tgatgtacag ctcgcttttt  22560
aataaatgta aagactgtgc actttattta tacacgggct ctttctggtt atttattcaa  22620
caccgccgtc gccatctaga aatcgaaagg gttctgccgc gcgtcgccgt gcgccacggg  22680
cagagacacg ttgcgatact ggaagcggct cgcccactta aactcgggca ccaccatgcg  22740
gggcagtggt tcctcgggga agttctcgcc ccacagggtg cgggtcagct gcagcgcgct  22800
caggaggtcg ggagccgaga tcttgaagtc gcagttgggg ccggaaccct gcgcgcgcga  22860
gttgcggtac acggggttgc agcactggaa caccagcagg gccggattat gcacgctggc  22920
cagcaggctc tcgtcgctga tcatgtcgct gtccagatcc tccgcgttgc tcagggcgaa  22980
```

cggggtcatc ttgcagacct gcctgcccag gaaaggcggc agcccgggct tgccgttgca 23040
gtcgcagcgc aggggcatca gcaggtgccc gcggcccgac tgcgcctgcg ggtacagcgc 23100
gcgcatgaag gcttcgatct gcctgaaagc cacctgcgtc ttggctccct ccgaaaagaa 23160
catcccacag gacttgctgg agaactggtt cgcgggacag ctggcatcgt gcaggcagca 23220
gcgcgcgtcg gtgttggcga tctgcaccac gttgcgaccc caccggttct tcactatctt 23280
ggccttggaa gcctgctcct tcagcgcgcg ctggccgttc tcgctggtca catccatctc 23340
tatcacctgc tccttgttga tcatgtttgt accgtgcaga cacttcaggt cgccctccgt 23400
ctgggtgcag cggtgctccc acagcgcgca accggtgggc tcccaatttt tgtgggtcac 23460
ccccgcgtag gcctgcaggt aggcctgcaa gaagcgcccc atcatggcca caaaggtctt 23520
ctggctcgta aaggtcagct gcaggccgcg atgctcttcg ttcagccagg tcttgcagat 23580
ggcggccagc gcctcggtct gctcgggcag catcctaaaa tttgtcttca ggtcgttatc 23640
cacgtggtac ttgtccatca tggcgcgcgc cgcctccatg cccttctccc aggcggacac 23700
catgggcagg cttagggggt ttatcacttc caccggcgag gacaccgtac tttcgatttc 23760
ttcttcctcc ccctcttccc ggcgcgcgcc cacgctgctg cgcgctctca ccgcctgcac 23820
caaggggtcg tcttcaggca agcgccgcac cgagcgcttg ccgcccttga cctgcttaat 23880
cagcaccggc gggttgctga agcccaccat ggtcagcgcc gcctgctctt cttcgtcttc 23940
gctgtctacc actatctctg gggaagggct tctccgctct gcggcggcgc gcttcttttt 24000
tttcttggga gcggccgtga tggagtccgc cacggcgacg gaggtcgagg gcgtggggct 24060
gggggtgcgc ggtaccaggg cctcgtcgcc ctcggactct tcctctgact ccaggcggcg 24120
gcggagtcgc ttctttgggg gcgcgcgcgt cagcggcggc ggagacgggg acggggacgg 24180
ggacgggacg ccctccacag gggtggtctt cgcgcagacc ccgcggccgc gctcgggggt 24240
cttctcgagc tggtcttggt cccgactggc cattgtatcc tcctcctcct aggcagagag 24300
acataaggag tctatcatgc aagtcgagaa ggaggagagc ttaaccaccc cctctgagac 24360
cgccgatgcg cccgccgtcg ccgtcgcccc cgctgccgcc gacgcgcccg ccacaccgag 24420
cgacaccccc gcggaccccc ccgccgacgc acccctgttc gaggaagcgg ccgtggagca 24480
ggacccgggc tttgtctcgg cagaggagga tttgcgagag gaggaggata aggagaagaa 24540
gccctcagtg ccaaaagatg ataaagagca agacgagcac gacgcagatg cacaccaggg 24600
tgaagtcggg cggggggacg gagggcatga cggcgccgac tacctagacg aagggaacga 24660
cgtgctcttg aagcacctgc atcgtcagtg cgccattgtt tgcgacgctc tgcaggagcg 24720
cagcgaagtg cccctcagcg tggcggaggt cagccacgcc tacgagctca gcctcttctc 24780
cccccgggtg cccccccgcc gccgcgaaaa cggcacatgc gagcccaacc cgcgcctcaa 24840
cttctacccc gcctttgtgg tacccgaggt cctggccacc tatcacatct tctttcaaaa 24900
ttgcaagatc cccctctcgt gccgcgccaa ccgtagccgc gccgataaga tgctggccct 24960
gcgccagggc gaccacatac ctgatatcgc cgctttggaa gatgtaccaa agatcttcga 25020
gggtctgggt cgcaacgaga agcgggcagc aaactctctg caacaggaaa acagcgaaaa 25080
tgagagtcac accggggtac tggtggagct cgagggcgac aacgcccgcc tggcggtggt 25140
caagcgcagc atcgaggtca cccactttgc ctaccccgcg ctaaacctgc cccccaaagt 25200
catgaacgcg gccatggacg ggctgatcat gcgccgcggc cggcccctcg ctccagatgc 25260
aaacttgcat gaggagaccg aggacggcca gcccgtggtc agcgacgagc agctggcgcg 25320
ctggctggag accgcggacc ccgccgaact ggaggagcgg cgcaagatga tgatggccgt 25380
ggtgctggtc accgtagagc tggagtgtct gcagcgcttc ttcggcgacc ccgagatgca 25440
gagaaaggtc gaggagaccc tgcactacac cttccgccag ggctacgtgc gccaggcttg 25500
caagatctcc aacgtggagc tcagcaacct ggtgtcctac ctgggcatct tgcatgagaa 25560
ccgcctcggg cagagcgtgc tgcactccac cctgcgcggg gaggcgcgcc gcgactacgt 25620
gcgcgactgc gtttacctct tcctctgcta cacctggcag acggccatgg gggtctggca 25680
gcagtgcctg gaggagcgca acctcaagga gctggagaag ctcctgcagc gcgcgctcaa 25740
agatctctgg acgggctaca acgagcgctc ggtggccgcc gcgctggccg acctcatctt 25800
ccccgagcgc ctgctcaaaa ccctccagca ggggctgccc gacttcacca gccaaagcat 25860
gttgcaaaac ttcaggaact ttatcctgga gcgttctggc atcctacccg ccacctgctg 25920
cgccctgccc agcgactttg tcccccctcgt gtaccgcgag tgcccccccgc cgctgtgggg 25980
tcactgctac ctgttccaac tggccaacta cctgtcctac cacgcggacc tcatggagga 26040
ctccagcggc gaggggctca tggagtgcca ctgccgctgc aacctctgca cgccccaccg 26100
ctccctggtc tgcaacaccc aactgctcag cgagagtcag attatcggta ccttcgagct 26160
acagggtccg tcctcctcag acgagaagtc cgcggctccg gggctaaaac tcactccggg 26220
gctgtggact tccgcctacc tgcgcaaatt tgtacctgaa gactaccacg cccacgagat 26280
caggttttac gaagaccaat cccgcccgcc caaggcggag ctgaccgcct gcgtcatcac 26340
ccagggcgag atcctaggcc aattgcaagc catccaaaaa gcccgccaag actttttgct 26400
gaagaagggt cgggggggtgt atctggaccc ccagtcgggt gaggagctca acccggttcc 26460
cccgctgccg ccgccgcggg accttgcttc ccaggataag catcgccatg gctcccagaa 26520
agaagcagca gcggccgcca ctgccgccac ccccacatgct ggaggaagag gaggaatact 26580
gggacagtca ggcagaggag gtttcggacg aggaggagcc ggagacggag atggaagagt 26640
gggaggagga cagcttagac gaggaggctt ccgaagccga agaggcagac gcaacaccgt 26700
caccctcggc cgcagccccc tcgcaggcgc ccccgaagtc cgctcccagc atcagcagca 26760
acagcagcgc tataacctcc gctcctccac cgccgcgacc cacggccgac cgcagaccca 26820
accgtagatg ggacaccacc ggaaccgggg ccggtaagtc ctccgggaga ggcaagcaag 26880
cgcagcgcca aggctaccgc tcgtggcgcg ctcacaagaa cgccatagtc gcttgcttgc 26940
aagactgcgg ggggaacatc tccttcgccc gccgcttcct gctcttccac cacggtgtgg 27000
ccttccccccg taacgtcctg cattactacc gtcatctcta cagcccctac tgcggcggca 27060
gtgagccaga gacggtcggc ggcggcggcg gcgcccgttt cggcgcctag gaagacccag 27120
ggcaagactt cagccaagaa actcgcggcg gccgcggcga acgcggtcgc gggggccctg 27180
cgcctgacgg tgaacgaacc cctgtcgacc cgcgaactga ggaaccgaat cttccccact 27240
ctctatgcca tcttccagca gagcagaggg caggatcagg aactgaaagt aaaaaacagg 27300
tctctgcgct ccctcacccg cagctgtctg tatcacaaga gcgaagacca gcttcggcgc 27360
acgctggagg acgctgaggc actcttcagc aaatactgcg cgctcactct taaggactag 27420
ctccgcgccc ttctcgaatt taggcgggaa cgcctacgtc atcgcagcgc cgccgtcatg 27480
agcaaggaca ttcccacgcc atacatgtgg agctatcagc cgcagatggg actcgcggcg 27540
ggcgcctccc aagactactc cacccgcatg aactggctca gtgccggccc acacatgatc 27600
tcacaggtta atgatatccg cacccatcga aaccaaatat tggtggagca ggcggcaatt 27660
accaccacgc cccgcaataa tcccaacccc agggagtggc ccgcgtccct ggtgtatcag 27720
gaaattcccg gccccaccac cgtactactt ccgcgtgatt cccaggccga agtccaaatg 27780
actaactcag gggcacagct cgcgggcggc tgtcgtcaca gggtgcggcc tcctcgccag 27840
ggtataactc acctggagat ccgaggcaga ggtattcagc tcaacgacga gtcggtgagc 27900
tcctcgctcg gtctcagacc tgacgggacc ttccagatag ccggagccgg ccgatcttcc 27960
ttcacgcccc gccaggcgta cctgactctg caaagctcgt cctcggcgcc gcgctcgggc 28020
ggcatcggga ctctccagtt cgtgcaggag tttgtgccct cggtctactt caacccccttc 28080 tcgggctctc ccggtcgcta cccggaccag ttcatctcga actttgacgc cgcgagggac 28140
tcggtggacg gctacgactg aatgtcgggt ggacccggtg cagagcaact tcgcctgaag 28200
cacctcgacc actgccgccg ccctcagtgc tttgcccgct gtcagaccgg tgagttccag 28260
tacttttccc tgcccgactc gcacccggac ggcccggcgc acggggtgcg ctttttcatc 28320
ccgagtcagg tgcgctctac cctaatcagg gagtttaccg cccgtcccct actggcggag 28380
ttggaaaagg ggccttctat cctaaccatt gcctgcatct gctctaaccc tggattgcac 28440
caagatcttt gctgtcattt gtgtgctgag tataataaag gctgagatca gaatctactc 28500
gggctcctgt cgccatcctg tcaacgccac cgtccaagcc cggcccgatc agcccgaggt 28560
gaacctcacc tgcggtctgc accggcgcct gaggaaatac ctagcttggt actacaacag 28620
cactcccttt gtggtttaca acagctttga ccaggacggg gtctcactga gggataacct 28680
ctcgaacctg agctactcca tcaggaagaa cagcaccctc gagctacttc ctccttacct 28740
gcccgggact taccagtgtg tcaccggtcc ctgcacccac acccacctgt tgatcgtaaa 28800
cgactctctt ccgagaacag acctcaataa ctcctcttcg cagttcccca gaacaggagg 28860
tgagctcagg aaaccccggg taaagaaggg tggacgagag ttaacacttg tggggtttct 28920
ggtgtatgtg acgctggtgg tggctctttt gattaaggct tttccttcca tgtctgaact 28980
ctccctcttc ttttatgaac aactcgacta gtgctaacgg gaccctaccc aacgaatcgg 29040
gattgaatat cggtaaccag gttgcagttt cacttttgat taccttcata gtcctcttcc 29100
tgctagtgct gtcgcttctg tgcctgcgga tcgggggctg ctgcatccac gtttatatct 29160
ggtgctggct gtttagaagg ttcggagacc atcgcaggta gaataaacat gctgctgctt 29220
accctctttg tcctggcgct ggccgccagc tgccaagcct tttccgaggc tgactttata 29280
gagccccagt gtaatgtgac ttttaaagcc catgcacagc gttgtcatac tataatcaaa 29340
tgtgccaccg aacacgatga ataccttatc cagtataaag ataaatcaca caaagtggca 29400
cttgttgaca tctggaaacc cgaagaccct ttggaataca atgtgaccgt tttccagggt 29460
gacctcttca aaatttacaa ttacactttc ccatttgacc agatgtgtga ctttgtcatg 29520
tacatggaaa agcagcacaa gctgtggcct ccgactcccc agggctgtgt ggaaaatcca 29580
ggctctttct gcatgatctc tctctgtgta actgtgctgg cactaatact cacgcttttg 29640
tatatcagat ttaaatcaag gcaaagcttc attgatgaaa agaaaatgcc ttaatcgctt 29700
tcacgcttga ttgctaacac cgggtttta tccgcagaat gattggaatc accctactaa 29760
tcacctccct ccttgcgatt gcccatgggt tggaacgaat cgaagtccct gtgggggcca 29820
atgttaccct ggtggggcct gtcggcaatg ctacattaat gtgggaaaaa tatactaaaa 29880
atcaatgggt ctcttactgc actaacaaaa atagccacaa gcccagagcc atctgcgatg 29940
ggcaaaatct aaccttgatt gatgttcaat tgctggatgc gggctactat tatgggcagc 30000
tgggtacaat gattaattac tggagacccc acagagatta catgctccac gtagtaaagg 30060
gtccccttag cagcccaccc actaccacct ctactacccc cactaccacc actactccca 30120

-continued ccaccagcac tgccgcccag cctcctcata gcagaacaac cacttttatc aattccaagt 30180
cccactcccc ccacattgcc ggcgggccct ccgcctcaga ctccgaaacc accgagatct 30240
gcttctgcaa atgctctgac gccattgccc aggatttgga agatcacgag gaagatgagc 30300
atgacttcgc agatgcatgc caggcatcag agccagaagc gctgccggtg gccctcaaac 30360
agtatgcaga cccccacacc acccccgacc ttcctccacc ttcccagaag ccaagtttcc 30420
tgggggaaaa tgaaactctg cctctctcca tactcgctct gacatctgtt gctatgttga 30480
ccgctctgct ggtgcttcta tgctctatat gctacctgat ctgctgcaga aagaaaaaat 30540
ctcacggcca tgctcaccag cccctcatgc acttccctta ccctccagag ctgggcgacc 30600
acaaacttta agtctgcagt aactatctgc ccatcccttg tcagtcgaca gcgatgagcc 30660
ccactaatct aacggcctct ggacttacaa catcgtctct taatgagacc accgctcctc 30720
aagacctgta cgatggtgtc tccgcgctgg ttaaccagtg ggatcacctg ggcatatggt 30780
ggctcctcat aggagcagtg accctgtgcc taatcctggt ctggatcatc tgctgcatca 30840
aaagcagaag acccaggcgg cggcccatct acaggccctt tgtcatcaca cctgaagatg 30900
atgatgacac cacttccagg ctgcagaggc taaagcagct actcttctct tttacagcat 30960
ggtaaattga atcatgcctc gcattttcat ctacttgtct ctccttccac tttttctggg 31020
ctcttctaca ttggccgctg tgtcccacat cgaggtagac tgcctcacgc ccttcacagt 31080
ctacctgctt ttcggctttg tcatctgcac ctttgtctgc agcgttatca ctgtagtgat 31140
ctgcttcata cagtgcatcg actacgtctg cgtgcgggtg gcttacttta gacaccaccc 31200
ccagtatcgc aacagggaca tagcggctct cctaagactt gtttaaaatc atggccaaat 31260
taactgtgat tggtcttctg atcatctgct gcgtcctagc cgcgattggg actcaagctc 31320
ctaccaccac cagcgctccc agaaagagac atgtatcctg cagcttcaag cgtccctgga 31380
atatacccca atgctttact gatgaacctg aaatctcttt ggcttggtac ttcagcgtca 31440
ccgcccttct tatcttctgc agtacggtta ttgcccttgc catctaccct tcccttgacc 31500
tgggctggaa tgctgtcaac tctatggaat atcccacctt cccagaacca gacctgccag 31560
acctggttgt tctaaacgcg tttcctcctc ctgctcccgt tcaaaatcag tttcgccctc 31620
cgtcccccac gcccactgag gtcagctact ttaatctaac aggcggagat gactgaaaac 31680
ctagacctag aaatggacgg tctctgcagc gagcaacgca cactagagag gcgccggcaa 31740
aaagagctcg agcgtcttaa acaagagctc caagacgcgg tggccataca ccagtgcaaa 31800
aaaggtgtct tctgtctggt aaaacaggcc acgctcacct atgaaaaaac aggtgacacc 31860
caccgcctag gatacaagct gcccacacag cgccaaaagt tcgccctcat gataggcgaa 31920
caacccatca ccgtgaccca gcactccgtg gagacagaag gctgcataca tgctccctgt 31980
aggggcgctg actgcctcta caccttgatc aaaaccctct gcggtctcag agaccttatc 32040
cctttcaatt aatcataact gtaatcaata aaaaatcact tacttgaaat ctgatagcaa 32100
gcctctgtcc aatttttttca gcaacacttc cttcccctcc tcccaactct ggtactctag 32160
gcgcctccta gctgcaaact tcctccacag tctgaaggga atgtcagatt cctcctcctg 32220
tccctccgca cccacgatct tcatgttgtt gcagatgaaa cgcgcgagat cgtctgacga 32280
gaccttcaac cccgtgtacc cctacgatac cgagatcgct ccgacttctg tccctttcct 32340 taccccctccc tttgtgtcat ccgcaggaat gcaagaaaat ccagctgggg tgctgtccct 32400
gcacttgtca gagcccctta ccacccacaa tggggccctg actctaaaaa tgggggggcgg 32460

-continued

```
cctgaccctg gacaaggaag ggaatctcac ttcccaaaac atcaccagtg tcgatccccc  32520
tctcaaaaaa agcaagaaca acatcagcct tcagaccgcc gcacccctcg ccgtcagctc  32580
cggggcccta acactttttg ccactccccc cctagcggtc agtggtgaca accttactgt  32640
gcagtctcag gcccctctca ctttggaaga ctcaaaacta actctggcca ccaaaggacc  32700
cctaactgtg tccgaaggca aacttgtcct agaaacagag gctcccctgc atgcaagtga  32760
cagcagcagc ctgggcctta gcgttacggc cccacttagc attaacaatg acagcctagg  32820
actagatctg caggcaccca ttgtctctca aaatggaaaa ctggctctaa atgtagcagg  32880
ccccctagct gtggccaatg gcattaatgc tttgacagta ggcacaggca aaggtattgg  32940
tctaaatgaa accagcactc acttgcaagc aaagttggtc gcccccctag gctttgatac  33000
caatggcaac attaagctaa gcgttgcagg aggcatgaga ctaaataatg acacacttat  33060
actagatgta aactacccat ttgaagctca aggccaacta agtctaagag tgggccaggg  33120
tccgctgtat gtagattcta gcagccataa cctgaccatt agatgcctta gaggattata  33180
cataacatcg tctaataacc aaaccggtct agaggccaac ataaaactaa caaaaggcct  33240
tgtctatgat ggaaatgcca tagcagtcaa tgttggtcaa ggattgcaat acagcactac  33300
tgccacatcg gaaggtgtgt atcctataca gtctaagata ggtttgggaa tggaatatga  33360
taccaacgga gccatgatga caaaactagg ctctggacta agctttgaca attcaggagc  33420
cattgtagtg ggaaacaaaa atgatgacag gcttactctg tggactacac cagacccatc  33480
tcctaactgt agaatttatt ctgaaaaaga tactaaacta accttggtgc tgactaagtg  33540
tggcagccaa atcctaggca cagtatctgc ccttgctgtc agaggcagcc ttgcgcccat  33600
cactaatgca tccagcatag tccaaatatt tctaagattt gatgaaaatg gactattgat  33660
gagcaactca tcgctagacg gtgattactg gaattacaga aatggggact ccactaatag  33720
cacaccatat acaaatgcag taggctttat gcctaatcta gcagcctatc ctaaaggtca  33780
ggctacagct gcaaaaagca gtattgtaag ccaggtatac atggatggtg acactactaa  33840
acctataaca ctaaaaataa acttcaatgg cattgatgaa acaacagaaa ataccccctgt  33900
tagtaaatat tccatgacat tctcatggag ctggcccacc gcaagctaca taggccacac  33960
ttttgcaaca aactctttta ctttctccta catcgcccaa gaataaagaa agcacagaga  34020
tgcttgtttt gatttcaaaa ttgtgtgctt ttatttattt tcagcttaca gtatttccag  34080
tagtcattcg aataaagctt aatcaaactg catgagaacc cttccacata gcttaaatta  34140
gcaccagtgc aaatggagaa aattcaacat accttttttta tccagatatc agagaactct  34200
agtggtcagt tttcccccac cctcccagct cacagaatac acagtccttt ccccccggct  34260
ggctttaaac aacactatct cattggtaac agacatattc ttaggtgtaa taatccacac  34320
ggtctcttgg cgggccaagc gctggtcggt gatgttaata aactccccag gcagctcttt  34380
caagttcacg tcgctgtcca actgctgaag cgctcgcggc tccgactgcg cctctagcgg  34440
aggcaacggc aacacccgat ccttgatcta taaaggagta gagtcataat cccccataag  34500
aatagggcgg tgatgcagca acaaggcgcg cagcaactcc tgccgccgcc tctccgtacg  34560
acaggaatgc aacggcgtgg tggtctcctc cgcgataatc cgcaccgctc gcagcatcag  34620
catcctcgtc ctccgggcac agcagcgcat cctgatctca ctgagatcgg cgcagtaagt  34680
gcagcacaaa accaagatgt tatttaagat cccacagtgc aaagcactgt acccaaagct  34740
catggcggga aggacagccc ccacgtgacc atcataccag atccttaggt aaatcaaatg  34800
acgacctctc ataaacacgc tggacatgta catcacctcc ttgggcatgc gctgattcac  34860
```

```
cacctctcga taccacaagc atcgctgatt aattaaagac ccctcaagca ccatcctgaa  34920
ccaggaagcc agcacctgac cccccgccag gcactgcagg gaccccggtg aattgcagtg  34980
gcagtgaaga ctccagcgct cgtagccgtg aaccatagag ccggtcatta tatccacatt  35040
ggcacaacac aaacacactt tcatacactt tttcatgatt agcagctcct ctctagtcag  35100
gaccatatcc caaggaatca cccactcttg aatcaaggta aatcccacac agcagggcag  35160
gcctctcaca taactcacgt tatgcatagt gagcgtgtcg caatctggaa ataccggatg  35220
atcttccatc accgaagctc gcgtctccgt ctcaaaggga ggtaaacggt ccctcgtgta  35280
gggacagtgg cgggataatc gagatcgtgt tgaacgtaga gtcatgccaa agggaacagc  35340
ggacgtactc atatttcctc cagcagaacc aagtgcgcgc gtggcagcta tccctgcgtc  35400
ttctgtctcg ccgcctgccc cgctcggtgt agtagttgta atacagccac tccctcagac  35460
cgtcaaggcg ctccctggcg tccggatcta taacaacacc gtcctgcagc gccgccctga  35520
tgacatccac caccgtagag tatgccaagc ccagccagga aatgcattca ctttgacagc  35580
gagagatagg aggagcggga agagatggaa gaaccatgat agtaaaagac ttttattcca  35640
atcgatcctc tacaatgtca aagtgtagat ctataagatg acactggtct cctccgctga  35700
gtcgatcaaa aataacagct aaaccacaaa caacacgatt ggtcaaatgc tccacaaggg  35760
cttgcagcat aaaatcgcct cgaaagtcca ccgcaagcat aacatcaaag ccaccgcccc  35820
tatcatgatc tataataaaa accccacagc tatccaccag acccataaag ttttcatctc  35880
tccatcgtga aaaaatattt acaagctcct cctttaaatc acctccaacc aattgaaaaa  35940
gttgagccaa accgccctcc accttcattt tcagcaagcg catcatgatt gcaaaaattc  36000
aggctcctga gacacctgta taagattgag aagcggaacg ttaacgtcaa tgtttcgctc  36060
gcgaagatcg cgcctcagtg caagcatgat ataatcccac aggtcggagc ggatcagcga  36120
ggacatctcc ccgccaggaa ccaactcaac ggagcctatg ctgattataa tacgcatatt  36180
cggggctatg ctgaccagca cggcccccaa ataggcgtac tgcataggcg gcgacaaaaa  36240
gtgaacagtt tgggttaaaa aatcaggcaa acagtcgcgc aaaaaagcaa gaacatcata  36300
accatgctca tgcaaataga tgcaagtaag ctcaggaacg accacagaaa aatgcacaat  36360
ttttctctca aacatgactg cgagccctgc aaaaaataaa aaagaaacat tacacaagag  36420
tagcctgtct tacgatggga tagactactc taaccaacat aagacgggcc acaacatcgc  36480
ccgcgtggcc ataaaaaaaa ttgtccgtgt gattaaaaag aagcacagat agctggccag  36540
tcatatccgg agtcatcacg tgtgaacccg tgtagacccc cgggttggac acatcggcca  36600
aacaaagaaa gcggccaatg tacccaggag gaatcataac actaagacga agatacaaca  36660
gaataacccc atgaggggga ataacaaagt tagtaggtga ataaaaacga taaacacccg  36720
aaactccctc ctgcgtaggc aaaatagcac cctccccttc caaaacaaca tatagcgctt  36780
ccacagcagc catgacaaaa gactcaaaac actcaaaaga ctcagtctta ccaggaaaat  36840
aaaagcactc tcacagcacc agcactaatc agagtgtgaa gagggccaag tgccgaacga  36900
gtatatatag gaataaaaaa tgacgtaaat gtgtaaaggt cagaaaacgc ccagaaaaat  36960
acacagacca acgcccgaaa cgaaaacccg cgaaaaaata cccagaactt cctcaacaac  37020
cgccacttcc ggtttctcac ggtacgtcac ttccgcaaga aaagcaaaac tacatttccc  37080
acatgtgtaa aaacgaaacc ccgccccttg taactgccca caacttacat catcaaaaca  37140
taaactccta cgtcacccgc cccgcctctc cccgcccacc tcattatcat attggccaca  37200
```

atccaaaata aggtatatta ttgatgatg 37229

<210> SEQ ID NO 22
<211> LENGTH: 37232
<212> TYPE: DNA
<213> ORGANISM: Gorilla beringei beringei

<400> SEQUENCE: 22
catcatcaat aatatacctt attttggatt gtggccaata tgataatgag gtgggcgggg 60
agaggcgggg cgggtgacgt aggacgcgcg agtagggttg ggaggtgtgg cggaagtgtg 120
gcatttgcaa gtgggaggag ctcacatgca agcttccgtc gcggaaaatg tgacgttttt 180
gatgagcgcc gcctacctcc ggaagtgcca attttcgcgc gcttttcacc ggatatcgta 240
gtaattttgg gcgggaccat gtaagatttg gccattttcg cgcgaaaagt gaaacgggga 300
agtgaaaact gaataatagg gcgttagtca tagcgcgtaa tatttaccga gggccgaggg 360
actttgaccg attacgtgga ggactcgccc aggtgttttt tacgtgaatt tccgcgttcc 420
gggtcaaagt ctccgttttt attgtcaccg tcatttgacg cggagggtat ttaaacccgc 480
tgcgctcctc aagaggccac tcttgagtgc cagcgagaag agttttctcc tctgctccgc 540
ttcggtgatc gaaaaatgag acacatagcc tgcactccgg gtcttttgtc cggtcgggcg 600
gcggccgagc ttttggacgc tttgatcaat gatgtcctaa gcgatgattt tccgtctact 660
acccacttta gcccacctac tcttcacgaa ctgtacgatc tggatgtact ggtggatgtg 720
aacgatccca acgaggaggc ggtttctgcg tttttcccg agtctgcgct gttggccgct 780
caggagggat ttgacctaca cactccgccg cctattttag agtctccgct gccggagccc 840
agtggtatac cttatatgcc tgaactgctt cccgaagtgg tagacctgac ctgccacgag 900
cctggctttc cgcccagcga cgatgagggt gagccttttg ttttagactt tgctgagata 960
cctgggcacg gttgcaggtc ttgtgcatat catcagaggg ttaccggaga ccccgaggtt 1020
aagtgttcgc tgtgctatat gaggatgacc tcttccttta tctacagtaa gtttttgtct 1080
aggtgggctt ttgggtaggt gggttttgtg tcagaacagg tgtaaacgtt gcttgtgttt 1140
tttgtacctg taggtccggt gtccgagcca gacccggagc ccgaccgcga tcccgagccg 1200
gatcccgagc ctcctcgcag gacaaggaaa ctaccttcca ttctgtgcaa gtctcagaca 1260
cctgtaagga ccagcgaggc agacagcacc gactctggca cttctacctc tccccctgaa 1320
attcacccag tggttcctct gggtatacat aaacctgttg ctgttaaagt ttgcgggcga 1380
cgccctgcag tacagtgcat tgaggacttg cttcacgatc ccgaggaacc tttggacttg 1440
agccttaaac gccctaggca ataaacccca cctaagtaat aaaccccacc taagtaataa 1500
accctgccgc ccttggttat tgagatgacg cccaatgttt gcttttgaat gacttcatgt 1560
gtgtaataaa agtgagtgtg atcataggtc tcttgtttgt ctgggcgggg cttaagggta 1620
tataagtctc ttggggctaa acttggttac acttgacccc aatggaggcg tgggggtgct 1680
tggaggagtt tgcggacgtg cgccgtttgc tggacgagag ctctagcaat acctatacta 1740
tttggaggta tctgtggggc tctactcagg ccaagttggt ttccagaatt aagcaggatt 1800
acaagtgcga ttttgaagag ctttttagtt cctgcggtga gcttttgcaa tccttgaatc 1860
tgggccatca ggctattttc caggaaaagg ttctctcgac tttggatttt tccactcccg 1920
ggcgcaccgc cgcttgtgtg gcttttgtgt cttttgtgca agataaatgg agcgaggaga 1980
cccacctgag tcacggctac gtactggatt tcatggcgat ggctctttgg agggctcaca 2040
acaaatggaa gattcagaag gaactgtacg gttccgccct acgtcgtcca cttctgtcgc 2100

-continued

```
gacaggggct gaggtttccc gaccatcggc agcatcagaa tctggaagac gagtcggagg   2160
agcgagcgga ggagaagatc agcttgagag ccggcctgga ccctcctcag gaggaatgaa   2220
tctcccgcag gtggttgacc tgtttccaga actgagacgg gtcctgacta tcagggagga   2280
tggtcagttt gtgaagaagt ttaagaggga tcggggtgag ggagatgatg aggcggctag   2340
caatttagct tttagtctga tgactcgcca ccgaccggaa tgtattacct atcagcagat   2400
taaggagagt tgtgccaacg agctggatct tttgggtcag aagtatagca tagaacagct   2460
taccacttac tggcttcagc ctggggatga ttgggaagag gcgatcaggg tgtatgcaaa   2520
ggtggccctg cggcccgatt gcaagtataa gattactaag ttggttaata ttagaaactg   2580
ctgctatatt tctgggaacg gggccgaagt ggagatagat actcaggaca gggtggcttt   2640
taggtgttgc atgataaaca tgtggcccgg gatactgggg atggatgggg tggtattcat   2700
gaatgtgagg tttacgggcc ccaactttaa tggcacggtg ttcatgggca acaccaactt   2760
gctcctgcat ggtgcgagtt tctatgggtt taataacacc tgtatagagg cctggaccga   2820
tgtaaaggtt cgaggttgtt ccttttatag ctgttggaag gcggtggtgt gtcgccctaa   2880
aagcaggggt tctgtgaaaa aatgcttgtt tgaaaggtgc accttaggca tcctctctga   2940
gggcaactcc agggtgcgcc ataatgtggc ttcgaactgc ggttgcttca tgcaagtgaa   3000
gggggtgagc gttatcaagc ataactcggt gtgtggaaac tgcgaggatc gcgcctccca   3060
gatgctgacc tgctttgatg gcaactgtca cctgttgaag accattcata taagcagcca   3120
ccccagaaag gcctggcccg tgtttgagca taacatcttg acccgctgct ccttgcatct   3180
gggggtcagg aggggtatgt tcctgcctta ccagtgtaac tttagccaca ctaaaatcct   3240
gctggaaccc gagtgcatga ccaaggtcag cctgaatggt gtgtttgatg tgactctgaa   3300
aatctggaag gtgctgaggt atgatgagac caggaccagg tgccgaccct gcgagtgcgg   3360
cggcaagcac atgagaaatc agcctgtgat gttggatgtg accgaggagc ttaggcctga   3420
ccatctggtg ctggcctgca ccagggccga gtttgggtct agcgatgagg ataccgattg   3480
aggtgggtaa ggtgggcgtg gctagaaggg tggggcgtgt ataaattggg ggtctaaggg   3540
tctctctgtt ttgtcttgca acagccgccg ccatgagcga caccggcaac agctttgatg   3600
gaagcatctt tagcccctat ctgacagtgc gcatgcctca ctgggctgga gtgcgtcaga   3660
atgtgatggg ttccaacgtg gatggacgcc ccgttctgcc ttcaaattcg tctacaatgg   3720
cctacgcgac cgtgggagga actccgctgg acgccgcgac ctccgccgcc gcctccgccg   3780
ccgccgcgac cgcgcgcagc atggctacgg acctttacag ctctttggtg gcgagcggcg   3840
cggcctctcg cgcgtctgct cgggatgaga aactgaccgc tctgctgctt aaactggaag   3900
acttgacccg ggagctgggt caactgaccc agcaggtctc cagcttgcgt gagagcagcc   3960
ttgcctcccc ctaatggccc ataatataaa taaaagccag tctgtttgga ttaagcaagt   4020
gtatgttctt tatttaactc tccgcgcgcg gtaagcccgg gaccagcggt ctcggtcgtt   4080
tagggtgcgg tggattcttt ccaacacgtg gtacaggtgg ctctggatgt ttagatacat   4140
gggcatgagt ccatccctgg ggtggaggta gcaccactgc agagcttcgt gctcgggggt   4200
ggtgttgtat atgatccagt cgtagcagga gcgctgggcg tggtgctgaa aaatgtcctt   4260
aagcaagagg cttatagcta gggggaggcc cttggtgtaa gtgtttacaa atctgctcag   4320
ttgggagggg tgcatccggg gggatataat gtgcatcttg gactggattt ttaggttggc   4380
tatgttccca cccagatccc ttctgggatt catgttgtgc aggaccacca gcacggtata   4440
```

-continued

```
tccagtgcac ttgggaaatt tatcgtggag cttagacggg aatgcatgga agaacttgga   4500
gacgcccttg tggcctccca gattttccat acattcgtcc atgatgatgg caatgggccc   4560
gtgggaagct gcctgagcaa aaatgtttct gggatcgctc acatcgtagt tatgttccag   4620
ggtgaggtca tcataggaca tctttacgaa tcgggggcgg agggtcccgg actgggggat   4680
gatggtaccc tcgggccccg gggcgtagtt cccctcacag atctgcatct cccaggcttt   4740
catttcagag ggagggatca tatccacctg cggagcgatg aaaaacacag tttctggcgc   4800
aggggagatt aactgggatg agagcaggtt tctgagcagc tgtgactttc cacagccggt   4860
gggcccatat atcacgccta tcaccggctg cagctggtag ttaagagagc tgcagctgcc   4920
gtcctcccgg agcagggggg ccacctcgtt cagcatatcc ctgacgtgga tgttctccct   4980
gaccaattcc gccagaaggc gctcgccgcc cagcgaaagc agctcttgca aggaagcaaa   5040
atttttcagc ggttttaggc cgtcggccgt gggcatgttt ttcagcgtct gggtcagcag   5100
ttccagcctg tcccacagct cggtgatgtg ctctacggca tctcgatcca gcagatctcc   5160
tcgtttcgcg ggttggggcg gctttcgctg tagggcacca gccgatgggc gtccagcggg   5220
gccagagtca tgtccttcca tgggcgcagg gtcctcgtca gggtggtctg ggtcacggtg   5280
aaggggtgcg ctccgggttg ggcgctggcc agggtgcgct tgaggctggt tctgctggtg   5340
ctgaatcgct gccgctcttc gccctgcgcg tcggccaggt agcatttgac catggtctcg   5400
tagtcgagac cctcggcggc gtgccccttg gcgcggagct ttcccttgga ggtggcgccg   5460
cacgaggggc actgcaggct cttcagggcg tagagcttgg gagcgagaaa cacggactct   5520
ggggagtagg cgtccgcgcc gcaggaagcg cagaccgtct cgcattccac cagccaagtg   5580
agctccgggc ggtcagggtc aaaaaccagg ttgcccccat gctttttgat gcgtttctta   5640
cctcggctct ccatgaggcg gtgtcccttc tcggtgacga agaggctgtc cgtgtccccg   5700
tagaccgact tcaggggcct gtcttccagc ggagtgcctc tgtcctcctc gtagagaaac   5760
tctgaccact ctgagacgaa ggcccgcgtc caggccagga cgaaggaggc cacgtgggag   5820
gggtagcggt cgttgtccac tagcgggtcc accttctcca gggtgtgcag gcacatgtcc   5880
ccctcctccg cgtccagaaa agtgattggc ttgtaggtgt aggacacgtg accgggggtt   5940
cccgacgggg gggtataaaa gggggtgggc gccctttcat cttcactctc ttccgcatcg   6000
ctgtctgcga gggccagctg ctggggtaag tattccctct cgaaggcggg catgacctca   6060
gcgctcaggt tgtcagtttc taaaaatgag gaggatttga tgttcacctg tccggaggtg   6120
ataccttga gggtacctgg gtccatctgg tcagaaaaca ctattttttt gttgtcaagc   6180
ttggtggcga acgacccgta gagggcgttg gagagcagct tggcgatgga gcgcagggtc   6240
tggtttttgt cgcggtcggc tcgctccttg gccgcgatgt tgagttgcac gtactcgcgg   6300
gccacgcact tccactcggg gaagacggtg gtgcgctcgt ctgggattag gcgcaccctc   6360
cagcctcggt tgtgcagggt gaccatgtcg acgctggtgg cgacctcgcc gcgcaggcgc   6420
tcgttggtcc agcagaggcg gccgcccttg cgcgagcaga aggggggtag ggggtccagc   6480
tggtcctcgt ttgggggtc cgcgtcgatg gtgaagaccc cggggagcaa gcgcgggtca   6540
aagtagtcga tcttgcaagc ttgcatgtcc agagcccgct gccattcgcg ggcggcgagc   6600
gcgcgctcgt aggggttgag ggcgggcccc cagggcatgg ggtgggtgag cgcggaggcg   6660
tacatgccgc agatgtcata cacgtacagg ggttccctga ggatgccgag gtaggtgggg   6720
tagcagcgcc ccccgcggat gctggcgcgc acgtagtcat agagctcgtg ggagggggcc   6780
agcatgttgg gcccgaggtt ggtgcgctgg gggcgctcgg cgcggaaggc gatctgcctg   6840
```

-continued aagatggcat gggagttgga ggagatggtg ggccgctgga agacgttgaa gcttgcttct 6900
tgcaagccca ccgagtccct gacgaaggag gcgtaggact cgcgcagctt gtgcaccagc 6960
tcggcggtga cctggacgtc gagcgcgcag tagtcgaggg tctcgcggat gatgtcatac 7020
ttatcctccc ccttcttttt ccacagctcg cggttgagga cgaactcttc gcggtctttc 7080
cagtactctt ggaggggaaa cccgtccgtg tccgaacggt aagagcctag catgtagaac 7140
tggttgacgg cctggtaggg gcaacagccc ttctccacgg gcagcgcgta ggcctgcgcc 7200
gccttgcgga gggaggtgtg ggtgagggcg aaagtgtccc tgaccatgac tttgaggtat 7260
tgatgtttga agtctgtgtc atcgcagccg ccctgttccc acagggtgta gtccgtgcgc 7320
tttttggagc gcgggttggg cagggagaag gtgaggtcat tgaagaggat cttccccgct 7380
cgaggcatga agtttctggt gatgcgaaag ggccctggga ccgaggagcg gttgttgatg 7440
acctgggcgg ccaggacgat ctcgtcaaag ccgtttatgt tgtggcccac gatgtagagc 7500
tccaaaaagc ggggctggcc cttgatggag gggagctttt tgagttcctc gtaggtgagc 7560
tcctcgggcg attccaggcc gtgctcctcc agggcccagt cttgcaagtg agggttggcc 7620
gccaggaagg atcgccagag gtcgcgggcc atgagggtct gcaggcggtc gcggaaggtt 7680
ctgaactgtc gccccacggc catcttttcg ggggtgatgc agtagaaggt gaggggggtct 7740
ttctcccagg ggtcccatct gagctctcgg gcgaggtcgc gcgcggcggc gaccagagcc 7800
tcgtcgcccc ccagtttcat gaccagcatg aagggcacga gctgcttgcc aaaggctccc 7860
atccaagtgt aggtctctac atcgtaggtg acaaagaggc gctccgtgcg aggatgagag 7920
ccgatcggga agaactggat ctcccgccac cagttggagg attggctgtt gatgtggtga 7980
aagtagaagt cccgtctgcg ggccgagcac tcgtgctggc ttttgtaaaa gcgaccgcag 8040
tactggcagc gctgcacggg ttgtatatct tgcacgaggt gaacctggcg acctctgacg 8100
aggaagcgca gcgggaatct aagtcccccg cctggggtcc cgtgtggctg gtggtcttct 8160
actttggttg tctggccgcc agcatctgtc tcctggaggg cgatggtgga gcagaccacc 8220
acgccgcgag agccgcaggt ccagatctcg gcgctcggcg ggcggagttt gatgacgaca 8280
tcgcgcacat tggagctgtc catggtctcc agctcccgcg gcggcaggtc agctgggagt 8340
tcctggaggt tcacctcgca gagacgggtc aaggcgcggg cagtgttgag atggtatctg 8400
atttcaaggg gcgtgttggc ggcggagtcg atggcttgca ggaggccgca gccccggggg 8460
gccacgatgg ttccccgcgg ggcgcgaggg gaggcggaag ctgggggtgt gttcagaagc 8520
ggtgacgcgg gcgggccccc ggaggtaggg ggggttccgg ccccacaggc atgggcggca 8580
ggggcacgtc ttcgccgcgc gcgggcaggg gctggtgctg gctccgaaga gcgcttgcgt 8640
gcgcgacgac gcgacggttg gtgtcctgta tctgacgcct ctgagtgaag accacgggtc 8700
ccgtgacctt gaacctgaaa gagagttcga cagaatcaat ctcggcatcg ttgacagcgg 8760
cctggcgcag gatctcctgc acgtcgcccg agttgtcctg gtaggcgatc tctgccatga 8820
actgctcgat ctcttcttcc tggagatctc ctcgtccggc gcgctccacg gtggccgcca 8880
ggtcgttgga gatgcgaccc atgagctgtg agaaggcgtt gagcccgccc tcgttccaga 8940
cccggctgta gaccacgccc ccctcggcgt cgcgagcgcg catgaccacc tgggccaggt 9000
tgagctccac gtgtcgcgtg aagacggcgt agttgcgcag gcgctggaaa aggtagttca 9060
gggtggtggc ggtgtgctcg gcgacgaaga agtacatgac ccagcgccgc aacgtggatt 9120
cattgatgtc ccccaaggcc tccaggcgct ccatggcctc gtagaagtcc acggcgaagt 9180

-continued

```
tgaaaaactg ggagttgcga gcggacacgg tcaactcctc ctccagaaga cggatgagct   9240
cggcgacagt gttgcgcacc tcgcgctcga aggccacggg gggcgcttct tcctcttcca   9300
cctcttcttc catgatcgct tcttcttctt cctcagccgg gacgggaggg ggcggcggcg   9360
gcgggggagg ggcgcggcgg cggcggcggc gcaccgggag gcggtcgatg aagcgctcga   9420
tcatctcccc ccgcatgcgg cgcatggtct cggtgacggc gcggccgttc tcccgggggc   9480
gcagctcgaa gacgccgcct ctcatctcgc cgcggggcga gcggccgtga ggtagcgaga   9540
cggcgctgac tatgcatctt aacaattgct gtgtaggtac accgccgagg gacctgattg   9600
agtccagatc caccggatcc gaaaaccttt ggaggaaagc gtctatccag tcgcagtcgc   9660
aaggtaggct gagcaccgtg gcgggcgggg gcgggtctgg agagttcctg gcggagatgc   9720
tgctgatgat gtaattaaag taggcggtct tgagaaggcg gatggtggac aggagcacca   9780
tgtctttggg tccggcctgt tggatgcgga ggcggtcggc catgccccag gcctcgttct   9840
gacaccggcg caggtctttg tagtagtctt gcatgagtct ttccaccggc acctcttctc   9900
cttcctcttc tccatctcgc cggtggtttc tcgcgccgcc catgcgcgtg accccaaagc   9960
ccctgagcgg ctgcagcagg gccaggtcgg cgaccacgcg ctcggccaag atggcctgct  10020
gcacctgagt gagggtcctc tcgaagtcat ccatgtccac gaagcggtgg taggcgcccg  10080
tgttgatggt gtaggtgcag ttggccatga cggaccagtt gacggtctgg tgtcccggct  10140
gcgagagctc cgtgtaccgc aggcgcgaga aggcgcggga atcgaacacg tagtcgttgc  10200
aagtccgcac cagatactgg tagcccacca ggaagtgcgg cggaggttgg cgatagaggg  10260
gccagcgctg ggtggcgggg gcgccgggcg ccaggtcttc cagcatgagg cggtggtatc  10320
cgtagatgta cctggacatc caggtgatgc cggcggcggt ggtggtggcg cgcgcgtagt  10380
cgcggacccg gttccagatg tttcgcaggg gcgagaagtg ttccatggtc ggcacgctct  10440
ggccggtgag gcgcgcgcag tcgttgacgc tctatacaca cacaaaaacg aaagcgttta  10500
cagggctttc gttctgtagc ctggaggaaa gtaaatgggt tgggttgcgg tgtgccccgg  10560
ttcgagacca agctgagctc ggccggctga agccgcagct aacgtggtat tggcagtccc  10620
gtctcgaccc aggccctgta tcctccagga tacggtcgag agcccttttg ctttcttggc  10680
caagcgcccg tggcgcgatc tgggatagat ggtcgcgatg agaggacaaa agcggctcgc  10740
ttccgtagtc tggagaaaca atcgccaggg ttgcgttgcg gcgtaccccg gttcgagccc  10800
ctatggcggc ttgaatcggc cggaaccgcg gctaacgagg gccgtggcag ccccgtcctc  10860
aggaccccgc cagccgactt ctccagttac gggagcgagc ccccttttgtt ttttattttt  10920
tagatgcatc ccgtgctgcg gcagatgcgc ccctcgcccc ggcccgatca gcagcagcaa  10980
cagcaggcat gcagaccccc ctctcccctt tccgccccgg tcaccacggc cgcggcggcc  11040
gtgtcgggcg cgggggggcgc gctggagtca gatgagccac cgcggcggcg acctaggcag  11100
tatctggact tggaagaggg cgagggactg gcgcggctgg gggcgaactc tccagagcgc  11160
cacccgcggg tgcagttgaa aagggacgcg cgcgaggcgt acctgccgcg gcagaacctg  11220
tttcgcgacc gcgggggcga ggagcccgag gagatgcgag actgcaggtt ccaagcgggg  11280
cgcgagctgc ggcgcgggct ggacagacag cgcctgctgc gcgaggagga ctttgagccc  11340
gacacgcaga cgggcatcag ccccgcgcgc gcgcacgtag ccgcggccga cctggtgacc  11400
gcctacgagc agacggtaaa ccaggagcgc aacttccaaa agagcttcaa caaccacgtg  11460
cgcacgctgg tggcgcgcga ggaggtgacc ctgggtctca tgcatctgtg ggacctggtg  11520
gaggcgatcg tgcagaaccc cagcagcaag cccctgaccg cgcagctgtt cctggtggtg  11580
```

-continued

```
cagcacagca gggacaacga ggccttcagg gaggcgctgc tgaacatcac cgagccggag  11640
gggcgctggc tcctggacct gataaacatc ctgcagagca tagtggtgca ggagcgcagc  11700
ctgagcctgg ccgagaaggt ggcggccatc aactactcta tgctgagcct gggcaagttc  11760
tacgcccgca agatctacaa gaccccctac gtgcccatag acaaggaggt gaagatagac  11820
agcttctaca tgcgcatggc gctgaaggtg ctgaccctga gcgacgacct gggagtgtac  11880
cgcaacgagc gcatccacaa ggccgtgagc gccagccggc ggcgcgagct gagcgaccgc  11940
gagctgatgc acagtctgca gcgcgcgctg accggcgcgg gcgagggcga cagggaggtc  12000
gagtcctact tcgacatggg ggccgacctg cactggcagc cgagccgccg cgccctggag  12060
gcggcgggggg cgtacggcgg ccccctggcg gccgatgacc aggaagagga ggactatgag  12120
ctagaggagg gcgagtacct ggaggactga cctggctggt ggtgttttgg tatagatgca  12180
agatccgaac gtggcggacc cggcggtccg ggcggcgctg caaagccagc cgtccggcat  12240
taactcctct gacgactggg ccgcggccat gggtcgcatc atggccctga ccgcgcgcaa  12300
ccccgaggct ttcaggcagc agcctcaggc caaccggctg gcggccatct tggaagcggt  12360
agtgcccgcg cgctccaacc ccacccacga gaaggtgctg gccatagtca acgcgctggc  12420
ggagagcagg gccatccgcg cggacgaggc cggactggtg tacgatgcgc tgctgcagcg  12480
ggtggcgcgg tacaacagcg gcaacgtgca gaccaacctg gaccgcctgg tgacggacgt  12540
gcgcgaggcc gtggcgcagc gcgagcgctt gcatcaggac ggtaacctgg gctcgctggt  12600
ggcgctaaac gccttcctca gcacccagcc ggccaacgta ccgcgggggc aggaggacta  12660
caccaacttt ttgagcgcgc tgcggctgat ggtgaccgag gtccctcaga gcgaggtgta  12720
ccagtcgggg cccgactact tcttccagac cagcagacag ggcttgcaaa ccgtgaacct  12780
gagccaggct ttcaagaacc tgcgggggct gtggggagtg aaggcgccca ccggcgaccg  12840
ggctacggtg tccagcctgc taacccccaa ctcgcgcctg ctgctgctgc tgatcgcgcc  12900
cttcacggac agcgggagcg tctcgcggga gacctatctg ggccacctgc tgacgctgta  12960
ccgcgaggcc atcgggcagg cgcaggtgga cgagcacacc ttccaagaga tcaccagcgt  13020
gagccacgcg ctggggcagg aggacacggg cagcctgcag gcgaccctga actacctgct  13080
gaccaacagg cggcagaaga ttcccacgct gcacagcctg acccaggagg aggagcgcat  13140
cttgcgctac gtgcagcaga gcgtgagcct gaacctgatg cgcgacggcg tgacgcccag  13200
cgtggcgctg gacatgaccg cgcgcaacat ggaaccgggc atgtacgcct cccaccggcc  13260
gtttatcaac cgcctgatgg actacttgca tcgggcggcg gccgtgaacc ccgagtactt  13320
cactaatgcc attctgaatc cccactggat gccccctccg ggtttctaca acggggactt  13380
tgaggtgccc gaggtcaacg acgggttcct ctgggatgac atggatgaca gtgtgttctc  13440
acccaacccg ctgcgcgccg cgtctctgcg attgaaggag ggctctgaca gggaaggacc  13500
gaggagtctg gcctcctccc tggctctggg agcggtgggc gccacgggcg cggcggcgcg  13560
gggcagtagc cccttcccca gcctggcaga ctctctgaac agcgggcggg tgagcaggcc  13620
ccgcttgcta ggcgaggagg agtatctgaa caactccctg ctgcagcccg cgagggacaa  13680
gaacgctcag cggcagcagt ttcccaacaa tgggatagag agcctggtgg acaagatgtc  13740
cagatggaag acgtatgcgc aggagtacaa ggagtgggag gaccgccagc cgcggccctt  13800
gccgccccct aggcagcgct ggcagcggcg cgcgtccaac cgccgctgga ggcaggggcc  13860
cgaggacgat gatgactctg cagatgacag cagcgtgttg gacctgggcg ggagcgggaa  13920
```

```
ccccttttcg cacctgcgcc cacgcctggg caagatgttt taaaagaaaa aaaaaaataa  13980
aactcaccaa ggccatggcg acgagcgttg gtttttttgtt cccttcctta gtatgcggcg  14040
cgcggcgatg ttcgaggagg ggcctccccc ctcttacgag agcgcgatgg ggatttctcc  14100
tgcggcgccc ctgcagcctc cctacgtgcc tcctcggtac ctgcaaccta caggggggag  14160
aaatagcatc tgttactctg agctgcagcc cctgtacgat accaccagac tgtacctggt  14220
ggacaacaag tccgcggacg tggcctccct gaactaccag aacgaccaca gcgatttttt  14280
gaccacggtg atccaaaaca acgacttcac cccaaccgag gccagcaccc agaccataaa  14340
cctggataac aggtcgaact ggggcggcga cctgaagacc atcttgcaca ccaacatgcc  14400
caacgtgaac gagttcatgt tcaccaactc ttttaaggcg cgggtgatgg tggcgcgcga  14460
gcagggggag gcgaagtacg agtgggtgga cttcacgctg cccgagggca actactcaga  14520
gaccatgact ctcgacctga tgaacaatgc gatcgtggaa cactatctga aagtgggcag  14580
gcagaacggg gtgaaggaaa gcgatatcgg ggtcaagttt gacaccagaa acttccgtct  14640
gggctgggac cccgtgaccg ggctggtcat gccgggggtc tacaccaacg aggcctttca  14700
tcccgacata gtgcttctgc ccggctgtgg ggtggacttc acccagagcc ggctgagcaa  14760
cctgctgggc attcgcaagc ggcagccttt ccaggagggt ttcaagatca cctatgagga  14820
tctgaagggg ggcaacattc ccgcgctcct tgatctggac gcctacgagg agagcttgaa  14880
acccgaggag agcgctggcg acagcggcga gagtggcgag gagcaagccg gcggcggtgg  14940
cggcgcgtcg gtagaaaacg aaagtacgcc cgcagtggcg gcggacgctg cggaggtcga  15000
gccggaggcc atgcagcagg acgcagagga gggcgcacag gagggcgcgc agaaggacat  15060
gaacgatggg gagatcaggg gagacacatt cgccacccgg ggcgaagaaa aagaggcaga  15120
ggcggcggcg gcggcgacgg cggaggccga aaccgaggtt gaggcagagg cagagcccga  15180
gaccgaagtt atggaagaca tgaatgatgg agaacgtagg ggcgacacgt tcgccacccg  15240
gggcgaagag aaggcggcgg aggcagaagc cgcggctgag gaggcggctg cggctgcggc  15300
caagactgag gctgcggcta aggctgaggt cgaagccaat gttgcggttg aggctcaggc  15360
tgaggaggag gcggcggctg aagcagttaa ggaaaaggcc caggcagagc aggaagagaa  15420
aaaacctgtc attcaacctc taaaagaaga tagcaaaaag cgcagttaca acgtcatcga  15480
gggcagcacc tttacccagt accgcagctg gtacctggcg tacaactacg gcgacccggt  15540
caagggggtg cgctcgtgga ccctgctctg cacgccggac gtcacctgcg gctccgagca  15600
gatgtactgg tcgctgccga acatgatgca agacccggtg accttccgct ccacgcggca  15660
ggttagcaac ttcccggtgg tgggcgccga actgctgccc gtgcactcca agagtttttta  15720
caacgagcag gccgtctact cccagctgat ccgccaggcc acctctctga cccacgtgtt  15780
caatcgcttt cccgagaacc agattttggc gcgcccgccg gcccccacca tcaccaccgt  15840
gagtgaaaac gttcctgccc tcacagatca cgggacgcta ccgctgcgca acagcatctc  15900
aggagtccag cgagtgacca ttactgacgc cagacgccgg acctgcccct acgtttacaa  15960
ggccttgggc atagtctcgc cgcgcgtcct ctccagtcgc actttttaaa acacatctac  16020
ccacacgttc caaaatcatg tccgtactca tctcacccag caacaacacc ggctgggggc  16080
tgcgcgcgcc cagcaagatg tttggagggg cgaggaagcg ctccgaccag caccctgtgc  16140
gcgtgcgcgg ccactaccgc gcgccctggg gagcgcacaa gcgcgggcgc acagggcgca  16200
ccactgtgga cgacgtcatt gactccgtag tggagcaagc gcgccactac acacccggcg  16260
cgccgaccgc ccccgccgtg tccaccgtgg accaggcgat cgaaagcgtg gtacagggcg  16320
```

-continued cgcggcacta tgccaacctt aaaagtcgcc gccgccgcgt ggcccgccgc catcgccgga 16380
gaccccgggc caccgccgcc gcgcgcctta ctaaggctct gctcaggcgc gccaggcgaa 16440
ctggccaccg ggccgccatg agggccgcac ggcgggctgc cgctgccgca agcgtcgtgg 16500
ccccgcgggc acgaaggcgc gcggccgctg ccgccgccgc cgccatttcc agcttggcct 16560
cgacgcggcg cggtaacata tactgggtgc gcgactcggt aaccggcacg cgggtacccg 16620
tgcgctttcg ccccccgcgg aattagcaca agacaacata cacactgagt ctcctgctgt 16680
tgtgtatccc agcggcgacc gtcagcagcg gcgacatgtc caagcgcaaa attaaagaag 16740
agatgctcca ggtcatcgcg ccggagatct atgggccccc gaagaaggag gaggatgatt 16800
acaagccccg caagctaaag cgggtcaaaa agaaaaagaa agatgatgat gacgaggcgg 16860
tggagtttgt ccgccgcatg gcacccaggc gccccgtgca gtggaagggc cggcgcgtgc 16920
agcgcgtttt gcgccccggc accgcggtgg tcttcacgcc cggcgagcgc tccacgcgca 16980
ctttcaagcg ggtgtacgat gaggtgtacg gcgacgagga cctgttggag caggccaacc 17040
agcgctttgg ggagtttgca tatgggaaac ggccccgcga gagtctaaaa gaggacctgc 17100
tggcgctacc gctggacgag ggcaatccca ccccgagtct gaagccggta accctgcaac 17160
aggtgctgcc tttgagcgcg cccagcgagc ataagcgagg gttgaagcgc gaaggcgggg 17220
acctggcgcc caccgtgcag ttgatggtgc ccaagcggca gaagctggag gacgtgctgg 17280
agaaaatgaa agtagagccc gggatccagc ccgagatcaa ggtccgcccc atcaagcagg 17340
tggcgcccgg cgtgggagtc cagaccgtgg acgttaggat tcccacggag gagatggaaa 17400
cccaaaccgc cactccctct tcggcggcca gcgccaccac cggcaccgct tcggtagagg 17460
tgcagacgga cccctggcta cccgccaccg ctgttgccgc cgccgccccc cgttcgcgcg 17520
ggcgcaagag aaattatcca gcggccagcg cgctcatgcc ccagtacgca ctgcatccat 17580
ccatcgtgcc cacccccggc taccgcgggt actcgtaccg cccgcgcaga tcagccggca 17640
ctcgcggccg ccgccgccgt gcgaccacaa ccagccgccg ccgtcgccgc cgccgccagc 17700
cagtgctgac cccgtgtct gtaaggaagg tggctcgctc ggggagcacg ctggtggtgc 17760
ccagagcgcg ctaccacccc agcatcgttt aaagccggtc tctgtatggt tcttgcagat 17820
atggccctca cttgtcgcct ccgcttcccg gtgccgggat accgaggaag aactcaccgc 17880
cgcagaggca tggcgggcag cggtctccgc ggcggccgtc gccatcgccg gcgcgcaaaa 17940
agcaggcgca tgcgcggcgg tgtgctgcct ctgctaatcc cgctaatcgc cgcggcgatc 18000
ggtgccgtac ccgggatcgc ctccgtggcc ctgcaggcgt cccagaaacg ttgactcttg 18060
caaccttgca agcttgcatt ttttggagga aaaaataaaa aaaaagtcta gactctcacg 18120
ctcgcttggt cctgtgacta ttttgtagaa aaaaagatgg aagacatcaa ctttgcgtcg 18180
ctggccccgc gtcacggctc gcgcccgttc atgggagact ggacagatat cggcaccagc 18240
aatatgagcg gtggcgcctt cagctggggc agtctgtgga gcggccttaa aaattttggt 18300
tccaccatta agaactatgg caacaaagcg tggaacagca gcacgggcca gatgctgaga 18360
gacaagttga aagagcagaa cttccaggag aaggtggcgc agggcctggc ctctggcatc 18420
agcggggtgg tggacatagc taaccaggcc gtgcagaaaa agataaacag tcatctggac 18480
ccccgtcctc aggtggagga aatgcctcca gcgatggaga cggtgtctcc cgagggcaaa 18540
ggcgaaaagc gcccgcggcc cgacagagaa gagaccctgg tgtcacacac cgaggagccg 18600
ccctcttacg aggaggcagt caaggccggc ctgcccacca ctcgccccat agcccccatg 18660
gccaccggtg tggtgggcca caggcaacac actcccgcaa cactagatct gcccccgccg 18720
tccgagccgc cgcgccagcc aaaggcggcg acggtgcccg ctccctccac ttccgccgcc 18780
aacagagtgc ccctgcgccg cgccgcgagc ggcccccggg cctcgcgagt tagcggcaac 18840
tggcagagca cactgaacag catcgtgggc ctgggagtga ggagtgtgaa gcgccgccgt 18900
tgctactgaa tgagcaagct agctaacgtg ttgtatgtgt gtatgcgtcc tatgtcgccg 18960
ccagaggagc tgttgagccg ccggcgccgt ctgcactcca gcgaatttca agatggcgac 19020
cccatcgatg atgcctcagt ggtcgtacat gcacatctcg ggccaggacg cttcggagta 19080
cctgagcccc gggctggtgc agttcgcccg cgccacagac acctacttca acatgagtaa 19140
caagttcagg aaccccactg tggcgcccac ccacgatgtg accacggacc ggtcgcagcg 19200
cctgacgctg cggttcatcc ccgtggatcg ggaggacacc gcctactctt acaaggcgcg 19260
gttcacgctg gccgtgggcg acaaccgcgt gctggacatg gcctccactt actttgacat 19320
caggggggtg ctggacaggg gccccacctt caagccctac tcgggtactg cctacaactc 19380
cctggccccc aagggcgctc ccaattcttg cgagtgggaa caagatgaac cagctcaggc 19440
agcaatagct gaagatgaag aagaacttga agaagaacaa gctcaggacg aacaggcgcc 19500
cactaagaaa acccatgtat acgcccaggc acctctttct ggtgaaaaaa ttactaagga 19560
tggtttgcaa ataggtgtgg atgccacaca ggcgggagat aaccctatat atgctgataa 19620
aacattccaa cccgaacctc agataggtga gtctcagtgg aacgaggctg atgccacagt 19680
agcaggaggc agagtcttaa aaaagaccac ccctatgaga ccttgctatg gatcctatgc 19740
caaacctact aatgccaatg gcggtcaagg gatcatggtg gccaatgatc agggagcgct 19800
tgaatctaaa gttgagatgc aatttttctc caccacaacg tctcttaatg taagggaagg 19860
tgaaaacaat cttcagccaa aagtagtgct atacagcgaa gatgttaact tggaatcccc 19920
tgacactcat ttgtcttaca aacctaaaaa ggatgacacc aactctaaaa tcatgttggg 19980
tcagcaagcc atgcccaaca gacccaacct cattgctttt agggacaact ttattggact 20040
tatgtactac aacagcacag gcaacatggg agtgctggca ggacaggcct cccagctaaa 20100
cgctgtggta gacttgcaag acagaaacac agagctgtca taccaactga tgcttgattc 20160
cattggagac agatcaagat acttttccat gtggaaccag gcagtggaca gctatgaccc 20220
agatgtcaga atcattgaaa accatggggt tgaagatgag ctgcccaact attgctttcc 20280
cctgggcggt attggaatta cagacacata ccagtgcata aaaccaaccg cagctgctaa 20340
taacactaca tggtctaagg atgaagaatt tagtgatcgc aatgaaatag gggtgggaaa 20400
caacttcgcc atggagatca acatccaggc caacctctgg aggaacttcc tctatgcgaa 20460
cgtggggctc tacctgccag acaagctcaa gtacaacccc accaacgtgg acatctctga 20520
caaccccaac acctatgact acatgaacaa gcgtgtggtg gctcccggcc tggtggactg 20580
ctttgtcaat gtgggagcca ggtggtccct ggactacatg gacaacgtca acccccttcaa 20640
ccaccaccgc aatgcgggtc tgcgctaccg ctccatgatc ctgggcaacg ggcgctacgt 20700
gcccttccac attcaggtgc cccagaagtt ctttgccatc aagaacctcc tcctcctgcc 20760
gggctcctac acttacgagt ggaacttcag gaaggatgtc aacatggtcc tgcagagctc 20820
tctgggcaat gaccttaggg tggacggggc cagcatcaag tttgacagcg tcaccctcta 20880
tgctaccttc ttccccatgg ctcacaacac cgcctccacg ctcgaggcca tgctgaggaa 20940
cgacaccaac gaccagtcct tcaatgacta cctctctggg gccaacatgc tctaccccat 21000
ccccgccaag gccaccaacg tgcccatctc cattccctct cgcaactggg ccgccttcag 21060
aggctgggcc tttacccgcc ttaagaccaa ggaaacccccc tccctgggct cgggttttga 21120
cccctacttt gtctactcgg gatccatccc ctacctggat ggcaccttct acctcaacca 21180
cacttttaag aagatatcca tcatgtatga ctcctccgtc agctggccgg gcaatgaccg 21240
cctgctcacc cccaatgagt tcgaggtcaa gcgcgccgtg gacggcgagg gctacaacgt 21300
ggcccagtgc aacatgacca aggactggtt cctggtgcag atgctggcca actacaacat 21360
aggctaccag ggcttctaca tcccagagag ctacaaggac aggatgtact ccttcttcag 21420
aaatttccaa cccatgagca ggcaggtggt ggacgagacc aaatacaagg actatcaggc 21480
cattggcatc actcaccagc acaacaactc gggattcgtg ggctacctgg ctcccaccat 21540
gcgcgagggg caggcctacc ccgccaactt cccctacccg ttgataggca aaaccgcggt 21600
cgacagcgtc acccagaaaa agttcctctg cgaccgcacc ctctggcgca tccccttctc 21660
tagcaacttc atgtccatgg gtgcgctcac ggacctgggc cagaacctgc tctatgccaa 21720
ctccgcccat gcgctggaca tgacttttga ggtggacccc atggacgagc ccacccttct 21780
ctatattgtg tttgaagtgt tcgacgtggt cagagtgcac cagccgcacc gcggtgtcat 21840
cgagaccgtg tacctgcgca cgcccttctc ggccggcaac gccaccacct aaggagacag 21900
cgccgccgcc tgcatgacgg gttccaccga gcaagagctc agggccatcg ccagagacct 21960
gggatgcgga ccctattttt tgggcaccta tgacaaacgc ttcccgggct tcatctcccg 22020
agacaagctc gcctgcgcca tcgtcaacac ggccgcgcgc gagaccgggg gcgtgcactg 22080
gctggccttt ggctgggacc cgcgctccaa aacctgctac ctcttcgacc cctttggctt 22140
ctccgatcag cgcctcagac agatctatga gtttgagtac gaggggctgc tgcgccgcag 22200
cgcgcttgcc tcctcgcccg accgctgcat caccccttgag aagtccaccg agaccgtgca 22260
ggggccccac tcggccgcct gcggtctctt ctgctgcatg tttttgcacg cctttgtgcg 22320
ctggccccag agtcccatgg atcgcaaccc caccatgaac ttgctcaagg gagtgcccaa 22380
cgccatgctc cagagccccc aggtccagcc caccctgcgc cacaaccagg aacagctcta 22440
ccgcttcctg gagcgccact cccccctactt ccgcagtcac agcgcgcaca tccgggggggc 22500 cacctctttc tgccacttgc aagaaaacat gcaagacgga aaatgatgta cagctcgctt 22560
tttaataaat gtaaagactg tgcactttat ttatacacgg gctctttctg gttatttatt 22620
caacaccgcc gtcgccatct agaaatcgaa agggttctgc cgcgcgtcgc cgtgcgccac 22680
gggcagagac acgttgcgat actggaagcg gctcgcccac ttaaactcgg gcaccaccat 22740
gcggggcagt ggttcctcgg ggaagttctc gccccacagg gtgcgggtca gctgcagcgc 22800
gctcaggagg tcgggagccg agatcttgaa gtcgcagttg ggcccggaac cctgcgcgcg 22860
cgagttgcgg tacacggggt tgcagcactg gaacaccagc agggccggat tatgcacgct 22920
ggccagcagg ctctcgtcgc tgatcatgtc gctgtccaga tcctccgcgt tgctcagggc 22980
gaacggggtc atcttgcaga cctgcctgcc caggaaaggc ggcagcccgg gcttgccgtt 23040
gcagtcgcag cgcaggggca tcagcaggtg cccgcggccc gactgcgcct gcgggtacag 23100
cgcgcgcatg aaggcttcga tctgcctgaa agccacctgc gtcttggctc cctccgaaaa 23160
gaacatccca caggacttgc tggagaactg gttcgcggga cagctggcat cgtgcaggca 23220
gcagcgcgcg tcggtgttgg cgatctgcac cacgttgcga ccccaccggt tcttcactat 23280
cttggccttg gaagcctgct ccttcagcgc gcgctggccg ttctcgctgg tcacatccat 23340
ctctatcacc tgctccttgt tgatcatgtt tgtaccgtgc agacacttca ggtcgccctc 23400

-continued

```
cgtctgggtg cagcggtgct cccacagcgc gcaaccggtg ggctcccaat ttttgtgggt  23460
cacccccgcg taggcctgca ggtaggcctg caagaagcgc cccatcatgg ccacaaaggt  23520
cttctggctc gtaaaggtca gctgcaggcc gcgatgctct tcgttcagcc aggtcttgca  23580
gatggcggcc agcgcctcgg tctgctcggg cagcatccta aaatttgtct tcaggtcgtt  23640
atccacgtgg tacttgtcca tcatggcgcg cgccgcctcc atgcccttct cccaggcgga  23700
caccatgggc aggcttaggg ggtttatcac ttccaccggc gaggacaccg tactttcgat  23760
ttcttcttcc tccccctctt cccggcgcgc gcccacgctg ctgcgcgctc tcaccgcctg  23820
caccaagggg tcgtcttcag gcaagcgccg caccgagcgc ttgccgccct tgacctgctt  23880
aatcagcacc ggcgggttgc tgaagcccac catggtcagc gccgcctgct cttcttcgtc  23940
ttcgctgtct accactatct ctggggaagg gcttctccgc tctgcggcgg cgcgcttctt  24000
ttttttcttg ggagcggccg tgatggagtc cgccacggcg acggaggtcg agggcgtggg  24060
gctgggggtg cgcggtacca gggcctcgtc gccctcggac tcttcctctg actccaggcg  24120
gcggcggagt cgcttctttg ggggcgcgcg cgtcagcggc ggcggagacg gggacgggga  24180
cggggacggg acgccctcca cagggggtgg tcttcgcgca gacccgcggc cgcgctcggg  24240
ggtcttctcg agctggtctt ggtcccgact ggccattgta tcctcctcct cctaggcaga  24300
gagacataag gagtctatca tgcaagtcga gaaggaggag agcttaacca ccccctctga  24360
gaccgccgat gcgcccgccg tcgccgtcgc ccccgctgcc gccgacgcgc ccgccacacc  24420
gagcgacacc cccgcggacc cccccgccga cgcacccctg ttcgaggaag cggccgtgga  24480
gcaggacccg ggctttgtct cggcagagga ggatttgcga gaggaggagg ataaggagaa  24540
gaagccctca gtgccaaaag atgataaaga gcaagacgag cacgacgcag atgcacacca  24600
gggtgaagtc gggcgggggg acggagggca tgacggcgcc gactacctag acgaagggaa  24660
cgacgtgctc ttgaagcacc tgcatcgtca gtgcgccatt gtttgcgacg ctctgcagga  24720
gcgcagcgaa gtgcccctca gcgtggcgga ggtcagccac gcctacgagc tcagcctctt  24780
ctcccccggg gtgccccccc gccgccgcga aaacggcaca tgcgagccca acccgcgcct  24840
caacttctac cccgcctttg tggtacccga ggtcctggcc acctatcaca tcttctttca  24900
aaattgcaag atccccctct cgtgccgcgc caaccgtagc cgcgccgata agatgctggc  24960
cctgcgccag ggcgaccaca tacctgatat cgccgctttg gaagatgtac caaagatctt  25020
cgagggtctg ggtcgcaacg agaagcgggc agcaaactct ctgcaacagg aaaacagcga  25080
aaatgagagt cacaccgggg tactggtgga gctcgagggc gacaacgccc gcctggcggt  25140
ggtcaagcgc agcatcgagg tcacccactt tgcctacccc gcgctaaacc tgccccccaa  25200
agtcatgaac gcggccatgg acgggctgat catgcgccgc ggccggcccc tcgctccaga  25260
tgcaaacttg catgaggaga ccgaggacgg ccagcccgtg gtcagcgacg agcagctggc  25320
gcgctggctg gagaccgcgg accccgccga actggaggag cggcgcaaga tgatgatggc  25380
cgtggtgctg gtcaccgtag agctggagtg tctgcagcgc ttcttcggcg accccgagat  25440
gcagagaaag gtcgaggaga ccctgcacta caccttccgc cagggctacg tgcgccaggc  25500
ttgcaagatc tccaacgtgg agctcagcaa cctggtgtcc tacctgggca tcttgcatga  25560
gaaccgcctc gggcagagcg tgctgcactc caccctgcgc ggggaggcgc gccgcgacta  25620
cgtgcgcgac tgcgtttacc tcttcctctg ctacacctgg cagacggcca tgggggtctg  25680
gcagcagtgc ctggaggagc gcaacctcaa ggagctggag aagctcctgc agcgcgcgct  25740
caaagatctc tggacgggct acaacgagcg ctcggtggcc gccgcgctgg ccgacctcat  25800
```

```
cttccccgag cgcctgctca aaaccctcca gcaggggctg cccgacttca ccagccaaag  25860
catgttgcaa aacttcagga actttatcct ggagcgttct ggcatcctac ccgccacctg  25920
ctgcgccctg cccagcgact ttgtccccct cgtgtaccgc gagtgccccc cgccgctgtg  25980
gggtcactgc tacctgttcc aactggccaa ctacctgtcc taccacgcgg acctcatgga  26040
ggactccagc ggcgaggggc tcatggagtg ccactgccgc tgcaacctct gcacgcccca  26100
ccgctccctg gtctgcaaca cccaactgct cagcgagagt cagattatcg gtaccttcga  26160
gctacagggt ccgtcctcct cagacgagaa gtccgcggct ccggggctaa aactcactcc  26220
ggggctgtgg acttccgcct acctgcgcaa atttgtacct gaagactacc acgcccacga  26280
gatcaggttt tacgaagacc aatcccgccc gcccaaggcg gagctgaccg cctgcgtcat  26340
cacccagggc gagatcctag gccaattgca agccatccaa aaagcccgcc aagacttttt  26400
gctgaagaag ggtcgggggg tgtatctgga cccccagtcg ggtgaggagc tcaacccggt  26460
tcccccgctg ccgccgccgc gggaccttgc ttcccaggat aagcatcgcc atggctccca  26520
gaaagaagca gcagcggccg ccactgccgc caccccacat gctggaggaa gaggaggaat  26580
actgggacag tcaggcagag gaggtttcgg acgaggagga gccggagacg gagatggaag  26640
agtgggagga ggacagctta gacgaggagg cttccgaagc cgaagaggca gacgcaacac  26700
cgtcaccctc ggccgcagcc ccctcgcagg cgcccccgaa gtccgctccc agcatcagca  26760
gcaacagcag cgctataacc tccgctcctc caccgccgcg acccacggcc gaccgcagac  26820
ccaaccgtag atgggacacc accggaaccg ggccggtaag gtcctccggg agaggcaagc  26880
aagcgcagcg ccaaggctac cgctcgtggc gcgctcacaa gaacgccata gtcgcttgct  26940
tgcaagactg cgggggggaac atctccttcg cccgccgctt cctgctcttc caccacggtg  27000
tggccttccc ccgtaacgtc ctgcattact accgtcatct ctacagcccc tactgcggcg  27060
gcagtgagcc agagacggtc ggcggcggcg gcggcgcccg tttcggcgcc taggaagacc  27120
cagggcaaga cttcagccaa gaaactcgcg gcggccgcgg cgaacgcggt cgcgggggcc  27180
ctgcgcctga cggtgaacga acccctgtcg acccgcgaac tgaggaaccg aatcttcccc  27240
actctctatg ccatcttcca gcagagcaga gggcaggatc aggaactgaa agtaaaaaac  27300
aggtctctgc gctccctcac ccgcagctgt ctgtatcaca agagcgaaga ccagcttcgg  27360
cgcacgctgg aggacgctga ggcactcttc agcaaatact gcgcgctcac tcttaaggac  27420
tagctccgcg cccttctcga atttaggcgg gaacgcctac gtcatcgcag cgccgccgtc  27480
atgagcaagg acattcccac gccatacatg tggagctatc agccgcagat gggactcgcg  27540
gcgggcgcct cccaagacta ctccacccgc atgaactggc tcagtgccgg cccacacatg  27600
atctcacagg ttaatgatat ccgcacccat cgaaaccaaa tattggtgga gcaggcggca  27660
attaccacca cgccccgcaa taatcccaac cccagggagt ggcccgcgtc cctggtgtat  27720
caggaaattc ccggccccac caccgtacta cttccgcgtg attcccaggc cgaagtccaa  27780
atgactaact caggggcaca gctcgcgggc ggctgtcgtc acagggtgcg gcctcctcgc  27840
cagggtataa ctcacctgga gatccgaggc agaggtattc agctcaacga cgagtcggtg  27900
agctcctcgc tcggtctcag acctgacggg accttccaga tagccggagc cggccgatct  27960
tccttcacgc cccgccaggc gtacctgact ctgcaaagct cgtcctcggc gccgcgctcg  28020
ggcggcatcg ggactctcca gttcgtgcag gagtttgtgc cctcggtcta cttcaacccc  28080
ttctcgggct ctcccggtcg ctacccggac cagttcatct cgaactttga cgccgcgagg  28140
```

gactcggtgg acggctacga ctgaatgtcg ggtggacccg gtgcagagca acttcgcctg 28200
aagcacctcg accactgccg ccgccctcag tgctttgccc gctgtcagac cggtgagttc 28260
cagtactttt ccctgcccga ctcgcacccg gacggcccgg cgcacggggt gcgctttttc 28320
atcccgagtc aggtgcgctc taccctaatc agggagttta ccgcccgtcc cctactggcg 28380
gagttggaaa aggggccttc tatcctaacc attgcctgca tctgctctaa ccctggattg 28440
caccaagatc tttgctgtca tttgtgtgct gagtataata aaggctgaga tcagaatcta 28500
ctcgggctcc tgtcgccatc ctgtcaacgc caccgtccaa gcccggcccg atcagcccga 28560
ggtgaacctc acctgcggtc tgcaccggcg cctgaggaaa tacctagctt ggtactacaa 28620
cagcactccc tttgtggttt acaacagctt tgaccaggac ggggtctcac tgagggataa 28680
cctctcgaac ctgagctact ccatcaggaa gaacagcacc ctcgagctac ttcctcctta 28740
cctgcccggg acttaccagt gtgtcaccgg tccctgcacc cacacccacc tgttgatcgt 28800
aaacgactct cttccgagaa cagacctcaa taactcctct tcgcagttcc ccagaacagg 28860
aggtgagctc aggaaacccc gggtaaagaa gggtggacga gagttaacac ttgtggggtt 28920
tctggtgtat gtgacgctgg tggtggctct tttgattaag gcttttcctt ccatgtctga 28980
actctccctc ttcttttatg aacaactcga ctagtgctaa cgggacccta cccaacgaat 29040
cgggattgaa tatcggtaac caggttgcag tttcactttt gattaccttc atagtcctct 29100
tcctgctagt gctgtcgctt ctgtgcctgc ggatcggggg ctgctgcatc cacgtttata 29160
tctggtgctg gctgtttaga aggttcggag accatcgcag gtagaataaa catgctgctg 29220
cttaccctct ttgtcctggc gctggccgcc agctgccaag ccttttccga ggctgacttt 29280
atagagcccc agtgtaatgt gacttttaaa gcccatgcac agcgttgtca tactataatc 29340
aaatgtgcca ccgaacacga tgaatacctt atccagtata aagataaatc acacaaagtg 29400
gcacttgttg acatctggaa acccgaagac cctttggaat acaatgtgac cgttttccag 29460
ggtgacctct tcaaaattta caattacact ttcccatttg accagatgtg tgactttgtc 29520
atgtacatgg aaaagcagca caagctgtgg cctccgactc cccagggctg tgtggaaaat 29580
ccaggctctt tctgcatgat ctctctctgt gtaactgtgc tggcactaat actcacgctt 29640
ttgtatatca gatttaaatc aaggcaaagc ttcattgatg aaaagaaaat gccttaatcg 29700
ctttcacgct tgattgctaa caccgggttt ttatccgcag aatgattgga atcaccctac 29760
taatcacctc cctccttgcg attgcccatg ggttggaacg aatcgaagtc cctgtggggg 29820
ccaatgttac cctggtgggg cctgtcggca atgctacatt aatgtgggaa aaatatacta 29880
aaaatcaatg ggtctcttac tgcactaaca aaaatagcca caagcccaga gccatctgcg 29940
atgggcaaaa tctaaccttg attgatgttc aattgctgga tgcgggctac tattatgggc 30000
agctgggtac aatgattaat tactggagac cccacagaga ttacatgctc cacgtagtaa 30060
agggtcccct tagcagccca cccactacca cctctactac cccactacc accactactc 30120
ccaccaccag cactgccgcc cagcctcctc atagcagaac aaccactttt atcaattcca 30180
agtcccactc cccccacatt gccggcgggc cctccgcctc agactccgaa accaccgaga 30240
tctgcttctg caaatgctct gacgccattg cccaggattt ggaagatcac gaggaagatg 30300
agcatgactt cgcagatgca tgccaggcat cagagccaga agcgctgccg gtggccctca 30360
aacagtatgc agaccccac accacccccg accttcctcc accttcccag aagccaagtt 30420
tcctggggga aaatgaaact ctgcctctct ccatactcgc tctgacatct gttgctatgt 30480
tgaccgctct gctggtgctt ctatgctcta tatgctacct gatctgctgc agaaagaaaa 30540

```
aatctcacgg ccatgctcac cagcccctca tgcacttccc ttaccctcca gagctgggcg  30600
accacaaact ttaagtctgc agtaactatc tgcccatccc ttgtcagtcg acagcgatga  30660
gccccactaa tctaacggcc tctggactta caacatcgtc tcttaatgag accaccgctc  30720
ctcaagacct gtacgatggt gtctccgcgc tggttaacca gtgggatcac ctgggcatat  30780
ggtggctcct cataggagca gtgaccctgt gcctaatcct ggtctggatc atctgctgca  30840
tcaaaagcag aagacccagg cggcggccca tctacaggcc ctttgtcatc acacctgaag  30900
atgatgatga caccacttcc aggctgcaga ggctaaagca gctactcttc tcttttacag  30960
catggtaaat tgaatcatgc ctcgcatttt catctacttg tctctccttc cactttttct  31020
gggctcttct acattggccg ctgtgtccca catcgaggta gactgcctca cgcccttcac  31080
agtctacctg cttttcggct ttgtcatctg caccttttgtc tgcagcgtta tcactgtagt  31140
gatctgcttc atacagtgca tcgactacgt ctgcgtgcgg gtggcttact ttagacacca  31200
cccccagtat cgcaacaggg acatagcggc tctcctaaga cttgtttaaa atcatggcca  31260
aattaactgt gattggtctt ctgatcatct gctgcgtcct agccgcgatt gggactcaag  31320
ctcctaccac caccagcgct cccagaaaga gacatgtatc ctgcagcttc aagcgtccct  31380
ggaatatacc ccaatgcttt actgatgaac ctgaaatctc tttggcttgg tacttcagcg  31440
tcaccgccct tcttatcttc tgcagtacgg ttattgccct tgccatctac ccttcccttg  31500
acctgggctg gaatgctgtc aactctatgg aatatcccac cttcccagaa ccagacctgc  31560
cagacctggt tgttctaaac gcgtttcctc ctcctgctcc cgttcaaaat cagtttcgcc  31620
ctccgtcccc cacgcccact gaggtcagct actttaatct aacaggcgga gatgactgaa  31680
aacctagacc tagaaatgga cggtctctgc agcgagcaac gcacactaga gaggcgccgg  31740
caaaaagagc tcgagcgtct taaacaagag ctccaagacg cggtggccat acaccagtgc  31800
aaaaaaggtg tcttctgtct ggtaaaacag gccacgctca cctatgaaaa aacaggtgac  31860
acccaccgcc taggatacaa gctgcccaca cagcgccaaa agttcgccct catgataggc  31920
gaacaaccca tcaccgtgac ccagcactcc gtggagacag aaggctgcat acatgctccc  31980
tgtaggggcg ctgactgcct ctacaccttg atcaaaaccc tctgcggtct cagagacctt  32040
atccctttca attaatcata actgtaatca ataaaaaatc acttacttga aatctgatag  32100
caagcctctg tccaattttt tcagcaacac ttccttcccc tcctcccaac tctggtactc  32160
taggcgcctc ctagctgcaa acttcctcca cagtctgaag ggaatgtcag attcctcctc  32220
ctgtccctcc gcacccacga tcttcatgtt gttgcagatg aaacgcgcga gatcgtctga  32280
cgagaccttc aaccccgtgt acccctacga taccgagatc gctccgactt ctgtcccttt  32340
ccttacccct ccctttgtgt catccgcagg aatgcaagaa aatccagctg gggtgctgtc  32400
cctgcacttg tcagagcccc ttaccaccca caatggggcc ctgactctaa aaatgggggg  32460
cggcctgacc ctggacaagg aagggaatct cacttcccaa aacatcacca gtgtcgatcc  32520
ccctctcaaa aaaagcaaga acaacatcag ccttcagacc gccgcacccc tcgccgtcag  32580
ctccggggcc ctaacacttt ttgccactcc cccccctagcg gtcagtggtg acaaccttac  32640
tgtgcagtct caggcccctc tcactttgga agactcaaaa ctaactctgg ccaccaaagg  32700
acccctaact gtgtccgaag gcaaacttgt cctagaaaca gaggctcccc tgcatgcaag  32760
tgacagcagc agcctgggcc ttagcgttac ggccccactt agcattaaca atgacagcct  32820
aggactagat ctgcaggcac ccattgtctc tcaaaatgga aaactggctc taaatgtagc  32880
```

-continued

```
aggcccccta gctgtggcca atggcattaa tgctttgaca gtaggcacag gcaaaggtat  32940
tggtctaaat gaaaccagca ctcacttgca agcaaagttg gtcgcccccc taggctttga  33000
taccaatggc aacattaagc taagcgttgc aggaggcatg agactaaata atgacacact  33060
tatactagat gtaaactacc catttgaagc tcaaggccaa ctaagtctaa gagtgggcca  33120
gggtccgctg tatgtagatt ctagcagcca taacctgacc attagatgcc ttagaggatt  33180
atacataaca tcgtctaata accaaaccgg tctagaggcc aacataaaac taacaaaagg  33240
ccttgtctat gatggaaatg ccatagcagt caatgttggt caaggattgc aatacagcac  33300
tactgccaca tcggaaggtg tgtatcctat acagtctaag ataggtttgg gaatggaata  33360
tgataccaac ggagccatga tgacaaaact aggctctgga ctaagctttg acaattcagg  33420
agccattgta gtgggaaaca aaaatgatga caggcttact ctgtggacta caccagaccc  33480
atctcctaac tgtagaattt attctgaaaa agatactaaa ctaaccttgg tgctgactaa  33540
gtgtggcagc caaatcctag gcacagtatc tgcccttgct gtcagaggca gccttgcgcc  33600
catcactaat gcatccagca tagtccaaat atttctaaga tttgatgaaa atggactatt  33660
gatgagcaac tcatcgctag acggtgatta ctggaattac agaaatgggg actccactaa  33720
tagcacacca tatacaaatg cagtaggctt tatgcctaat ctagcagcct atcctaaagg  33780
tcaggctaca gctgcaaaaa gcagtattgt aagccaggta tacatggatg gtgacactac  33840
taaacctata acactaaaaa taaacttcaa tggcattgat gaaacaacag aaaatacccc  33900
tgttagtaaa tattccatga cattctcatg gagctggccc accgcaagct acataggcca  33960
cacttttgca acaaactctt ttactttctc ctacatcgcc caagaataaa gaaagcacag  34020
agatgcttgt tttgatttca aaattgtgtg cttttattta ttttcagctt acagtatttc  34080
cagtagtcat tcgaataaag cttaatcaaa ctgcatgaga acccttccac atagcttaaa  34140
ttagcaccag tgcaaatgga gaaaattcaa catacctttt ttatccagat atcagagaac  34200
tctagtggtc agttttcccc caccctccca gctcacagaa tacacagtcc tttccccccg  34260
gctggcttta aacaacacta tctcattggt aacagacata ttcttaggtg taataatcca  34320
cacggtctct tggcgggcca agcgctggtc ggtgatgtta ataaactccc caggcagctc  34380
tttcaagttc acgtcgctgt ccaactgctg aagcgctcgc ggctccgact gcgcctctag  34440
cggaggcaac ggcaacaccc gatccttgat ctataaagga gtagagtcat aatcccccat  34500
aagaataggg cggtgatgca gcaacaaggc gcgcagcaac tcctgccgcc gcctctccgt  34560
acgacaggaa tgcaacggcg tggtggtctc ctccgcgata atccgcaccg ctcgcagcat  34620
cagcatcctc gtcctccggg cacagcagcg catcctgatc tcactgagat cggcgcagta  34680
agtgcagcac aaaaccaaga tgttatttaa gatcccacag tgcaaagcac tgtacccaaa  34740
gctcatggcg ggaaggacag cccccacgtg accatcatac cagatcctta ggtaaatcaa  34800
atgacgacct ctcataaaca cgctggacat gtacatcacc tccttgggca tgcgctgatt  34860
caccacctct cgataccaca agcatcgctg attaattaaa gacccctcaa gcaccatcct  34920
gaaccaggaa gccagcacct gaccccccgc caggcactgc agggaccccg gtgaattgca  34980
gtggcagtga agactccagc gctcgtagcc gtgaaccata gagccggtca ttatatccac  35040
attggcacaa cacaaacaca ctttcataca ctttttcatg attagcagct cctctctagt  35100
caggaccata tcccaaggaa tcacccactc ttgaatcaag gtaaatccca cacagcaggg  35160
caggcctctc acataactca cgttatgcat agtgagcgtg tcgcaatctg gaaataccgg  35220
atgatcttcc atcaccgaag ctcgcgtctc cgtctcaaag ggaggtaaac ggtccctcgt  35280
```

```
gtagggacag tggcgggata atcgagatcg tgttgaacgt agagtcatgc caaagggaac  35340
agcggacgta ctcatatttc ctccagcaga accaagtgcg cgcgtggcag ctatccctgc  35400
gtcttctgtc tcgccgcctg ccccgctcgg tgtagtagtt gtaatacagc cactccctca  35460
gaccgtcaag gcgctccctg gcgtccggat ctataacaac accgtcctgc agcgccgccc  35520
tgatgacatc caccaccgta gagtatgcca agcccagcca ggaaatgcat tcactttgac  35580
agcgagagat aggaggagcg ggaagagatg gaagaaccat gatagtaaaa gacttttatt  35640
ccaatcgatc ctctacaatg tcaaagtgta gatctataag atgacactgg tctcctccgc  35700
tgagtcgatc aaaaataaca gctaaaccac aaacaacacg attggtcaaa tgctccacaa  35760
gggcttgcag cataaaatcg cctcgaaagt ccaccgcaag cataacatca aagccaccgc  35820
ccctatcatg atctataata aaaaccccac agctatccac cagacccata aagttttcat  35880
ctctccatcg tgaaaaaata tttacaagct cctcctttaa atcacctcca accaattgaa  35940
aaagttgagc caaaccgccc tccaccttca ttttcagcaa gcgcatcatg attgcaaaaa  36000
ttcaggctcc tgagacacct gtataagatt gagaagcgga acgttaacgt caatgtttcg  36060
ctcgcgaaga tcgcgcctca gtgcaagcat gatataatcc cacaggtcgg agcggatcag  36120
cgaggacatc tccccgccag gaaccaactc aacggagcct atgctgatta taatacgcat  36180
attcggggct atgctgacca gcacggcccc caaataggcg tactgcatag gcggcgacaa  36240
aaagtgaaca gtttgggtta aaaaatcagg caaacagtcg cgcaaaaaag caagaacatc  36300
ataaccatgc tcatgcaaat agatgcaagt aagctcagga acgaccacag aaaaatgcac  36360
aatttttctc tcaaacatga ctgcgagccc tgcaaaaaat aaaaaagaaa cattacacaa  36420
gagtagcctg tcttacgatg ggatagacta ctctaaccaa cataagacgg gccacaacat  36480
cgcccgcgtg gccataaaaa aaattgtccg tgtgattaaa aagaagcaca gatagctggc  36540
cagtcatatc cggagtcatc acgtgtgaac ccgtgtagac ccccgggttg gacacatcgg  36600
ccaaacaaag aaagcggcca atgtacccag gaggaatcat aacactaaga cgaagataca  36660
acagaataac cccatgaggg ggaataacaa agttagtagg tgaataaaaa cgataaacac  36720
ccgaaactcc ctcctgcgta ggcaaaatag caccctcccc ttccaaaaca acatatagcg  36780
cttccacagc agccatgaca aaagactcaa aacactcaaa agactcagtc ttaccaggaa  36840
aataaaagca ctctcacagc accagcacta atcagagtgt gaagagggcc aagtgccgaa  36900
cgagtatata taggaataaa aaatgacgta aatgtgtaaa ggtcagaaaa cgcccagaaa  36960
aatacacaga ccaacgcccg aaacgaaaac ccgcgaaaaa atacccagaa cttcctcaac  37020
aaccgccact tccggtttct cacggtacgt cacttccgca agaaaagcaa aactacattt  37080
cccacatgtg taaaaacgaa accccgcccc ttgtaactgc ccacaactta catcatcaaa  37140
acataaactc ctacgtcacc cgccccgcct ctccccgccc acctcattat catattggcc  37200
acaatccaaa ataaggtata ttattgatga tg                                37232
```

<210> SEQ ID NO 23
<211> LENGTH: 37213
<212> TYPE: DNA
<213> ORGANISM: Gorilla beringei beringei

<400> SEQUENCE: 23

```
ataatatacc ttattttgga ttgtggccaa tatgataatg aggtgggcgg ggagaggcgg     60
ggcgggtgac gtaggacgcg cgagtagggt tgggaggtgt ggcggaagtg tggcatttgc    120
```

```
aagtgggagg agctcacatg caagcttccg tcgcggaaaa tgtgacgttt ttgatgagcg    180
ccgcctacct ccggaagtgc caattttcgc gcgcttttca ccggatatcg tagtaatttt    240
gggcgggacc atgtaagatt tggccatttt cgcgcgaaaa gtgaaacggg gaagtgaaaa    300
ctgaataata gggcgttagt catagcgcgt aatatttacc gagggccgag ggactttgac    360
cgattacgtg gaggactcgc ccaggtgttt tttacgtgaa tttccgcgtt ccgggtcaaa    420
gtctccgttt ttattgtcac cgtcatttga cgcggagggt atttaaaccc gctgcgctcc    480
tcaagaggcc actcttgagt gccagcgaga agagttttct cctctgctcc gcttcggtga    540
tcgaaaaatg agacacatag cctgcactcc gggtcttttg tccggtcggg cggcggccga    600
gcttttggac gctttgatca atgatgtcct aagcgatgat tttccgtcta ctacccactt    660
tagcccacct actcttcacg aactgtacga tctggatgta ctggtggatg tgaacgatcc    720
caacgaggag gcggtttctg cgtttttttcc cgagtctgcg ctgttggccg ctcaggaggg    780
atttgaccta cacactccgc cgcctatttt agagtctccg ctgccggagc ccagtggtat    840
accttatatg cctgaactgc ttcccgaagt ggtagacctg acctgccacg agcctggctt    900
tccgcccagc gacgatgagg gtgagccttt tgttttagac tttgctgaga tacctgggca    960
cggttgcagg tcttgtgcat atcatcagag ggttaccgga gaccccgagg ttaagtgttc   1020
gctgtgctat atgaggatga cctcttcctt tatctacagt aagtttttgt ctaggtgggc   1080
ttttgggtag gtgggttttg tgtcagaaca ggtgtaaacg ttgcttgtgt tttttgtacc   1140
tgtaggtccg gtgtccgagc cagacccgga gcccgaccgc gatcccgagc cggatcccga   1200
gcctcctcgc aggacaagga aactaccttc cattctgtgc aagtctcaga cacctgtaag   1260
gaccagcgag gcagacagca ccgactctgg cacttctacc tctcccccctg aaattcaccc   1320
agtggttcct ctgggtatac ataaacctgt tgctgttaaa gtttgcgggc gacgccctgc   1380
agtacagtgc attgaggact tgcttcacga tcccgaggaa cctttggact tgagccttaa   1440
acgccctagg caataaaccc cacctaagta ataaacccca cctaagtaat aaaccctgcc   1500
gcccttggtt attgagatga cgcccaatgt ttgcttttga atgacttcat gtgtgtaata   1560
aaagtgagtg tgatcatagg tctcttgttt gtctgggcgg ggcttaaggg tatataagtc   1620
tcttggggct aaacttggtt acacttgacc ccaatggagg cgtgggggtg cttggaggag   1680
tttgcggacg tgcgccgttt gctggacgag agctctagca atacctatac tatttggagg   1740
tatctgtggg gctctactca ggccaagttg gtttccagaa ttaagcagga ttacaagtgc   1800
gattttgaag agctttttag ttcctgcggt gagcttttgc aatccttgaa tctgggccat   1860
caggctattt tccaggaaaa ggttctctcg actttggatt tttccactcc cgggcgcacc   1920
gccgcttgtg tggcttttgt gtcttttgtg caagataaat ggagcgagga gacccacctg   1980
agtcacggct acgtactgga tttcatggcg atggctcttt ggagggctca caacaaatgg   2040
aagattcaga aggaactgta cggttccgcc ctacgtcgtc cacttctgtc gcgacagggg   2100
ctgaggtttc ccgaccatcg gcagcatcag aatctggaag acgagtcgga ggagcgagcg   2160
gaggagaaga tcagcttgag agccggcctg gaccctcctc aggaggaatg aatctcccgc   2220
aggtggttga cctgtttcca gaactgagac gggtcctgac tatcagggag gatggtcagt   2280
ttgtgaagaa gtttaagagg gatcggggtg agggagatga tgaggcggct agcaatttag   2340
cttttagtct gatgactcgc caccgaccgg aatgtattac ctatcagcag attaaggaga   2400
gttgtgccaa cgagctggat cttttgggtc agaagtatag catagaacag cttaccactt   2460
actggcttca gcctggggat gattgggaag aggcgatcag ggtgtatgca aaggtggccc   2520
```

tgcggcccga ttgcaagtat aagattacta agttggttaa tattagaaac tgctgctata 2580
tttctgggaa cggggccgaa gtggagatag atactcagga cagggtggct tttaggtgtt 2640
gcatgataaa catgtggccc gggatactgg ggatggatgg ggtggtattc atgaatgtga 2700
ggtttacggg ccccaacttt aatggcacgg tgttcatggg caacaccaac ttgctcctgc 2760
atggtgcgag tttctatggg tttaataaca cctgtataga ggcctggacc gatgtaaagg 2820
ttcgaggttg ttccttttat agctgttgga aggcggtggt gtgtcgccct aaaagcaggg 2880
gttctgtgaa aaaatgcttg tttgaaaggt gcaccttagg catcctctct gagggcaact 2940
ccagggtgcg ccataatgtg gcttcgaact gcggttgctt catgcaagtg aagggggtga 3000
gcgttatcaa gcataactcg gtgtgtggaa actgcgagga tcgcgcctcc cagatgctga 3060
cctgctttga tggcaactgt cacctgttga agaccattca tataagcagc caccccagaa 3120
aggcctggcc cgtgtttgag cataacatct tgacccgctg ctccttgcat ctgggggtca 3180
ggaggggtat gttcctgcct taccagtgta actttagcca cactaaaatc ctgctggaac 3240
ccgagtgcat gaccaaggtc agcctgaatg gtgtgtttga tgtgactctg aaaatctgga 3300
aggtgctgag gtatgatgag accaggacca ggtgccgacc ctgcgagtgc ggcggcaagc 3360
acatgagaaa tcagcctgtg atgttggatg tgaccgagga gcttaggcct gaccatctgg 3420
tgctggcctg caccagggcc gagtttgggt ctagcgatga ggataccgat tgaggtgggt 3480
aaggtgggcg tggctagaag ggtggggcgt gtataaattg gggtctaag ggtctctctg 3540 ttttgtcttg caacagccgc cgccatgagc gacaccggca acagctttga tggaagcatc 3600
tttagcccct atctgacagt gcgcatgcct cactgggctg gagtgcgtca gaatgtgatg 3660
ggttccaacg tggatggacg ccccgttctg ccttcaaatt cgtctacaat ggcctacgcg 3720
accgtgggag gaactccgct ggacgccgcg acctccgccg ccgcctccgc cgccgccgcg 3780
accgcgcgca gcatggctac ggacctttac agctctttgg tggcgagcgg cgcggcctct 3840
cgcgcgtctg ctcgggatga gaaactgacc gctctgctgc ttaaactgga agacttgacc 3900
cgggagctgg gtcaactgac ccagcaggtc tccagcttgc gtgagagcag ccttgcctcc 3960
ccctaatggc ccataatata aataaaagcc agtctgtttg gattaagcaa gtgtatgttc 4020
tttatttaac tctccgcgcg cggtaagccc gggaccagcg gtctcggtcg tttagggtgc 4080
ggtggattct ttccaacacg tggtacaggt ggctctggat gtttagatac atgggcatga 4140
gtccatccct ggggtggagg tagcaccact gcagagcttc gtgctcgggg gtggtgttgt 4200
atatgatcca gtcgtagcag gagcgctggg cgtggtgctg aaaaatgtcc ttaagcaaga 4260
ggcttatagc taggggggagg cccttggtgt aagtgtttac aaatctgctc agttgggagg 4320
ggtgcatccg gggggatata atgtgcatct tggactggat ttttaggttg gctatgttcc 4380
cacccagatc ccttctggga ttcatgttgt gcaggaccac cagcacggta tatccagtgc 4440
acttgggaaa tttatcgtgg agcttagacg ggaatgcatg gaagaacttg gagacgccct 4500
tgtggcctcc cagattttcc atacattcgt ccatgatgat ggcaatgggc ccgtgggaag 4560
ctgcctgagc aaaaatgttt ctgggatcgc tcacatcgta gttatgttcc agggtgaggt 4620
catcatagga catctttacg aatcgggggc ggagggtccc ggactggggg atgatggtac 4680
cctcgggccc cggggcgtag ttcccctcac agatctgcat ctcccaggct ttcatttcag 4740
agggagggat catatccacc tgcggagcga tgaaaaacac agtttctggc gcaggggaga 4800
ttaactggga tgagagcagg tttctgagca gctgtgactt tccacagccg gtgggcccat 4860

-continued atatcacgcc tatcaccggc tgcagctggt agttaagaga gctgcagctg ccgtcctccc 4920
ggagcagggg ggccacctcg ttcagcatat ccctgacgtg gatgttctcc ctgaccaatt 4980
ccgccagaag gcgctcgccg cccagcgaaa gcagctcttg caaggaagca aaatttttca 5040
gcggttttag gccgtcggcc gtgggcatgt ttttcagcgt ctgggtcagc agttccagcc 5100
tgtcccacag ctcggtgatg tgctctacgg catctcgatc cagcagatct cctcgtttcg 5160
cgggttgggg cggctttcgc tgtagggcac cagccgatgg gcgtccagcg ggggccagagt 5220 catgtccttc catgggcgca gggtcctcgt cagggtggtc tgggtcacgg tgaaggggtg 5280
cgctccgggt tgggcgctgg ccagggtgcg cttgaggctg gttctgctgg tgctgaatcg 5340
ctgccgctct tcgccctgcg cgtcggccag gtagcatttg accatggtct cgtagtcgag 5400
accctcggcg gcgtgcccct tggcgcggag ctttcccttg gaggtggcgc cgcacgaggg 5460
gcactgcagg ctcttcaggg cgtagagctt gggagcgaga aacacggact ctggggagta 5520
ggcgtccgcg ccgcaggaag cgcagaccgt ctcgcattcc accagccaag tgagctccgg 5580
gcggtcaggg tcaaaaacca ggttgccccc atgctttttg atgcgtttct tacctcggct 5640
ctccatgagg cggtgtccct tctcggtgac gaagaggctg tccgtgtccc cgtagaccga 5700
cttcaggggc ctgtcttcca gcggagtgcc tctgtcctcc tcgtagagaa actctgacca 5760
ctctgagacg aaggcccgcg tccaggccag gacgaaggag gccacgtggg aggggtagcg 5820
gtcgttgtcc actagcgggt ccaccttctc cagggtgtgc aggcacatgt ccccctcctc 5880
cgcgtccaga aaagtgattg gcttgtaggt gtaggacacg tgaccggggg ttcccgacgg 5940
gggggtataa aagggggtgg gcgccctttc atcttcactc tcttccgcat cgctgtctgc 6000
gagggccagc tgctggggta agtattccct ctcgaaggcg ggcatgacct cagcgctcag 6060
gttgtcagtt tctaaaaatg aggaggattt gatgttcacc tgtccggagg tgataccttt 6120
gagggtacct gggtccatct ggtcagaaaa cactattttt ttgttgtcaa gcttggtggc 6180
gaacgacccg tagagggcgt tggagagcag cttggcgatg gagcgcaggg tctggttttt 6240
gtcgcggtcg gctcgctcct tggccgcgat gttgagttgc acgtactcgc gggccacgca 6300
cttccactcg gggaagacgg tggtgcgctc gtctgggatt aggcgcaccc tccagcctcg 6360
gttgtgcagg gtgaccatgt cgacgctggt ggcgacctcg ccgcgcaggc gctcgttggt 6420
ccagcagagg cggccgccct tgcgcgagca gaagggggggt agggggtcca gctggtcctc 6480
gtttgggggg tccgcgtcga tggtgaagac cccggggagc aagcgcgggt caaagtagtc 6540
gatcttgcaa gcttgcatgt ccagagcccg ctgccattcg cgggcggcga gcgcgcgctc 6600
gtaggggttg aggggcgggc cccagggcat ggggtgggtg agcgcggagg cgtacatgcc 6660
gcagatgtca tacacgtaca ggggttccct gaggatgccg aggtaggtgg ggtagcagcg 6720
ccccccgcgg atgctggcgc gcacgtagtc atagagctcg tgggaggggg ccagcatgtt 6780
gggcccgagg ttggtgcgct gggggcgctc ggcgcggaag gcgatctgcc tgaagatggc 6840
atgggagttg gaggagatgg tgggccgctg gaagacgttg aagcttgctt cttgcaagcc 6900
caccgagtcc ctgacgaagg aggcgtagga ctcgcgcagc ttgtgcacca gctcggcggt 6960
gacctggacg tcgagcgcgc agtagtcgag ggtctcgcgg atgatgtcat acttatcctc 7020
ccccttcttt ttccacagct cgcggttgag gacgaactct tcgcggtctt tccagtactc 7080
ttggagggga aacccgtccg tgtccgaacg gtaagagcct agcatgtaga actggttgac 7140
ggcctggtag ggcaacagcc ccttctccac gggcagcgcg taggcctgcg ccgccttgcg 7200
gagggaggtg tgggtgaggg cgaaagtgtc cctgaccatg actttgaggt attgatgttt 7260
gaagtctgtg tcatcgcagc cgccctgttc ccacagggtg tagtccgtgc gctttttgga 7320
gcgcgggttg ggcagggaga aggtgaggtc attgaagagg atcttccccg ctcgaggcat 7380
gaagtttctg gtgatgcgaa agggccctgg gaccgaggag cggttgttga tgacctgggc 7440
ggccaggacg atctcgtcaa agccgtttat gttgtggccc acgatgtaga gctccaaaaa 7500
gcggggctgg cccttgatgg aggggagctt tttgagttcc tcgtaggtga gctcctcggg 7560
cgattccagg ccgtgctcct ccagggccca gtcttgcaag tgagggttgg ccgccaggaa 7620
ggatcgccag aggtcgcggg ccatgagggt ctgcaggcgg tcgcggaagg ttctgaactg 7680
tcgccccacg gccatctttt cggggggtgat gcagtagaag gtgagggggt ctttctccca 7740
ggggtcccat ctgagctctc gggcgaggtc gcgcgcggcg gcgaccagag cctcgtcgcc 7800
ccccagtttc atgaccagca tgaagggcac gagctgcttg ccaaaggctc ccatccaagt 7860
gtaggtctct acatcgtagg tgacaaagag gcgctccgtg cgaggatgag agccgatcgg 7920
gaagaactgg atctcccgcc accagttgga ggattggctg ttgatgtggt gaaagtagaa 7980
gtcccgtctg cgggccgagc actcgtgctg gcttttgtaa aagcgaccgc agtactggca 8040
gcgctgcacg ggttgtatat cttgcacgag gtgaacctgg cgacctctga cgaggaagcg 8100
cagcgggaat ctaagtcccc cgcctggggt cccgtgtggc tggtggtctt ctactttggt 8160
tgtctggccg ccagcatctg tctcctggag ggcgatggtg gagcagacca ccacgccgcg 8220
agagccgcag gtccagatct cggcgctcgg cgggcggagt ttgatgacga catcgcgcac 8280
attggagctg tccatggtct ccagctcccg cggcggcagg tcagctggga gttcctggag 8340
gttcacctcg cagagacggg tcaaggcgcg ggcagtgttg agatggtatc tgatttcaag 8400
gggcgtgttg gcggcggagt cgatggcttg caggaggccg cagcccgggg gggccacgat 8460
ggttccccgc ggggcgcgag gggaggcgga agctgggggt gtgttcagaa gcggtgacgc 8520
gggcgggccc ccggaggtag ggggggttcc ggccccacag gcatgggcgg caggggcacg 8580
tcttcgccgc gcgcgggcag ggctggtgc tggctccgaa gagcgcttgc gtgcgcgacg 8640
acgcgacggt tggtgtcctg tatctgacgc ctctgagtga agaccacggg tcccgtgacc 8700
ttgaacctga aagagagttc gacagaatca atctcggcat cgttgacagc ggcctggcgc 8760
aggatctcct gcacgtcgcc cgagttgtcc tggtaggcga tctctgccat gaactgctcg 8820
atctcttctt cctggagatc tcctcgtccg gcgcgctcca cggtggccgc caggtcgttg 8880
gagatgcgac ccatgagctg tgagaaggcg ttgagcccgc cctcgttcca gacccggctg 8940
tagaccacgc ccccctcggc gtcgcgagcg cgcatgacca cctgggccag gttgagctcc 9000
acgtgtcgcg tgaagacggc gtagttgcgc aggcgctgga aaaggtagtt cagggtggtg 9060
gcggtgtgct cggcgacgaa gaagtacatg acccagcgcc gcaacgtgga ttcattgatg 9120
tcccccaagg cctccaggcg ctccatggcc tcgtagaagt ccacggcgaa gttgaaaaac 9180
tgggagttgc gagcggacac ggtcaactcc tcctccagaa gacggatgag ctcggcgaca 9240
gtgttgcgca cctcgcgctc gaaggccacg gggggcgctt cttcctcttc cacctcttct 9300
tccatgatcg cttcttcttc ttcctcagcc gggacgggag ggggcggcgg cggcggggga 9360
ggggcgcggc ggcggcggcg gcgcaccggg aggcggtcga tgaagcgctc gatcatctcc 9420
ccccgcatgc ggcgcatggt ctcggtgacg gcgcggccgt tctcccgggg gcgcagctcg 9480
aagacgccgc ctctcatctc gccgcggggc gagcggccgt gaggtagcga gacggcgctg 9540
actatgcatc ttaacaattg ctgtgtaggt acaccgccga gggacctgat tgagtccaga 9600

-continued

```
tccaccggat ccgaaaacct ttggaggaaa gcgtctatcc agtcgcagtc gcaaggtagg   9660
ctgagcaccg tggcgggcgg gggcgggtct ggagagttcc tggcggagat gctgctgatg   9720
atgtaattaa agtaggcggt cttgagaagg cggatggtgg acaggagcac catgtctttg   9780
ggtccggcct gttggatgcg gaggcggtcg gccatgcccc aggcctcgtt ctgacaccgg   9840
cgcaggtctt tgtagtagtc ttgcatgagt ctttccaccg gcacctcttc tccttcctct   9900
tctccatctc gccggtggtt tctcgcgccg cccatgcgcg tgaccccaaa gcccctgagc   9960
ggctgcagca gggccaggtc ggcgaccacg cgctcggcca agatggcctg ctgcacctga  10020
gtgagggtcc tctcgaagtc atccatgtcc acgaagcggt ggtaggcgcc cgtgttgatg  10080
gtgtaggtgc agttggccat gacggaccag ttgacggtct ggtgtcccgg ctgcgagagc  10140
tccgtgtacc gcaggcgcga gaaggcgcgg gaatcgaaca cgtagtcgtt gcaagtccgc  10200
accagatact ggtagcccac caggaagtgc ggcggaggtt ggcgatagag gggccagcgc  10260
tgggtggcgg gggcgccggg cgccaggtct tccagcatga ggcggtggta tccgtagatg  10320
tacctggaca tccaggtgat gccggcggcg gtggtggtgg cgcgcgcgta gtcgcggacc  10380
cggttccaga tgtttcgcag ggcgagaaag tgttccatgg tcggcacgct ctggccggtg  10440
aggcgcgcgc agtcgttgac gctctataca cacacaaaaa cgaaagcgtt tacagggctt  10500
tcgttctgta gcctggagga aagtaaatgg gttgggttgc ggtgtgcccc ggttcgagac  10560
caagctgagc tcggccggct gaagccgcag ctaacgtggt attggcagtc ccgtctcgac  10620
ccaggccctg tatcctccag gatacggtcg agagcccttt tgctttcttg gccaagcgcc  10680
cgtggcgcga tctgggatag atggtcgcga tgagaggaca aaagcggctc gcttccgtag  10740
tctggagaaa caatcgccag ggttgcgttg cggcgtaccc cggttcgagc ccctatggcg  10800
gcttgaatcg gccggaaccg cggctaacga gggccgtggc agccccgtcc tcaggacccc  10860
gccagccgac ttctccagtt acgggagcga gccccttttg ttttttattt tttagatgca  10920
tcccgtgctg cggcagatgc gcccctcgcc ccggcccgat cagcagcagc aacagcaggc  10980
atgcagaccc ccctctcccc tttccgcccc ggtcaccacg gccgcggcgg ccgtgtcggg  11040
cgcgggggc gcgctggagt cagatgagcc accgcggcgg cgacctaggc agtatctgga  11100
cttggaagag ggcgagggac tggcgcggct gggggcgaac tctccagagc gccacccgcg  11160
ggtgcagttg aaaagggacg cgcgcgaggc gtacctgccg cggcagaacc tgtttcgcga  11220
ccgcgggggc gaggagcccg aggagatgcg agactgcagg ttccaagcgg ggcgcgagct  11280
gcggcgcggg ctggacagac agcgcctgct gcgcgaggag gactttgagc ccgacacgca  11340
gacgggcatc agccccgcgc gcgcgcacgt agccgcggcc gacctggtga ccgcctacga  11400
gcagacggta aaccaggagc gcaacttcca aaagagcttc aacaaccacg tgcgcacgct  11460
ggtggcgcgc gaggaggtga ccctgggtct catgcatctg tgggacctgg tggaggcgat  11520
cgtgcagaac cccagcagca agcccctgac cgcgcagctg ttcctggtgg tgcagcacag  11580
cagggacaac gaggccttca gggaggcgct gctgaacatc accgagccgg aggggcgctg  11640
gctcctggac ctgataaaca tcctgcagag catagtggtg caggagcgca gcctgagcct  11700
ggccgagaag gtggcggcca tcaactactc tatgctgagc ctgggcaagt tctacgcccg  11760
caagatctac aagacccccct acgtgcccat agacaaggag gtgaagatag acagcttcta  11820
catgcgcatg gcgctgaagg tgctgaccct gagcgacgac ctgggagtgt accgcaacga  11880
gcgcatccac aaggccgtga gcgccagccg gcggcgcgag ctgagcgacc gcgagctgat  11940
gcacagtctg cagcgcgcgc tgaccggcgc gggcgagggc gacagggagg tcgagtccta  12000
```

```
cttcgacatg gggccgacc tgcactggca gccgagccgc cgcgccctgg aggcggcggg  12060
ggcgtacggc ggcccccctgg cggccgatga ccaggaagag gaggactatg agctagagga  12120
gggcgagtac ctggaggact gacctggctg gtggtgtttt ggtatagatg caagatccga  12180
acgtggcgga cccggcggtc cgggcggcgc tgcaaagcca gccgtccggc attaactcct  12240
ctgacgactg ggccgcggcc atgggtcgca tcatggccct gaccgcgcgc aaccccgagg  12300
ctttcaggca gcagcctcag gccaaccggc tggcggccat cttggaagcg gtagtgcccg  12360
cgcgctccaa ccccacccac gagaaggtgc tggccatagt caacgcgctg gcggagagca  12420
gggccatccg cgcggacgag gccggactgg tgtacgatgc gctgctgcag cgggtggcgc  12480
ggtacaacag cggcaacgtg cagaccaacc tggaccgcct ggtgacggac gtgcgcgagg  12540
ccgtggcgca gcgcgagcgc ttgcatcagg acggtaacct gggctcgctg gtggcgctaa  12600
acgccttcct cagcacccag ccggccaacg taccgcgggg gcaggaggac tacaccaact  12660
ttttgagcgc gctgcggctg atggtgaccg aggtccctca gagcgaggtg taccagtcgg  12720
ggcccgacta cttcttccag accagcagac agggcttgca aaccgtgaac ctgagccagg  12780
ctttcaagaa cctgcggggg ctgtggggag tgaaggcgcc caccggcgac cgggctacgg  12840
tgtccagcct gctaaccccc aactcgcgcc tgctgctgct gctgatcgcg cccttcacgg  12900
acagcgggag cgtctcgcgg gagacctatc tgggccacct gctgacgctg taccgcgagg  12960
ccatcgggca ggcgcaggtg gacgagcaca ccttccaaga gatcaccagc gtgagccacg  13020
cgctggggca ggaggacacg ggcagcctgc aggcgaccct gaactacctg ctgaccaaca  13080
ggcggcagaa gattcccacg ctgcacagcc tgacccagga ggaggagcgc atcttgcgct  13140
acgtgcagca gagcgtgagc ctgaacctga tgcgcgacgg cgtgacgccc agcgtggcgc  13200
tggacatgac cgcgcgcaac atggaaccgg gcatgtacgc ctcccaccgg ccgtttatca  13260
accgcctgat ggactacttg catcgggcgg cggccgtgaa ccccgagtac ttcactaatg  13320
ccattctgaa tccccactgg atgcccccctc cgggtttcta caacggggac tttgaggtgc  13380
ccgaggtcaa cgacgggttc ctctgggatg acatggatga cagtgtgttc tcacccaacc  13440
cgctgcgcgc cgcgtctctg cgattgaagg agggctctga cagggaagga ccgaggagtc  13500
tggcctcctc cctggctctg ggagcggtgg gcgccacggg cgcggcggcg cggggcagta  13560
gccccttccc cagcctggca gactctctga acagcgggcg ggtgagcagg ccccgcttgc  13620
taggcgagga ggagtatctg aacaactccc tgctgcagcc cgcgagggac aagaacgctc  13680
agcggcagca gtttcccaac aatgggatag agagcctggt ggacaagatg tccagatgga  13740
agacgtatgc gcaggagtac aaggagtggg aggaccgcca gccgcggccc ttgccgcccc  13800
ctaggcagcg ctggcagcgg cgcgcgtcca accgccgctg gaggcagggg cccgaggacg  13860
atgatgactc tgcagatgac agcagcgtgt tggacctggg cgggagcggg aacccctttt  13920
cgcacctgcg cccacgcctg ggcaagatgt tttaaaagaa aaaaaaaata aaactcacca  13980
aggccatggc gacgagcgtt ggtttttgt tcccttcctt agtatgcggc gcgcggcgat  14040
gttcgaggag ggcctcccc cctcttacga gagcgcgatg ggatttctc ctgcggcgcc  14100
cctgcagcct ccctacgtgc ctcctcggta cctgcaacct acaggggga gaaatagcat  14160
ctgttactct gagctgcagc ccctgtacga taccaccaga ctgtacctgg tggacaacaa  14220
gtccgcggac gtggcctccc tgaactacca gaacgaccac agcgattttt tgaccacggt  14280
gatccaaaac aacgacttca ccccaaccga ggccagcacc cagaccataa acctggataa  14340
```

-continued

```
caggtcgaac tggggcggcg acctgaagac catcttgcac accaacatgc ccaacgtgaa  14400
cgagttcatg ttcaccaact cttttaaggc gcgggtgatg gtggcgcgcg agcaggggga  14460
ggcgaagtac gagtgggtgg acttcacgct gcccgagggc aactactcag agaccatgac  14520
tctcgacctg atgaacaatg cgatcgtgga acactatctg aaagtgggca ggcagaacgg  14580
ggtgaaggaa agcgatatcg gggtcaagtt tgacaccaga aacttccgtc tgggctggga  14640
ccccgtgacc gggctggtca tgccggggt ctacaccaac gaggcctttc atcccgacat  14700
agtgcttctg cccggctgtg gggtggactt cacccagagc cggctgagca acctgctggg  14760
cattcgcaag cggcagcctt tccaggaggg tttcaagatc acctatgagg atctgaaggg  14820
gggcaacatt cccgcgctcc ttgatctgga cgcctacgag gagagcttga aacccgagga  14880
gagcgctggc gacagcggcg agagtggcga ggagcaagcc ggcggcggtg gcggcgcgtc  14940
ggtagaaaac gaaagtacgc ccgcagtggc ggcggacgct gcggaggtcg agccggaggc  15000
catgcagcag gacgcagagg agggcgcaca ggagggcgcg cagaaggaca tgaacgatgg  15060
ggagatcagg ggagacacat tcgccacccg gggcgaagaa aaagaggcag aggcggcggc  15120
ggcggcgacg gcggaggccg aaaccgaggt tgaggcagag gcagagcccg agaccgaagt  15180
tatggaagac atgaatgatg gagaacgtag ggcgacacg ttcgccaccc ggggcgaaga  15240
gaaggcggcg gaggcagaag ccgcggctga ggaggcggct gcggctgcgg ccaagactga  15300
ggctgcggct aaggctgagg tcgaagccaa tgttgcggtt gaggctcagg ctgaggagga  15360
ggcggcggct gaagcagtta aggaaaaggc ccaggcagag caggaagaga aaaaacctgt  15420
cattcaacct ctaaaagaag atagcaaaaa gcgcagttac aacgtcatcg agggcagcac  15480
ctttacccag taccgcagct ggtacctggc gtacaactac ggcgacccgg tcaagggggt  15540
gcgctcgtgg accctgctct gcacgccgga cgtcacctgc ggctccgagc agatgtactg  15600
gtcgctgccg aacatgatgc aagacccggt gaccttccgc tccacgcggc aggttagcaa  15660
cttcccggtg gtgggcgccg aactgctgcc cgtgcactcc aagagttttt acaacgagca  15720
ggccgtctac tcccagctga tccgccaggc cacctctctg acccacgtgt tcaatcgctt  15780
tcccgagaac cagattttgg cgcgcccgcc ggcccccacc atcaccaccg tgagtgaaaa  15840
cgttcctgcc ctcacagatc acgggacgct accgctgcgc aacagcatct caggagtcca  15900
gcgagtgacc attactgacg ccagacgccg gacctgcccc tacgtttaca aggccttggg  15960
catagtctcg ccgcgcgtcc tctccagtcg cactttttaa aacacatcta cccacacgtt  16020
ccaaaatcat gtccgtactc atctcaccca gcaacaacac cggctggggg ctgcgcgcgc  16080
ccagcaagat gtttggaggg gcgaggaagc gctccgacca gcaccctgtg cgcgtgcgcg  16140
gccactaccg cgcgccctgg ggagcgcaca agcgcgggcg cacagggcgc accactgtgg  16200
acgacgtcat tgactccgta gtggagcaag cgcgccacta cacacccggc gcgccgaccg  16260
cccccgccgt gtccaccgtg gaccaggcga tcgaaagcgt ggtacagggc gcgcggcact  16320
atgccaacct taaaagtcgc cgccgccgcg tggcccgccg ccatcgccgg agaccccggg  16380
ccaccgccgc cgcgcgcctt actaaggctc tgctcaggcg cgccaggcga actggccacc  16440
gggccgccat gagggccgca cggcgggctg ccgctgccgc aagcgtcgtg gccccgcggg  16500
cacgaaggcg cgcggccgct gccgccgccg ccgccatttc cagcttggcc tcgacgcggc  16560
gcggtaacat atactgggtg cgcgactcgg taaccggcac gcgggtaccc gtgcgctttc  16620
gccccccgcg gaattagcac aagacaacat acacactgag tctcctgctg ttgtgtatcc  16680
cagcggcgac cgtcagcagc ggcgacatgt ccaagcgcaa aattaaagaa gagatgctcc  16740
```

```
aggtcatcgc gccggagatc tatgggcccc cgaagaagga ggaggatgat tacaagcccc  16800
gcaagctaaa gcgggtcaaa aagaaaaaga aagatgatga tgacgaggcg gtggagtttg  16860
tccgccgcat ggcacccagg cgccccgtgc agtggaaggg ccggcgcgtg cagcgcgttt  16920
tgcgccccgg caccgcggtg gtcttcacgc ccggcgagcg ctccacgcgc actttcaagc  16980
gggtgtacga tgaggtgtac ggcgacgagg acctgttgga gcaggccaac cagcgctttg  17040
gggagtttgc atatgggaaa cggccccgcg agagtctaaa agaggacctg ctggcgctac  17100
cgctggacga gggcaatccc accccgagtc tgaagccggt aaccctgcaa caggtgctgc  17160
ctttgagcgc gcccagcgag cataagcgag ggttgaagcg cgaaggcggg gacctggcgc  17220
ccaccgtgca gttgatggtg cccaagcggc agaagctgga ggacgtgctg gagaaaatga  17280
aagtagagcc cgggatccag cccgagatca aggtccgccc catcaagcag gtggcgcccg  17340
gcgtgggagt ccagaccgtg gacgttagga ttcccacgga ggagatggaa acccaaaccg  17400
ccactccctc ttcggcggcc agcgccacca ccggcaccgc ttcggtagag gtgcagacgg  17460
acccctggct acccgccacc gctgttgccg ccgccgcccc ccgttcgcgc gggcgcaaga  17520
gaaattatcc agcggccagc gcgctcatgc cccagtacgc actgcatcca tccatcgtgc  17580
ccaccccggg ctaccgcggg tactcgtacc gcccgcgcag atcagccggc actcgcggcc  17640
gccgccgccg tgcgaccaca accagccgcc gccgtcgccg ccgccgccag ccagtgctga  17700
cccccgtgtc tgtaaggaag gtggctcgct cggggagcac gctggtggtg cccagagcgc  17760
gctaccaccc cagcatcgtt taaagccggt ctctgtatgg ttcttgcaga tatggccctc  17820
acttgtcgcc tccgcttccc ggtgccggga taccgaggaa gaactcaccg ccgcagaggc  17880
atggcgggca gcggtctccg cggcggccgt cgccatcgcc ggcgcgcaaa aagcaggcgc  17940
atgcgcggcg gtgtgctgcc tctgctaatc ccgctaatcg ccgcggcgat cggtgccgta  18000
cccgggatcg cctccgtggc cctgcaggcg tcccagaaac gttgactctt gcaaccttgc  18060
aagcttgcat tttttggagg aaaaataaaa aaaagtctag actctcacgc tcgcttggtc  18120
ctgtgactat tttgtagaaa aaaagatgga agacatcaac tttgcgtcgc tggccccgcg  18180
tcacggctcg cgcccgttca tgggagactg gacagatatc ggcaccagca atatgagcgg  18240
tggcgccttc agctggggca gtctgtggag cggccttaaa aattttggtt ccaccattaa  18300
gaactatggc aacaaagcgt ggaacagcag cacgggccag atgctgagag acaagttgaa  18360
agagcagaac ttccaggaga aggtggcgca gggcctggcc tctggcatca gcggggtggt  18420
ggacatagct aaccaggccg tgcagaaaaa gataaacagt catctggacc cccgtcctca  18480
ggtggaggaa atgcctccag cgatggagac ggtgtctccc gagggcaaag gcgaaaagcg  18540
cccgcggccc gacagagaag agaccctggt gtcacacacc gaggagccgc cctcttacga  18600
ggaggcagtc aaggccggcc tgcccaccac tcgccccata gcccccatgg ccaccggtgt  18660
ggtgggccac aggcaacaca ctcccgcaac actagatctg cccccgccgt ccgagccgcc  18720
gcgccagcca aaggcggcga cggtgcccgc tccctccact tccgccgcca acagagtgcc  18780
cctgcgccgc gccgcgagcg gcccccgggc ctcgcgagtt agcggcaact ggcagagcac  18840
actgaacagc atcgtgggcc tgggagtgag gagtgtgaag cgccgccgtt gctactgaat  18900
gagcaagcta gctaacgtgt tgtatgtgtg tatgcgtcct atgtcgccgc cagaggagct  18960
gttgagccgc cggcgccgtc tgcactccag cgaatttcaa gatggcgacc ccatcgatga  19020
tgcctcagtg gtcgtacatg cacatctcgg gccaggacgc ttcggagtac ctgagccccg  19080
```

-continued ggctggtgca gttcgcccgc gccacagaca cctacttcaa catgagtaac aagttcagga 19140
accccactgt ggcgcccacc cacgatgtga ccacggaccg gtcgcagcgc ctgacgctgc 19200
ggttcatccc cgtggatcgg gaggacaccg cctactctta caaggcgcgg ttcacgctgg 19260
ccgtgggcga caaccgcgtg ctggacatgg cctccactta ctttgacatc aggggggtgc 19320
tggacagggg ccccaccttc aagccctact cgggtactgc ctacaactcc ctggccccca 19380
agggcgctcc caattcttgc gagtgggaac aagatgaacc agctcaggca gcaatagctg 19440
aagatgaaga agaacttgaa gaagaacaag ctcaggacga acaggcgccc actaagaaaa 19500
cccatgtata cgcccaggca cctctttctg gtgaaaaaat tactaaggat ggtttgcaaa 19560
taggtgtgga tgccacacag gcgggagata accctatata tgctgataaa acattccaac 19620
ccgaacctca gataggtgag tctcagtgga acgaggctga tgccacagta gcaggaggca 19680
gagtcttaaa aaagaccacc cctatgagac cttgctatgg atcctatgcc aaacctacta 19740
atgccaatgg cggtcaaggg atcatggtgg ccaatgatca gggagcgctt gaatctaaag 19800
ttgagatgca atttttctcc accacaacgt ctcttaatgt aagggaaggt gaaaacaatc 19860
ttcagccaaa agtagtgcta tacagcgaag atgttaactt ggaatcccct gacactcatt 19920
tgtcttacaa acctaaaaag gatgacacca actctaaaat catgttgggt cagcaagcca 19980
tgcccaacag acccaacctc attgctttta gggacaactt tattggactt atgtactaca 20040
acagcacagg caacatggga gtgctggcag gacaggcctc ccagctaaac gctgtggtag 20100
acttgcaaga cagaaacaca gagctgtcat accaactgat gcttgattcc attggagaca 20160
gatcaagata cttttccatg tggaaccagg cagtggacag ctatgaccca gatgtcagaa 20220
tcattgaaaa ccatggggtt gaagatgagc tgcccaacta ttgctttccc ctgggcggta 20280
ttggaattac agacacatac cagtgcataa aaccaaccgc agctgctaat aacactacat 20340
ggtctaagga tgaagaattt agtgatcgca atgaaatagg ggtgggaaac aacttcgcca 20400
tggagatcaa catccaggcc aacctctgga ggaacttcct ctatgcgaac gtggggctct 20460
acctgccaga caagctcaag tacaacccca ccaacgtgga catctctgac aaccccaaca 20520
cctatgacta catgaacaag cgtgtggtgg ctcccggcct ggtggactgc tttgtcaatg 20580
tgggagccag gtggtccctg gactacatgg acaacgtcaa ccccttcaac caccaccgca 20640
atgcgggtct gcgctaccgc tccatgatcc tgggcaacgg gcgctacgtg cccttccaca 20700
ttcaggtgcc ccagaagttc tttgccatca agaacctcct cctcctgccg ggctcctaca 20760
cttacgagtg gaacttcagg aaggatgtca acatggtcct gcagagctct ctgggcaatg 20820
accttagggt ggacggggcc agcatcaagt ttgacagcgt caccctctat gctaccttct 20880
tccccatggc tcacaacacc gcctccacgc tcgaggccat gctgaggaac gacaccaacg 20940
accagtcctt caatgactac ctctctgggg ccaacatgct ctaccccatc cccgccaagg 21000
ccaccaacgt gcccatctcc attccctctc gcaactgggc cgccttcaga ggctgggcct 21060
ttacccgcct taagaccaag gaaacccccct ccctgggctc gggttttgac ccctactttg 21120
tctactcggg atccatcccc tacctggatg gcaccttcta cctcaaccac acttttaaga 21180
agatatccat catgtatgac tcctccgtca gctggccggg caatgaccgc ctgctcaccc 21240
ccaatgagtt cgaggtcaag cgcgccgtgg acggcgaggg ctacaacgtg gcccagtgca 21300
acatgaccaa ggactggttc ctggtgcaga tgctggccaa ctacaacata ggctaccagg 21360
gcttctacat cccagagagc tacaaggaca ggatgtactc cttcttcaga aatttccaac 21420
ccatgagcag gcaggtggtg gacgagacca aatacaagga ctatcaggcc attggcatca 21480
ctcaccagca caacaactcg ggattcgtgg gctacctggc tcccaccatg cgcgaggggc 21540
aggcctaccc cgccaacttc ccctacccgt tgataggcaa aaccgcggtc gacagcgtca 21600
cccagaaaaa gttcctctgc gaccgcaccc tctggcgcat ccccttctct agcaacttca 21660
tgtccatggg tgcgctcacg gacctgggcc agaacctgct ctatgccaac tccgcccatg 21720
cgctggacat gacttttgag gtggacccca tggacgagcc cacccttctc tatattgtgt 21780
ttgaagtgtt cgacgtggtc agagtgcacc agccgcaccg cggtgtcatc gagaccgtgt 21840
acctgcgcac gcccttctcg gccggcaacg ccaccaccta aggagacagc gccgccgcct 21900
gcatgacggg ttccaccgag caagagctca gggccatcgc cagagacctg ggatgcggac 21960
cctatttttt gggcacctat gacaaacgct tcccgggctt catctcccga gacaagctcg 22020
cctgcgccat cgtcaacacg gccgcgcgcg agaccggggg cgtgcactgg ctggcctttg 22080
gctgggaccc gcgctccaaa acctgctacc tcttcgaccc ctttggcttc tccgatcagc 22140
gcctcagaca gatctatgag tttgagtacg aggggctgct gcgccgcagc gcgcttgcct 22200
cctcgcccga ccgctgcatc acccttgaga agtccaccga gaccgtgcag gggccccact 22260
cggccgcctg cggtctcttc tgctgcatgt ttttgcacgc ctttgtgcgc tggccccaga 22320
gtcccatgga tcgcaacccc accatgaact tgctcaaggg agtgcccaac gccatgctcc 22380
agagccccca ggtccagccc accctgcgcc acaaccagga acagctctac cgcttcctgg 22440
agcgccactc cccctacttc cgcagtcaca gcgcgcacat ccgggggccc acctctttct 22500
gccacttgca agaaaacatg caagacggaa aatgatgtac agctcgcttt ttaataaatg 22560
taaagactgt gcactttatt tatacacggg ctctttctgg ttatttattc aacaccgccg 22620
tcgccatcta gaaatcgaaa gggttctgcc gcgcgtcgcc gtgcgccacg ggcagagaca 22680
cgttgcgata ctggaagcgg ctcgcccact taaactcggg caccaccatg cggggcagtg 22740
gttcctcggg gaagttctcg ccccacaggg tgcgggtcag ctgcagcgcg ctcaggaggt 22800
cgggagccga gatcttgaag tcgcagttgg ggccggaacc ctgcgcgcgc gagttgcggt 22860
acacggggtt gcagcactgg aacaccagca gggccggatt atgcacgctg gccagcaggc 22920
tctcgtcgct gatcatgtcg ctgtccagat cctccgcgtt gctcagggcg aacggggtca 22980
tcttgcagac ctgcctgccc aggaaaggcg gcagcccggg cttgccgttg cagtcgcagc 23040
gcaggggcat cagcaggtgc ccgcggcccg actgcgcctg cgggtacagc gcgcgcatga 23100
aggcttcgat ctgcctgaaa gccacctgcg tcttggctcc ctccgaaaag aacatcccac 23160
aggacttgct ggagaactgg ttcgcgggac agctggcatc gtgcaggcag cagcgcgcgt 23220
cggtgttggc gatctgcacc acgttgcgac cccaccggtt cttcactatc ttggccttgg 23280
aagcctgctc cttcagcgcg cgctggccgt tctcgctggt cacatccatc tctatcacct 23340
gctccttgtt gatcatgttt gtaccgtgca gacacttcag gtcgccctcc gtctgggtgc 23400
agcggtgctc ccacagcgcg caaccggtgg gctcccaatt tttgtgggtc acccccgcgt 23460
aggcctgcag gtaggcctgc aagaagcgcc ccatcatggc cacaaaggtc ttctggctcg 23520
taaaggtcag ctgcaggccg cgatgctctt cgttcagcca ggtcttgcag atggcggcca 23580
gcgcctcggt ctgctcgggc agcatcctaa aatttgtctt caggtcgtta tccacgtggt 23640
acttgtccat catggcgcgc gccgcctcca tgcccttctc ccaggcggac accatgggca 23700
ggcttagggg gtttatcact tccaccggcg aggacaccgt actttcgatt tcttcttcct 23760
ccccctcttc ccggcgcgcg cccacgctgc tgcgcgctct caccgcctgc accaaggggt 23820

-continued

```
cgtcttcagg caagcgccgc accgagcgct tgccgccctt gacctgctta atcagcaccg  23880
gcgggttgct gaagcccacc atggtcagcg ccgcctgctc ttcttcgtct tcgctgtcta  23940
ccactatctc tggggaaggg cttctccgct ctgcggcggc gcgcttcttt tttttcttgg  24000
gagcggccgt gatggagtcc gccacggcga cggaggtcga gggcgtgggg ctgggggtgc  24060
gcggtaccag ggcctcgtcg ccctcggact cttcctctga ctccaggcgg cggcggagtc  24120
gcttctttgg gggcgcgcgc gtcagcggcg gcggagacgg ggacggggac ggggacggga  24180
cgccctccac agggggtggt cttcgcgcag acccgcggcc gcgctcgggg gtcttctcga  24240
gctggtcttg gtcccgactg gccattgtat cctcctcctc ctaggcagag agacataagg  24300
agtctatcat gcaagtcgag aaggaggaga gcttaaccac cccctctgag accgccgatg  24360
cgcccgccgt cgccgtcgcc cccgctgccg ccgacgcgcc cgccacaccg agcgacaccc  24420
ccgcggaccc ccccgccgac gcacccctgt tcgaggaagc ggccgtggag caggacccgg  24480
gctttgtctc ggcagaggag gatttgcgag aggaggagga taaggagaag aagccctcag  24540
tgccaaaaga tgataaagag caagacgagc acgacgcaga tgcacaccag ggtgaagtcg  24600
ggcgggggga cggagggcat gacggcgccg actacctaga cgaagggaac gacgtgctct  24660
tgaagcacct gcatcgtcag tgcgccattg tttgcgacgc tctgcaggag cgcagcgaag  24720
tgcccctcag cgtggcggag gtcagccacg cctacgagct cagcctcttc tccccccggg  24780
tgcccccccg ccgccgcgaa aacggcacat gcgagcccaa cccgcgcctc aacttctacc  24840
ccgcctttgt ggtacccgag gtcctggcca cctatcacat cttctttcaa aattgcaaga  24900
tcccctctc gtgccgcgcc aaccgtagcc gcgccgataa gatgctggcc ctgcgccagg  24960
gcgaccacat acctgatatc gccgctttgg aagatgtacc aaagatcttc gagggtctgg  25020
gtcgcaacga gaagcgggca gcaaactctc tgcaacagga aaacagcgaa aatgagagtc  25080
acaccggggt actggtggag ctcgagggcg acaacgcccg cctggcggtg gtcaagcgca  25140
gcatcgaggt cacccacttt gcctaccccg cgctaaacct gccccccaaa gtcatgaacg  25200
cggccatgga cgggctgatc atgcgccgcg gccggcccct cgctccagat gcaaacttgc  25260
atgaggagac cgaggacggc cagcccgtgg tcagcgacga gcagctggcg cgctggctgg  25320
agaccgcgga ccccgccgaa ctggaggagc ggcgcaagat gatgatggcc gtggtgctgg  25380
tcaccgtaga gctggagtgt ctgcagcgct tcttcggcga ccccgagatg cagagaaagg  25440
tcgaggagac cctgcactac accttccgcc agggctacgt gcgccaggct tgcaagatct  25500
ccaacgtgga gctcagcaac ctggtgtcct acctgggcat cttgcatgag aaccgcctcg  25560
ggcagagcgt gctgcactcc accctgcgcg gggaggcgcg ccgcgactac gtgcgcgact  25620
gcgtttacct cttcctctgc tacacctggc agacggccat gggggtctgg cagcagtgcc  25680
tggaggagcg caacctcaag gagctggaga agctcctgca gcgcgcgctc aaagatctct  25740
ggacgggcta caacgagcgc tcggtggccg ccgcgctggc cgacctcatc ttccccgagc  25800
gcctgctcaa aaccctccag caggggctgc ccgacttcac cagccaaagc atgttgcaaa  25860
acttcaggaa ctttatcctg gagcgttctg gcatcctacc cgccacctgc tgcgccctgc  25920
ccagcgactt tgtcccctc gtgtaccgcg agtgcccccc gccgctgtgg ggtcactgct  25980
acctgttcca actggccaac tacctgtcct accacgcgga cctcatggag gactccagcg  26040
gcgaggggct catggagtgc cactgccgct gcaacctctg cacgccccac cgctccctgg  26100
tctgcaacac ccaactgctc agcgagagtc agattatcgg taccttcgag ctacagggtc  26160
cgtcctcctc agacgagaag tccgcggctc cggggctaaa actcactccg ggctgtgga  26220
```

-continued cttccgccta cctgcgcaaa tttgtacctg aagactacca cgcccacgag atcaggtttt 26280
acgaagacca atcccgcccg cccaaggcgg agctgaccgc ctgcgtcatc acccagggcg 26340
agatcctagg ccaattgcaa gccatccaaa aagcccgcca agactttttg ctgaagaagg 26400 gtcgggggt gtatctggac ccccagtcgg gtgaggagct caacccggtt cccccgctgc 26460
cgccgccgcg ggaccttgct tcccaggata agcatcgcca tggctcccag aaagaagcag 26520
cagcggccgc cactgccgcc accccacatg ctggaggaag aggaggaata ctgggacagt 26580
caggcagagg aggtttcgga cgaggaggag ccggagacgg agatggaaga gtgggaggag 26640
gacagcttag acgaggaggc ttccgaagcc gaagaggcag acgcaacacc gtcaccctcg 26700
gccgcagccc cctcgcaggc gcccccgaag tccgctccca gcatcagcag caacagcagc 26760
gctataacct ccgctcctcc accgccgcga cccacggccg accgcagacc caaccgtaga 26820
tgggacacca ccggaaccgg ggccggtaag tcctccggga gaggcaagca agcgcagcgc 26880
caaggctacc gctcgtggcg cgctcacaag aacgccatag tcgcttgctt gcaagactgc 26940
ggggggaaca tctccttcgc ccgccgcttc ctgctcttcc accacggtgt ggccttcccc 27000
cgtaacgtcc tgcattacta ccgtcatctc tacagcccct actgcggcgg cagtgagcca 27060
gagacggtcg gcggcggcgg cggcgcccgt ttcggcgcct aggaagaccc agggcaagac 27120
ttcagccaag aaactcgcgg cggccgcggc gaacgcggtc gcgggggccc tgcgcctgac 27180
ggtgaacgaa cccctgtcga cccgcgaact gaggaaccga atcttcccca ctctctatgc 27240
catcttccag cagagcagag ggcaggatca ggaactgaaa gtaaaaaaca ggtctctgcg 27300
ctccctcacc cgcagctgtc tgtatcacaa gagcgaagac cagcttcggc gcacgctgga 27360
ggacgctgag gcactcttca gcaaatactg cgcgctcact cttaaggact agctccgcgc 27420
ccttctcgaa tttaggcggg aacgcctacg tcatcgcagc gccgccgtca tgagcaagga 27480
cattcccacg ccatacatgt ggagctatca gccgcagatg ggactcgcgg cgggcgcctc 27540
ccaagactac tccacccgca tgaactggct cagtgccggc ccacacatga tctcacaggt 27600
taatgatatc cgcacccatc gaaaccaaat attggtggag caggcggcaa ttaccaccac 27660
gccccgcaat aatcccaacc ccagggagtg gcccgcgtcc ctggtgtatc aggaaattcc 27720
cggccccacc accgtactac ttccgcgtga ttcccaggcc gaagtccaaa tgactaactc 27780
aggggcacag ctcgcgggcg gctgtcgtca cagggtgcgg cctcctcgcc agggtataac 27840
tcacctggag atccgaggca gaggtattca gctcaacgac gagtcggtga gctcctcgct 27900
cggtctcaga cctgacggga ccttccagat agccggagcc ggccgatctt ccttcacgcc 27960
ccgccaggcg tacctgactc tgcaaagctc gtcctcggcg ccgcgctcgg gcggcatcgg 28020
gactctccag ttcgtgcagg agtttgtgcc ctcggtctac ttcaacccct tctcgggctc 28080
tcccggtcgc tacccggacc agttcatctc gaactttgac gccgcgaggg actcggtgga 28140
cggctacgac tgaatgtcgg gtggacccgg tgcagagcaa cttcgcctga agcacctcga 28200
ccactgccgc cgccctcagt gctttgcccg ctgtcagacc ggtgagttcc agtacttttc 28260
cctgcccgac tcgcacccgg acggcccggc gcacggggtg cgctttttca tcccgagtca 28320
ggtgcgctct accctaatca gggagtttac cgcccgtccc ctactggcgg agttggaaaa 28380
ggggccttct atcctaacca ttgcctgcat ctgctctaac cctggattgc accaagatct 28440
ttgctgtcat ttgtgtgctg agtataataa aggctgagat cagaatctac tcgggctcct 28500
gtcgccatcc tgtcaacgcc accgtccaag cccggcccga tcagcccgag gtgaacctca 28560

-continued

```
cctgcggtct gcaccggcgc ctgaggaaat acctagcttg gtactacaac agcactccct  28620
ttgtggttta caacagcttt gaccaggacg gggtctcact gagggataac ctctcgaacc  28680
tgagctactc catcaggaag aacagcaccc tcgagctact tcctccttac ctgcccggga  28740
cttaccagtg tgtcaccggt ccctgcaccc acacccacct gttgatcgta aacgactctc  28800
ttccgagaac agacctcaat aactcctctt cgcagttccc cagaacagga ggtgagctca  28860
ggaaaccccg ggtaaagaag ggtggacgag agttaacact tgtggggttt ctggtgtatg  28920
tgacgctggt ggtggctctt ttgattaagg cttttccttc catgtctgaa ctctccctct  28980
tcttttatga acaactcgac tagtgctaac gggaccctac ccaacgaatc gggattgaat  29040
atcggtaacc aggttgcagt ttcactttg attaccttca tagtcctctt cctgctagtg  29100
ctgtcgcttc tgtgcctgcg gatcgggggc tgctgcatcc acgtttatat ctggtgctgg  29160
ctgtttagaa ggttcggaga ccatcgcagg tagaataaac atgctgctgc ttaccctctt  29220
tgtcctggcg ctggccgcca gctgccaagc cttttccgag gctgacttta tagagcccca  29280
gtgtaatgtg acttttaaag cccatgcaca gcgttgtcat actataatca aatgtgccac  29340
cgaacacgat gaataccttta tccagtataa agataaatca cacaaagtgg cacttgttga  29400
catctggaaa cccgaagacc ctttggaata caatgtgacc gttttccagg gtgacctctt  29460
caaaatttac aattacactt tcccatttga ccagatgtgt gactttgtca tgtacatgga  29520
aaagcagcac aagctgtggc ctccgactcc ccagggctgt gtggaaaatc caggctcttt  29580
ctgcatgatc tctctctgtg taactgtgct ggcactaata ctcacgcttt tgtatatcag  29640
atttaaatca aggcaaagct tcattgatga aaagaaaatg ccttaatcgc tttcacgctt  29700
gattgctaac accgggtttt tatccgcaga atgattggaa tcaccctact aatcacctcc  29760
ctccttgcga ttgcccatgg gttggaacga atcgaagtcc ctgtgggggc caatgttacc  29820
ctggtggggc ctgtcggcaa tgctacatta atgtgggaaa aatatactaa aaatcaatgg  29880
gtctcttact gcactaacaa aaatagccac aagcccagag ccatctgcga tgggcaaaat  29940
ctaaccttga ttgatgttca attgctggat gcgggctact attatgggca gctgggtaca  30000
atgattaatt actggagacc ccacagagat tacatgctcc acgtagtaaa gggtcccctt  30060
agcagcccac ccactaccac ctctactacc cccactacca ccactactcc caccaccagc  30120
actgccgccc agcctcctca tagcagaaca accactttta tcaattccaa gtcccactcc  30180
ccccacattg ccggcgggcc ctccgcctca gactccgaaa ccaccgagat ctgcttctgc  30240
aaatgctctg acgccattgc ccaggatttg gaagatcacg aggaagatga gcatgacttc  30300
gcagatgcat gccaggcatc agagccagaa gcgctgccgg tggccctcaa acagtatgca  30360
gacccccaca ccacccccga ccttcctcca ccttcccaga agccaagttt cctgggggaa  30420
aatgaaactc tgcctctctc catactcgct ctgacatctg ttgctatgtt gaccgctctg  30480
ctggtgcttc tatgctctat atgctacctg atctgctgca gaaagaaaaa atctcacggc  30540
catgctcacc agcccctcat gcacttccct taccctccag agctgggcga ccacaaactt  30600
taagtctgca gtaactatct gcccatccct tgtcagtcga cagcgatgag ccccactaat  30660
ctaacggcct ctggacttac aacatcgtct cttaatgaga ccaccgctcc tcaagacctg  30720
tacgatggtg tctccgcgct ggttaaccag tgggatcacc tgggcatatg gtggctcctc  30780
ataggagcag tgaccctgtg cctaatcctg gtctggatca tctgctgcat caaaagcaga  30840
agacccaggc ggcggcccat ctacaggccc tttgtcatca cacctgaaga tgatgatgac  30900
accacttcca ggctgcagag gctaaagcag ctactcttct cttttacagc atggtaaatt  30960
```

```
gaatcatgcc tcgcattttc atctacttgt ctctccttcc actttttctg ggctcttcta  31020
cattggccgc tgtgtcccac atcgaggtag actgcctcac gcccttcaca gtctacctgc  31080
ttttcggctt tgtcatctgc acctttgtct gcagcgttat cactgtagtg atctgcttca  31140
tacagtgcat cgactacgtc tgcgtgcggg tggcttactt tagacaccac ccccagtatc  31200
gcaacaggga catagcggct ctcctaagac ttgtttaaaa tcatggccaa attaactgtg  31260
attggtcttc tgatcatctg ctgcgtccta gccgcgattg ggactcaagc tcctaccacc  31320
accagcgctc ccagaaagag acatgtatcc tgcagcttca agcgtccctg gaatataccc  31380
caatgcttta ctgatgaacc tgaaatctct ttggcttggt acttcagcgt caccgccctt  31440
cttatcttct gcagtacggt tattgccctt gccatctacc cttcccttga cctgggctgg  31500
aatgctgtca actctatgga atatcccacc ttcccagaac cagacctgcc agacctggtt  31560
gttctaaacg cgtttcctcc tcctgctccc gttcaaaatc agtttcgccc tccgtccccc  31620
acgcccactg aggtcagcta ctttaatcta acaggcggag atgactgaaa acctagacct  31680
agaaatggac ggtctctgca gcgagcaacg cacactagag aggcgccggc aaaaagagct  31740
cgagcgtctt aaacaagagc tccaagacgc ggtggccata caccagtgca aaaaaggtgt  31800
cttctgtctg gtaaaacagg ccacgctcac ctatgaaaaa acaggtgaca cccaccgcct  31860
aggatacaag ctgcccacac agcgccaaaa gttcgccctc atgataggcg aacaacccat  31920
caccgtgacc cagcactccg tggagacaga aggctgcata catgctccct gtaggggcgc  31980
tgactgcctc tacaccttga tcaaaaccct ctgcggtctc agagacctta tccctttcaa  32040
ttaatcataa ctgtaatcaa taaaaaatca cttacttgaa atctgatagc aagcctctgt  32100
ccaatttttt cagcaacact tccttcccct cctcccaact ctggtactct aggcgcctcc  32160
tagctgcaaa cttcctccac agtctgaagg gaatgtcaga ttcctcctcc tgtccctccg  32220
cacccacgat cttcatgttg ttgcagatga aacgcgcgag atcgtctgac gagaccttca  32280
accccgtgta cccctacgat accgagatcg ctccgacttc tgtccctttc cttacccctc  32340
cctttgtgtc atccgcagga atgcaagaaa atccagctgg ggtgctgtcc ctgcacttgt  32400
cagagcccct taccacccac aatggggccc tgactctaaa aatgggggc ggcctgaccc  32460
tggacaagga agggaatctc acttcccaaa acatcaccag tgtcgatccc cctctcaaaa  32520
aaagcaagaa caacatcagc cttcagaccg ccgcacccct cgccgtcagc tccggggccc  32580
taacactttt tgccactccc cccctagcgg tcagtggtga caaccttact gtgcagtctc  32640
aggcccctct cactttggaa gactcaaaac taactctggc caccaaagga cccctaactg  32700
tgtccgaagg caaacttgtc ctagaaacag aggctcccct gcatgcaagt gacagcagca  32760
gcctgggcct tagcgttacg gccccactta gcattaacaa tgacagccta ggactagatc  32820
tgcaggcacc cattgtctct caaaatggaa aactggctct aaatgtagca ggcccccctag  32880
ctgtggccaa tggcattaat gctttgacag taggcacagg caaaggtatt ggtctaaatg  32940
aaaccagcac tcacttgcaa gcaaagttgg tcgccccccct aggctttgat accaatggca  33000
acattaagct aagcgttgca ggaggcatga gactaaataa tgacacactt atactagatg  33060
taaactaccc atttgaagct caaggccaac taagtctaag agtgggccag ggtccgctgt  33120
atgtagattc tagcagccat aacctgacca ttagatgcct tagaggatta tacataacat  33180
cgtctaataa ccaaaccggt ctagaggcca acataaaact aacaaaaggc cttgtctatg  33240
atggaaatgc catagcagtc aatgttggtc aaggattgca atacagcact actgccacat  33300
```

-continued

```
cggaaggtgt gtatcctata cagtctaaga taggtttggg aatggaatat gataccaacg  33360
gagccatgat gacaaaacta ggctctggac taagctttga caattcagga gccattgtag  33420
tgggaaacaa aaatgatgac aggcttactc tgtggactac accagaccca tctcctaact  33480
gtagaattta ttctgaaaaa gatactaaac taaccttggt gctgactaag tgtggcagcc  33540
aaatcctagg cacagtatct gcccttgctg tcagaggcag ccttgcgccc atcactaatg  33600
catccagcat agtccaaata tttctaagat ttgatgaaaa tggactattg atgagcaact  33660
catcgctaga cggtgattac tggaattaca gaaatgggga ctccactaat agcacaccat  33720
atacaaatgc agtaggcttt atgcctaatc tagcagccta tcctaaaggt caggctacag  33780
ctgcaaaaag cagtattgta agccaggtat acatggatgg tgacactact aaacctataa  33840
cactaaaaat aaacttcaat ggcattgatg aaacaacaga aaatacccct gttagtaaat  33900
attccatgac attctcatgg agctggccca ccgcaagcta cataggccac acttttgcaa  33960
caaactcttt tactttctcc tacatcgccc aagaataaag aaagcacaga gatgcttgtt  34020
ttgatttcaa aattgtgtgc ttttatttat tttcagctta cagtatttcc agtagtcatt  34080
cgaataaagc ttaatcaaac tgcatgagaa cccttccaca tagcttaaat tagcaccagt  34140
gcaaatggag aaaattcaac atacctttt tatccagata tcagagaact ctagtggtca  34200
gttttccccc accctcccag ctcacagaat acacagtcct ttcccccgg ctggctttaa  34260
acaacactat ctcattggta acagacatat tcttaggtgt aataatccac acggtctctt  34320
ggcgggccaa gcgctggtcg gtgatgttaa taaactcccc aggcagctct ttcaagttca  34380
cgtcgctgtc caactgctga agcgctcgcg gctccgactg cgcctctagc ggaggcaacg  34440
gcaacacccg atccttgatc tataaaggag tagagtcata atccccata agaatagggc  34500
ggtgatgcag caacaaggcg cgcagcaact cctgccgccg cctctccgta cgacaggaat  34560
gcaacggcgt ggtggtctcc tccgcgataa tccgcaccgc tcgcagcatc agcatcctcg  34620
tcctccgggc acagcagcgc atcctgatct cactgagatc ggcgcagtaa gtgcagcaca  34680
aaaccaagat gttatttaag atcccacagt gcaaagcact gtacccaaag ctcatggcgg  34740
gaaggacagc cccacgtga ccatcatacc agatccttag gtaaatcaaa tgacgacctc  34800
tcataaacac gctggacatg tacatcacct ccttgggcat gcgctgattc accacctctc  34860
gataccacaa gcatcgctga ttaattaaag acccctcaag caccatcctg aaccaggaag  34920
ccagcacctg accccccgcc aggcactgca gggaccccgg tgaattgcag tggcagtgaa  34980
gactccagcg ctcgtagccg tgaaccatag agccggtcat tatatccaca ttggcacaac  35040
acaaacacac tttcatacac tttttcatga ttagcagctc ctctctagtc aggaccatat  35100
cccaaggaat cacccactct tgaatcaagg taaatcccac acagcagggc aggcctctca  35160
cataactcac gttatgcata gtgagcgtgt cgcaatctgg aaataccgga tgatcttcca  35220
tcaccgaagc tcgcgtctcc gtctcaaagg gaggtaaacg gtccctcgtg tagggacagt  35280
ggcgggataa tcgagatcgt gttgaacgta gagtcatgcc aaagggaaca gcggacgtac  35340
tcatatttcc tccagcagaa ccaagtgcgc gcgtggcagc tatccctgcg tcttctgtct  35400
cgccgcctgc cccgctcggt gtagtagttg taatacagcc actccctcag accgtcaagg  35460
cgctccctgg cgtccggatc tataacaaca ccgtcctgca gcgccgccct gatgacatcc  35520
accaccgtag agtatgccaa gcccagccag gaaatgcatt cactttgaca gcgagagata  35580
ggaggagcgg gaagagatgg aagaaccatg atagtaaaag acttttattc caatcgatcc  35640
tctacaatgt caaagtgtag atctataaga tgacactggt ctcctccgct gagtcgatca  35700
```

aaaataacag ctaaaccaca aacaacacga ttggtcaaat gctccacaag ggcttgcagc 35760
ataaaatcgc ctcgaaagtc caccgcaagc ataacatcaa agccaccgcc cctatcatga 35820
tctataataa aaaccccaca gctatccacc agacccataa agttttcatc tctccatcgt 35880
gaaaaaatat ttacaagctc ctcctttaaa tcacctccaa ccaattgaaa aagttgagcc 35940
aaaccgccct ccaccttcat tttcagcaag cgcatcatga ttgcaaaaat tcaggctcct 36000
gagacacctg tataagattg agaagcggaa cgttaacgtc aatgtttcgc tcgcgaagat 36060
cgcgcctcag tgcaagcatg atataatccc acaggtcgga gcggatcagc gaggacatct 36120
ccccgccagg aaccaactca acggagccta tgctgattat aatacgcata ttcggggcta 36180
tgctgaccag cacggccccc aaataggcgt actgcatagg cggcgacaaa aagtgaacag 36240
tttgggttaa aaaatcaggc aaacagtcgc gcaaaaaagc aagaacatca taaccatgct 36300
catgcaaata gatgcaagta agctcaggaa cgaccacaga aaaatgcaca atttttctct 36360
caaacatgac tgcgagccct gcaaaaaata aaaaagaaac attacacaag agtagcctgt 36420
cttacgatgg gatagactac tctaaccaac ataagacggg ccacaacatc gcccgcgtgg 36480
ccataaaaaa aattgtccgt gtgattaaaa agaagcacag atagctggcc agtcatatcc 36540
ggagtcatca cgtgtgaacc cgtgtagacc cccgggttgg acacatcggc caaacaaaga 36600
aagcggccaa tgtacccagg aggaatcata acactaagac gaagatacaa cagaataacc 36660
ccatgagggg gaataacaaa gttagtaggt gaataaaaac gataaacacc cgaaactccc 36720
tcctgcgtag gcaaaatagc accctcccct tccaaaacaa catatagcgc ttccacagca 36780
gccatgacaa aagactcaaa acactcaaaa gactcagtct taccaggaaa ataaaagcac 36840
tctcacagca ccagcactaa tcagagtgtg aagagggcca agtgccgaac gagtatatat 36900
aggaataaaa aatgacgtaa atgtgtaaag gtcagaaaac gcccagaaaa atacacagac 36960
caacgcccga aacgaaaacc cgcgaaaaaa tacccagaac ttcctcaaca accgccactt 37020
ccggtttctc acggtacgtc acttccgcaa gaaaagcaaa actacatttc ccacatgtgt 37080
aaaaacgaaa ccccgcccct tgtaactgcc cacaacttac atcatcaaaa cataaactcc 37140
tacgtcaccc gccccgcctc tccccgccca cctcattatc atattggcca caatccaaaa 37200
taaggtatat tat 37213

<210> SEQ ID NO 24
<211> LENGTH: 37216
<212> TYPE: DNA
<213> ORGANISM: Gorilla beringei beringei

<400> SEQUENCE: 24
ataatatacc ttattttgga ttgtggccaa tatgataatg aggtgggcgg ggagaggcgg 60
ggcgggtgac gtaggacgcg cgagtagggt tgggaggtgt ggcggaagtg tggcatttgc 120
aagtgggagg agctcacatg caagcttccg tcgcggaaaa tgtgacgttt ttgatgagcg 180
ccgcctacct ccggaagtgc caattttcgc gcgcttttca ccggatatcg tagtaatttt 240
gggcgggacc atgtaagatt tggccatttt cgcgcgaaaa gtgaaacggg gaagtgaaaa 300
ctgaataata gggcgttagt catagcgcgt aatatttacc gagggccgag ggactttgac 360
cgattacgtg gaggactcgc ccaggtgttt tttacgtgaa tttccgcgtt ccgggtcaaa 420
gtctccgttt ttattgtcac cgtcatttga cgcggagggt atttaaaccc gctgcgctcc 480
tcaagaggcc actcttgagt gccagcgaga agagttttct cctctgctcc gcttcggtga 540

-continued

```
tcgaaaaatg agacacatag cctgcactcc gggtcttttg tccggtcggg cggcggccga    600
gcttttggac gctttgatca atgatgtcct aagcgatgat tttccgtcta ctacccactt    660
tagcccacct actcttcacg aactgtacga tctggatgta ctggtggatg tgaacgatcc    720
caacgaggag gcggtttctg cgtttttttcc cgagtctgcg ctgttggccg ctcaggaggg    780
atttgaccta cacactccgc cgcctatttt agagtctccg ctgccggagc ccagtggtat    840
accttatatg cctgaactgc ttcccgaagt ggtagacctg acctgccacg agcctggctt    900
tccgcccagc gacgatgagg gtgagccttt tgttttagac tttgctgaga tacctgggca    960
cggttgcagg tcttgtgcat atcatcagag ggttaccgga gaccccgagg ttaagtgttc   1020
gctgtgctat atgaggatga cctcttcctt tatctacagt aagtttttgt ctaggtgggc   1080
ttttgggtag gtgggttttg tgtcagaaca ggtgtaaacg ttgcttgtgt tttttgtacc   1140
tgtaggtccg gtgtccgagc cagacccgga gcccgaccgc gatcccgagc cggatcccga   1200
gcctcctcgc aggacaagga aactaccttc cattctgtgc aagtctcaga cacctgtaag   1260
gaccagcgag gcagacagca ccgactctgg cacttctacc tctcccctg aaattcaccc    1320
agtggttcct ctgggtatac ataaacctgt tgctgttaaa gtttgcgggc gacgccctgc   1380
agtacagtgc attgaggact tgcttcacga tcccgaggaa cctttggact tgagccttaa   1440
acgccctagg caataaaccc cacctaagta ataaacccca cctaagtaat aaaccctgcc   1500
gcccttggtt attgagatga cgcccaatgt ttgcttttga atgacttcat gtgtgtaata   1560
aaagtgagtg tgatcatagg tctcttgttt gtctgggcgg ggcttaaggg tatataagtc   1620
tcttggggct aaacttggtt acacttgacc ccaatggagg cgtgggggtg cttggaggag   1680
tttgcggacg tgcgccgttt gctggacgag agctctagca atacctatac tatttggagg   1740
tatctgtggg gctctactca ggccaagttg gtttccagaa ttaagcagga ttacaagtgc   1800
gattttgaag agctttttag ttcctgcggt gagcttttgc aatccttgaa tctgggccat   1860
caggctattt tccaggaaaa ggttctctcg actttggatt tttccactcc cgggcgcacc   1920
gccgcttgtg tggcttttgt gtcttttgtg caagataaat ggagcgagga gacccacctg   1980
agtcacggct acgtactgga tttcatggcg atggctcttt ggagggctca caacaaatgg   2040
aagattcaga aggaactgta cggttccgcc ctacgtcgtc cacttctgtc gcgacagggg   2100
ctgaggtttc ccgaccatcg gcagcatcag aatctggaag acgagtcgga ggagcgagcg   2160
gaggagaaga tcagcttgag agccggcctg gaccctcctc aggaggaatg aatctcccgc   2220
aggtggttga cctgtttcca gaactgagac gggtcctgac tatcagggag gatggtcagt   2280
ttgtgaagaa gtttaagagg gatcggggtg agggagatga tgaggcggct agcaatttag   2340
cttttagtct gatgactcgc caccgaccgg aatgtattac ctatcagcag attaaggaga   2400
gttgtgccaa cgagctggat cttttgggtc agaagtatag catagaacag cttaccactt   2460
actggcttca gcctggggat gattgggaag aggcgatcag ggtgtatgca aaggtggccc   2520
tgcggcccga ttgcaagtat aagattacta agttggttaa tattagaaac tgctgctata   2580
tttctgggaa cggggccgaa gtggagatag atactcagga cagggtggct tttaggtgtt   2640
gcatgataaa catgtggccc gggatactgg ggatggatgg ggtggtattc atgaatgtga   2700
ggtttacggg ccccaacttt aatggcacgg tgttcatggg caacaccaac ttgctcctgc   2760
atggtgcgag tttctatggg tttaataaca cctgtataga ggcctggacc gatgtaaagg   2820
ttcgaggttg ttccttttat agctgttgga aggcggtggt gtgtcgccct aaaagcaggg   2880
gttctgtgaa aaaatgcttg tttgaaaggt gcaccttagg catcctctct gagggcaact   2940
```

-continued

```
ccagggtgcg ccataatgtg gcttcgaact gcggttgctt catgcaagtg aagggggtga   3000
gcgttatcaa gcataactcg gtgtgtggaa actgcgagga tcgcgcctcc cagatgctga   3060
cctgctttga tggcaactgt cacctgttga agaccattca tataagcagc caccccagaa   3120
aggcctggcc cgtgtttgag cataacatct tgacccgctg ctccttgcat ctgggggtca   3180
ggagggggtat gttcctgcct taccagtgta actttagcca cactaaaatc ctgctggaac   3240
ccgagtgcat gaccaaggtc agcctgaatg gtgtgtttga tgtgactctg aaaatctgga   3300
aggtgctgag gtatgatgag accaggacca ggtgccgacc ctgcgagtgc ggcggcaagc   3360
acatgagaaa tcagcctgtg atgttggatg tgaccgagga gcttaggcct gaccatctgg   3420
tgctggcctg caccagggcc gagtttgggt ctagcgatga ggataccgat tgaggtgggt   3480
aaggtgggcg tggctagaag ggtggggcgt gtataaattg gggtctaag ggtctctctg   3540
ttttgtcttg caacagccgc cgccatgagc gacaccggca acagctttga tggaagcatc   3600
tttagcccct atctgacagt gcgcatgcct cactgggctg gagtgcgtca gaatgtgatg   3660
ggttccaacg tggatggacg ccccgttctg ccttcaaatt cgtctacaat ggcctacgcg   3720
accgtgggag gaactccgct ggacgccgcg acctccgccg ccgcctccgc cgccgccgcg   3780
accgcgcgca gcatggctac ggacctttac agctctttgg tggcgagcgg cgcggcctct   3840
cgcgcgtctg ctcgggatga gaaactgacc gctctgctgc ttaaactgga agacttgacc   3900
cgggagctgg gtcaactgac ccagcaggtc tccagcttgc gtgagagcag ccttgcctcc   3960
ccctaatggc ccataatata aataaaagcc agtctgtttg gattaagcaa gtgtatgttc   4020
tttatttaac tctccgcgcg cggtaagccc gggaccagcg gtctcggtcg tttagggtgc   4080
ggtggattct ttccaacacg tggtacaggt ggctctggat gtttagatac atgggcatga   4140
gtccatccct ggggtggagg tagcaccact gcagagcttc gtgctcgggg gtggtgttgt   4200
atatgatcca gtcgtagcag gagcgctggg cgtggtgctg aaaaatgtcc ttaagcaaga   4260
ggcttatagc tagggggagg cccttggtgt aagtgtttac aaatctgctc agttgggagg   4320
ggtgcatccg gggggatata atgtgcatct tggactggat tttaggttg gctatgttcc   4380
cacccagatc ccttctggga ttcatgttgt gcaggaccac cagcacggta tatccagtgc   4440
acttgggaaa tttatcgtgg agcttagacg ggaatgcatg gaagaacttg gagacgccct   4500
tgtggcctcc cagattttcc atacattcgt ccatgatgat ggcaatgggc ccgtgggaag   4560
ctgcctgagc aaaaatgttt ctgggatcgc tcacatcgta gttatgttcc agggtgaggt   4620
catcatagga catctttacg aatcgggggc ggagggtccc ggactggggg atgatggtac   4680
cctcgggccc cggggcgtag ttcccctcac agatctgcat ctcccaggct ttcatttcag   4740
agggagggat catatccacc tgcggagcga tgaaaaacac agtttctggc gcagggggaga   4800
ttaactggga tgagagcagg tttctgagca gctgtgactt tccacagccg gtgggcccat   4860
atatcacgcc tatcaccggc tgcagctggt agttaagaga gctgcagctg ccgtcctccc   4920
ggagcagggg ggccacctcg ttcagcatat ccctgacgtg gatgttctcc ctgaccaatt   4980
ccgccagaag gcgctcgccg cccagcgaaa gcagctcttg caaggaagca aaatttttca   5040
gcggttttag gccgtcggcc gtgggcatgt tttcagcgt ctgggtcagc agttccagcc   5100
tgtcccacag ctcggtgatg tgctctacgg catctcgatc cagcagatct cctcgtttcg   5160
cgggttgggg cggctttcgc tgtagggcac cagccgatgg gcgtccagcg ggccagagt   5220
catgtccttc catgggcgca gggtcctcgt cagggtggtc tgggtcacgg tgaaggggtg   5280
```

-continued

```
cgctccgggt tgggcgctgg ccagggtgcg cttgaggctg gttctgctgg tgctgaatcg   5340
ctgccgctct tcgccctgcg cgtcggccag gtagcatttg accatggtct cgtagtcgag   5400
accctcggcg gcgtgcccct tggcgcggag ctttcccttg gaggtggcgc cgcacgaggg   5460
gcactgcagg ctcttcaggg cgtagagctt gggagcgaga aacacggact ctggggagta   5520
ggcgtccgcg ccgcaggaag cgcagaccgt ctcgcattcc accagccaag tgagctccgg   5580
gcggtcaggg tcaaaaacca ggttgccccc atgctttttg atgcgtttct tacctcggct   5640
ctccatgagg cggtgtccct tctcggtgac gaagaggctg tccgtgtccc cgtagaccga   5700
cttcaggggc ctgtcttcca gcggagtgcc tctgtcctcc tcgtagagaa actctgacca   5760
ctctgagacg aaggcccgcg tccaggccag gacgaaggag gccacgtggg aggggtagcg   5820
gtcgttgtcc actagcgggt ccaccttctc cagggtgtgc aggcacatgt ccccctcctc   5880
cgcgtccaga aaagtgattg gcttgtaggt gtaggacacg tgaccggggg ttcccgacgg   5940
gggggtataa aagggggtgg gcgccctttc atcttcactc tcttccgcat cgctgtctgc   6000
gagggccagc tgctggggta agtattccct ctcgaaggcg ggcatgacct cagcgctcag   6060
gttgtcagtt tctaaaaatg aggaggattt gatgttcacc tgtccggagg tgataccttt   6120
gagggtacct gggtccatct ggtcagaaaa cactattttt ttgttgtcaa gcttggtggc   6180
gaacgacccg tagagggcgt tggagagcag cttggcgatg gagcgcaggg tctggttttt   6240
gtcgcggtcg gctcgctcct tggccgcgat gttgagttgc acgtactcgc gggccacgca   6300
cttccactcg gggaagacgg tggtgcgctc gtctgggatt aggcgcaccc tccagcctcg   6360
gttgtgcagg gtgaccatgt cgacgctggt ggcgacctcg ccgcgcaggc gctcgttggt   6420
ccagcagagg cggccgccct tgcgcgagca gaagggggt agggggtcca gctggtcctc    6480
gtttgggggg tccgcgtcga tggtgaagac cccggggagc aagcgcgggt caaagtagtc   6540
gatcttgcaa gcttgcatgt ccagagcccg ctgccattcg cgggcggcga gcgcgcgctc   6600
gtaggggttg aggggcgggc cccagggcat ggggtgggtg agcgcggagg cgtacatgcc   6660
gcagatgtca tacacgtaca ggggttccct gaggatgccg aggtaggtgg ggtagcagcg   6720
ccccccgcgg atgctggcgc gcacgtagtc atagagctcg tgggaggggg ccagcatgtt   6780
gggcccgagg ttggtgcgct gggggcgctc ggcgcggaag gcgatctgcc tgaagatggc   6840
atgggagttg gaggagatgg tgggccgctg gaagacgttg aagcttgctt cttgcaagcc   6900
caccgagtcc ctgacgaagg aggcgtagga ctcgcgcagc ttgtgcacca gctcggcggt   6960
gacctggacg tcgagcgcgc agtagtcgag ggtctcgcgg atgatgtcat acttatcctc   7020
ccccttcttt ttccacagct cgcggttgag gacgaactct tcgcggtctt tccagtactc   7080
ttggagggga aacccgtccg tgtccgaacg gtaagagcct agcatgtaga actggttgac   7140
ggcctggtag ggcaacagcc ccttctccac gggcagcgcg taggcctgcg ccgccttgcg   7200
gagggaggtg tgggtgaggg cgaaagtgtc cctgaccatg actttgaggt attgatgttt   7260
gaagtctgtg tcatcgcagc cgccctgttc ccacagggtg tagtccgtgc gctttttgga   7320
gcgcgggttg ggcagggaga aggtgaggtc attgaagagg atcttccccg ctcgaggcat   7380
gaagtttctg gtgatgcgaa agggccctgg gaccgaggag cggttgttga tgacctgggc   7440
ggccaggacg atctcgtcaa agccgtttat gttgtggccc acgatgtaga gctccaaaaa   7500
gcggggctgg cccttgatgg aggggagctt tttgagttcc tcgtaggtga gctcctcggg   7560
cgattccagg ccgtgctcct ccagggccca gtcttgcaag tgagggttgg ccgccaggaa   7620
ggatcgccag aggtcgcggg ccatgagggt ctgcaggcgg tcgcggaagg ttctgaactg   7680
```

-continued

```
tcgccccacg gccatctttt cgggggtgat gcagtagaag gtgagggggt ctttctccca   7740
ggggtcccat ctgagctctc gggcgaggtc gcgcgcggcg gcgaccagag cctcgtcgcc   7800
ccccagtttc atgaccagca tgaagggcac gagctgcttg ccaaaggctc ccatccaagt   7860
gtaggtctct acatcgtagg tgacaaagag gcgctccgtg cgaggatgag agccgatcgg   7920
gaagaactgg atctcccgcc accagttgga ggattggctg ttgatgtggt gaaagtagaa   7980
gtcccgtctg cgggccgagc actcgtgctg gcttttgtaa aagcgaccgc agtactggca   8040
gcgctgcacg ggttgtatat cttgcacgag gtgaacctgg cgacctctga cgaggaagcg   8100
cagcgggaat ctaagtcccc cgcctggggt cccgtgtggc tggtggtctt ctactttggt   8160
tgtctggccg ccagcatctg tctcctggag ggcgatggtg gagcagacca ccacgccgcg   8220
agagccgcag gtccagatct cggcgctcgg cgggcggagt ttgatgacga catcgcgcac   8280
attggagctg tccatggtct ccagctcccg cggcggcagg tcagctggga gttcctggag   8340
gttcacctcg cagagacggg tcaaggcgcg ggcagtgttg agatggtatc tgatttcaag   8400
gggcgtgttg gcggcggagt cgatggcttg caggaggccg cagcccgggg gggccacgat   8460
ggttccccgc ggggcgcgag gggaggcgga agctgggggt gtgttcagaa gcggtgacgc   8520
gggcgggccc ccggaggtag ggggggttcc ggccccacag gcatgggcgg caggggcacg   8580
tcttcgccgc gcgcgggcag ggctggtgc tggctccgaa gagcgcttgc gtgcgcgacg   8640
acgcgacggt tggtgtcctg tatctgacgc ctctgagtga agaccacggg tcccgtgacc   8700
ttgaacctga aagagagttc gacagaatca atctcggcat cgttgacagc ggcctggcgc   8760
aggatctcct gcacgtcgcc cgagttgtcc tggtaggcga tctctgccat gaactgctcg   8820
atctcttctt cctggagatc tcctcgtccg gcgcgctcca cggtggccgc caggtcgttg   8880
gagatgcgac ccatgagctg tgagaaggcg ttgagcccgc cctcgttcca gacccggctg   8940
tagaccacgc ccccctcggc gtcgcgagcg cgcatgacca cctgggccag gttgagctcc   9000
acgtgtcgcg tgaagacggc gtagttgcgc aggcgctgga aaaggtagtt cagggtggtg   9060
gcggtgtgct cggcgacgaa gaagtacatg acccagcgcc gcaacgtgga ttcattgatg   9120
tcccccaagg cctccaggcg ctccatggcc tcgtagaagt ccacggcgaa gttgaaaaac   9180
tgggagttgc gagcggacac ggtcaactcc tcctccagaa gacggatgag ctcggcgaca   9240
gtgttgcgca cctcgcgctc gaaggccacg gggggcgctt cttcctcttc cacctcttct   9300
tccatgatcg cttcttcttc ttcctcagcc gggacgggag gggggcggcgg cggcggggga   9360
ggggcgcggc ggcggcggcg gcgcaccggg aggcggtcga tgaagcgctc gatcatctcc   9420
ccccgcatgc ggcgcatggt ctcggtgacg gcgcggccgt tctcccgggg gcgcagctcg   9480
aagacgccgc ctctcatctc gccgcggggc gagcggccgt gaggtagcga gacggcgctg   9540
actatgcatc ttaacaattg ctgtgtaggt acaccgccga gggacctgat tgagtccaga   9600
tccaccggat ccgaaaacct ttggaggaaa gcgtctatcc agtcgcagtc gcaaggtagg   9660
ctgagcaccg tggcgggcgg gggcgggtct ggagagttcc tggcggagat gctgctgatg   9720
atgtaattaa agtaggcggt cttgagaagg cggatggtgg acaggagcac catgtctttg   9780
ggtccggcct gttggatgcg gaggcggtcg gccatgcccc aggcctcgtt ctgacaccgg   9840
cgcaggtctt tgtagtagtc ttgcatgagt ctttccaccg gcacctcttc tccttcctct   9900
tctccatctc gccggtggtt tctcgcgccg cccatgcgcg tgaccccaaa gcccctgagc   9960
ggctgcagca gggccaggtc ggcgaccacg cgctcggcca agatggcctg ctgcacctga  10020
```

```
gtgagggtcc tctcgaagtc atccatgtcc acgaagcggt ggtaggcgcc cgtgttgatg  10080
gtgtaggtgc agttggccat gacggaccag ttgacggtct ggtgtcccgg ctgcgagagc  10140
tccgtgtacc gcaggcgcga gaaggcgcgg gaatcgaaca cgtagtcgtt gcaagtccgc  10200
accagatact ggtagcccac caggaagtgc ggcggaggtt ggcgatagag gggccagcgc  10260
tgggtggcgg gggcgccggg cgccaggtct tccagcatga ggcggtggta tccgtagatg  10320
tacctggaca tccaggtgat gccggcggcg gtggtggtgg cgcgcgcgta gtcgcggacc  10380
cggttccaga tgtttcgcag ggcgagaag tgttccatgg tcggcacgct ctggccggtg  10440
aggcgcgcgc agtcgttgac gctctataca cacacaaaaa cgaaagcgtt tacagggctt  10500
tcgttctgta gcctggagga aagtaaatgg gttgggttgc ggtgtgcccc ggttcgagac  10560
caagctgagc tcggccggct gaagccgcag ctaacgtggt attggcagtc ccgtctcgac  10620
ccaggccctg tatcctccag gatacggtcg agagcccttt tgctttcttg gccaagcgcc  10680
cgtggcgcga tctgggatag atggtcgcga tgagaggaca aaagcggctc gcttccgtag  10740
tctggagaaa caatcgccag ggttgcgttg cggcgtaccc cggttcgagc ccctatggcg  10800
gcttgaatcg gccggaaccg cggctaacga gggccgtggc agccccgtcc tcaggacccc  10860
gccagccgac ttctccagtt acgggagcga gccccttttg tttttattt tttagatgca  10920
tcccgtgctg cggcagatgc gcccctcgcc ccggcccgat cagcagcagc aacagcaggc  10980
atgcagaccc ccctctcccc tttccgcccc ggtcaccacg gccgcggcgg ccgtgtcggg  11040
cgcgggggc gcgctggagt cagatgagcc accgcggcgg cgacctaggc agtatctgga  11100
cttggaagag ggcgagggac tggcgcggct gggggcgaac tctccagagc gccacccgcg  11160
ggtgcagttg aaaagggacg cgcgcgaggc gtacctgccg cggcagaacc tgtttcgcga  11220
ccgcgggggc gaggagcccg aggagatgcg agactgcagg ttccaagcgg ggcgcgagct  11280
gcggcgcggg ctggacagac agcgcctgct gcgcgaggag gactttgagc ccgacacgca  11340
gacgggcatc agccccgcgc gcgcgcacgt agccgcggcc gacctggtga ccgcctacga  11400
gcagacggta aaccaggagc gcaacttcca aaagagcttc aacaaccacg tgcgcacgct  11460
ggtggcgcgc gaggaggtga ccctgggtct catgcatctg tgggacctgg tggaggcgat  11520
cgtgcagaac cccagcagca agcccctgac cgcgcagctg ttcctggtgg tgcagcacag  11580
cagggacaac gaggccttca gggaggcgct gctgaacatc accgagccgg aggggcgctg  11640
gctcctggac ctgataaaca tcctgcagag catagtggtg caggagcgca gcctgagcct  11700
ggccgagaag gtggcggcca tcaactactc tatgctgagc ctgggcaagt tctacgcccg  11760
caagatctac aagacccct acgtgcccat agacaaggag gtgaagatag acagcttcta  11820
catgcgcatg gcgctgaagg tgctgaccct gagcgacgac ctgggagtgt accgcaacga  11880
gcgcatccac aaggccgtga gcgccagccg gcggcgcgag ctgagcgacc gcgagctgat  11940
gcacagtctg cagcgcgcgc tgaccggcgc gggcgagggc gacagggagg tcgagtccta  12000
cttcgacatg gggccgacc tgcactggca gccgagccgc cgcgccctgg aggcggcggg  12060
ggcgtacggc ggcccctgg cggccgatga ccaggaagag gaggactatg agctagagga  12120
gggcgagtac ctggaggact gacctggctg gtggtgtttt ggtatagatg caagatccga  12180
acgtggcgga cccggcggtc cgggcggcgc tgcaaagcca gccgtccggc attaactcct  12240
ctgacgactg ggccgcggcc atgggtcgca tcatggccct gaccgcgcgc aaccccgagg  12300
ctttcaggca gcagcctcag gccaaccggc tggcggccat cttggaagcg gtagtgcccg  12360
cgcgctccaa ccccacccac gagaaggtgc tggccatagt caacgcgctg gcggagagca  12420
```

-continued

```
gggccatccg cgcggacgag gccggactgg tgtacgatgc gctgctgcag cgggtggcgc  12480
ggtacaacag cggcaacgtg cagaccaacc tggaccgcct ggtgacggac gtgcgcgagg  12540
ccgtggcgca gcgcgagcgc ttgcatcagg acggtaacct gggctcgctg gtggcgctaa  12600
acgccttcct cagcacccag ccggccaacg taccgcgggg gcaggaggac tacaccaact  12660
ttttgagcgc gctgcggctg atggtgaccg aggtccctca gagcgaggtg taccagtcgg  12720
ggcccgacta cttcttccag accagcagac agggcttgca aaccgtgaac ctgagccagg  12780
ctttcaagaa cctgcggggg ctgtggggag tgaaggcgcc caccggcgac cgggctacgg  12840
tgtccagcct gctaaccccc aactcgcgcc tgctgctgct gctgatcgcg cccttcacgg  12900
acagcgggag cgtctcgcgg gagacctatc tgggccacct gctgacgctg taccgcgagg  12960
ccatcgggca ggcgcaggtg gacgagcaca ccttccaaga gatcaccagc gtgagccacg  13020
cgctggggca ggaggacacg ggcagcctgc aggcgaccct gaactacctg ctgaccaaca  13080
ggcggcagaa gattcccacg ctgcacagcc tgacccagga ggaggagcgc atcttgcgct  13140
acgtgcagca gagcgtgagc ctgaacctga tgcgcgacgg cgtgacgccc agcgtggcgc  13200
tggacatgac cgcgcgcaac atggaaccgg gcatgtacgc ctcccaccgg ccgtttatca  13260
accgcctgat ggactacttg catcgggcgg cggccgtgaa ccccgagtac ttcactaatg  13320
ccattctgaa tccccactgg atgccccctc cgggtttcta caacggggac tttgaggtgc  13380
ccgaggtcaa cgacgggttc ctctgggatg acatggatga cagtgtgttc tcacccaacc  13440
cgctgcgcgc cgcgtctctg cgattgaagg agggctctga cagggaagga ccgaggagtc  13500
tggcctcctc cctggctctg ggagcggtgg gcgccacggg cgcggcggcg cggggcagta  13560
gccccttccc cagcctggca gactctctga acagcgggcg ggtgagcagg ccccgcttgc  13620
taggcgagga ggagtatctg aacaactccc tgctgcagcc cgcgagggac aagaacgctc  13680
agcggcagca gtttcccaac aatgggatag agagcctggt ggacaagatg tccagatgga  13740
agacgtatgc gcaggagtac aaggagtggg aggaccgcca gccgcggccc ttgccgcccc  13800
ctaggcagcg ctggcagcgg cgcgcgtcca accgccgctg gaggcagggg cccgaggacg  13860
atgatgactc tgcagatgac agcagcgtgt tggacctggg cgggagcggg aacccctttt  13920
cgcacctgcg cccacgcctg ggcaagatgt tttaaaagaa aaaaaaaaat aaaactcacc  13980
aaggccatgg cgacgagcgt tggttttttg ttcccttcct tagtatgcgg cgcgcggcga  14040
tgttcgagga ggggcctccc ccctcttacg agagcgcgat ggggatttct cctgcggcgc  14100
ccctgcagcc tccctacgtg cctcctcggt acctgcaacc tacagggggg agaaatagca  14160
tctgttactc tgagctgcag cccctgtacg ataccaccag actgtacctg gtggacaaca  14220
agtccgcgga cgtggcctcc ctgaactacc agaacgacca cagcgatttt ttgaccacgg  14280
tgatccaaaa caacgacttc accccaaccg aggccagcac ccagaccata aacctggata  14340
acaggtcgaa ctggggcggc gacctgaaga ccatcttgca caccaacatg cccaacgtga  14400
acgagttcat gttcaccaac tcttttaagg cgcgggtgat ggtggcgcgc gagcaggggg  14460
aggcgaagta cgagtgggtg gacttcacgc tgcccgaggg caactactca gagaccatga  14520
ctctcgacct gatgaacaat gcgatcgtgg aacactatct gaaagtgggc aggcagaacg  14580
gggtgaagga aagcgatatc ggggtcaagt ttgacaccag aaacttccgt ctgggctggg  14640
accccgtgac cgggctggtc atgccggggg tctacaccaa cgaggccttt catcccgaca  14700
tagtgcttct gcccggctgt ggggtggact tcacccagag ccggctgagc aacctgctgg  14760
```

-continued

```
gcattcgcaa gcggcagcct ttccaggagg gtttcaagat cacctatgag gatctgaagg  14820
ggggcaacat tcccgcgctc cttgatctgg acgcctacga ggagagcttg aaacccgagg  14880
agagcgctgg cgacagcggc gagagtggcg aggagcaagc cggcggcggt ggcggcgcgt  14940
cggtagaaaa cgaaagtacg cccgcagtgg cggcggacgc tgcggaggtc gagccggagg  15000
ccatgcagca ggacgcagag gagggcgcac aggagggcgc gcagaaggac atgaacgatg  15060
gggagatcag gggagacaca ttcgccaccc ggggcgaaga aaaagaggca gaggcggcgg  15120
cggcggcgac ggcggaggcc gaaaccgagg ttgaggcaga ggcagagccc gagaccgaag  15180
ttatggaaga catgaatgat ggagaacgta ggggcgacac gttcgccacc cggggcgaag  15240
agaaggcggc ggaggcagaa gccgcggctg aggaggcggc tgcggctgcg gccaagactg  15300
aggctgcggc taaggctgag gtcgaagcca atgttgcggt tgaggctcag gctgaggagg  15360
aggcggcggc tgaagcagtt aaggaaaagg cccaggcaga gcaggaagag aaaaaacctg  15420
tcattcaacc tctaaaagaa gatagcaaaa agcgcagtta caacgtcatc gagggcagca  15480
cctttaccca gtaccgcagc tggtacctgg cgtacaacta cggcgacccg gtcaaggggg  15540
tgcgctcgtg gaccctgctc tgcacgccgg acgtcacctg cggctccgag cagatgtact  15600
ggtcgctgcc gaacatgatg caagacccgg tgaccttccg ctccacgcgg caggttagca  15660
acttcccggt ggtgggcgcc gaactgctgc ccgtgcactc caagagtttt tacaacgagc  15720
aggccgtcta ctcccagctg atccgccagg ccacctctct gacccacgtg ttcaatcgct  15780
ttcccgagaa ccagattttg gcgcgcccgc cggcccccac catcaccacc gtgagtgaaa  15840
acgttcctgc cctcacagat cacgggacgc taccgctgcg caacagcatc tcaggagtcc  15900
agcgagtgac cattactgac gccagacgcc ggacctgccc ctacgtttac aaggccttgg  15960
gcatagtctc gccgcgcgtc ctctccagtc gcactttttta aaacacatct acccacacgt  16020
tccaaaatca tgtccgtact catctcaccc agcaacaaca ccggctgggg gctgcgcgcg  16080
cccagcaaga tgtttggagg ggcgaggaag cgctccgacc agcaccctgt gcgcgtgcgc  16140
ggccactacc gcgcgccctg gggagcgcac aagcgcgggc gcacagggcg caccactgtg  16200
gacgacgtca ttgactccgt agtggagcaa gcgcgccact acacacccgg cgcgccgacc  16260
gcccccgccg tgtccaccgt ggaccaggcg atcgaaagcg tggtacaggg cgcgcggcac  16320
tatgccaacc ttaaaagtcg ccgccgccgc gtggcccgcc gccatcgccg gagaccccgg  16380
gccaccgccg ccgcgcgcct tactaaggct ctgctcaggc gcgccaggcg aactggccac  16440
cgggccgcca tgagggccgc acggcgggct gccgctgccg caagcgtcgt ggccccgcgg  16500
gcacgaaggc gcgcggccgc tgccgccgcc gccgccattt ccagcttggc ctcgacgcgg  16560
cgcggtaaca tatactgggt gcgcgactcg gtaaccggca cgcgggtacc cgtgcgcttt  16620
cgcccccgc ggaattagca caagacaaca tacacactga gtctcctgct gttgtgtatc  16680
ccagcggcga ccgtcagcag cggcgacatg tccaagcgca aaattaaaga agagatgctc  16740
caggtcatcg cgccggagat ctatgggccc ccgaagaagg aggaggatga ttacaagccc  16800
cgcaagctaa agcgggtcaa aaagaaaaag aaagatgatg atgacgaggc ggtggagttt  16860
gtccgccgca tggcacccag gcgccccgtg cagtggaagg gccggcgcgt gcagcgcgtt  16920
ttgcgccccg gcaccgcggt ggtcttcacg cccggcgagc gctccacgcg cactttcaag  16980
cgggtgtacg atgaggtgta cggcgacgag gacctgttgg agcaggccaa ccagcgcttt  17040
ggggagtttg catatgggaa acggccccgc gagagtctaa aagaggacct gctggcgcta  17100
ccgctggacg agggcaatcc caccccgagt ctgaagccgg taaccctgca acaggtgctg  17160
```

cctttgagcg cgcccagcga gcataagcga gggttgaagc gcgaaggcgg ggacctggcg 17220
cccaccgtgc agttgatggt gcccaagcgg cagaagctgg aggacgtgct ggagaaaatg 17280
aaagtagagc ccgggatcca gcccgagatc aaggtccgcc ccatcaagca ggtggcgccc 17340
ggcgtgggag tccagaccgt ggacgttagg attcccacgg aggagatgga aacccaaacc 17400
gccactccct cttcggcggc cagcgccacc accggcaccg cttcggtaga ggtgcagacg 17460
gacccctggc tacccgccac cgctgttgcc gccgccgccc cccgttcgcg cgggcgcaag 17520
agaaattatc cagcggccag cgcgctcatg ccccagtacg cactgcatcc atccatcgtg 17580
cccacccccg gctaccgcgg gtactcgtac cgcccgcgca gatcagccgg cactcgcggc 17640
cgccgccgcc gtgcgaccac aaccagccgc cgccgtcgcc gccgccgcca gccagtgctg 17700
acccccgtgt ctgtaaggaa ggtggctcgc tcggggagca cgctggtggt gcccagagcg 17760
cgctaccacc ccagcatcgt ttaaagccgg tctctgtatg gttcttgcag atatggccct 17820
cacttgtcgc ctccgcttcc cggtgccggg ataccgagga agaactcacc gccgcagagg 17880
catggcgggc agcggtctcc gcggcggccg tcgccatcgc cggcgcgcaa aaagcaggcg 17940
catgcgcggc ggtgtgctgc ctctgctaat cccgctaatc gccgcggcga tcggtgccgt 18000
acccgggatc gcctccgtgg ccctgcaggc gtcccagaaa cgttgactct tgcaaccttg 18060
caagcttgca ttttttggag gaaaaaataa aaaaaaagtc tagactctca cgctcgcttg 18120
gtcctgtgac tattttgtag aaaaaaagat ggaagacatc aactttgcgt cgctggcccc 18180
gcgtcacggc tcgcgcccgt tcatgggaga ctggacagat atcggcacca gcaatatgag 18240
cggtggcgcc ttcagctggg gcagtctgtg gagcggcctt aaaaattttg gttccaccat 18300
taagaactat ggcaacaaag cgtggaacag cagcacgggc cagatgctga gagacaagtt 18360
gaaagagcag aacttccagg agaaggtggc gcagggcctg gcctctggca tcagcggggt 18420
ggtggacata gctaaccagg ccgtgcagaa aaagataaac agtcatctgg acccccgtcc 18480
tcaggtggag gaaatgcctc cagcgatgga gacggtgtct cccgagggca aaggcgaaaa 18540
gcgcccgcgg cccgacagag aagagaccct ggtgtcacac accgaggagc cgccctctta 18600
cgaggaggca gtcaaggccg gcctgcccac cactcgcccc atagccccca tggccaccgg 18660
tgtggtgggc cacaggcaac acactcccgc aacactagat ctgcccccgc cgtccgagcc 18720
gccgcgccag ccaaaggcgg cgacggtgcc cgctccctcc acttccgccg ccaacagagt 18780
gcccctgcgc cgcgccgcga gcggcccccg ggcctcgcga gttagcggca actggcagag 18840
cacactgaac agcatcgtgg gcctgggagt gaggagtgtg aagcgccgcc gttgctactg 18900
aatgagcaag ctagctaacg tgttgtatgt gtgtatgcgt cctatgtcgc cgccagagga 18960
gctgttgagc cgccggcgcc gtctgcactc cagcgaattt caagatggcg accccatcga 19020
tgatgcctca gtggtcgtac atgcacatct cgggccagga cgcttcggag tacctgagcc 19080
ccgggctggt gcagttcgcc cgcgccacag acacctactt caacatgagt aacaagttca 19140
ggaaccccac tgtggcgccc acccacgatg tgaccacgga ccggtcgcag cgcctgacgc 19200
tgcggttcat ccccgtggat cgggaggaca ccgcctactc ttacaaggcg cggttcacgc 19260
tggccgtggg cgacaaccgc gtgctggaca tggcctccac ttactttgac atcagggggg 19320
tgctggacag gggccccacc ttcaagccct actcgggtac tgcctacaac tccctggccc 19380
ccaagggcgc tcccaattct tgcgagtggg aacaagatga accagctcag gcagcaatag 19440
ctgaagatga agaagaactt gaagaagaac aagctcagga cgaacaggcg cccactaaga 19500
aaacccatgt atacgcccag gcacctcttt ctggtgaaaa aattactaag gatggtttgc 19560
aaataggtgt ggatgccaca caggcgggag ataaccctat atatgctgat aaaacattcc 19620
aacccgaacc tcagataggt gagtctcagt ggaacgaggc tgatgccaca gtagcaggag 19680
gcagagtctt aaaaaagacc acccctatga gaccttgcta tggatcctat gccaaaccta 19740
ctaatgccaa tggcggtcaa gggatcatgg tggccaatga tcagggagcg cttgaatcta 19800
aagttgagat gcaatttttc tccaccacaa cgtctcttaa tgtaagggaa ggtgaaaaca 19860
atcttcagcc aaaagtagtg ctatacagcg aagatgttaa cttggaatcc cctgacactc 19920
atttgtctta caaacctaaa aaggatgaca ccaactctaa aatcatgttg ggtcagcaag 19980
ccatgcccaa cagacccaac ctcattgctt ttagggacaa ctttattgga cttatgtact 20040
acaacagcac aggcaacatg ggagtgctgg caggacaggc ctcccagcta aacgctgtgg 20100
tagacttgca agacagaaac acagagctgt cataccaact gatgcttgat tccattggag 20160
acagatcaag atacttttcc atgtggaacc aggcagtgga cagctatgac ccagatgtca 20220
gaatcattga aaaccatggg gttgaagatg agctgcccaa ctattgcttt cccctgggcg 20280
gtattggaat tacagacaca taccagtgca taaaaccaac cgcagctgct aataacacta 20340
catggtctaa ggatgaagaa tttagtgatc gcaatgaaat aggggtggga aacaacttcg 20400
ccatggagat caacatccag gccaacctct ggaggaactt cctctatgcg aacgtggggc 20460
tctacctgcc agacaagctc aagtacaacc ccaccaacgt ggacatctct gacaacccca 20520
acacctatga ctacatgaac aagcgtgtgg tggctcccgg cctggtggac tgctttgtca 20580
atgtgggagc caggtggtcc ctggactaca tggacaacgt caacccctc aaccaccacc 20640
gcaatgcggg tctgcgctac cgctccatga tcctgggcaa cgggcgctac gtgcccttcc 20700
acattcaggt gccccagaag ttctttgcca tcaagaacct cctcctcctg ccgggctcct 20760
acacttacga gtggaacttc aggaaggatg tcaacatggt cctgcagagc tctctgggca 20820
atgaccttag ggtggacggg gccagcatca agtttgacag cgtcaccctc tatgctacct 20880
tcttccccat ggctcacaac accgcctcca cgctcgaggc catgctgagg aacgacacca 20940
acgaccagtc cttcaatgac tacctctctg ggccaacat gctctacccc atccccgcca 21000
aggccaccaa cgtgcccatc tccattccct ctcgcaactg ggccgccttc agaggctggg 21060
cctttacccg ccttaagacc aaggaaaccc cctccctggg ctcgggtttt gacccctact 21120
ttgtctactc gggatccatc ccctacctgg atggcacctt ctacctcaac cacactttta 21180
agaagatatc catcatgtat gactcctccg tcagctggcc gggcaatgac cgcctgctca 21240
cccccaatga gttcgaggtc aagcgcgccg tggacggcga gggctacaac gtggcccagt 21300
gcaacatgac caaggactgg ttcctggtgc agatgctggc caactacaac atagctacc 21360
agggcttcta catcccagag agctacaagg acaggatgta ctccttcttc agaaatttcc 21420
aacccatgag caggcaggtg gtggacgaga ccaaatacaa ggactatcag gccattggca 21480
tcactcacca gcacaacaac tcgggattcg tgggctacct ggctcccacc atgcgcgagg 21540
ggcaggccta ccccgccaac ttcccctacc cgttgatagg caaaaccgcg gtcgacagcg 21600
tcacccagaa aaagttcctc tgcgaccgca ccctctggcg catccccttc tctagcaact 21660
tcatgtccat gggtgcgctc acggacctgg gccagaacct gctctatgcc aactccgccc 21720
atgcgctgga catgactttt gaggtggacc ccatggacga gcccaccctt ctctatattg 21780
tgtttgaagt gttcgacgtg gtcagagtgc accagccgca ccgcggtgtc atcgagaccg 21840
tgtacctgcg cacgcccttc tcggccggca acgccaccac ctaaggagac agcgccgccg 21900

```
cctgcatgac gggttccacc gagcaagagc tcagggccat cgccagagac ctgggatgcg  21960
gaccctattt tttgggcacc tatgacaaac gcttcccggg cttcatctcc cgagacaagc  22020
tcgcctgcgc catcgtcaac acggccgcgc gcgagaccgg gggcgtgcac tggctggcct  22080
ttggctggga cccgcgctcc aaaacctgct acctcttcga ccccttttggc ttctccgatc  22140
agcgcctcag acagatctat gagtttgagt acgaggggct gctgcgccgc agcgcgcttg  22200
cctcctcgcc cgaccgctgc atcacccttg agaagtccac cgagaccgtg caggggcccc  22260
actcggccgc ctgcggtctc ttctgctgca tgtttttgca cgcctttgtg cgctggcccc  22320
agagtcccat ggatcgcaac cccaccatga acttgctcaa gggagtgccc aacgccatgc  22380
tccagagccc ccaggtccag cccaccctgc gccacaacca ggaacagctc taccgcttcc  22440
tggagcgcca ctcccccctac ttccgcagtc acagcgcgca catccggggg gccacctctt  22500
tctgccactt gcaagaaaac atgcaagacg gaaaatgatg tacagctcgc tttttaataa  22560
atgtaaagac tgtgcacttt atttatacac gggctctttc tggttattta ttcaacaccg  22620
ccgtcgccat ctagaaatcg aaagggttct gccgcgcgtc gccgtgcgcc acgggcagag  22680
acacgttgcg atactggaag cggctcgccc acttaaactc gggcaccacc atgcggggca  22740
gtggttcctc ggggaagttc tcgccccaca gggtgcgggt cagctgcagc gcgctcagga  22800
ggtcgggagc cgagatcttg aagtcgcagt tggggccgga accctgcgcg cgcgagttgc  22860
ggtacacggg gttgcagcac tggaacacca gcagggccgg attatgcacg ctggccagca  22920
ggctctcgtc gctgatcatg tcgctgtcca gatcctccgc gttgctcagg gcgaacgggg  22980
tcatcttgca gacctgcctg cccaggaaag gcggcagccc gggcttgccg ttgcagtcgc  23040
agcgcagggg catcagcagg tgcccgcggc ccgactgcgc ctgcgggtac agcgcgcgca  23100
tgaaggcttc gatctgcctg aaagccacct gcgtcttggc tccctccgaa aagaacatcc  23160
cacaggactt gctggagaac tggttcgcgg gacagctggc atcgtgcagg cagcagcgcg  23220
cgtcggtgtt ggcgatctgc accacgttgc gaccccaccg gttcttcact atcttggcct  23280
tggaagcctg ctccttcagc gcgcgctggc cgttctcgct ggtcacatcc atctctatca  23340
cctgctcctt gttgatcatg tttgtaccgt gcagacactt caggtcgccc tccgtctggg  23400
tgcagcggtg ctcccacagc gcgcaaccgg tgggctccca atttttgtgg gtcacccccg  23460
cgtaggcctg caggtaggcc tgcaagaagc gccccatcat ggccacaaag gtcttctggc  23520
tcgtaaaggt cagctgcagg ccgcgatgct cttcgttcag ccaggtcttg cagatggcgg  23580
ccagcgcctc ggtctgctcg ggcagcatcc taaaatttgt cttcaggtcg ttatccacgt  23640
ggtacttgtc catcatggcg cgcgccgcct ccatgccctt ctcccaggcg gacaccatgg  23700
gcaggcttag gggtttatc acttccaccg gcgaggacac cgtactttcg atttcttctt  23760
cctcccccctc ttcccggcgc gcgcccacgc tgctgcgcgc tctcaccgcc tgcaccaagg  23820
ggtcgtcttc aggcaagcgc cgcaccgagc gcttgccgcc cttgacctgc ttaatcagca  23880
ccggcgggtt gctgaagccc accatggtca gcgccgcctg ctcttcttcg tcttcgctgt  23940
ctaccactat ctctggggaa gggcttctcc gctctgcggc ggcgcgcttc tttttttttct  24000
tgggagcggc cgtgatggag tccgccacgg cgacggaggt cgagggcgtg ggctggggg  24060
tgcgcggtac cagggcctcg tcgccctcgg actcttcctc tgactccagg cggcggcgga  24120
gtcgcttctt tgggggcgcg cgcgtcagcg gcggcggaga cggggacggg gacggggacg  24180
ggacgccctc cacagggggt ggtcttcgcg cagacccgcg gccgcgctcg gggtcttct  24240
```

-continued cgagctggtc ttggtcccga ctggccattg tatcctcctc ctcctaggca gagagacata 24300
aggagtctat catgcaagtc gagaaggagg agagcttaac cacccccctct gagaccgccg 24360
atgcgcccgc cgtcgccgtc gcccccgctg ccgccgacgc gcccgccaca ccgagcgaca 24420
cccccgcgga cccccccgcc gacgcacccc tgttcgagga agcggccgtg gagcaggacc 24480
cgggctttgt ctcggcagag gaggatttgc gagaggagga ggataaggag aagaagccct 24540
cagtgccaaa agatgataaa gagcaagacg agcacgacgc agatgcacac cagggtgaag 24600
tcgggcgggg ggacggaggg catgacggcg ccgactacct agacgaaggg aacgacgtgc 24660
tcttgaagca cctgcatcgt cagtgcgcca ttgtttgcga cgctctgcag gagcgcagcg 24720
aagtgcccct cagcgtggcg gaggtcagcc acgcctacga gctcagcctc ttctcccccc 24780
gggtgccccc ccgccgccgc gaaaacggca catgcgagcc caacccgcgc ctcaacttct 24840
accccgcctt tgtggtaccc gaggtcctgg ccacctatca catcttcttt caaaattgca 24900
agatcccccct ctcgtgccgc gccaaccgta gccgcgccga taagatgctg gccctgcgcc 24960
agggcgacca catacctgat atcgccgctt tggaagatgt accaaagatc ttcgagggtc 25020
tgggtcgcaa cgagaagcgg gcagcaaact ctctgcaaca ggaaaacagc gaaaatgaga 25080
gtcacaccgg ggtactggtg gagctcgagg gcgacaacgc ccgcctggcg gtggtcaagc 25140
gcagcatcga ggtcacccac tttgcctacc ccgcgctaaa cctgcccccc aaagtcatga 25200
acgcggccat ggacgggctg atcatgcgcc gcggccggcc cctcgctcca gatgcaaact 25260
tgcatgagga gaccgaggac ggccagcccg tggtcagcga cgagcagctg gcgcgctggc 25320
tggagaccgc ggaccccgcc gaactggagg agcggcgcaa gatgatgatg gccgtggtgc 25380
tggtcaccgt agagctggag tgtctgcagc gcttcttcgg cgaccccgag atgcagagaa 25440
aggtcgagga gaccctgcac tacaccttcc gccagggcta cgtgcgccag gcttgcaaga 25500
tctccaacgt ggagctcagc aacctggtgt cctacctggg catcttgcat gagaaccgcc 25560
tcgggcagag cgtgctgcac tccaccctgc gcggggaggc gcgccgcgac tacgtgcgcg 25620
actgcgttta cctcttcctc tgctacacct ggcagacggc catgggggtc tggcagcagt 25680
gcctggagga gcgcaacctc aaggagctgg agaagctcct gcagcgcgcg ctcaaagatc 25740
tctggacggg ctacaacgag cgctcggtgg ccgccgcgct ggccgacctc atcttccccg 25800
agcgcctgct caaaaccctc cagcaggggc tgcccgactt caccagccaa agcatgttgc 25860
aaaacttcag gaactttatc ctggagcgtt ctggcatcct acccgccacc tgctgcgccc 25920
tgcccagcga ctttgtcccc ctcgtgtacc gcgagtgccc cccgccgctg tggggtcact 25980
gctacctgtt ccaactggcc aactacctgt cctaccacgc ggacctcatg gaggactcca 26040
gcggcgaggg gctcatggag tgccactgcc gctgcaacct ctgcacgccc caccgctccc 26100
tggtctgcaa cacccaactg ctcagcgaga gtcagattat cggtaccttc gagctacagg 26160
gtccgtcctc ctcagacgag aagtccgcgg ctccggggct aaaactcact ccggggctgt 26220
ggacttccgc ctacctgcgc aaatttgtac ctgaagacta ccacgcccac gagatcaggt 26280
tttacgaaga ccaatcccgc ccgcccaagg cggagctgac cgcctgcgtc atcacccagg 26340
gcgagatcct aggccaattg caagccatcc aaaaagcccg ccaagacttt ttgctgaaga 26400
agggtcgggg ggtgtatctg gacccccagt cgggtgagga gctcaacccg gttcccccgc 26460
tgccgccgcc gcgggacctt gcttcccagg ataagcatcg ccatggctcc cagaaagaag 26520
cagcagcggc cgccactgcc gccaccccac atgctggagg aagaggagga atactgggac 26580
agtcaggcag aggaggtttc ggacgaggag gagccggaga cggagatgga agagtgggag 26640

```
gaggacagct tagacgagga ggcttccgaa gccgaagagg cagacgcaac accgtcaccc  26700
tcggccgcag ccccctcgca ggcgcccccg aagtccgctc ccagcatcag cagcaacagc  26760
agcgctataa cctccgctcc tccaccgccg cgacccacgg ccgaccgcag acccaaccgt  26820
agatgggaca ccaccggaac cggggccggt aagtcctccg ggagaggcaa gcaagcgcag  26880
cgccaaggct accgctcgtg gcgcgctcac aagaacgcca tagtcgcttg cttgcaagac  26940
tgcgggggga acatctcctt cgcccgccgc ttcctgctct tccaccacgg tgtggccttc  27000
ccccgtaacg tcctgcatta ctaccgtcat ctctacagcc cctactgcgg cggcagtgag  27060
ccagagacgg tcggcggcgg cggcggcgcc cgtttcggcg cctaggaaga cccagggcaa  27120
gacttcagcc aagaaactcg cggcggccgc ggcgaacgcg gtcgcggggg ccctgcgcct  27180
gacggtgaac gaacccctgt cgacccgcga actgaggaac cgaatcttcc ccactctcta  27240
tgccatcttc cagcagagca gagggcagga tcaggaactg aaagtaaaaa acaggtctct  27300
gcgctccctc acccgcagct gtctgtatca caagagcgaa gaccagcttc ggcgcacgct  27360
ggaggacgct gaggcactct tcagcaaata ctgcgcgctc actcttaagg actagctccg  27420
cgcccttctc gaatttaggc gggaacgcct acgtcatcgc agcgccgccg tcatgagcaa  27480
ggacattccc acgccataca tgtggagcta tcagccgcag atgggactcg cggcgggcgc  27540
ctcccaagac tactccaccc gcatgaactg gctcagtgcc ggcccacaca tgatctcaca  27600
ggttaatgat atccgcaccc atcgaaacca aatattggtg gagcaggcgg caattaccac  27660
cacgccccgc aataatccca accccaggga gtggcccgcg tccctggtgt atcaggaaat  27720
tcccggcccc accaccgtac tacttccgcg tgattcccag gccgaagtcc aaatgactaa  27780
ctcaggggca cagctcgcgg gcggctgtcg tcacagggtg cggcctcctc gccagggtat  27840
aactcacctg gagatccgag gcagaggtat tcagctcaac gacgagtcgg tgagctcctc  27900
gctcggtctc agacctgacg ggaccttcca gatagccgga gccggccgat cttccttcac  27960
gccccgccag gcgtacctga ctctgcaaag ctcgtcctcg gcgccgcgct cgggcggcat  28020
cgggactctc cagttcgtgc aggagtttgt gccctcggtc tacttcaacc ccttctcggg  28080
ctctcccggt cgctacccgg accagttcat ctcgaacttt gacgccgcga gggactcggt  28140
ggacggctac gactgaatgt cgggtggacc cggtgcagag caacttcgcc tgaagcacct  28200
cgaccactgc cgccgccctc agtgctttgc ccgctgtcag accggtgagt tccagtactt  28260
ttccctgccc gactcgcacc cggacggccc ggcgcacggg gtgcgctttt tcatcccgag  28320
tcaggtgcgc tctaccctaa tcagggagtt taccgcccgt cccctactgg cggagttgga  28380
aaaggggcct tctatcctaa ccattgcctg catctgctct aaccctggat tgcaccaaga  28440
tctttgctgt catttgtgtg ctgagtataa taaaggctga gatcagaatc tactcgggct  28500
cctgtcgcca tcctgtcaac gccaccgtcc aagcccggcc cgatcagccc gaggtgaacc  28560
tcacctgcgg tctgcaccgg cgcctgagga aatacctagc ttggtactac aacagcactc  28620
cctttgtggt ttacaacagc tttgaccagg acggggtctc actgagggat aacctctcga  28680
acctgagcta ctccatcagg aagaacagca ccctcgagct acttcctcct tacctgcccg  28740
ggacttacca gtgtgtcacc ggtccctgca cccacaccca cctgttgatc gtaaacgact  28800
ctcttccgag aacagacctc aataactcct cttcgcagtt ccccagaaca ggaggtgagc  28860
tcaggaaacc ccgggtaaag aagggtggac gagagttaac acttgtgggg tttctggtgt  28920
atgtgacgct ggtggtggct cttttgatta aggcttttcc ttccatgtct gaactctccc  28980
```

-continued

```
tcttctttta tgaacaactc gactagtgct aacgggaccc tacccaacga atcgggattg  29040
aatatcggta accaggttgc agtttcactt ttgattacct tcatagtcct cttcctgcta  29100
gtgctgtcgc ttctgtgcct gcggatcggg ggctgctgca tccacgttta tatctggtgc  29160
tggctgttta gaaggttcgg agaccatcgc aggtagaata aacatgctgc tgcttaccct  29220
ctttgtcctg gcgctggccg ccagctgcca agccttttcc gaggctgact ttatagagcc  29280
ccagtgtaat gtgactttta aagcccatgc acagcgttgt catactataa tcaaatgtgc  29340
caccgaacac gatgaatacc ttatccagta taaagataaa tcacacaaag tggcacttgt  29400
tgacatctgg aaacccgaag accctttgga atacaatgtg accgttttcc agggtgacct  29460
cttcaaaatt tacaattaca ctttcccatt tgaccagatg tgtgactttg tcatgtacat  29520
ggaaaagcag cacaagctgt ggcctccgac tccccagggc tgtgtggaaa atccaggctc  29580
tttctgcatg atctctctct gtgtaactgt gctggcacta atactcacgc ttttgtatat  29640
cagatttaaa tcaaggcaaa gcttcattga tgaaaagaaa atgccttaat cgctttcacg  29700
cttgattgct aacaccgggt ttttatccgc agaatgattg gaatcaccct actaatcacc  29760
tccctccttg cgattgccca tgggttggaa cgaatcgaag tccctgtggg ggccaatgtt  29820
accctggtgg ggcctgtcgg caatgctaca ttaatgtggg aaaaatatac taaaaatcaa  29880
tgggtctctt actgcactaa caaaaatagc cacaagccca gagccatctg cgatgggcaa  29940
aatctaacct tgattgatgt tcaattgctg gatgcgggct actattatgg gcagctgggt  30000
acaatgatta attactggag accccacaga gattacatgc tccacgtagt aaagggtccc  30060
cttagcagcc cacccactac cacctctact acccccacta ccaccactac tcccaccacc  30120
agcactgccg cccagcctcc tcatagcaga acaaccactt ttatcaattc caagtcccac  30180
tccccccaca ttgccggcgg gccctccgcc tcagactccg aaaccaccga gatctgcttc  30240
tgcaaatgct ctgacgccat tgcccaggat ttggaagatc acgaggaaga tgagcatgac  30300
ttcgcagatg catgccaggc atcagagcca gaagcgctgc cggtggccct caaacagtat  30360
gcagaccccc acaccacccc cgaccttcct ccaccttccc agaagccaag tttcctgggg  30420
gaaaatgaaa ctctgcctct ctccatactc gctctgacat ctgttgctat gttgaccgct  30480
ctgctggtgc ttctatgctc tatatgctac ctgatctgct gcagaaagaa aaaatctcac  30540
ggccatgctc accagcccct catgcacttc ccttaccctc cagagctggg cgaccacaaa  30600
ctttaagtct gcagtaacta tctgcccatc ccttgtcagt cgacagcgat gagccccact  30660
aatctaacgg cctctggact tacaacatcg tctcttaatg agaccaccgc tcctcaagac  30720
ctgtacgatg gtgtctccgc gctggttaac cagtgggatc acctgggcat atggtggctc  30780
ctcataggag cagtgaccct gtgcctaatc ctggtctgga tcatctgctg catcaaaagc  30840
agaagaccca ggcggcggcc catctacagg ccctttgtca tcacacctga agatgatgat  30900
gacaccactt ccaggctgca gaggctaaag cagctactct tctcttttac agcatggtaa  30960
attgaatcat gcctcgcatt ttcatctact tgtctctcct tccacttttt ctgggctctt  31020
ctacattggc cgctgtgtcc cacatcgagg tagactgcct cacgcccttc acagtctacc  31080
tgcttttcgg ctttgtcatc tgcacctttg tctgcagcgt tatcactgta gtgatctgct  31140
tcatacagtg catcgactac gtctgcgtgc gggtggctta ctttagacac caccccccagt  31200
atcgcaacag ggacatagcg gctctcctaa gacttgttta aaatcatggc caaattaact  31260
gtgattggtc ttctgatcat ctgctgcgtc ctagccgcga ttgggactca agctcctacc  31320
accaccagcg ctcccagaaa gagacatgta tcctgcagct tcaagcgtcc ctggaatata  31380
```

-continued

```
ccccaatgct ttactgatga acctgaaatc tctttggctt ggtacttcag cgtcaccgcc  31440
cttcttatct tctgcagtac ggttattgcc cttgccatct acccttccct tgacctgggc  31500
tggaatgctg tcaactctat ggaatatccc accttcccag aaccagacct gccagacctg  31560
gttgttctaa acgcgtttcc tcctcctgct cccgttcaaa atcagtttcg ccctccgtcc  31620
cccacgccca ctgaggtcag ctactttaat ctaacaggcg gagatgactg aaaacctaga  31680
cctagaaatg gacggtctct gcagcgagca acgcacacta gagaggcgcc ggcaaaaaga  31740
gctcgagcgt cttaaacaag agctccaaga cgcggtggcc atacaccagt gcaaaaaagg  31800
tgtcttctgt ctggtaaaac aggccacgct cacctatgaa aaaacaggtg acacccaccg  31860
cctaggatac aagctgccca cacagcgcca aaagttcgcc ctcatgatag gcgaacaacc  31920
catcaccgtg acccagcact ccgtggagac agaaggctgc atacatgctc cctgtagggg  31980
cgctgactgc ctctacacct tgatcaaaac cctctgcggt ctcagagacc ttatcccttt  32040
caattaatca taactgtaat caataaaaaa tcacttactt gaaatctgat agcaagcctc  32100
tgtccaattt tttcagcaac acttccttcc cctcctccca actctggtac tctaggcgcc  32160
tcctagctgc aaacttcctc cacagtctga agggaatgtc agattcctcc tcctgtccct  32220
ccgcacccac gatcttcatg ttgttgcaga tgaaacgcgc gagatcgtct gacgagacct  32280
tcaaccccgt gtacccctac gataccgaga tcgctccgac ttctgtccct ttccttaccc  32340
ctccctttgt gtcatccgca ggaatgcaag aaaatccagc tggggtgctg tccctgcact  32400
tgtcagagcc ccttaccacc cacaatgggg ccctgactct aaaaatgggg ggcggcctga  32460
ccctggacaa ggaagggaat ctcacttccc aaaacatcac cagtgtcgat ccccctctca  32520
aaaaaagcaa gaacaacatc agccttcaga ccgccgcacc cctcgccgtc agctccgggg  32580
ccctaacact ttttgccact cccccccctag cggtcagtgg tgacaacctt actgtgcagt  32640
ctcaggcccc tctcactttg gaagactcaa aactaactct ggccaccaaa ggacccctaa  32700
ctgtgtccga aggcaaactt gtcctagaaa cagaggctcc cctgcatgca agtgacagca  32760
gcagcctggg ccttagcgtt acggccccac ttagcattaa caatgacagc ctaggactag  32820
atctgcaggc acccattgtc tctcaaaatg gaaaactggc tctaaatgta gcaggccccc  32880
tagctgtggc caatggcatt aatgctttga cagtaggcac aggcaaaggt attggtctaa  32940
atgaaaccag cactcacttg caagcaaagt tggtcgcccc cctaggcttt gataccaatg  33000
gcaacattaa gctaagcgtt gcaggaggca tgagactaaa taatgacaca cttatactag  33060
atgtaaacta cccatttgaa gctcaaggcc aactaagtct aagagtgggc cagggtccgc  33120
tgtatgtaga ttctagcagc cataacctga ccattagatg ccttagagga ttatacataa  33180
catcgtctaa taaccaaacc ggtctagagg ccaacataaa actaacaaaa ggccttgtct  33240
atgatggaaa tgccatagca gtcaatgttg gtcaaggatt gcaatacagc actactgcca  33300
catcggaagg tgtgtatcct atacagtcta agataggttt gggaatggaa tatgatacca  33360
acggagccat gatgacaaaa ctaggctctg gactaagctt tgacaattca ggagccattg  33420
tagtgggaaa caaaaatgat gacaggctta ctctgtggac tacaccagac ccatctccta  33480
actgtagaat ttattctgaa aaagatacta aactaacctt ggtgctgact aagtgtggca  33540
gccaaatcct aggcacagta tctgcccttg ctgtcagagg cagccttgcg cccatcacta  33600
atgcatccag catagtccaa atatttctaa gatttgatga aaatggacta ttgatgagca  33660
actcatcgct agacggtgat tactggaatt acagaaatgg ggactccact aatagcacac  33720
```

catatacaaa tgcagtaggc tttatgccta atctagcagc ctatcctaaa ggtcaggcta 33780
cagctgcaaa aagcagtatt gtaagccagg tatacatgga tggtgacact actaaaccta 33840
taacactaaa aataaacttc aatggcattg atgaaacaac agaaaatacc cctgttagta 33900
aatattccat gacattctca tggagctggc ccaccgcaag ctacataggc cacacttttg 33960
caacaaactc ttttactttc tcctacatcg cccaagaata aagaaagcac agagatgctt 34020
gttttgattt caaaattgtg tgcttttatt tattttcagc ttacagtatt tccagtagtc 34080
attcgaataa agcttaatca aactgcatga gaacccttcc acatagctta aattagcacc 34140
agtgcaaatg gagaaaattc aacatacctt ttttatccag atatcagaga actctagtgg 34200
tcagttttcc cccaccctcc cagctcacag aatacacagt cctttccccc cggctggctt 34260
taaacaacac tatctcattg gtaacagaca tattcttagg tgtaataatc cacacggtct 34320
cttggcgggc caagcgctgg tcggtgatgt taataaactc cccaggcagc tctttcaagt 34380
tcacgtcgct gtccaactgc tgaagcgctc gcggctccga ctgcgcctct agcggaggca 34440
acggcaacac ccgatccttg atctataaag gagtagagtc ataatccccc ataagaatag 34500
ggcggtgatg cagcaacaag gcgcgcagca actcctgccg ccgcctctcc gtacgacagg 34560
aatgcaacgg cgtggtggtc tcctccgcga taatccgcac cgctcgcagc atcagcatcc 34620
tcgtcctccg ggcacagcag cgcatcctga tctcactgag atcggcgcag taagtgcagc 34680
acaaaaccaa gatgttattt aagatcccac agtgcaaagc actgtaccca aagctcatgg 34740
cgggaaggac agcccccacg tgaccatcat accagatcct taggtaaatc aaatgacgac 34800
ctctcataaa cacgctggac atgtacatca cctccttggg catgcgctga ttcaccacct 34860
ctcgatacca caagcatcgc tgattaatta aagacccctc aagcaccatc ctgaaccagg 34920
aagccagcac ctgaccccc gccaggcact gcagggaccc cggtgaattg cagtggcagt 34980
gaagactcca gcgctcgtag ccgtgaacca tagagccggt cattatatcc acattggcac 35040
aacacaaaca cactttcata cactttttca tgattagcag ctcctctcta gtcaggacca 35100
tatcccaagg aatcacccac tcttgaatca aggtaaatcc cacacagcag ggcaggcctc 35160
tcacataact cacgttatgc atagtgagcg tgtcgcaatc tggaaatacc ggatgatctt 35220
ccatcaccga agctcgcgtc tccgtctcaa agggaggtaa acggtccctc gtgtagggac 35280
agtggcggga taatcgagat cgtgttgaac gtagagtcat gccaaaggga acagcggacg 35340
tactcatatt tcctccagca gaaccaagtg cgcgcgtggc agctatccct gcgtcttctg 35400
tctcgccgcc tgccccgctc ggtgtagtag ttgtaataca gccactccct cagaccgtca 35460
aggcgctccc tggcgtccgg atctataaca acaccgtcct gcagcgccgc cctgatgaca 35520
tccaccaccg tagagtatgc caagcccagc caggaaatgc attcactttg acagcgagag 35580
ataggaggag cgggaagaga tggaagaacc atgatagtaa aagactttta ttccaatcga 35640
tcctctacaa tgtcaaagtg tagatctata agatgacact ggtctcctcc gctgagtcga 35700
tcaaaaataa cagctaaacc acaaacaaca cgattggtca aatgctccac aagggcttgc 35760
agcataaaat cgcctcgaaa gtccaccgca agcataacat caaagccacc gcccctatca 35820
tgatctataa taaaaacccc acagctatcc accagaccca taaagttttc atctctccat 35880
cgtgaaaaaa tatttacaag ctcctccttt aaatcacctc caaccaattg aaaaagttga 35940
gccaaaccgc cctccacctt cattttcagc aagcgcatca tgattgcaaa aattcaggct 36000
cctgagacac ctgtataaga ttgagaagcg gaacgttaac gtcaatgttt cgctcgcgaa 36060
gatcgcgcct cagtgcaagc atgatataat cccacaggtc ggagcggatc agcgaggaca 36120
tctccccgcc aggaaccaac tcaacggagc ctatgctgat tataatacgc atattcgggg 36180
ctatgctgac cagcacggcc cccaaatagg cgtactgcat aggcggcgac aaaaagtgaa 36240
cagtttgggt taaaaaatca ggcaaacagt cgcgcaaaaa agcaagaaca tcataaccat 36300
gctcatgcaa atagatgcaa gtaagctcag gaacgaccac agaaaaatgc acaatttttc 36360
tctcaaacat gactgcgagc cctgcaaaaa ataaaaaaga aacattacac aagagtagcc 36420
tgtcttacga tgggatagac tactctaacc aacataagac gggccacaac atcgcccgcg 36480
tggccataaa aaaaattgtc cgtgtgatta aaaagaagca cagatagctg gccagtcata 36540
tccggagtca tcacgtgtga acccgtgtag acccccgggt tggacacatc ggccaaacaa 36600
agaaagcggc caatgtaccc aggaggaatc ataacactaa gacgaagata caacagaata 36660
accccatgag gggggaataac aaagttagta ggtgaataaa aacgataaac acccgaaact 36720
ccctcctgcg taggcaaaat agcaccctcc ccttccaaaa caacatatag cgcttccaca 36780
gcagccatga caaaagactc aaaacactca aaagactcag tcttaccagg aaaataaaag 36840
cactctcaca gcaccagcac taatcagagt gtgaagaggg ccaagtgccg aacgagtata 36900
tataggaata aaaaatgacg taaatgtgta aaggtcagaa aacgcccaga aaaatacaca 36960
gaccaacgcc cgaaacgaaa acccgcgaaa aaatacccag aacttcctca acaaccgcca 37020
cttccggttt ctcacggtac gtcacttccg caagaaaagc aaaactacat ttcccacatg 37080
tgtaaaaacg aaaccccgcc ccttgtaact gcccacaact tacatcatca aaacataaac 37140
tcctacgtca cccgccccgc ctctccccgc ccacctcatt atcatattgg ccacaatcca 37200
aaataaggta tattat 37216

<210> SEQ ID NO 25
<211> LENGTH: 34029
<212> TYPE: DNA
<213> ORGANISM: Gorilla beringei beringei

<400> SEQUENCE: 25
catcatcaat aatatacctt attttggatt gtggccaata tgataatgag gtgggcgggg 60
agaggcgggg cgggtgacgt aggacgcgcg agtagggttg ggaggtgtgg cggaagtgtg 120
gcatttgcaa gtgggaggag ctcacatgca agcttccgtc gcggaaaatg tgacgttttt 180
gatgagcgcc gcctacctcc ggaagtgcca attttcgcgc gcttttcacc ggatatcgta 240
gtaattttgg gcgggaccat gtaagatttg gccattttcg cgcgaaaagt gaaacgggga 300
agtgaaaact gaataatagg gcgttagtca tagtgcgtaa tatttaccga gggccgaggg 360
actttgaccg attacgtgga ggactcgccc aggtgttttt tacgtgaatt tccgcgttcc 420
gggtcaaagt ctccgtttta ttgtcaccgt catttgacgc ttaggcctga ccatctggtg 480
ctggcctgca ccagggccga gtttgggtct agcgatgagg ataccgattg aggtgggtaa 540
ggtgggcgtg gctagaaggg tggggcgtgt ataaattggg ggtctaaggg tctctctgtt 600
ttgtcttgca acagccgccg ccatgagcga caccggcaac agctttgatg gaagcatctt 660
tagcccctat ctgacagtgc gcatgcctca ctgggctgga gtgcgtcaga atgtgatggg 720
ttccaacgtg gatggacgcc ccgttctgcc ttcaaattcg tctacaatgg cctacgcgac 780
cgtgggagga actccgctgg acgccgcgac ctccgccgcc gcctccgccg ccgccgcgac 840
cgcgcgcagc atggctacgg acctttacag ctctttggtg gcgagcggcg cggcctctcg 900
cgcgtctgct cgggatgaga aactgaccgc tctgctgctt aaactggaag acttgacccg 960

-continued

```
ggagctgggt caactgaccc agcaggtctc cagcttgcgt gagagcagcc ttgcctcccc   1020
ctaatggccc ataatataaa taaaagccag tctgtttgga ttaagcaagt gtatgttctt   1080
tatttaactc tccgcgcgcg gtaagcccgg gaccagcggt ctcggtcgtt tagggtgcgg   1140
tggattcttt ccaacacgtg gtacaggtgg ctctggatgt ttagatacat gggcatgagt   1200
ccatccctgg ggtggaggta gcaccactgc agagcttcgt gctcgggggt ggtgttgtat   1260
atgatccagt cgtagcagga gcgctgggcg tggtgctgaa aaatgtcctt aagcaagagg   1320
cttatagcta gggggaggcc cttggtgtaa gtgtttacaa atctgctcag ttgggagggg   1380
tgcatccggg ggatataat gtgcatcttg gactggattt ttaggttggc tatgttccca   1440
cccagatccc ttctgggatt catgttgtgc aggaccacca gcacggtata tccagtgcac   1500
ttgggaaatt tatcgtggag cttagacggg aatgcatgga agaacttgga gacgcccttg   1560
tggcctccca gattttccat acattcgtcc atgatgatgg caatgggccc gtgggaagct   1620
gcctgagcaa aaatgtttct gggatcgctc acatcgtagt tatgttccag ggtgaggtca   1680
tcataggaca tctttacgaa tcgggggcgg agggtcccgg actgggggat gatggtaccc   1740
tcgggccccg gggcgtagtt cccctcacag atctgcatct cccaggcttt catttcagag   1800
ggagggatca tatccacctg cggagcgatg aaaaacacag tttctggcgc aggggagatt   1860
aactgggatg agagcaggtt tctgagcagc tgtgactttc cacagccggt gggcccatat   1920
atcacgccta tcaccggctg cagctggtag ttaagagagc tgcagctgcc gtcctcccgg   1980
agcagggggg ccacctcgtt cagcatatcc ctgacgtgga tgttctccct gaccaattcc   2040
gccagaaggc gctcgccgcc cagcgaaagc agctcttgca aggaagcaaa atttttcagc   2100
ggttttaggc cgtcggccgt gggcatgttt ttcagcgtct gggtcagcag ttccagcctg   2160
tcccacagct cggtgatgtg ctctacggca tctcgatcca gcagatctcc tcgtttcgcg   2220
ggttggggcg gctttcgctg tagggcacca gccgatgggc gtccagcggg gccagagtca   2280
tgtccttcca tgggcgcagg gtcctcgtca gggtggtctg ggtcacggtg aaggggtgcg   2340
ctccgggttg ggcgctggcc agggtgcgct tgaggctggt tctgctggtg ctgaatcgct   2400
gccgctcttc gccctgcgcg tcggccaggt agcatttgac catggtctcg tagtcgagac   2460
cctcggcggc gtgccccttg gcgcggagct ttcccttgga ggtggcgccg cacgaggggc   2520
actgcaggct cttcagggcg tagagcttgg gagcgagaaa cacggactct ggggagtagg   2580
cgtccgcgcc gcaggaagcg cagaccgtct cgcattccac cagccaagtg agctccgggc   2640
ggtcagggtc aaaaaccagg ttgcccccat gctttttgat gcgtttctta cctcggctct   2700
ccatgaggcg gtgtcccttc tcggtgacga agaggctgtc cgtgtccccg tagaccgact   2760
tcaggggcct gtcttccagc ggagtgcctc tgtcctcctc gtagagaaac tctgaccact   2820
ctgagacgaa ggcccgcgtc caggccagga cgaaggaggc cacgtgggag ggtagcggt   2880
cgttgtccac tagcgggtcc accttctcca gggtgtgcag gcacatgtcc ccctcctccg   2940
cgtccagaaa agtgattggc ttgtaggtgt aggacacgtg accgggggtt cccgacgggg   3000
gggtataaaa gggggtgggc gccctttcat cttcactctc ttccgcatcg ctgtctgcga   3060
gggccagctg ctggggtaag tattccctct cgaaggcggg catgacctca gcgctcaggt   3120
tgtcagtttc taaaaatgag gaggatttga tgttcacctg tccggaggtg atacctttga   3180
gggtacctgg gtccatctgg tcagaaaaca ctatttttt gttgtcaagc ttggtggcga   3240
acgacccgta gagggcgttg gagagcagct tggcgatgga gcgcagggtc tggtttttgt   3300
cgcggtcggc tcgctccttg gccgcgatgt tgagttgcac gtactcgcgg gccacgcact   3360
```

tccactcggg gaagacggtg gtgcgctcgt ctgggattag gcgcaccctc cagcctcggt 3420
tgtgcagggt gaccatgtcg acgctggtgg cgacctcgcc gcgcaggcgc tcgttggtcc 3480
agcagaggcg gccgcccttg cgcgagcaga aggggggtag ggggtccagc tggtcctcgt 3540
ttggggggtc cgcgtcgatg gtgaagaccc cggggagcaa gcgcgggtca aagtagtcga 3600
tcttgcaagc ttgcatgtcc agagcccgct gccattcgcg ggcggcgagc gcgcgctcgt 3660
aggggttgag gggcgggccc cagggcatgg ggtgggtgag cgcggaggcg tacatgccgc 3720
agatgtcata cacgtacagg ggttccctga ggatgccgag gtaggtgggg tagcagcgcc 3780
ccccgcggat gctggcgcgc acgtagtcat agagctcgtg ggaggggggcc agcatgttgg 3840
gcccgaggtt ggtgcgctgg gggcgctcgg cgcggaaggc gatctgcctg aagatggcat 3900
gggagttgga ggagatggtg ggccgctgga agacgttgaa gcttgcttct tgcaagccca 3960
ccgagtccct gacgaaggag gcgtaggact cgcgcagctt gtgcaccagc tcggcggtga 4020
cctggacgtc gagcgcgcag tagtcgaggg tctcgcggat gatgtcatac ttatcctccc 4080
ccttcttttt ccacagctcg cggttgagga cgaactcttc gcggtctttc cagtactctt 4140
ggaggggaaa cccgtccgtg tccgaacggt aagagcctag catgtagaac tggttgacgg 4200
cctggtaggg gcaacagccc ttctccacgg gcagcgcgta ggcctgcgcc gccttgcgga 4260
gggaggtgtg ggtgagggcg aaagtgtccc tgaccatgac tttgaggtat tgatgtttga 4320
agtctgtgtc atcgcagccg ccctgttccc acagggtgta gtccgtgcgc tttttggagc 4380
gcgggttggg cagggagaag gtgaggtcat tgaagaggat cttccccgct cgaggcatga 4440
agtttctggt gatgcgaaag ggccctggga ccgaggagcg gttgttgatg acctgggcgg 4500
ccaggacgat ctcgtcaaag ccgtttatgt tgtggcccac gatgtagagc tccaaaaagc 4560
ggggctggcc cttgatggag gggagctttt tgagttcctc gtaggtgagc tcctcgggcg 4620
attccaggcc gtgctcctcc agggcccagt cttgcaagtg agggttggcc gccaggaagg 4680
atcgccagag gtcgcgggcc atgagggtct gcaggcggtc gcggaaggtt ctgaactgtc 4740
gccccacggc catcttttcg gggtgatgc agtagaaggt gagggggtct ttctcccagg 4800
ggtcccatct gagctctcgg gcgaggtcgc gcgcggcggc gaccagagcc tcgtcgcccc 4860
ccagtttcat gaccagcatg aagggcacga gctgcttgcc aaaggctccc atccaagtgt 4920
aggtctctac atcgtaggtg acaaagaggc gctccgtgcg aggatgagag ccgatcggga 4980
agaactggat ctcccgccac cagttggagg attggctgtt gatgtggtga aagtagaagt 5040
cccgtctgcg ggccgagcac tcgtgctggc ttttgtaaaa gcgaccgcag tactggcagc 5100
gctgcacggg ttgtatatct tgcacgaggt gaacctggcg acctctgacg aggaagcgca 5160
gcgggaatct aagtcccccg cctggggtcc cgtgtggctg gtggtcttct actttggttg 5220
tctggccgcc agcatctgtc tcctggaggg cgatggtgga gcagaccacc acgccgcgag 5280
agccgcaggt ccagatctcg gcgctcggcg ggcggagttt gatgacgaca tcgcgcacat 5340
tggagctgtc catggtctcc agctcccgcg gcggcaggtc agctgggagt tcctggaggt 5400
tcacctcgca gagacgggtc aaggcgcggg cagtgttgag atggtatctg atttcaaggg 5460
gcgtgttggc ggcggagtcg atggcttgca ggaggccgca gccccggggg gccacgatgg 5520
ttccccgcgg ggcgcgaggg gaggcggaag ctgggggtgt gttcagaagc ggtgacgcgg 5580
gcgggccccc ggaggtaggg ggggttccgg ccccacaggc atgggcggca ggggcacgtc 5640
ttcgccgcgc gcgggcaggg gctggtgctg gctccgaaga gcgcttgcgt gcgcgacgac 5700

-continued

```
gcgacggttg gtgtcctgta tctgacgcct ctgagtgaag accacgggtc ccgtgacctt   5760
gaacctgaaa gagagttcga cagaatcaat ctcggcatcg ttgacagcgg cctggcgcag   5820
gatctcctgc acgtcgcccg agttgtcctg gtaggcgatc tctgccatga actgctcgat   5880
ctcttcttcc tggagatctc ctcgtccggc gcgctccacg gtggccgcca ggtcgttgga   5940
gatgcgaccc atgagctgtg agaaggcgtt gagcccgccc tcgttccaga cccggctgta   6000
gaccacgccc ccctcggcgt cgcgagcgcg catgaccacc tgggccaggt tgagctccac   6060
gtgtcgcgtg aagacggcgt agttgcgcag gcgctggaaa aggtagttca gggtggtggc   6120
ggtgtgctcg gcgacgaaga agtacatgac ccagcgccgc aacgtggatt cattgatgtc   6180
ccccaaggcc tccaggcgct ccatggcctc gtagaagtcc acggcgaagt tgaaaaactg   6240
ggagttgcga gcggacacgg tcaactcctc ctccagaaga cggatgagct cggcgacagt   6300
gttgcgcacc tcgcgctcga aggccacggg gggcgcttct tcctcttcca cctcttcttc   6360
catgatcgct tcttcttctt cctcagccgg gacgggaggg ggcggcggcg gcgggggagg   6420
ggcgcggcgg cggcggcggc gcaccgggag gcggtcgatg aagcgctcga tcatctcccc   6480
ccgcatgcgg cgcatggtct cggtgacggc gcggccgttc tcccgggggc gcagctcgaa   6540
gacgccgcct ctcatctcgc cgcggggcga gcggccgtga ggtagcgaga cggcgctgac   6600
tatgcatctt aacaattgct gtgtaggtac accgccgagg gacctgattg agtccagatc   6660
caccggatcc gaaaaccttt ggaggaaagc gtctatccag tcgcagtcgc aaggtaggct   6720
gagcaccgtg gcgggcgggg gcgggtctgg agagttcctg gcggagatgc tgctgatgat   6780
gtaattaaag taggcggtct tgagaaggcg gatggtggac aggagcacca tgtctttggg   6840
tccggcctgt tggatgcgga ggcggtcggc catgccccag gcctcgttct gacaccggcg   6900
caggtctttg tagtagtctt gcatgagtct ttccaccggc acctcttctc cttcctcttc   6960
tccatctcgc cggtggtttc tcgcgccgcc catgcgcgtg accccaaagc ccctgagcgg   7020
ctgcagcagg gccaggtcgg cgaccacgcg ctcggccaag atggcctgct gcacctgagt   7080
gagggtcctc tcgaagtcat ccatgtccac gaagcggtgg taggcgcccg tgttgatggt   7140
gtaggtgcag ttggccatga cggaccagtt gacggtctgg tgtcccggct gcgagagctc   7200
cgtgtaccgc aggcgcgaga aggcgcggga atcgaacacg tagtcgttgc aagtccgcac   7260
cagatactgg tagcccacca ggaagtgcgg cggaggttgg cgatagaggg gccagcgctg   7320
ggtggcgggg gcgccgggcg ccaggtcttc cagcatgagg cggtggtatc cgtagatgta   7380
cctggacatc caggtgatgc cggcggcggt ggtggtggcg cgcgcgtagt cgcggacccg   7440
gttccagatg tttcgcaggg gcgagaagtg ttccatggtc ggcacgctct ggccggtgag   7500
gcgcgcgcag tcgttgacgc tctatacaca cacaaaaacg aaagcgttta cagggctttc   7560
gttctgtagc ctggaggaaa gtaaatgggt tgggttgcgg tgtgccccgg ttcgagacca   7620
agctgagctc ggccggctga agccgcagct aacgtggtat tggcagtccc gtctcgaccc   7680
aggccctgta tcctccagga tacggtcgag agccctttg ctttcttggc caagcgcccg   7740
tggcgcgatc tgggatagat ggtcgcgatg agaggacaaa agcggctcgc ttccgtagtc   7800
tggagaaaca atcgccaggg ttgcgttgcg gcgtaccccg gttcgagccc ctatggcggc   7860
ttgaatcggc cggaaccgcg gctaacgagg gccgtggcag ccccgtcctc aggaccccgc   7920
cagccgactt ctccagttac gggagcgagc cccttttgtt ttttattttt tagatgcatc   7980
ccgtgctgcg gcagatgcgc ccctcgcccc ggcccgatca gcagcagcaa cagcaggcat   8040
gcagaccccc ctctcccctt tccgccccgg tcaccacggc cgcggcggcc gtgtcgggcg   8100
```

-continued

```
cggggggcgc gctggagtca gatgagccac cgcggcggcg acctaggcag tatctggact   8160
tggaagaggg cgagggactg gcgcggctgg gggcgaactc tccagagcgc cacccgcggg   8220
tgcagttgaa aagggacgcg cgcgaggcgt acctgccgcg gcagaacctg tttcgcgacc   8280
gcgggggcga ggagcccgag gagatgcgag actgcaggtt ccaagcgggg cgcgagctgc   8340
ggcgcgggct ggacagacag cgcctgctgc gcgaggagga ctttgagccc gacacgcaga   8400
cgggcatcag ccccgcgcgc gcgcacgtag ccgcggccga cctggtgacc gcctacgagc   8460
agacggtaaa ccaggagcgc aacttccaaa agagcttcaa caaccacgtg cgcacgctgg   8520
tggcgcgcga ggaggtgacc ctgggtctca tgcatctgtg ggacctggtg gaggcgatcg   8580
tgcagaaccc cagcagcaag cccctgaccg cgcagctgtt cctggtggtg cagcacagca   8640
gggacaacga ggccttcagg gaggcgctgc tgaacatcac cgagccggag gggcgctggc   8700
tcctggacct gataaacatc ctgcagagca tagtggtgca ggagcgcagc ctgagcctgg   8760
ccgagaaggt ggcggccatc aactactcta tgctgagcct gggcaagttc tacgcccgca   8820
agatctacaa gacccccta c gtgcccatag acaaggaggt gaagatagac agcttctaca   8880
tgcgcatggc gctgaaggtg ctgaccctga gcgacgacct gggagtgtac cgcaacgagc   8940
gcatccacaa ggccgtgagc gccagccggc ggcgcgagct gagcgaccgc gagctgatgc   9000
acagtctgca gcgcgcgctg accggcgcgg gcgagggcga cagggaggtc gagtcctact   9060
tcgacatggg ggccgacctg cactggcagc cgagccgccg cgccctggag gcggcggggg   9120
cgtacggcgg cccccctggcg gccgatgacc aggaagagga ggactatgag ctagaggagg   9180
gcgagtacct ggaggactga cctggctggt ggtgttttgg tatagatgca agatccgaac   9240
gtggcggacc cggcggtccg ggcggcgctg caaagccagc cgtccggcat taactcctct   9300
gacgactggg ccgcggccat gggtcgcatc atggccctga ccgcgcgcaa ccccgaggct   9360
ttcaggcagc agcctcaggc caaccggctg gcggccatct tggaagcggt agtgcccgcg   9420
cgctccaacc ccacccacga gaaggtgctg gccatagtca acgcgctggc ggagagcagg   9480
gccatccgcg cggacgaggc cggactggtg tacgatgcgc tgctgcagcg ggtggcgcgg   9540
tacaacagcg gcaacgtgca gaccaacctg gaccgcctgg tgacggacgt gcgcgaggcc   9600
gtggcgcagc gcgagcgctt gcatcaggac ggtaacctgg gctcgctggt ggcgctaaac   9660
gccttcctca gcacccagcc ggccaacgta ccgcgggggc aggaggacta caccaacttt   9720
ttgagcgcgc tgcggctgat ggtgaccgag gtccctcaga gcgaggtgta ccagtcgggg   9780
cccgactact tcttccagac cagcagacag ggcttgcaaa ccgtgaacct gagccaggct   9840
ttcaagaacc tgcgggggct gtggggagtg aaggcgccca ccggcgaccg ggctacggtg   9900
tccagcctgc taacccccaa ctcgcgcctg ctgctgctgc tgatcgcgcc cttcacggac   9960
agcgggagcg tctcgcggga gacctatctg ggccacctgc tgacgctgta ccgcgaggcc  10020
atcgggcagg cgcaggtgga cgagcacacc ttccaagaga tcaccagcgt gagccacgcg  10080
ctggggcagg aggacacggg cagcctgcag gcgaccctga actacctgct gaccaacagg  10140
cggcagaaga ttcccacgct gcacagcctg acccaggagg aggagcgcat cttgcgctac  10200
gtgcagcaga gcgtgagcct gaacctgatg cgcgacggcg tgacgcccag cgtggcgctg  10260
gacatgaccg cgcgcaacat ggaaccgggc atgtacgcct cccaccggcc gtttatcaac  10320
cgcctgatgg actacttgca tcgggcggcg gccgtgaacc ccgagtactt cactaatgcc  10380
attctgaatc cccactggat gccccctccg ggtttctaca acggggactt tgaggtgccc  10440
```

gaggtcaacg acgggttcct ctgggatgac atggatgaca gtgtgttctc acccaacccg 10500
ctgcgcgccg cgtctctgcg attgaaggag ggctctgaca gggaaggacc gaggagtctg 10560
gcctcctccc tggctctggg agcggtgggc gccacgggcg cggcggcgcg gggcagtagc 10620
cccttcccca gcctggcaga ctctctgaac agcgggcggg tgagcaggcc ccgcttgcta 10680
ggcgaggagg agtatctgaa caactccctg ctgcagcccg cgagggacaa gaacgctcag 10740
cggcagcagt ttcccaacaa tgggatagag agcctggtgg acaagatgtc cagatggaag 10800
acgtatgcgc aggagtacaa ggagtgggag gaccgccagc cgcggccctt gccgccccct 10860
aggcagcgct ggcagcggcg cgcgtccaac cgccgctgga ggcaggggcc cgaggacgat 10920
gatgactctg cagatgacag cagcgtgttg gacctgggcg ggagcgggaa ccccttttcg 10980
cacctgcgcc cacgcctggg caagatgttt taaaagaaaa aaaaaataaa actcaccaag 11040
gccatggcga cgagcgttgg ttttttgttc ccttccttag tatgcggcgc gcggcgatgt 11100
tcgaggaggg gcctcccccc tcttacgaga gcgcgatggg gatttctcct gcggcgcccc 11160
tgcagcctcc ctacgtgcct cctcggtacc tgcaacctac aggggggaga aatagcatct 11220
gttactctga gctgcagccc ctgtacgata ccaccagact gtacctggtg gacaacaagt 11280
ccgcggacgt ggcctccctg aactaccaga acgaccacag cgattttttg accacggtga 11340
tccaaaacaa cgacttcacc ccaaccgagg ccagcaccca gaccataaac ctggataaca 11400
ggtcgaactg gggcggcgac ctgaagacca tcttgcacac caacatgccc aacgtgaacg 11460
agttcatgtt caccaactct tttaaggcgc gggtgatggt ggcgcgcgag caggggggagg 11520
cgaagtacga gtgggtggac ttcacgctgc ccgagggcaa ctactcagag accatgactc 11580
tcgacctgat gaacaatgcg atcgtggaac actatctgaa agtgggcagg cagaacgggg 11640
tgaaggaaag cgatatcggg gtcaagtttg acaccagaaa cttccgtctg ggctgggacc 11700
ccgtgaccgg gctggtcatg ccgggggtct acaccaacga ggcctttcat cccgacatag 11760
tgcttctgcc cggctgtggg gtggacttca cccagagccg gctgagcaac ctgctgggca 11820
ttcgcaagcg gcagcctttc caggagggtt tcaagatcac ctatgaggat ctgaaggggg 11880
gcaacattcc cgcgctcctt gatctggacg cctacgagga gagcttgaaa cccgaggaga 11940
gcgctggcga cagcggcgag agtggcgagg agcaagccgg cggcggtggc ggcgcgtcgg 12000
tagaaaacga aagtacgccc gcagtggcgg cggacgctgc ggaggtcgag ccggaggcca 12060
tgcagcagga cgcagaggag ggcgcacagg agggcgcgca gaaggacatg aacgatgggg 12120
agatcagggg agacacattc gccacccggg gcgaagaaaa agaggcagag gcggcggcgg 12180
cggcgacggc ggaggccgaa accgaggttg aggcagaggc agagcccgag accgaagtta 12240
tggaagacat gaatgatgga gaacgtaggg gcgacacgtt cgccacccgg ggcgaagaga 12300
aggcggcgga ggcagaagcc gcggctgagg aggcggctgc ggctgcggcc aagactgagg 12360
ctgcggctaa ggctgaggtc gaagccaatg ttgcggttga ggctcaggct gaggaggagg 12420
cggcggctga agcagttaag gaaaaggccc aggcagagca ggaagagaaa aaacctgtca 12480
ttcaacctct aaaagaagat agcaaaaagc gcagttacaa cgtcatcgag ggcagcacct 12540
ttacccagta ccgcagctgg tacctggcgt acaactacgg cgacccggtc aagggggtgc 12600
gctcgtggac cctgctctgc acgccggacg tcacctgcgg ctccgagcag atgtactggt 12660
cgctgccgaa catgatgcaa gacccggtga ccttccgctc cacgcggcag gttagcaact 12720
tcccggtggt gggcgccgaa ctgctgcccg tgcactccaa gagtttttac aacgagcagg 12780
ccgtctactc ccagctgatc cgccaggcca cctctctgac ccacgtgttc aatcgctttc 12840

-continued

```
ccgagaacca gattttggcg cgcccgccgg cccccaccat caccaccgtg agtgaaaacg  12900
ttcctgccct cacagatcac gggacgctac cgctgcgcaa cagcatctca ggagtccagc  12960
gagtgaccat tactgacgcc agacgccgga cctgccccta cgtttacaag gccttgggca  13020
tagtctcgcc gcgcgtcctc tccagtcgca ctttttaaaa cacatctacc cacacgttcc  13080
aaaatcatgt ccgtactcat ctcacccagc aacaacaccg gctgggggct gcgcgcgccc  13140
agcaagatgt ttggaggggc gaggaagcgc tccgaccagc accctgtgcg cgtgcgcggc  13200
cactaccgcg cgccctgggg agcgcacaag cgcgggcgca cagggcgcac cactgtggac  13260
gacgtcattg actccgtagt ggagcaagcg cgccactaca cacccggcgc gccgaccgcc  13320
cccgccgtgt ccaccgtgga ccaggcgatc gaaagcgtgg tacagggcgc gcggcactat  13380
gccaacctta aaagtcgccg ccgccgcgtg gcccgccgcc atcgccggag accccgggcc  13440
accgccgccg cgcgccttac taaggctctg ctcaggcgcg ccaggcgaac tggccaccgg  13500
gccgccatga gggccgcacg gcgggctgcc gctgccgcaa gcgtcgtggc cccgcgggca  13560
cgaaggcgcg cggccgctgc cgccgccgcc gccatttcca gcttggcctc gacgcggcgc  13620
ggtaacatat actgggtgcg cgactcggta accggcacgc gggtacccgt gcgctttcgc  13680
cccccgcgga attagcacaa gacaacatac acactgagtc tcctgctgtt gtgtatccca  13740
gcggcgaccg tcagcagcgg cgacatgtcc aagcgcaaaa ttaaagaaga gatgctccag  13800
gtcatcgcgc cggagatcta tgggcccccg aagaaggagg aggatgatta caagccccgc  13860
aagctaaagc gggtcaaaaa gaaaaagaaa gatgatgatg acgaggcggt ggagtttgtc  13920
cgccgcatgg cacccaggcg ccccgtgcag tggaagggcc ggcgcgtgca gcgcgttttg  13980
cgccccggca ccgcggtggt cttcacgccc ggcgagcgct ccacgcgcac tttcaagcgg  14040
gtgtacgatg aggtgtacgg cgacgaggac ctgttggagc aggccaacca gcgctttggg  14100
gagtttgcat atgggaaacg gccccgcgag agtctaaaag aggacctgct ggcgctaccg  14160
ctggacgagg gcaatcccac cccgagtctg aagccggtaa ccctgcaaca ggtgctgcct  14220
ttgagcgcgc ccagcgagca taagcgaggg ttgaagcgcg aaggcgggga cctggcgccc  14280
accgtgcagt tgatggtgcc caagcggcag aagctggagg acgtgctgga gaaaatgaaa  14340
gtagagcccg ggatccagcc cgagatcaag gtccgcccca tcaagcaggt ggcgcccggc  14400
gtgggagtcc agaccgtgga cgttaggatt ccccacggag agatggaaac ccaaaccgcc  14460
actccctctt cggcggccag cgccaccacc ggcaccgctt cggtagaggt gcagacggac  14520
ccctggctac ccgccaccgc tgttgccgcc gccgcccccc gttcgcgcgg gcgcaagaga  14580
aattatccag cggccagcgc gctcatgccc cagtacgcac tgcatccatc catcgtgccc  14640
acccccggct accgcgggta ctcgtaccgc ccgcgcagat cagccggcac tcgcggccgc  14700
cgccgccgtg cgaccacaac cagccgccgc cgtcgccgcc gccgccagcc agtgctgacc  14760
cccgtgtctg taaggaaggt ggctcgctcg gggagcacgc tggtggtgcc cagagcgcgc  14820
taccacccca gcatcgttta aagccggtct ctgtatggtt cttgcagata tggccctcac  14880
ttgtcgcctc cgcttcccgg tgccgggata ccgaggaaga actcaccgcc gcagaggcat  14940
ggcgggcagc ggtctccgcg gcggccgtcg ccatcgccgg cgcgcaaaaa gcaggcgcat  15000
gcgcggcggt gtgctgcctc tgctaatccc gctaatcgcc gcggcgatcg gtgccgtacc  15060
cgggatcgcc tccgtggccc tgcaggcgtc ccagaaacgt tgactcttgc aaccttgcaa  15120
gcttgcattt tttggaggaa aaataaaaaa aagtctagac tctcacgctc gcttggtcct  15180
gtgactattt tgtagaaaaa aagatggaag acatcaactt tgcgtcgctg gccccgcgtc  15240
```

acggctcgcg cccgttcatg ggagactgga cagatatcgg caccagcaat atgagcggtg 15300
gcgccttcag ctggggcagt ctgtggagcg gccttaaaaa ttttggttcc accattaaga 15360
actatggcaa caaagcgtgg aacagcagca cgggccagat gctgagagac aagttgaaag 15420
agcagaactt ccaggagaag gtggcgcagg gcctggcctc tggcatcagc ggggtggtgg 15480
acatagctaa ccaggccgtg cagaaaaaga taaacagtca tctggacccc cgtcctcagg 15540
tggaggaaat gcctccagcg atggagacgg tgtctcccga gggcaaaggc gaaaagcgcc 15600
cgcggcccga cagagaagag accctggtgt cacacaccga ggagccgccc tcttacgagg 15660
aggcagtcaa ggccggcctg cccaccactc gccccatagc ccccatggcc accggtgtgg 15720
tgggccacag gcaacacact cccgcaacac tagatctgcc cccgccgtcc gagccgccgc 15780
gccagccaaa ggcggcgacg gtgcccgctc cctccacttc cgccgccaac agagtgcccc 15840
tgcgccgcgc cgcgagcggc ccccgggcct cgcgagttag cggcaactgg cagagcacac 15900
tgaacagcat cgtgggcctg ggagtgagga gtgtgaagcg ccgccgttgc tactgaatga 15960
gcaagctagc taacgtgttg tatgtgtgta tgcgtcctat gtcgccgcca gaggagctgt 16020
tgagccgccg gcgccgtctg cactccagcg aatttcaaga tggcgacccc atcgatgatg 16080
cctcagtggt cgtacatgca catctcgggc caggacgctt cggagtacct gagccccggg 16140
ctggtgcagt tcgcccgcgc cacagacacc tacttcaaca tgagtaacaa gttcaggaac 16200
cccactgtgg cgcccaccca cgatgtgacc acggaccggt cgcagcgcct gacgctgcgg 16260
ttcatccccg tggatcggga ggacaccgcc tactcttaca aggcgcggtt cacgctggcc 16320
gtgggcgaca accgcgtgct ggacatggcc tccacttact ttgacatcag gggggtgctg 16380
gacaggggcc ccaccttcaa gccctactcg ggtactgcct acaactccct ggcccccaag 16440
ggcgctccca attcttgcga gtgggaacaa gatgaaccag ctcaggcagc aatagctgaa 16500
gatgaagaag aacttgaaga agaacaagct caggacgaac aggcgcccac taagaaaacc 16560
catgtatacg cccaggcacc tctttctggt gaaaaaatta ctaaggatgg tttgcaaata 16620
ggtgtggatg ccacacaggc gggagataac cctatatatg ctgataaaac attccaaccc 16680
gaacctcaga taggtgagtc tcagtggaac gaggctgatg ccacagtagc aggaggcaga 16740
gtcttaaaaa agaccacccc tatgagacct tgctatggat cctatgccaa acctactaat 16800
gccaatggcg gtcaagggat catggtggcc aatgatcagg gagcgcttga atctaaagtt 16860
gagatgcaat tttctccac cacaacgtct cttaatgtaa gggaaggtga aaacaatctt 16920
cagccaaaag tagtgctata cagcgaagat gttaacttgg aatcccctga cactcatttg 16980
tcttacaaac ctaaaaagga tgacaccaac tctaaaatca tgttgggtca gcaagccatg 17040
cccaacagac ccaacctcat tgcttttagg gacaacttta ttggacttat gtactacaac 17100
agcacaggca acatgggagt gctggcagga caggcctccc agctaaacgc tgtggtagac 17160
ttgcaagaca gaaacacaga gctgtcatac caactgatgc ttgattccat tggagacaga 17220
tcaagatact tttccatgtg gaaccaggca gtggacagct atgacccaga tgtcagaatc 17280
attgaaaacc atggggttga agatgagctg cccaactatt gctttcccct gggcggtatt 17340
ggaattacag acacatacca gtgcataaaa ccaaccgcag ctgctaataa cactacatgg 17400
tctaaggatg aagaatttag tgatcgcaat gaaatagggg tgggaaacaa cttcgccatg 17460
gagatcaaca tccaggccaa cctctggagg aacttcctct atgcgaacgt ggggctctac 17520
ctgccagaca agctcaagta caaccccacc aacgtggaca tctctgacaa ccccaacacc 17580
tatgactaca tgaacaagcg tgtggtggct cccggcctgg tggactgctt tgtcaatgtg 17640

-continued ggagccaggt ggtccctgga ctacatggac aacgtcaacc ccttcaacca ccaccgcaat 17700
gcgggtctgc gctaccgctc catgatcctg ggcaacgggc gctacgtgcc cttccacatt 17760
caggtgcccc agaagttctt tgccatcaag aacctcctcc tcctgccggg ctcctacact 17820
tacgagtgga acttcaggaa ggatgtcaac atggtcctgc agagctctct gggcaatgac 17880
cttagggtgg acggggccag catcaagttt gacagcgtca ccctctatgc taccttcttc 17940
cccatggctc acaacaccgc ctccacgctc gaggccatgc tgaggaacga caccaacgac 18000
cagtccttca atgactacct ctctggggcc aacatgctct accccatccc cgccaaggcc 18060
accaacgtgc ccatctccat tccctctcgc aactgggccg ccttcagagg ctgggccttt 18120
acccgcctta agaccaagga aaccccctcc ctgggctcgg gttttgaccc ctactttgtc 18180
tactcgggat ccatccccta cctggatggc accttctacc tcaaccacac ttttaagaag 18240
atatccatca tgtatgactc ctccgtcagc tggccgggca atgaccgcct gctcaccccc 18300
aatgagttcg aggtcaagcg cgccgtggac ggcgagggct acaacgtggc ccagtgcaac 18360
atgaccaagg actggttcct ggtgcagatg ctggccaact acaacatagg ctaccagggc 18420
ttctacatcc cagagagcta caaggacagg atgtactcct tcttcagaaa tttccaaccc 18480
atgagcaggc aggtggtgga cgagaccaaa tacaaggact atcaggccat tggcatcact 18540
caccagcaca acaactcggg attcgtgggc tacctggctc ccaccatgcg cgaggggcag 18600
gcctaccccg ccaacttccc ctacccgttg ataggcaaaa ccgcggtcga cagcgtcacc 18660
cagaaaaagt tcctctgcga ccgcaccctc tggcgcatcc ccttctctag caacttcatg 18720
tccatgggtg cgctcacgga cctgggccag aacctgctct atgccaactc cgcccatgcg 18780
ctggacatga cttttgaggt ggaccccatg gacgagccca cccttctcta tattgtgttt 18840
gaagtgttcg acgtggtcag agtgcaccag ccgcaccgcg gtgtcatcga gaccgtgtac 18900
ctgcgcacgc ccttctcggc cggcaacgcc accacctaag gagacagcgc cgccgcctgc 18960
atgacgggtt ccaccgagca agagctcagg gccatcgcca gagacctggg atgcggaccc 19020
tatttttggg gcacctatga caaacgcttc ccgggcttca tctcccgaga caagctcgcc 19080
tgcgccatcg tcaacacggc cgcgcgcgag accgggggcg tgcactggct ggcctttggc 19140
tgggacccgc gctccaaaac ctgctacctc ttcgacccct ttggcttctc cgatcagcgc 19200
ctcagacaga tctatgagtt tgagtacgag gggctgctgc gccgcagcgc gcttgcctcc 19260
tcgcccgacc gctgcatcac ccttgagaag tccaccgaga ccgtgcaggg gccccactcg 19320
gccgcctgcg gtctcttctg ctgcatgttt ttgcacgcct ttgtgcgctg gccccagagt 19380
cccatggatc gcaaccccac catgaacttg ctcaagggag tgcccaacgc catgctccag 19440
agcccccagg tccagcccac cctgcgccac aaccaggaac agctctaccg cttcctggag 19500
cgccactccc cctacttccg cagtcacagc gcgcacatcc ggggggccac ctctttctgc 19560
cacttgcaag aaaacatgca agacggaaaa tgatgtacag ctcgcttttt aataaatgta 19620
aagactgtgc actttattta tacacgggct ctttctggtt atttattcaa caccgccgtc 19680
gccatctaga aatcgaaagg gttctgccgc gcgtcgccgt gcgccacggg cagagacacg 19740
ttgcgatact ggaagcggct cgcccactta aactcgggca ccaccatgcg gggcagtggt 19800
tcctcgggga agttctcgcc ccacagggtg cgggtcagct gcagcgcgct caggaggtcg 19860
ggagccgaga tcttgaagtc gcagttgggg ccggaaccct gcgcgcgcga gttgcggtac 19920
acggggttgc agcactggaa caccagcagg gccggattat gcacgctggc cagcaggctc 19980
tcgtcgctga tcatgtcgct gtccagatcc tccgcgttgc tcagggcgaa cggggtcatc 20040
ttgcagacct gcctgcccag gaaaggcggc agcccgggct tgccgttgca gtcgcagcgc 20100
aggggcatca gcaggtgccc gcggcccgac tgcgcctgcg ggtacagcgc gcgcatgaag 20160
gcttcgatct gcctgaaagc cacctgcgtc ttggctccct ccgaaaagaa catcccacag 20220
gacttgctgg agaactggtt cgcgggacag ctggcatcgt gcaggcagca gcgcgcgtcg 20280
gtgttggcga tctgcaccac gttgcgaccc caccggttct tcactatctt ggccttggaa 20340
gcctgctcct tcagcgcgcg ctggccgttc tcgctggtca catccatctc tatcacctgc 20400
tccttgttga tcatgtttgt accgtgcaga cacttcaggt cgccctccgt ctgggtgcag 20460
cggtgctccc acagcgcgca accggtgggc tcccaatttt tgtgggtcac cccgcgtag 20520
gcctgcaggt aggcctgcaa gaagcgcccc atcatggcca caaaggtctt ctggctcgta 20580
aaggtcagct gcaggccgcg atgctcttcg ttcagccagg tcttgcagat ggcggccagc 20640
gcctcggtct gctcgggcag catcctaaaa tttgtcttca ggtcgttatc cacgtggtac 20700
ttgtccatca tggcgcgcgc cgcctccatg cccttctccc aggcggacac catgggcagg 20760
cttagggggt ttatcacttc caccggcgag gacaccgtac tttcgatttc ttcttcctcc 20820
ccctcttccc ggcgcgcgcc cacgctgctg cgcgctctca ccgcctgcac caaggggtcg 20880
tcttcaggca agcgccgcac cgagcgcttg ccgcccttga cctgcttaat cagcaccggc 20940
gggttgctga agcccaccat ggtcagcgcc gcctgctctt cttcgtcttc gctgtctacc 21000
actatctctg gggaagggct tctccgctct gcggcggcgc gcttcttttt tttcttggga 21060
gcggccgtga tggagtccgc cacggcgacg gaggtcgagg gcgtggggct gggggtgcgc 21120
ggtaccaggg cctcgtcgcc ctcggactct tcctctgact ccaggcggcg gcggagtcgc 21180
ttctttgggg gcgcgcgcgt cagcggcggc ggagacgggg acggggacgg ggacgggacg 21240
ccctccacag gggggtggtct tcgcgcagac ccgcggccgc gctcgggggt cttctcgagc 21300
tggtcttggt cccgactggc cattgtatcc tcctcctcct aggcagagag acataaggag 21360
tctatcatgc aagtcgagaa ggaggagagc ttaaccaccc cctctgagac cgccgatgcg 21420
cccgccgtcg ccgtcgcccc cgctgccgcc gacgcgcccg ccacaccgag cgacaccccc 21480
gcggaccccc ccgccgacgc acccctgttc gaggaagcgg ccgtggagca ggacccgggc 21540
tttgtctcgg cagaggagga tttgcgagag gaggaggata aggagaagaa gccctcagtg 21600
ccaaaagatg ataaagagca agacgagcac gacgcagatg cacaccaggg tgaagtcggg 21660
cggggggacg gagggcatga cggcgccgac tacctagacg aagggaacga cgtgctcttg 21720
aagcacctgc atcgtcagtg cgccattgtt tgcgacgctc tgcaggagcg cagcgaagtg 21780
cccctcagcg tggcggaggt cagccacgcc tacgagctca gcctcttctc ccccccgggtg 21840
ccccccgcc gccgcgaaaa cggcacatgc gagcccaacc cgcgcctcaa cttctacccc 21900
gcctttgtgg tacccgaggt cctggccacc tatcacatct tctttcaaaa ttgcaagatc 21960
cccctctcgt gccgcgccaa ccgtagccgc gccgataaga tgctggccct gcgccagggc 22020
gaccacatac ctgatatcgc cgctttggaa gatgtaccaa agatcttcga gggtctgggt 22080
cgcaacgaga agcgggcagc aaactctctg caacaggaaa acagcgaaaa tgagagtcac 22140
accggggtac tggtggagct cgagggcgac aacgcccgcc tggcggtggt caagcgcagc 22200
atcgaggtca cccactttgc ctaccccgcg ctaaacctgc cccccaaagt catgaacgcg 22260
gccatggacg ggctgatcat gcgccgcggc cggcccctcg ctccagatgc aaacttgcat 22320
gaggagaccg aggacggcca gcccgtggtc agcgacgagc agctggcgcg ctggctggag 22380
accgcggacc ccgccgaact ggaggagcgg cgcaagatga tgatggccgt ggtgctggtc 22440

```
accgtagagc tggagtgtct gcagcgcttc ttcggcgacc ccgagatgca gagaaaggtc   22500

gaggagaccc tgcactacac cttccgccag ggctacgtgc gccaggcttg caagatctcc   22560

aacgtggagc tcagcaacct ggtgtcctac ctgggcatct tgcatgagaa ccgcctcggg   22620

cagagcgtgc tgcactccac cctgcgcggg gaggcgcgcc gcgactacgt gcgcgactgc   22680

gtttacctct tcctctgcta cacctggcag acggccatgg gggtctggca gcagtgcctg   22740

gaggagcgca acctcaagga gctggagaag ctcctgcagc gcgcgctcaa agatctctgg   22800

acgggctaca acgagcgctc ggtggccgcc gcgctggccg acctcatctt ccccgagcgc   22860

ctgctcaaaa ccctccagca ggggctgccc gacttcacca gccaaagcat gttgcaaaac   22920

ttcaggaact ttatcctgga gcgttctggc atcctacccg ccacctgctg cgccctgccc   22980

agcgactttg tccccctcgt gtaccgcgag tgccccccgc cgctgtgggg tcactgctac   23040

ctgttccaac tggccaacta cctgtcctac cacgcggacc tcatggagga ctccagcggc   23100

gaggggctca tggagtgcca ctgccgctgc aacctctgca cgccccaccg ctccctggtc   23160

tgcaacaccc aactgctcag cgagagtcag attatcggta ccttcgagct acagggtccg   23220

tcctcctcag acgagaagtc cgcggctccg gggctaaaac tcactccggg gctgtggact   23280

tccgcctacc tgcgcaaatt tgtacctgaa gactaccacg cccacgagat caggttttac   23340

gaagaccaat cccgcccgcc caaggcggag ctgaccgcct gcgtcatcac ccagggcgag   23400

atcctaggcc aattgcaagc catccaaaaa gcccgccaag actttttgct gaagaagggt   23460

cgggggggtgt atctggaccc ccagtcgggt gaggagctca acccggttcc cccgctgccg   23520

ccgccgcggg accttgcttc ccaggataag catcgccatg gctcccagaa agaagcagca   23580

gcggccgcca ctgccgccac cccacatgct ggaggaagag gaggaatact gggacagtca   23640

ggcagaggag gtttcggacg aggaggagcc ggagacggaa atggaagagt gggaggagga   23700

cagcttagac gaggaggctt ccgaagccga agaggcagac gcaacaccgt caccctcggc   23760

cgcagccccc tcgcaggcgc ccccgaagtc cgctcccagc atcagcagca acagcagcgc   23820

tataacctcc gctcctccac cgccgcgacc cacggccgac cgcagaccca accgtagatg   23880

ggacaccacc ggaaccgggg ccggtaagtc ctccgggaga ggcaagcaag cgcagcgcca   23940

aggctaccgc tcgtggcgcg ctcacaagaa cgccatagtc gcttgcttgc aagactgcgg   24000

ggggaacatc tccttcgccc gccgcttcct gctcttccac cacggtgtgg ccttcccccg   24060

taacgtcctg cattactacc gtcatctcta cagcccctac tgcggcggca gtgagccaga   24120

gacggtcggc ggcggcggcg gcgcccgttt cggcgcctag gaagacccag ggcaagactt   24180

cagccaagaa actcgcggcg gccgcggcga acgcggtcgc gggggccctg cgcctgacgg   24240

tgaacgaacc cctgtcgacc cgcgaactga ggaaccgaat cttccccact ctctatgcca   24300

tcttccagca gagcagaggg caggatcagg aactgaaagt aaaaaacagg tctctgcgct   24360

ccctcacccg cagctgtctg tatcacaaga gcgaagacca gcttcggcgc acgctggagg   24420

acgctgaggc actcttcagc aaatactgcg cgctcactct taaggactag ctccgcgccc   24480

ttctcgaatt taggcgggaa cgcctacgtc atcgcagcgc cgccgtcatg agcaaggaca   24540

ttcccacgcc atacatgtgg agctatcagc cgcagatggg actcgcggcg ggcgcctccc   24600

aagactactc cacccgcatg aactggctca gtgccggccc acacatgatc tcacaggtta   24660

atgatatccg cacccatcga aaccaaatat tggtggagca ggcggcaatt accaccacgc   24720

cccgcaataa tcccaacccc agggagtggc ccgcgtccct ggtgtatcag gaaattcccg   24780

gccccaccac cgtactactt ccgcgtgatt cccaggccga agtccaaatg actaactcag   24840
```

```
gggcacagct cgcgggcggc tgtcgtcaca gggtgcggcc tcctcgccag ggtataactc  24900
acctggagat ccgaggcaga ggtattcagc tcaacgacga gtcggtgagc tcctcgctcg  24960
gtctcagacc tgacgggacc ttccagatag ccggagccgg ccgatcttcc ttcacgcccc  25020
gccaggcgta cctgactctg caaagctcgt cctcggcgcc gcgctcgggc ggcatcggga  25080
ctctccagtt cgtgcaggag tttgtgccct cggtctactt caaccccttc tcgggctctc  25140
ccggtcgcta cccggaccag ttcatctcga actttgacgc cgcgagggac tcggtggacg  25200
gctacgactg aatgtcgggt ggacccggtg cagagcaact tcgcctgaag cacctcgacc  25260
actgccgccg ccctcagtgc tttgcccgct gtcagaccgg tgagttccag tacttttccc  25320
tgcccgactc gcacccggac ggcccggcgc acggggtgcg ctttttcatc ccgagtcagg  25380
tgcgctctac cctaatcagg gagtttaccg cccgtcccct actggcggag ttggaaaagg  25440
ggccttctat cctaaccatt gcctgcatct gctctaaccc tggattgcac caagatcttt  25500
gctgtcattt gtgtgctgag tataataaag gctgagatca gaatctactc gggctcctgt  25560
cgccatcctg tcaacgccac cgtccaagcc cggcccgatc agcccgaggt gaacctcacc  25620
tgcggtctgc accggcgcct gaggaaatac ctagcttggt actacaacag cactcccttt  25680
gtggtttaca acagctttga ccaggacggg gtctcactga gggataacct ctcgaacctg  25740
agctactcca tcaggaagaa cagcaccctc gagctacttc ctccttacct gcccgggact  25800
taccagtgtg tcaccggtcc ctgcacccac acccacctgt tgatcgtaaa cgactctctt  25860
ccgagaacag acctcaataa ctcctcttcg cagttcccca gaacaggagg tgagctcagg  25920
aaaccccggg taaagaaggg tggacgagag ttaacacttg tggggtttct ggtgtatgtg  25980
acgctggtgg tggctctttt gattaaggct tttccttcca tgtctgaact ctccctcttc  26040
ttttatgaac aactcgacta gtgctaacgg gaccctaccc aacgaatcgg gattgaatat  26100
cggtaaccag gttgcagttt cacttttgat taccttcata gtcctcttcc tgctagtgct  26160
gtcgcttctg tgcctgcgga tcgggggctg ctgcatccac gtttatatct ggtgctggct  26220
gtttagaagg ttcggagacc atcgcaggta gaataaacat gctgctgctt accctctttg  26280
tcctggcgct ggccgccagc tgccaagcct tttccgaggc tgactttata gagccccagt  26340
gtaatgtgac ttttaaagcc catgcacagc gttgtcatac tataatcaaa tgtgccaccg  26400
aacacgatga ataccttatc cagtataaag ataaatcaca caaagtggca cttgttgaca  26460
tctggaaacc cgaagaccct ttggaataca atgtgaccgt tttccagggt gacctcttca  26520
aaatttacaa ttacactttc ccatttgacc agatgtgtga ctttgtcatg tacatggaaa  26580
agcagcacaa gctgtggcct ccgactcccc agggctgtgt ggaaaatcca ggctctttct  26640
gcatgatctc tctctgtgta actgtgctgg cactaatact cacgcttttg tatatcagat  26700
ttaaatcaag gcaaagcttc attgatgaaa agaaaatgcc ttaatcgctt tcacgcttga  26760
ttgctaacac cgggttttta tccgcagaat gattggaatc accctactaa tcacctccct  26820
ccttgcgatt gcccatgggt tggaacgaat cgaagtccct gtgggggcca atgttaccct  26880
ggtggggcct gtcggcaatg ctacattaat gtgggaaaaa tatactaaaa atcaatgggt  26940
ctcttactgc actaacaaaa atagccacaa gcccagagcc atctgcgatg ggcaaaatct  27000
aaccttgatt gatgttcaat tgctggatgc gggctactat tatgggcagc tgggtacaat  27060
gattaattac tggagacccc acagagatta catgctccac gtagtaaagg gtccccttag  27120
cagcccaccc actaccacct ctactacccc cactaccacc actactccca ccaccagcac  27180
tgccgcccag cctcctcata gcagaacaac cacttttatc aattccaagt cccactcccc  27240
```

```
ccacattgcc ggcgggccct ccgcctcaga ctccgaaacc accgagatct gcttctgcaa  27300
atgctctgac gccattgccc aggatttgga agatcacgag gaagatgagc atgacttcgc  27360
agatgcatgc caggcatcag agccagaagc gctgccggtg gccctcaaac agtatgcaga  27420
cccccacacc acccccgacc ttcctccacc ttcccagaag ccaagtttcc tgggggaaaa  27480
tgaaactctg cctctctcca tactcgctct gacatctgtt gctatgttga ccgctctgct  27540
ggtgcttcta tgctctatat gctacctgat ctgctgcaga aagaaaaaat ctcacggcca  27600
tgctcaccag cccctcatgc acttccctta ccctccagag ctgggcgacc acaaacttta  27660
agtctgcagt aactatctgc ccatcccttg tcagtcgaca gcgatgagcc ccactaatct  27720
aacggcctct ggacttacaa catcgtctct taatgagacc accgctcctc aagacctgta  27780
cgatggtgtc tccgcgctgg ttaaccagtg ggatcacctg ggcatatggt ggctcctcat  27840
aggagcagtg accctgtgcc taatcctggt ctggatcatc tgctgcatca aaagcagaag  27900
acccaggcgg cggcccatct acaggccctt tgtcatcaca cctgaagatg atgatgacac  27960
cacttccagg ctgcagaggc taaagcagct actcttctct tttacagcat ggtaaattga  28020
atcatgcctc gcattttcat ctacttgtct ctccttccac tttttctggg ctcttctaca  28080
ttggccgctg tgtcccacat cgaggtagac tgcctcacgc ccttcacagt ctacctgctt  28140
ttcggctttg tcatctgcac ctttgtctgc agcgttatca ctgtagtgat ctgcttcata  28200
cagtgcatcg actacgtctg cgtgcgggtg gcttacttta gacaccaccc ccagtatcgc  28260
aacagggaca tagcggctct cctaagactt gtttaaaatc atggccaaat taactgtgat  28320
tggtcttctg atcatctgct gcgtcctagc cgcgattggg actcaagctc ctaccaccac  28380
cagcgctccc agaaagagac atgtatcctg cagcttcaag cgtccctgga atataccccca  28440
atgctttact gatgaacctg aaatctcttt ggcttggtac ttcagcgtca ccgcccttct  28500
tatcttctgc agtacggtta ttgcccttgc catctaccct tcccttgacc tgggctggaa  28560
tgctgtcaac tctatggaat atcccacctt cccagaacca gacctgccag acctggttgt  28620
tctaaacgcg tttcctcctc ctgctcccgt tcaaaatcag tttcgccctc cgtcccccac  28680
gcccactgag gtcagctact ttaatctaac aggcggagat gactgaaaac ctagacctag  28740
aaatggacgg tctctgcagc gagcaacgca cactagagag gcgccggcaa aaagagctcg  28800
agcgtcttaa acaagagctc caagacgcgg tggccataca ccagtgcaaa aaaggtgtct  28860
tctgtctggt aaaacaggcc acgctcacct atgaaaaaac aggtgacacc caccgcctag  28920
gatacaagct gcccacacag cgccaaaagt tcgccctcat gataggcgaa caacccatca  28980
ccgtgaccca gcactccgtg gagacagaag gctgcataca tgctccctgt aggggcgctg  29040
actgcctcta caccttgatc aaaaccctct gcggtctcag agaccttatc cctttcaatt  29100
aatcataact gtaatcaata aaaaatcact tacttgaaat ctgatagcaa gcctctgtcc  29160
aatttttca gcaacacttc cttcccctcc tcccaactct ggtactctag gcgcctccta  29220
gctgcaaact tcctccacag tctgaaggga atgtcagatt cctcctcctg tccctccgca  29280
cccacgatct tcatgttgtt gcagatgaaa cgcgcgagat cgtctgacga gaccttcaac  29340
cccgtgtacc cctacgatac cgagatcgct ccgacttctg tccctttcct tacccctccc  29400
tttgtgtcat ccgcaggaat gcaagaaaat ccagctgggg tgctgtccct gcacttgtca  29460
gagcccctta ccacccacaa tggggccctg actctaaaaa tgggggggcgg cctgaccctg  29520
gacaaggaag ggaatctcac ttcccaaaac atcaccagtg tcgatccccc tctcaaaaaa  29580
agcaagaaca acatcagcct tcagaccgcc gcacccctcg ccgtcagctc cggggcccta  29640
```

acactttttg ccactccccc cctagcggtc agtggtgaca accttactgt gcagtctcag 29700
gcccctctca ctttggaaga ctcaaaacta actctggcca ccaaaggacc cctaactgtg 29760
tccgaaggca aacttgtcct agaaacagag gctcccctgc atgcaagtga cagcagcagc 29820
ctgggcctta gcgttacggc cccacttagc attaacaatg acagcctagg actagatctg 29880
caggcaccca ttgtctctca aaatggaaaa ctggctctaa atgtagcagg ccccctagct 29940
gtggccaatg gcattaatgc tttgacagta ggcacaggca aaggtattgg tctaaatgaa 30000
accagcactc acttgcaagc aaagttggtc gccccccctag gctttgatac caatggcaac 30060
attaagctaa gcgttgcagg aggcatgaga ctaaataatg acacacttat actagatgta 30120
aactacccat ttgaagctca aggccaacta agtctaagag tgggccaggg tccgctgtat 30180
gtagattcta gcagccataa cctgaccatt agatgcctta gaggattata cataacatcg 30240
tctaataacc aaaccggtct agaggccaac ataaaactaa caaaaggcct tgtctatgat 30300
ggaaatgcca tagcagtcaa tgttggtcaa ggattgcaat acagcactac tgccacatcg 30360
gaaggtgtgt atcctataca gtctaagata ggtttgggaa tggaatatga taccaacgga 30420
gccatgatga caaaactagg ctctggacta agctttgaca attcaggagc cattgtagtg 30480
ggaaacaaaa atgatgacag gcttactctg tggactacac cagacccatc tcctaactgt 30540
agaatttatt ctgaaaaaga tactaaacta accttggtgc tgactaagtg tggcagccaa 30600
atcctaggca cagtatctgc ccttgctgtc agaggcagcc ttgcgcccat cactaatgca 30660
tccagcatag tccaaatatt tctaagattt gatgaaaatg gactattgat gagcaactca 30720
tcgctagacg gtgattactg gaattacaga aatggggact ccactaatag cacaccatat 30780
acaaatgcag taggctttat gcctaatcta gcagcctatc ctaaaggtca ggctacagct 30840 gcaaaaaagca gtattgtaag ccaggtatac atggatggtg acactactaa acctataaca 30900
ctaaaaataa acttcaatgg cattgatgaa acaacagaaa atacccctgt tagtaaatat 30960
tccatgacat tctcatggag ctggcccacc gcaagctaca taggccacac ttttgcaaca 31020
aactctttta ctttctccta catcgcccaa gaataaagaa agcacagaga tgcttgtttt 31080
gatttcaaaa ttgtgtgctt ttatttattt tcagcttaca gtatttccag tagtcattcg 31140
aataaagctt aatcaaactg catgagaacc cttccacata gcttaaatta gcaccagtgc 31200
aaatggagaa aagcctcgag gtcgttgcgc ggccgggatc ggtgatcacc gatccagaca 31260
tgataagata cattgatgag tttggacaaa ccacaactag aatgcagtga aaaaaatgct 31320
ttatttgtga aatttgtgat gctattgctt tatttgtaac cattataagc tgcaataaac 31380
aagttcccgg atcgcgatcc ggcccgaggc tgtagccgac gatggtgcgc caggagagtt 31440
gttgattcat tgtttgcctc cctgctgcgg tttttcaccg aagttcatgc cagtccagcg 31500
tttttgcagc agaaaagccg ccgacttcgg tttgcggtcg cgagtgaaga tccctttctt 31560
gttaccgcca acgcgcaata tgccttgcga ggtcgcaaaa tcggcgaaat tccatacctg 31620
ttcaccgacg acggcgctga cgcgatcaaa gacgcggtga tacatatcca gccatgcaca 31680
ctgatactct tcactccaca tgtcggtgta cattgagtgc agcccggcta acgtatccac 31740
gccgtattcg gtgatgataa tcggctgatg cagtttctcc tgccaggcca gaagttcttt 31800
ttccagtacc ttctctgccg tttccaaatc gccgctttgg acataccatc cgtaataacg 31860
gttcaggcac agcacatcaa agagatcgct gatggtatcg gtgtgagcgt cgcagaacat 31920
tacattgacg caggtgatcg gacgcgtcgg gtcgagttta cgcgttgctt ccgccagtgg 31980
cgcgaaatat tcccgtgcac cttgcggacg ggtatccggt tcgttggcaa tactccacat 32040

-continued

```
caccacgctt gggtggtttt tgtcacgcgc tatcagctct ttaatcgcct gtaagtgcgc  32100
ttgctgagtt tccccgttga ctgcctcttc gctgtacagt tctttcggct tgttgcccgc  32160
ttcgaaacca atgcctaaag agaggttaaa gccgacagca gcagtttcat caatcaccac  32220
gatgccatgt tcatctgccc agtcgagcat ctcttcagcg taagggtaat gcgaggtacg  32280
gtaggagttg gccccaatcc agtccattaa tgcgtggtcg tgcaccatca gcacgttatc  32340
gaatcctttg ccacgcaagt ccgcatcttc atgacgacca aagccagtaa agtagaacgg  32400
tttgtggtta atcaggaact gttcgccctt cactgccact gaccggatgc cgacgcgaag  32460
cgggtagata tcacactctg tctggctttt ggctgtgacg cacagttcat agagataacc  32520
ttcacccggt tgccagaggt gcggattcac cacttgcaaa gtcccgctag tgccttgtcc  32580
agttgcaacc acctgttgat ccgcatcacg cagttcaacg ctgacatcac cattggccac  32640
cacctgccag tcaacagacg cgtggttaca gtcttgcgcg acatgcgtca ccacggtgat  32700
atcgtccacc caggtgttcg gcgtggtgta gagcattacg ctgcgatgga ttccggcata  32760
gttaaagaaa tcatggaagt aagactgctt tttcttgccg ttttcgtcgg taatcaccat  32820
tcccggcggg atagtctgcc agttcagttc gttgttcaca caaacggtga tacgtacact  32880
tttcccggca ataacatacg gcgtgacatc ggcttcaaat ggcgtatagc cgccctgatg  32940
ctccatcact tcctgattat tgacccacac tttgccgtaa tgagtgaccg catcgaaacg  33000
cagcacgata cgctggcctg cccaaccttt cggtataaag acttcgcgct gataccagac  33060
gttgcccgca taattacgaa tatctgcatc ggcgaactga tcgttaaaac tgcctggcac  33120
agcaattgcc cggctttctt gtaacgcgct ttcccaccaa cgctgatcaa ttccacagtt  33180
ttcgcgatcc agactgaatg cccacaggcc gtcgagtttt ttgatttcac gggttggggt  33240
ttctacagga cggaccatgc gttcgacctt tctcttcttt tttgggccca tgatggcaga  33300
tccgtatagt gagtcgtatt agctggttct ttccgcctca gaagccatag agcccaccgc  33360
atccccagca tgcctgctat tgtcttccca atcctccccc ttgctgtcct gccccacccc  33420
acccccccaga atagaatgac acctactcag acaatgcgat gcaatttcct cattttatta  33480
ggaaaggaca gtgggagtgg caccttccag ggtcaaggaa ggcacggggg aggggcaaac  33540
aacagatggc tggcaactag aaggcacagt cgaggctgat cagcgagctc tagatgcatg  33600
ctcgagcggc cgcacgtcgt accggcaatt gccgcggcaa ttgccgacgc cgcgtaacta  33660
taacggtcct aaggtagcga gagggccaag tgccgaacga gtatatatag gaataaaaaa  33720
tgacgtaaat gtgtaaaggt cagaaaacgc ccagaaaaat acacagacca acgcccgaaa  33780
cgaaaacccg cgaaaaaata cccagaactt cctcaacaac cgccacttcc ggtttctcac  33840
ggtacgtcac ttccgcaaga aaagcaaaac tacatttccc acatgtgtaa aaacgaaacc  33900
ccgccccttg taactgccca caacttacat catcaaaaca taaactccta cgtcacccgc  33960
cccgcctctc cccgcccacc tcattatcat attggccaca atccaaaata aggtatatta  34020
ttgatgatg                                                          34029
```